(12) United States Patent
Khattri et al.

(10) Patent No.: US 7,507,542 B2
(45) Date of Patent: Mar. 24, 2009

(54) METHOD FOR REGULATING IMMUNE FUNCTION USING THE FOXP3 PROTEIN

(75) Inventors: Roli Khattri, Kirkland, WA (US); Mary E Brunkow, Seattle, WA (US); Fred Ramsdell, Bainbridge Island, WA (US)

(73) Assignee: UCB SA, Slough, Berkshire (GB)

( * ) Notice: Subject to any disclaimer, the term of this patent is extended or adjusted under 35 U.S.C. 154(b) by 146 days.

(21) Appl. No.: 10/142,667

(22) Filed: May 8, 2002

(65) Prior Publication Data

US 2003/0170648 A1    Sep. 11, 2003

Related U.S. Application Data

(60) Provisional application No. 60/333,409, filed on Nov. 26, 2001, provisional application No. 60/289,654, filed on May 8, 2001.

(51) Int. Cl.
*G01N 33/53*    (2006.01)
(52) U.S. Cl. .......................... 435/7.2; 435/6
(58) Field of Classification Search .................... 435/4, 435/6, 29, DIG. 2, DIG. 4
See application file for complete search history.

(56) References Cited

U.S. PATENT DOCUMENTS

| 6,084,067 A | 7/2000 | Freeman et al. ............ 530/350 |
| 6,414,129 B1 | 7/2002 | Brunkow et al. ........... 536/23.5 |
| 6,878,523 B2 * | 4/2005 | Nelson et al. ............... 435/7.1 |
| 2003/0170648 A1 * | 9/2003 | Khattri et al. .................. 435/6 |

FOREIGN PATENT DOCUMENTS

| WO | WO 00/09693 | 2/2000 |
| WO | WO-02/16656 | 2/2002 |

OTHER PUBLICATIONS

Genebank Accession No. AF235087, Oct. 11, 2000.
Genebank Accession No. AF235097, Apr. 5, 2000.
Asano et al., "Autoimmune disease as a consequence of developmental abnormality of a T cell subpopulation," *J. Exp. Med.* 184(2):387-396, Aug. 1, 1996.
Bennett et al., "The immune dysregulation, polyendocrinopathy, enteropathy, X-linked syndrome (IPEX) is caused by mutations of FOXP3," *Nat. Genet.* 27(1):20-21, Jan. 2001.
Blair et al., "CD4$^+$CD8$^-$ T cells are the effector cells in disease pathogenesis in the scurfy (sf) mouse," *J. Immunol.* 153(8):3764-3774, Oct. 15, 1994.
Brunkow et al., "Disruption of a new forkhead/winged-helix protein, scurfin, results in the fatal lymphoproliferative disorder of the scurfy mouse," *Nat. Genet.* 27(1):68-73, Jan. 2001.
Chatila et al., "JM2, encoding a fork head-related protein, is mutated in X-linked autoimmunity-allergic disregulation syndrome," *J. Clin. Invest.* 106(12):R75-R81, Dec. 2000.
Clark et al., "Cellular and molecular characterization of the *scurfy* mouse mutant," *J. Immunol.* 162(5):2546-2554, Mar. 1, 1999.

Cottrez and Groux, "Regulation of TGF-β response during T cell activation is modulated by IL-10," *J. Immunol.* 167(2):773-778, Jul. 15, 2001.
Garvin, "Disruption of thymocyte development and lymphomagenesis induced by SV40 T-antigen," *Int. Immunol.* 2(2):173-180, 1990.
Godfrey et al., "Fatal lymphoreticular disease in the scurfy (sf) mouse requires T cells that mature in a sf thymic environment: potential model for thymic education," *Proc. Natl. Acad. Sci. U S A.* 88(13):5528-5532, Jul. 1, 1991.
Godfrey et al., "Transplantation of T cell-mediated, lymphoreticular disease from the scurfy (sf) mouse," *Am. J. Pathol.* 145(2):281-286, Aug. 1994.
Godfrey et al., "X-linked lymphoreticular disease in the scurfy (sf) mutant mouse," *Am. J. Pathol.* 138(6):1379-1387, Jun. 1991.
Kanangat et al., "Disease in the scurfy (sf) mouse is associated with overexpression of cytokine genes," *Eur. J. Immunol.* 26(1):161-165, Jan. 1996.
Kulkarni et al., "Transforming growth factor β 1 null mutation in mice causes excessive inflammatory response and early death," *Proc. Nat. Acad Sci. U S A.* 90(2):770-774, Jan. 15, 1993.
Lenardo et al., "Mature T lymphocyte apoptosis—immune regulation in a dynamic and unpredictable antigenic environment," *Annu. Rev. Immunol.* 17:221-253, 1999.
Lyon et al., "The scurfy mouse mutant has previously unrecognized hematological abnormalities and resembles Wiskott-Aldrich syndrome," *Proc. Natl. Acad. Sci. U S A.* 87(7):2433-2437, Apr. 1990.
McHugh et al., "CD4$^+$CD25$^+$ immunoregulatory T cells: gene expression analysis reveals a functional role for the glucocorticoid-induced TNF receptor," *Immunity* 16(2):311-323, Feb. 2002.
Oosterwegel et al., "CTLA-4 and T cell activation," *Curr. Opin. Immunol.* 11(3):294-300, Jun. 1999.
Read et al., "Cytotoxic T lymphocyte-associated antigen 4 plays an essential role in the function of CD25$^+$CD4$^+$ regulatory cells that control intestinal inflammation," *J. Exp. Med.* 192(2):295-302, Jul. 17, 2000.
Roncarolo and Levings, "The role of different subsets of T regulatory cells in controlling autoimmunity," *Curr. Opin. Immunol.* 12(6):676-683, Dec. 2000.
Saito, "Negative regulation of T cell activation," *Curr. Opin. Immunol.* 10(3):313-321, Jun. 1998.
Sakaguchi, "Regulatory T cells: key controllers of immunologic self-tolerance," *Cell* 101(5):455-458, May 26, 2000.
Sakaguchi et al., "Immunologic self-tolerance maintained by activated T cells expressing IL-2 receptor α-chains (CD25). Breakdown of a single mechanism of self-tolerance causes various autoimmune diseases," *J. Immunol.* 155(3):1151-1164, Aug. 1, 1995.

(Continued)

*Primary Examiner*—Michael Pak
(74) *Attorney, Agent, or Firm*—Jane E. R. Potter; Davis Wright Tremaine LLP

(57) ABSTRACT

Isolated nucleic acid molecules are provided which encode Fkh$^{sf}$, as well as mutant forms thereof. Also provided are expression vectors suitable for expressing such nucleic acid molecules, and host cells containing such expression vectors. Also provided are pharmaceutical compounds and methods of identifying such compounds that can modulate the immune system. In addition are provided methods for identifying proteins regulated by Scurfin (Fkh$^{sf}$) and proteins that induce or inhibit Scurfin or Foxp3 expression.

7 Claims, 19 Drawing Sheets

OTHER PUBLICATIONS

Shevach, "Regulatory T cells in autoimmmunity," *Annu. Rev. Immunol.* 18:423-449, 2000.

Shimizu et al., "Stimulation of CD25$^+$CD4$^+$ regulatory T cells through GITR breaks immunological self-tolerance," *Nat. Immunol.* 3(2):135-142, Feb. 2002.

Shull et al., "Targeted disruption of the mouse transforming growth factor-β 1 gene results in multifocal inflammatory disease," *Nature.* 359(6397):693-699, Oct. 22, 1992.

Suri-Payer et al., "CD4$^+$CD25$^+$ T cells inhibit both the induction and effector function of autoreactive T cells and represent a unique lineage of immunoregulatory cells," *J. Immunol.* 160(3):1212-1218, Feb. 1, 1998.

Takahashi et al., "Generalized lymphoproliferative disease in mice, caused by a point mutation in the Fas ligand," *Cell* 76(6)969-976, Mar. 25, 1994.

Takahashi et al., "Immunologic self-tolerance maintained by CD25$^+$CD4$^+$ regulatory T cells constitutively expressing cytotoxic T lymphocyte-associated antigen 4," *J. Exp. Med.* 192(2):303-310, Jul. 17, 2000.

Thornton and Shevach, "CD4$^+$CD25$^+$ immunoregulatory T cells suppress polyclonal T cell activation in vitro by inhibiting interleukin 2 production," *J. Exp. Med.* 188(2):287-296, Jul. 20, 1998.

Thornton and Shevach, "Suppressor effector function of CD4$^+$CD25$^+$ immunoregulatory T cells is antigen nonspecific," *J Immunol.* 164(1):183-190, Jan. 1, 2000.

Tivol et al., "Loss of CTLA-4 leads to massive lymphoproliferation and fatal multiorgan tissue destruction, revealing a critical negative regulatory role of CTLA-4," *Immunity.* 3(5):541-547, Nov. 1995.

Wallach, "Tumor necrosis factor receptor and Fas signaling mechanisms," *Annu. Rev. Immunol.* 17:331-367, 1999.

Watanabe-Fukunaga et al., "Lymphoproliferation disorder in mice explained by defects in Fas antigen that mediates apoptosis," *Nature* 356(6367):314-317, Mar. 26, 1992.

Waterhouse et al., "Lymphoproliferative disorders with early lethality in mice deficient in Ctla-4," *Science* 270(5238):985-988, Nov. 10, 1995.

Wildin et al., "X-linked neonatal diabetes mellitus, enteropathy and endocrinopathy syndrome is the human equivalent of mouse scurfy," *Nat. Genet.* 27(1):18-20, Jan. 2001.

Bassuny, Wafaa, M, et al., "A Functional Polymorphism in the Promoter/Enhancer Region of the FOXP3/Scurfin Gene Associated with Type 1 Diabetes," *Immunogenetics,* 2003, 55:149-156.

Karagiannidis, Christian, et al., "Glucocorticoids Upregulate FOXP3 Expression and Regulatory T Cells in Asthma," *J.Allergy Clin Immunol,* Dec. 2004, 114(6);1425-1433.

Website Reference: http://grants.nih.gov/grants/guide/notice-files/NOT-RM-04-003.html (RFP Announcement: Molecular Libraries Small Molecule Repository—RFP-RM-04-001, notice released Dec. 23, 2003.

Zavattari, Patricia, et al., "No Association Between Variation of the FOXP3 Gene and Common Type 1 Diabetes in the Sardinian Population," *Diabetes,* Jul. 2004, 53:1911-1914.

Khattri et al., *An Essential Role for Scurfin in CD$+CD25+ T Regulatory Cells,* Nature Immunology 4(4):337-342, 2003.

Khattri et al., *The amoung of Scurfin Protein Determines Peripheral T Cell Number and Responsiveness,* Journal of Immunology 167(11):6312-6320, 2001.

Schubert et al., *Scurfin (FOXP3) Acts as a Repressor of Transcription and regulates T Cell Activation,* Journal of Biological Chemistry, 276(40):37672-37679, 2001.

Means, G. D. et al., A Transcript Map of a 2-Mb BAC Contig in the Promimal Portion of the Mouse X Chromosome and Regional Mapping of the Scurfy Mutation, *Genomics* 65:213-223, 2000.

Scherf, M. et al., Highly Specific Localization of promoter Regions in Large Genomic Sequences by Promoterinspector: A Novel Context Analysis Approach, *J. Mol. Biol.* 297:599-606, 2000.

Scherf, M. et al., First Pass Annotation of Promoters on Human Chromosome 22, *Genome Res.* 11:333-340, 2001.

Werner, T., Finding and Decrypting of Promoters Contributes to the Elucidation of Gene Function, *In Silico Biology* 2:0023, 2002.

\* cited by examiner

MOUSE Fkh<sup>sf</sup> cDNA SEQUENCE

```
   1  GCTGATCCCC CTCTAGCAGT CCACTTCACC AAGGTGAGCG AGTGTCCCTG
  51  CTCTCCCCCA CCAGACACAG CTCTGCTGGC GAAAGTGGCA GAGAGGTATT
 101  GAGGGTGGGT GTCAGGAGCC CACCAGTACA GCTGGAAACA CCCAGCCACT
 151  CCAGCTCCCG GCAACTTCTC CTGACTCTGC CTTCAGACGA GACTTGGAAG
 201  ACAGTCACAT CTCAGCAGCT CCTCTGCCGT TATCCAGCCT GCCTCTGACA
 251  AGAACCCAAT GCCCAACCCT AGGCCAGCCA AGCCTATGGC TCCTTCCTTG
 301  GCCCTTGGCC CATCCCCAGG AGTCTTGCCA AGCTGGAAGA CTGCACCCAA
 351  GGGCTCAGAA CTTCTAGGGA CCAGGGGCTC TGGGGGACCC TTCCAAGGTC
 401  GGGACCTGCG AAGTGGGGCC CACACCTCTT CTTCCTTGAA CCCCCTGCCA
 451  CCATCCCAGC TGCAGCTGCC TACAGTGCCC CTAGTCATGG TGGCACCGTC
 501  TGGGGCCCGA CTAGGTCCCT CACCCCACCT ACAGGCCCTT CTCCAGGACA
 551  GACCACACTT CATGCATCAG CTCTCCACTG TGGATGCCCA TGCCCAGACC
 601  CCTGTGCTCC AAGTGCGTCC ACTGGACAAC CCAGCCATGA TCAGCCTCCC
 651  ACCACCTTCT GCTGCCACTG GGTCTTCTC CCTCAAGGCC CGGCCTGGCC
 701  TGCCACCTGG GATCAATGTG GCCAGTCTGG AATGGGTGTC CAGGGAGCCA
 751  GCTCTACTCT GCACCTTCCC ACGCTCGGGT ACACCCAGGA AAGACAGCAA
 801  CCTTTTGGCT GCACCCCAAG GATCCTACCC ACTGCTGGCA AATGGAGTCT
 851  GCAAGTGGCC TGGTTGTGAG AAGGTCTTCG AGGAGCCAGA AGAGTTTCTC
 901  AAGCACTGCC AAGCAGATCA TCTCCTGGAT GAGAAAGGCA AGGCCCAGTG
 951  CCTCCTCCAG AGAGAAGTGG TGCAGTCTCT GGAGCAGCAG CTGGAGCTGG
1001  AAAAGGAGAA GCTGGGAGCT ATGCAGGCCC ACCTGGCTGG GAAGATGGCG
1051  CTGGCCAAGG CTCCATCTGT GGCCTCAATG GACAAGAGCT CTTGCTGCAT
1101  CGTAGCCACC AGTACTCAGG GCAGTGTGCT CCCGGCCTGG TCTGCTCCTC
```

FIG. 1A

```
1101  CGTAGCCACC AGTACTCAGG GCAGTGTGCT CCCGGCCTGG TCTGCTCCTC
1151  GGGAGGCTCC AGACGGCGGC CTGTTTGCAG TGCGGAGGCA CCTCTGGGGA
1201  AGCCATGGCA ATAGTTCCTT CCCAGAGTTC TTCCACAACA TGGACTACTT
1251  CAAGTACCAC AATATGCGAC CCCCTTTCAC CTATGCCACC CTTATCCGAT
1301  GGGCCATCCT GGAAGCCCCG GAGAGGCAGA GGACACTCAA TGAAATCTAC
1351  CATTGGTTTA CTCGCATGTT CGCCTACTTC AGAAACCACC CCGCCACCTG
1401  GAAGAATGCC ATCCGCCACA ACCTGAGCCT GCACAAGTGC TTTGTGCGAG
1451  TGGAGAGCGA GAAGGGAGCA GTGTGGACCG TAGATGAATT TGAGTTTCGC
1501  AAGAAGAGGA GCCAACGCCC CAACAAGTGC TCCAATCCCT GCCCTTGACC
1551  TCAAAACCAA GAAAAGGTGG GCGGGGGAGG GGGCCAAAAC CATGAGACTG
1601  AGGCTGTGGG GGCAAGGAGG CAAGTCCTAC GTGTACCTAT GGAAACCGGG
1651  CGATGATGTG CCTGCTATCA GGGCCTCTGC TCCCTATCTA GCTGCCCTCC
1701  TAGATCATAT CATCTGCCTT ACAGCTGAGA GGGGTGCCAA TCCCAGCCTA
1751  GCCCCTAGTT CCAACCTAGC CCCAAGATGA ACTTTCCAGT CAAAGAGCCC
1801  TCACAACCAG CTATACATAT CTGCCTTGGC CACTGCCAAG CAGAAAGATG
1851  ACAGACACCA TCCTAATATT TACTCAACCC AAACCCTAAA ACATGAAGAG
1901  CCTGCCTTGG TACATTCGTG AACTTTCAAA GTTAGTCATG CAGTCACACA
1951  TGACTGCAGT CCTACTGACT CACACCCCAA AGCACTCACC CACAACATCT
2001  GGAACCACGG GCACTATCAC ACATAGGTGT ATATACAGAC CCTTACACAG
2051  CAACAGCACT GGAACCTTCA CAATTACATC CCCCCAAACC ACACAGGCAT
2101  AACTGATCAT ACGCAGCCTC AAGCAATGCC CAAAATACAA GTCAGACACA
2151  GCTTGTCAGA
```

FIG. 1B

MOUSE Fkh$^{sf}$ PROTEIN SEQUENCE

```
  1  MPNPRPAKPM APSLALGPSP GVLPSWKTAP KGSELLGTRG SGGPFQGRDL
 51  RSGAHTSSSL NPLPPSQLQL PTVPLVMVAP SGARLGPSPH LQALLQDRPH
101  FMHQLSTVDA HAQTPVLQVR PLDNPAMISL PPPSAATGVF SLKARPGLPP
151  GINVASLEWV SREPALLCTF PRSGTPRKDS NLLAAPQGSY PLLANGVCKW
201  PGCEKVFEEP EEFLKHCQAD HLLDEKGKAQ CLLQREVVQS LEQQLELEKE
251  KLGAMQAHLA GKMALAKAPS VASMDKSSCC IVATSTQGSV LPAWSAPREA
301  PDGGLFAVRR HLWGSHGNSS FPEFFHNMDY FKYHNMRPPF TYATLIRWAI
351  LEAPERQRTL NEIYHWFTRM FAYFRNHPAT WKNAIRHNLS LHKCFVRVES
401  EKGAVWTVDE FEFRKKRSQR PNKCSNPCP*
```

FIG. 2

HUMAN *FKH*$^{sf}$ cDNA Sequence

```
   1  GCACACACTC ATCGAAAAAA ATTTGGATTA TTAGAAGAGA GAGGTCTGCG
  51  GCTTCCACAC CGTACAGCGT GGTTTTTCTT CTCGGTATAA AAGCAAAGTT
 101  GTTTTTGATA CGTGACAGTT TCCCACAAGC CAGGCTGATC CTTTTCTGTC
 151  AGTCCACTTC ACCAAGCCTG CCCTTGGACA AGGACCCGAT GCCCAACCCC
 201  AGGCCTGGCA AGCCCTCGGC CCCTTCCTTG GCCCTTGGCC CATCCCCAGG
 251  AGCCTCGCCC AGCTGGAGGG CTGCACCCAA AGCCTCAGAC CTGCTGGGGG
 301  CCCGGGGCCC AGGGGGAACC TTCCAGGGCC GAGATCTTCG AGGCGGGGCC
 351  CATGCCTCCT CTTCTTCCTT GAACCCCATG CCACCATCGC AGCTGCAGCT
 401  GCCCACACTG CCCCTAGTCA TGGTGGCACC CTCCGGGGCA CGGCTGGGCC
 451  CCTTGCCCCA CTTACAGGCA CTCCTCCAGG ACAGGCCACA TTTCATGCAC
 501  CAGCTCTCAA CGGTGGATGC CCACGCCCGG ACCCCTGTGC TGCAGGTGCA
 551  CCCCCTGGAG AGCCCAGCCA TGATCAGCCT CACACCACCC ACCACCGCCA
 601  CTGGGGTCTT CTCCCTCAAG GCCCGGCCTG GCCTCCCACC TGGGATCAAC
 651  GTGGCCAGCC TGGAATGGGT GTCCAGGGAG CCGGCACTGC TCTGCACCTT
 701  CCCAAATCCC AGTGCACCCA GGAAGGACAG CACCCTTTCG GCTGTGCCCC
 751  AGAGCTCCTA CCCACTGCTG GCAAATGGTG TCTGCAAGTG GCCCGGATGT
 801  GAGAAGGTCT TCGAAGAGCC AGAGGACTTC CTCAAGCACT GCCAGGCGGA
 851  CCATCTTCTG GATGAGAAGG GCAGGGCACA ATGTCTCCTC CAGAGAGAGA
 901  TGGTACAGTC TCTGGAGCAG CAGCTGGTGC TGGAGAAGGA GAAGCTGAGT
 951  GCCATGCAGG CCCACCTGGC TGGGAAAATG GCACTGACCA AGGCTTCATC
1001  TGTGGCATCA TCCGACAAGG CTCCTGCTG CATCGTAGCT GCTGGCAGCC
1051  AAGGCCCTGT CGTCCCAGCC TGGTCTGGCC CCCGGGAGGC CCCTGACAGC
1101  CTGTTTGCTG TCCGGAGGCA CCTGTGGGGT AGCCATGGAA ACAGCACATT
```

FIG. 3A

```
1151 CCCAGAGTTC CTCCACAACA TGGACTACTT CAAGTTCCAC AACATGCGAC
1201 CCCCTTTCAC CTACGCCACG CTCATCCGCT GGGCCATCCT GGAGGCTCCA
1251 GAGAAGCAGC GGACACTCAA TGAGATCTAC CACTGGTTCA CACGCATGTT
1301 TGCCTTCTTC AGAAACCATC CTGCCACCTG GAAGAACGCC ATCCGCCACA
1351 ACCTGAGTCT GCACAAGTGC TTTGTGCGGG TGGAGAGCGA GAAGGGGGCT
1401 GTGTGGACCG TGGATGAGCT GGAGTTCCGC AAGAAACGGA GCCAGAGGCC
1451 CAGCAGGTGT TCCAACCCTA CACCTGGCCC CTGACCTCAA GATCAAGGAA
1501 AGGAGGATGG ACGAACAGGG GCCAAACTGG TGGGAGGCAG AGGTGGTGGG
1551 GGCAGGGATG ATAGGCCCTG GATGTGCCCA CAGGGACCAA GAAGTGAGGT
1601 TTCCACTGTC TTGCCTGCCA GGGCCCCTGT TCCCCCGCTG GCAGCCACCC
1651 CCTCCCCCAT CATATCCTTT GCCCAAGGC TGCTCAGAGG GGCCCCGGTC
1701 CTGGCCCCAG CCCCCACCTC CGCCCCAGAC ACACCCCCCA GTCGAGCCCT
1751 GCAGCCAAAC AGAGCCTTCA CAACCAGCCA CACAGAGCCT GCCTCAGCTG
1801 CTCGCACAGA TTACTTCAGG GCTGGAAAAG TCACACAGAC ACACAAAATG
1851 TCACAATCCT GTCCCTCAC
```

FIG. 3B

HUMAN FKH$^{sf}$ PROTEIN SEQUENCE

```
  1 MPNPRPGKPS APSLALGPSP GASPSWRAAP KASDLLGARG PGGTFQGRDL
 51 RGGAHASSSS LNPMPPSQLQ LPTLPLVMVA PSGARLGPLP HLQALLQDRP
101 HFMHQLSTVD AHARTPVLQV HPLESPAMIS LTPPTTATGV FSLKARPGLP
151 PGINVASLEW VSREPALLCT FPNPSAPRKD STLSAVPQSS YPLLANGVCK
201 WPGCEKVFEE PEDFLKHCQA DHLLDEKGRA QCLLQREMVQ SLEQQLVLEK
251 EKLSAMQAHL AGKMALTKAS SVASSDKGSC CIVAAGSQGP VVPAWSGPRE
301 APDSLFAVRR HLWGSHGNST FPEFLHNMDY FKFHNMRPPF TYATLIRWAI
351 LEAPEKQRTL NEIYHWFTRM FAFFRNHPAT WKNAIRHNLS LHKCFVRVES
401 EKGAVWTVDE LEFRKKRSQR PSRCSNPTPG P*
```

FIG. 4

FKHsf Transgene corrects the defect in scurfy animals

FKHsf tg mice have reduce lymph node cells
compared to normal cells

| Cell number | Mouse genotype | | |
|---|---|---|---|
| | Normal | Scurfy | Transgenic |
| Cells / LN | 0.92 | 1.97 | 0.29 |
| Cells / Thymus | 0.76 | 0.54 | 0.76 |

FIG. 7

FKHsf trangenic mice respond poorly to in vitro stimulation

| Proliferation | Mouse genotype | | |
|---|---|---|---|
| | Normal | Scurfy | Transgenic |
| No stimulation | 778 | 23488 | 596 |
| Anti-CD3+Anti-CD28 | 22932 | 225981 | 9106 |

FIG. 8

| N-terminal | ZNF | Mid | Forkhead |
|---|---|---|---|
| 83.4% | 95.8% | 82.8% | 96.4% |

Human FKH<sup>sf</sup>

Mouse Fkh<sup>sf</sup>

Human and mouse FKH<sup>sf</sup> proteins are highly conserved.

SEQUENCE LISTING

<160> NUMBER OF SEQ ID NOS: 22

<210> SEQ ID NO 1
<211> LENGTH: 2160
<212> TYPE: DNA
<213> ORGANISM: Mus musculus

<400> SEQUENCE: 1

```
gctgatcccc ctctagcagt ccacttcacc aaggtgagcg agtgtccctg ctctccccca      60
ccagacacag ctctgctggc gaaagtggca gagaggtatt gagggtgggt gtcaggagcc     120
caccagtaca gctggaaaca cccagccact ccagctcccg gcaacttctc ctgactctgc     180
cttcagacga gacttggaag acagtcacat ctcagcagct cctctgccgt tatccagcct     240
gcctctgaca agaacccaat gcccaaccct aggccagcca agcctatggc tccttccttg     300
gcccttggcc catccccagg agtcttgcca agctggaaga ctgcacccaa gggctcagaa     360
cttctaggga ccaggggctc tgggggaccc ttccaaggtc gggacctgcg aagtggggcc     420
cacacctctt cttccttgaa cccctgcca ccatcccagc tgcagctgcc tacagtgccc     480
ctagtcatgg tggcaccgtc tggggcccga ctaggtccct cacccacct acaggccctt     540 ctccaggaca gaccacactt catgcatcag ctctccactg tggatgccca tgcccagacc     600
cctgtgctcc aagtgcgtcc actggacaac ccagccatga tcagcctccc accaccttct     660
gctgccactg gggtcttctc cctcaaggcc cggcctggcc tgccacctgg gatcaatgtg     720
gccagtctgg aatgggtgtc cagggagcca gctctactct gcaccttccc acgctcgggt     780
acacccagga aagacagcaa ccttttggct gcacccaag gatcctaccc actgctggca     840
```

-continued

```
aatggagtct gcaagtggcc tggttgtgag aaggtcttcg aggagccaga agagtttctc      900
aagcactgcc aagcagatca tctcctggat gagaaaggca aggcccagtg cctcctccag      960
agagaagtgg tgcagtctct ggagcagcag ctggagctgg aaaaggagaa gctgggagct     1020
atgcaggccc acctggctgg gaagatggcg ctggccaagg ctccatctgt ggcctcaatg     1080
gacaagagct cttgctgcat cgtagccacc agtactcagg gcagtgtgct cccggcctgg     1140
tctgctcctc gggaggctcc agacggcggc ctgtttgcag tgcggaggca cctctgggga     1200
agccatggca atagttcctt cccagagttc ttccacaaca tggactactt caagtaccac     1260
aatatgcgac ccccttttcac ctatgccacc cttatccgat gggccatcct ggaagccccg     1320
gagaggcaga ggacactcaa tgaaatctac cattggttta ctcgcatgtt cgcctacttc     1380
agaaaccacc ccgccacctg gaagaatgcc atccgccaca acctgagcct gcacaagtgc     1440
tttgtgcgag tggagagcga aagggagca gtgtggaccg tagatgaatt tgagtttcgc     1500
aagaaggagga gccaacgccc caacaagtgc tccaatccct gcccttgacc tcaaaaccaa     1560
gaaaaggtgg gcggggagg gggccaaaac catgagactg aggctgtggg ggcaaggagg     1620
caagtcctac gtgtacctat ggaaaccggg cgatgatgtg cctgctatca gggcctctgc     1680
tccctatcta gctgccctcc tagatcatat catctgcctt acagctgaga ggggtgccaa     1740
tcccagccta gccctagtt ccaacctagc cccaagatga actttccagt caaagagccc     1800
tcacaaccag ctatacatat ctgccttggc cactgccaag cagaaagatg acagacacca     1860
tcctaatatt tactcaaccc aaaccctaaa acatgaagag cctgccttgg tacattcgtg     1920
aactttcaaa gttagtcatg cagtcacaca tgactgcagt cctactgact cacacccaa     1980
agcactcacc cacaacatct ggaaccacgg gcactatcac ataggtgt atatacagac     2040
ccttacacag caacagcact ggaaccttca caattacatc ccccaaaacc acacaggcat     2100
aactgatcat acgcagcctc aagcaatgcc caaaatacaa gtcagacaca gcttgtcaga     2160
```

<210> SEQ ID NO 2
<211> LENGTH: 429
<212> TYPE: PRT
<213> ORGANISM: Mus musculus

<400> SEQUENCE: 2

```
Met Pro Asn Pro Arg Pro Ala Lys Pro Met Ala Pro Ser Leu Ala Leu
 1               5                  10                  15

Gly Pro Ser Pro Gly Val Leu Pro Ser Trp Lys Thr Ala Pro Lys Gly
            20                  25                  30

Ser Glu Leu Leu Gly Thr Arg Gly Ser Gly Gly Pro Phe Gln Gly Arg
        35                  40                  45

Asp Leu Arg Ser Gly Ala His Thr Ser Ser Ser Leu Asn Pro Leu Pro
    50                  55                  60

Pro Ser Gln Leu Gln Leu Pro Thr Val Pro Leu Val Met Val Ala Pro
65                  70                  75                  80

Ser Gly Ala Arg Leu Gly Pro Ser Pro His Leu Gln Ala Leu Leu Gln
                85                  90                  95

Asp Arg Pro His Phe Met His Gln Leu Ser Thr Val Asp Ala His Ala
            100                 105                 110

Gln Thr Pro Val Leu Gln Val Arg Pro Leu Asp Asn Pro Ala Met Ile
        115                 120                 125

Ser Leu Pro Pro Pro Ser Ala Ala Thr Gly Val Phe Ser Leu Lys Ala
    130                 135                 140
```

```
Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
            180                 185                 190

Leu Ala Asn Gly Val Cys Lys Trp Pro Gly Cys Glu Lys Val Phe Glu
        195                 200                 205

Glu Pro Glu Glu Phe Leu Lys His Cys Gln Ala Asp His Leu Leu Asp
    210                 215                 220

Glu Lys Gly Lys Ala Gln Cys Leu Leu Gln Arg Glu Val Val Gln Ser
225                 230                 235                 240

Leu Glu Gln Gln Leu Glu Leu Glu Lys Glu Lys Leu Gly Ala Met Gln
                245                 250                 255

Ala His Leu Ala Gly Lys Met Ala Leu Ala Lys Ala Pro Ser Val Ala
                260                 265                 270

Ser Met Asp Lys Ser Ser Cys Cys Ile Val Ala Thr Ser Thr Gln Gly
            275                 280                 285

Ser Val Leu Pro Ala Trp Ser Ala Pro Arg Glu Ala Pro Asp Gly Gly
        290                 295                 300

Leu Phe Ala Val Arg Arg His Leu Trp Gly Ser His Gly Asn Ser Ser
305                 310                 315                 320

Phe Pro Glu Phe Phe His Asn Met Asp Tyr Phe Lys Tyr His Asn Met
                325                 330                 335

Arg Pro Pro Phe Thr Tyr Ala Thr Leu Ile Arg Trp Ala Ile Leu Glu
                340                 345                 350

Ala Pro Glu Arg Gln Arg Thr Leu Asn Glu Ile Tyr His Trp Phe Thr
            355                 360                 365

Arg Met Phe Ala Tyr Phe Arg Asn His Pro Ala Thr Trp Lys Asn Ala
        370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Phe Glu Phe Arg Lys Lys
                405                 410                 415

Arg Ser Gln Arg Pro Asn Lys Cys Ser Asn Pro Cys Pro
            420                 425

<210> SEQ ID NO 3
<211> LENGTH: 1869
<212> TYPE: DNA
<213> ORGANISM: Homo sapien

<400> SEQUENCE: 3
gcacacactc atcgaaaaaa atttggatta ttagaagaga gaggtctgcg gcttccacac      60
cgtacagcgt ggttttcttt ctcggtataa aagcaaagtt gttttgata cgtgacagtt     120 tcccacaagc caggctgatc ctttctgtc agtccacttc accaagcctg cccttggaca     180
aggacccgat gccaaccccc aggcctggca agccctcggc ccttccttg gcccttggcc     240 catccccagg agcctcgccc agctggaggg ctgcacccaa agcctcagac tgctggggg     300 cccggggccc aggggaacc ttccaggcc gagatcttcg aggcgggcc catgcctcct     360 cttcttcctt gaacccccatg ccaccatcgc agctgcagct gcccacactg ccctagtca     420 tggtggcacc ctccggggca cggctgggcc ccttgcccca cttacaggca ctcctccagg     480
acaggccaca tttcatgcac cagctctcaa cggtggatgc ccacgcccgg acccctgtgc     540
```

-continued

```
tgcaggtgca ccccctggag agcccagcca tgatcagcct cacaccaccc accaccgcca     600
ctggggtctt ctccctcaag gcccggcctg gcctcccacc tgggatcaac gtggccagcc     660
tggaatgggt gtccagggag ccggcactgc tctgcacctt cccaaatccc agtgcaccca     720
ggaaggacag cacccttttcg gctgtgcccc agagctccta cccactgctg gcaaatggtg    780
tctgcaagtg gcccggatgt gagaaggtct cgaagagcc agaggacttc ctcaagcact      840
gccaggcgga ccatcttctg gatgagaagg gcagggcaca atgtctcctc cagagagaga    900
tggtacagtc tctggagcag cagctggtgc tggagaagga gaagctgagt gccatgcagg   960
cccacctggc tgggaaaatg gcactgacca aggcttcatc tgtggcatca tccgacaagg   1020
gctcctgctg catcgtagct gctggcagcc aaggccctgt cgtcccagcc tggtctggcc   1080
cccgggaggc ccctgacagc ctgtttgctg tccggaggca cctgtggggt agccatggaa   1140
acagcacatt cccagagttc ctccacaaca tggactactt caagttccac aacatgcgac   1200
cccctttcac ctacgccacg ctcatccgct gggccatcct ggaggctcca gagaagcagc   1260
ggacactcaa tgagatctac cactggttca cacgcatgtt tgccttcttc agaaaccatc   1320
ctgccacctg gaagaacgcc atccgccaca acctgagtct gcacaagtgc tttgtgcggg   1380
tggagagcga gaagggggct gtgtggaccg tggatgagct ggagttccgc aagaaacgga   1440
gccagaggcc cagcaggtgt tccaacccta cacctggccc ctgacctcaa gatcaaggaa   1500
aggaggatgg acgaacaggg gccaaactgg tgggaggcag aggtggtggg ggcagggatg   1560
ataggccctg gatgtgccca cagggaccaa gaagtgaggt ttccactgtc ttgcctgcca   1620
gggcccctgt tccccgctg gcagccaccc cctcccccat catatccttt gccccaaggc    1680
tgctcagagg ggccccggtc ctggcccag ccccacctc cgcccagac acaccccca       1740 gtcgagccct gcagccaaac agagccttca aaccagcca cacagagcct gcctcagctg    1800
ctcgcacaga ttacttcagg gctggaaaag tcacacagac acacaaaatg tcacaatcct   1860
gtccctcac                                                          1869
```

<210> SEQ ID NO 4
<211> LENGTH: 431
<212> TYPE: PRT
<213> ORGANISM: Homo sapien

<400> SEQUENCE: 4

```
Met Pro Asn Pro Arg Pro Gly Lys Pro Ser Ala Pro Ser Leu Ala Leu
  1               5                  10                  15

Gly Pro Ser Pro Gly Ala Ser Pro Ser Trp Arg Ala Ala Pro Lys Ala
             20                  25                  30

Ser Asp Leu Leu Gly Ala Arg Gly Pro Gly Gly Thr Phe Gln Gly Arg
         35                  40                  45

Asp Leu Arg Gly Gly Ala His Ala Ser Ser Ser Leu Asn Pro Met
     50                  55                  60

Pro Pro Ser Gln Leu Gln Leu Pro Thr Leu Pro Leu Val Met Val Ala
 65                  70                  75                  80

Pro Ser Gly Ala Arg Leu Gly Pro Leu Pro His Leu Gln Ala Leu Leu
                 85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125
```

```
Ile Ser Leu Thr Pro Pro Thr Ala Thr Gly Val Phe Ser Leu Lys
    130                 135                 140
Ala Arg Pro Gly Leu Pro Pro Gly Ile Asn Val Ala Ser Leu Glu Trp
145                 150                 155                 160
Val Ser Arg Glu Pro Ala Leu Leu Cys Thr Phe Pro Asn Pro Ser Ala
                165                 170                 175
Pro Arg Lys Asp Ser Thr Leu Ser Ala Val Pro Gln Ser Ser Tyr Pro
            180                 185                 190
Leu Leu Ala Asn Gly Val Cys Lys Trp Pro Gly Cys Glu Lys Val Phe
        195                 200                 205
Glu Glu Pro Glu Asp Phe Leu Lys His Cys Gln Ala Asp His Leu Leu
    210                 215                 220
Asp Glu Lys Gly Arg Ala Gln Cys Leu Leu Gln Arg Glu Met Val Gln
225                 230                 235                 240
Ser Leu Glu Gln Gln Leu Val Leu Glu Lys Glu Lys Leu Ser Ala Met
                245                 250                 255
Gln Ala His Leu Ala Gly Lys Met Ala Leu Thr Lys Ala Ser Ser Val
            260                 265                 270
Ala Ser Ser Asp Lys Gly Ser Cys Cys Ile Val Ala Ala Gly Ser Gln
        275                 280                 285
Gly Pro Val Val Pro Ala Trp Ser Gly Pro Arg Glu Ala Pro Asp Ser
    290                 295                 300
Leu Phe Ala Val Arg Arg His Leu Trp Gly Ser His Gly Asn Ser Thr
305                 310                 315                 320
Phe Pro Glu Phe Leu His Asn Met Asp Tyr Phe Lys Phe His Asn Met
                325                 330                 335
Arg Pro Pro Phe Thr Tyr Ala Thr Leu Ile Arg Trp Ala Ile Leu Glu
            340                 345                 350
Ala Pro Glu Lys Gln Arg Thr Leu Asn Glu Ile Tyr His Trp Phe Thr
        355                 360                 365
Arg Met Phe Ala Phe Phe Arg Asn His Pro Ala Thr Trp Lys Asn Ala
    370                 375                 380
Ile Arg His Asn Leu Ser Leu His Lys Cys Phe Val Arg Val Glu Ser
385                 390                 395                 400
Glu Lys Gly Ala Val Trp Thr Val Asp Glu Leu Glu Phe Arg Lys Lys
                405                 410                 415
Arg Ser Gln Arg Pro Ser Arg Cys Ser Asn Pro Thr Pro Gly Pro
            420                 425                 430

<210> SEQ ID NO 5
<211> LENGTH: 23
<212> TYPE: DNA
<213> ORGANISM: Artificial Sequence
<220> FEATURE:
<223> OTHER INFORMATION: Primer for generation of mouse Fkh cDNA

<400> SEQUENCE: 5
gcagatctcc tgactctgcc ttc                                          23

<210> SEQ ID NO 6
<211> LENGTH: 23
<212> TYPE: DNA
<213> ORGANISM: Artificial Sequence
<220> FEATURE:
<223> OTHER INFORMATION: Primer for generation of mouse Fkh cDNA

<400> SEQUENCE: 6
```

-continued gcagatctga caagctgtgt ctg                                          23

<210> SEQ ID NO 7
<211> LENGTH: 21
<212> TYPE: DNA
<213> ORGANISM: Artificial Sequence
<220> FEATURE:
<223> OTHER INFORMATION: Primer for generation of human Fkh cDNA

<400> SEQUENCE: 7
agcctgccct tggacaagga c                                            21

<210> SEQ ID NO 8
<211> LENGTH: 21
<212> TYPE: DNA
<213> ORGANISM: Artificial Sequence
<220> FEATURE:
<223> OTHER INFORMATION: Primer for generation of human Fkh cDNA

<400> SEQUENCE: 8
gcaagacagt ggaaacctca c                                            21

<210> SEQ ID NO 9
<211> LENGTH: 20
<212> TYPE: DNA
<213> ORGANISM: Artificial Sequence
<220> FEATURE:
<223> OTHER INFORMATION: Primer for PCR amplification of mouse Fkh cDNA

<400> SEQUENCE: 9
ctacccactg ctggcaaatg                                              20

<210> SEQ ID NO 10
<211> LENGTH: 23
<212> TYPE: DNA
<213> ORGANISM: Artificial Sequence
<220> FEATURE:
<223> OTHER INFORMATION: Primer for PCR amplification of mouse Fkh cDNA

<400> SEQUENCE: 10
gaaggaacta ttgccatggc ttc                                          23

<210> SEQ ID NO 11
<211> LENGTH: 28
<212> TYPE: DNA
<213> ORGANISM: Artificial Sequence
<220> FEATURE:
<223> OTHER INFORMATION: Oligonucleotide for hybridization reaction

<400> SEQUENCE: 11
atgcagcaag agctcttgtc cattgagg                                     28

<210> SEQ ID NO 12
<211> LENGTH: 28
<212> TYPE: DNA
<213> ORGANISM: Artificial Sequence
<220> FEATURE:
<223> OTHER INFORMATION: Oligonucleotide for hybridization reaction

<400> SEQUENCE: 12
gcagcaagag ctcttttgtc cattgagg                                     28

<210> SEQ ID NO 13
<211> LENGTH: 22
<212> TYPE: DNA
<213> ORGANISM: Artificial Sequence

```
<220> FEATURE:
<223> OTHER INFORMATION: Primer for amplification of Fkh cDNA
<220> FEATURE:
<221> NAME/KEY: modified_base
<222> LOCATION: (7)...(7)
<223> OTHER INFORMATION: I

<400> SEQUENCE: 13
catcggngag atgctaagat gg                                              22

<210> SEQ ID NO 14
<211> LENGTH: 28
<212> TYPE: DNA
<213> ORGANISM: Artificial Sequence
<220> FEATURE:
<223> OTHER INFORMATION: Primer for amplification of Fkh cDNA

<400> SEQUENCE: 14
gaaaccagat tagtaagtat cttcgatt                                        28

<210> SEQ ID NO 15
<211> LENGTH: 22
<212> TYPE: DNA
<213> ORGANISM: Artificial Sequence
<220> FEATURE:
<223> OTHER INFORMATION: PCR primer

<400> SEQUENCE: 15
attttgatta cagcatgtcc cc                                              22

<210> SEQ ID NO 16
<211> LENGTH: 21
<212> TYPE: DNA
<213> ORGANISM: Artificial Sequence
<220> FEATURE:
<223> OTHER INFORMATION: PCR primer

<400> SEQUENCE: 16
acggaaacac tcttatgtgc g                                               21

<210> SEQ ID NO 17
<211> LENGTH: 19
<212> TYPE: DNA
<213> ORGANISM: Artificial Sequence
<220> FEATURE:
<223> OTHER INFORMATION: PCR primer

<400> SEQUENCE: 17
ggcccttctc caggacaga                                                  19

<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18
gctgatcatg gctgggttgt                                                 20

<210> SEQ ID NO 19
<211> LENGTH: 31
<212> TYPE: DNA
<213> ORGANISM: Artificial Sequence
<220> FEATURE:
<223> OTHER INFORMATION: PCR primer
```

```
<400> SEQUENCE: 19
agcttcatcc tagcggtttg cctgagaata c                                 31

<210> SEQ ID NO 20
<211> LENGTH: 24
<212> TYPE: DNA
<213> ORGANISM: Artificial Sequence
<220> FEATURE:
<223> OTHER INFORMATION: PCR primer

<400> SEQUENCE: 20
cctctctggc ttcatctctt gtgt                                         24

<210> SEQ ID NO 21
<211> LENGTH: 19
<212> TYPE: DNA
<213> ORGANISM: Artificial Sequence
<220> FEATURE:
<223> OTHER INFORMATION: PCR primer

<400> SEQUENCE: 21
ccggagagat gccttggaa                                               19

<210> SEQ ID NO 22
<211> LENGTH: 31
<212> TYPE: DNA
<213> ORGANISM: Artificial Sequence
<220> FEATURE:
<223> OTHER INFORMATION: PCR primer

<400> SEQUENCE: 22
agcttcatcc tagcggtttg cctgagaata c                                 31
```

METHOD FOR REGULATING IMMUNE FUNCTION USING THE FOXP3 PROTEIN

CROSS-REFERENCE TO RELATED APPLICATIONS

This application claims the benefit of U.S. Provisional Patent Application No. 60/333,409 filed Nov. 26, 2001 and 60/289,654 filed May 8, 2001, where these applications are incorporated herein by reference in their entireties.

BACKGROUND OF THE INVENTION

1. Field of the Invention

The present invention relates generally to pharmaceutical products and methods and, more specifically, to methods for identifying compounds which can modulate the immune system, further, to methods for identifying proteins regulated by Scurfin and those that induce or inhibit Foxp3 expression.

2. Description of the Related Art

A number of autoimmune diseases, such as Inflammatory Bowel Disease, Multiple Sclerosis, rheumatoid Arthritis, and Asthma, involve immune dysregulation. In all these diseases, subsets of T cells are hyper-activated and contribute to an immune reaction towards self. In recent years, mice with mutations in CD95, CD95-ligand, CTLA-4 or TGF-β have proven useful for dissecting a number of pathways involved in T cell regulation and immune system homeostasis. Mice with mutations in any one if the above genes have profoundly altered immune responses, attributed to a failure to control T cell function.

T cell activation in the periphery involves signaling via the T cell receptor and CD28 costimulation (reviewed in Bluestone, J. A., *Immunity* 2:555-559 (1995); Jenkins, M. K., *Immunity* 1:443-448 (1994); Rudd, C. E., *Immunity* 4:527-534 (1996)). Down regulation of peripheral T cell responses involves several pathways. Some of these include apoptosis mediated by members of the TNFR family, including CD95 and its ligand, activation induced death due to cytokine withdrawal, and negative signaling through CTLA-4 (CD152) (Lenardo et al., *Ann. Rev. Immun.* 17:221-253 (1999); Oosterwegel et al., *Curr. Opin. Immun.* 11:294-300 (1999); Saito, T., *Curr. Opin. Immun.* 10:313-321 (1998); Wallach et al., *Ann. Rev. Immun.* 17:331-367 (1999)). Mutations or expression of dominant negative forms of some of these genes have proven their critical role in the regulation of peripheral T cell responses. Mutations in CD95, CD95L, TGF-β or CTLA-4 lead to progressive autoimmune lymphoproliferative disorders (Kulkarni et al., *Proc. Nat'l. Acad. Sci. USA* 90:770-774 (1993); Shull et al., *Nature* 359:693-699 (1992); Takahashi et al., *Cell* 76:969-976 (1994); Tivol et al., *Immunity* 3:541-547 (1995); Watanbe-Fukunaga et al., *Nature* 356:314-347 (1992); Waterhouse et al., *Science* 270:985-988 (1995)). More recent data suggests that regulation of T cell activity by $CD4^+CD25^+$ regulatory T cells is also important for maintaining peripheral T cell tolerance (Roncarolo et al., *Curr. Opin. Immun.* 12:676-683 (2000); Sakaguchi, S., *Cell* 101:455-458 (2000); Shevach, E. M., *Ann. Rev. Immun.* 18:423-449 (2000)). Depletion of such regulatory T cells from normal animals leads to development of various autoimmune diseases and the adoptive transfer of these regulatory cells can also prevent disease in vivo in a number of systems (Asano et al., *J. Exp. Med.* 184:387-396 (1996); Sakaguchi et al., *J. Immun.* 155:1151-1164 (1995); Suri-Payer et al., *J. Immun.* 160:1212-1218 (1998)).

The specific mechanism by which regulatory T cells (T-reg cells) mediate their suppressive effect is currently unclear. While TGFB and IL-10 can mediate suppressive effects, and blocking these cytokines eliminates suppression in some in vivo models, there is good evidence to indicate other molecules are also involved. Mounting evidence indicates a role for CD152 in the activation and/or function of $CD4^+CD25^+$ T cells (Read et al., *J. Exp. Med.* 192:295-302 (2000); Takahashi et al., *J. Exp. Med.* 192:303-310 (2000)). Intriguingly, several studies suggest that signaling through CD152 results in the induction of TGFB (Chen et al., *J. Exp. Med.* 188:1849-1857 (1998); Gomes et al., *J. Immunol.* 164:2001-2008 (2000); Kitani et al., *J. Immunol.* 165:691-702 (2000)), providing a potential link between TGFB-mediated inhibition and the inhibitory activity of $CD4^+CD25^+$ cells.

The X-linked lymphoproliferative disease observed in the scurfy (sf) mouse, a spontaneous mutant animal that shares many characteristics with the pathogenesis seen in targeted deletions of CTLA-4 (Tivol et al., *Immunity* 3:541-547 (1995); Waterhouse et al., *Science* 270:985-988 (1995)) as well as TGF-β (Kulkarni et al., *Proc. Nat'l. Acad. Sci. USA* 90:770-774 (1993); Shull et al., *Nature* 359:693-699 (1992)), including death by three weeks of age (Godfrey et al., *Am. J. Pathol.* 145:281-286 (1994); Godfrey et al., *Proc. Nat'l. Acad. Sci. USA* 88:5528-5532 (1991); Godfrey et al., *Am. J. Pathol.* 138:1379-1387 (1991); Kanangat et al., *Eur. J. Immunol.* 26:161-165 (1996); Lyon et al., *Proc. Nat'l. Acad. Sci. USA* 87:2433-2437 (1990)). In sf animals, disease is mediated by $CD4^+$ T cells, and these cells exhibit an activated phenotype both in vivo and in vitro (Blair et al., *J. Immunol.* 153:3764-774 (1994)). The specific mutation responsible for the disease has been recently cloned and the gene shown to be a new member of the forkhead family of transcription factors (Brunkow et al., *Nature Genetics* 27:68-72 (2001)). The gene has been designated Foxp3 and the protein product, scurfin. Mutations in the orthologous human gene cause a similar lymphoproliferative disorder among affected male progeny, which if left untreated is generally fatal (Bennett et al., *Nature Genetics* 27:20-21 (2001); Chatila et al., JM2, *J. Clin. Invest.* 106:R75-81 (2000); Wildin et al., *Nature Genetics* 27:18-20 (2001)).

The present invention discloses methods and compositions useful for diagnosing scurfy-related diseases, more specifically, to methods for identifying compounds which can modulate the immune system, further, to methods for identifying proteins regulated by Scurfin and those that induce or inhibit Foxp3 expression

BRIEF SUMMARY OF THE INVENTION

The present invention relates generally to the discovery of novel genes which, when mutated, results in a profound lymphoproliferative disorder. In particular, a mutant mouse, designated 'Scurfy', was used to identify the gene responsible for this disorder through backcross analysis, physical mapping and large-scale DNA sequencing. Analysis of the sequence of this gene indicated that it belongs to a family of related genes, all containing a winged-helix DNA binding domain.

Thus, within one aspect of the invention isolated nucleic acid molecules are provided which encode $FKH^{sf}$ or $Fkh^{sf}$, including mutant forms thereof. Within certain embodiments, $Fkh^{sf}$ of any type may be from a warm-blooded animal, such as a mouse or human. Within further embodiments, isolated nucleic acid molecules are provided wherein the nucleic acid molecule is selected from the group consisting of (a) a nucleic acid molecule that encodes an amino acid sequence comprising SEQ ID NOs:2 or 4, (b) a nucleic acid molecule that hybridizes under stringent conditions to a nucleic acid molecule having the nucleotide sequence of SEQ ID NOs:1 or 3, or its complement, and (c) a nucleic acid molecule that encodes a functional fragment of the polypeptide encoded by either (a) or (b). Preferably, the nucleic acid molecule is not JM2. Within related aspects, vectors (including expression vectors), and recombinant host cells are also provided, as well as proteins which are encoded by the above-noted nucleic acid molecules. Further, fusion proteins are also provided which combine at least a portion of the above-described nucleic acid molecules with the coding region of another protein. Also provided are oligonucleotide fragments (including probes and primers) which are based upon the above sequence. Such fragments are at least 8,10, 12,15, 20, or 25 nucleotides in length, and may extend up to 100, 200, 500, 1000, 1500, or, 2000 nucleotides in length.

Within other aspects methods of using the above noted expression vector for producing a $Fkh^{sf}$ protein (of any type) are provided, comprising the general steps of (a) culturing recombinant host cells that comprise the expression vector and that produce $Fkh^{sf}$ protein, and (b) isolating protein from the cultured recombinant host cells.

Also provided are antibodies and antibody fragments that specifically bind to $Fkh^{sf}$ proteins. Representative examples of such antibodies include both polyclonal and monoclonal antibodies (whether obtained from a murine hybridoma, or derived into human form). Repesentative examples of antibody fragments include $F(ab')_2$, $F(ab)_2$, Fab', Fab, Fv, sFv, and minimal recognition units or complementarity determining regions.

Within yet other aspects, methods are provided for detecting the presence of a $Fkh^{sf}$ nucleic acid sequence in a biological sample from a subject, comprising the steps of (a) contacting a $Fkh^{sf}$ specific nucleic acid probe under hybridizing conditions with either (i) test nucleic acid molecules isolated from said biological sample, or (ii) nucleic acid molecules synthesized from RNA molecules, wherein the probe recognizes at least a portion of nucleotide sequence of SEQ ID NOs:1 or 3, and (b) detecting the formation of hybrids of the nucleic acid probe and (i) or (ii).

Within another related embodiment, methods are provided for detecting the presence of an $Fkh^{sf}$, or a mutant form thereof, in a biological sample, comprising the steps of: (a) contacting a biological sample with an anti-$Fkh^{sf}$ antibody or an antibody fragment, wherein the contacting is performed under conditions that allow the binding of the antibody or antibody fragment to the biological sample, and (b) detecting any of the bound antibody or bound antibody fragment.

Within other aspects of the invention, methods are provided for introducing $Fkh^{sf}$ nucleic acid molecules to an animal, comprising the step of administering a $Fkh^{sf}$ nucleic acid molecule as described herein to an animal (e.g., a human, monkey, dog, cat, rat, or, mouse). Within one embodiment, the nucleic acid molecule is contained within and expressed by a viral vector (e.g., a vector generated at least in part from a retrovirus, adenovirus, adeno-associated virus, herpes virus, or, alphavirus). Within another embodiment the nucleic acid molecule is expressed by, or contained within a plasmid vector. Such vectors may be administered either in vivo, or ex vivo (e.g., to hematopoietic cells such as T cells).

Within other embodiments, transgenic non-human animals are provided wherein the cells of the animal express a transgene that contains a sequence encoding $Fkh^{sf}$ protein.

In one preferred embodiment, a method is provided for regulating an immune function in a primate. The method comprises inserting a plurality of nucleic acid sequences that encode the Foxp3 protein into the lymphocytes of the primate; placing the nucleic acid sequence under the control of cytokine c; and activating expression of the nucleic acid sequences to increase the amount of the Foxp3 protein in the primate with cytokine c.

Accordingly, it is an object of the present invention to provide an assay for use in identifying agents that alter expression of Foxp3. Specifically, an assay is provided to measure the induction or inhibition of Foxp3 under varying conditions. The expression altering agents include small molecules, peptides, polynucleotides, cytokines, antibodies and Fab∝ fragments.

In one preferred embodiment, a method is provided for identifying a compound that modulates the level of expression of scurfin. The method comprises providing a composition comprising a reporter gene ligated to a scurfin promoter; contacting the composition with a test compound; determining the level of reporter gene expression; and comparing the level of reporter gene expression in (c) with the predetermined level of expression and thereby determining if the test compound modulates the expression of scurfin.

In a preferred embodiment, the compound decreases the level of scurfin expression.

In another embodiment, the compound increases the level of scurfin.

In one embodiment the test compound is selected from the group consisting of: a monoclonal antibody, a polyclonal antibody, a peptide, and a small molecule.

In another embodiment the test compound is selected from the group consisting of an organic molecule, a natural product, a peptide, an oligosaccharide, a nucleic acid, a lipid, an antibody or binding fragment thereof, and a cell.

In yet another embodiment, the test compound is from a library of compounds.

With other embodiments, the library is selected from the group consisting of a random peptide library, a natural products library, a combinatorial library, an oligosaccharide library and a phage display library.

In one preferred embodiment, a method is provided for suppressing an immune response comprising contacting T cells of the mammal with a compound that increases scurfin expression in the T cell, wherein an immune response is suppressed.

In one preferred embodiment, a method is provided for enhancing an immune response comprising contacting T cells with a compound that decreases scurfin expression in the T cell, wherein an immune response is enhanced.

Within another related embodiment, a method for inhibiting an autoimmune response in a subject, wherein the method comprises administering to the subject a compound which increases scurfin expression, thereby inhibiting an autoimmune response by the subject.

In a related embodiment the autoimmune response is selected from the group consisting of Inflammatory Bowel Disease, Psoriasis, Diabetes, Multiple Sclerosis, Rheumatoid Arthritis, and Asthma.

In one preferred embodiment, a method is provided for enhancing an immune response to a disease in a subject, wherein the method comprises administering to the subject a compound which decreases scurfin expression, thereby treating the disease in the subject.

In a related embodiment, a method is provided for enhancing an immune response to HIV or cancer in a subject, wherein the method comprises administering to the subject a compound which decreases scurfin expression, thereby treating HIV and cancer.

In one preferred embodiment, a method for inhibiting graft versus host disease in a subject wherein the method comprises administering to the subject a compound that increases scurfin expression, thereby inhibiting tissue transplant rejection by the subject.

In one preferred embodiment, a method is provided for inhibiting an autoimmune response in a patient comprising. The method comprising: isolating T cells from the patient; transducing the T cells with the scurfin gene; expanding the tranduced T cells; and reintroducing the transduced T cells into said patient, wherein an autoimmune disease in the patient is inhibited.

In a related embodiment, a method is provided for inhibiting an autoimmune response in a patient comprising. The method comprising: isolating CD4+CD25+ regulatory T cells from the patient; transducing the CD4+CD25+ regulatory T cells with the scurfin gene; expanding the tranduced CD4+CD25+ regulatory T cells; and reintroducing the transduced CD4+CD25+ regulatory T cells into the patient, wherein an autoimmune disease in the patient is inhibited.

In one preferred embodiment, a method is provided for inhibiting an autoimmune response in a patient, wherein the autoimmune disease is selected from the group consisting of Inflammatory Bowel Disease, Multiple Sclerosis, Rheumatoid Arthritis, Psoriasis, Diabetes and Asthma. The method comprising: isolating T cells from the patient; transducing the T cells with the scurfin gene; expanding the tranduced T cells; and reintroducing the transduced T cells into said patient, wherein an autoimmune disease in the patient is inhibited.

In one preferred embodiment, a method is provided for inhibiting an autoimmune response in a patient comprising. The method comprising: isolating T cells from the patient; transducing the T cells with the scurfin gene contained in a retroviral vector; expanding the tranduced T cells; and reintroducing the transduced T cells into said patient, wherein an autoimmune disease in the patient is inhibited.

In yet another preferred embodiment, a method for enhancing an immune response to a disease in a patient is provided. The method comprising: isolating T cells from the patient; transfecting the T cells with a test compound that inhibits scurfin expression; expanding the transfected T cells; and reintroducing the transfected T cells into said patient, wherein an immune response to a disease in the patient is enhanced.

In yet another preferred embodiment, a method for enhancing an immune response to a HIV and cancer in a patient is provided. The method comprising: isolating T cells from the patient; transfecting the T cells with a test compound that inhibits scurfin expression; expanding the transfected T cells; and reintroducing the transfected T cells into said patient, wherein an immune response to HIV or cancer in the patient is enhanced.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE SEVERAL VIEWS OF THE DRAWINGS

FIGS. 1A and 1B depict a nucleotide sequence of mouse Fkh$^{sf}$ cDNA (SEQ ID NO:1); translation is predicted to initiate at position 259 and terminate at position 1546.

FIG. 2 depicts the amino acid sequence of mouse Fkh$^{sf}$ (SEQ ID NO:2).

FIGS. 3A and 3B depict a nucleotide sequence of 1735 bp corresponding to human FKHsf cDNA (SEQ ID NO: 3; including a 1293 bp coding region); translation is predicted to initiate at position 55 and terminate at position 1348.

FIG. 4 depicts the sequence of a 431 amino acid human FKH$^{sf}$ protein (SEQ ID NO: 4).

FIG. 7 is a diagram which shows that FKH$^{sf}$ tg mice have reduced lymph node cells, as compared to normal cells.

FIG. 8 is a diagram which shows that FKH$^{sf}$ transgenic mice respond poorly to in vitro stimulation.

FIG. 10 compares homology in various regions of human FKH$^{sf}$ and murine Fkh$^{sf}$.

DETAILED DESCRIPTION OF THE INVENTION

Figure 5:
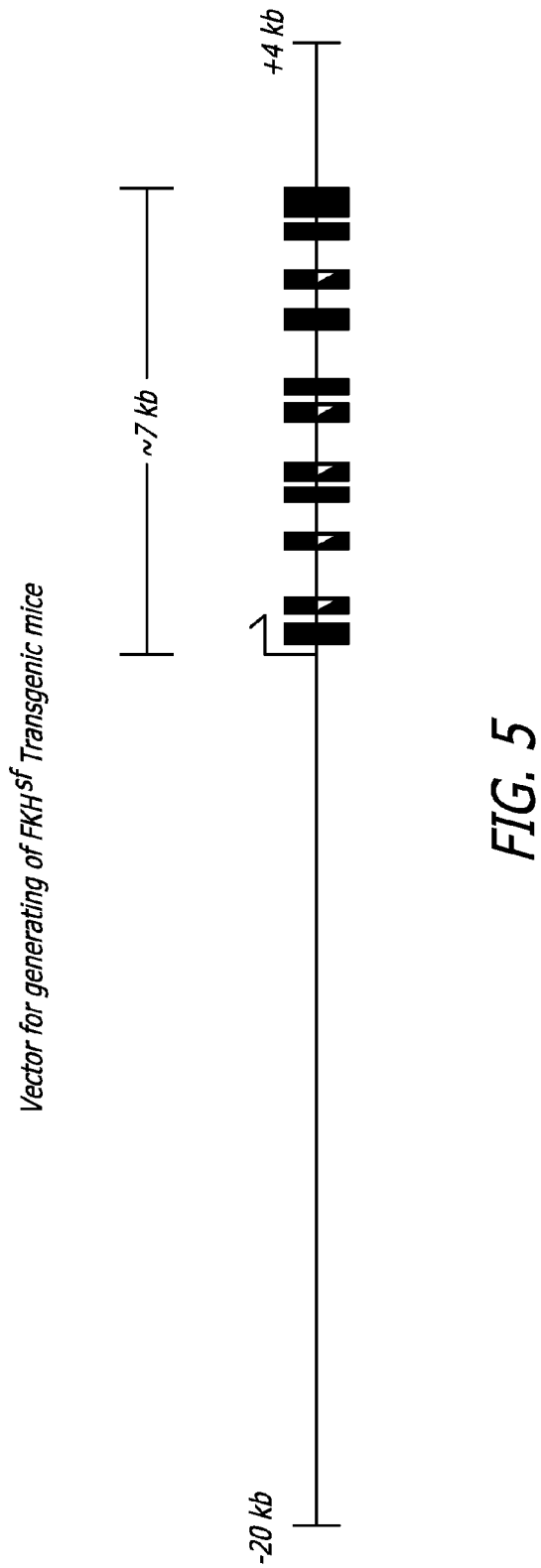
FIG. 5 diagrammatically depicts a vector for generation of FKH$^{sf}$ transgenic mice.

The invention relates to the discovery that the scurfin protein is involved in the generation and/or activity of the CD4+ CD25+ subset of regulatory T cells. Foxp3 expression is directly correlated with cells of this regulatory phenotype and its expression is uniquely increased upon activation of this specific subset. Mutant (sf) animals appear to lack this subset, whereas Foxp3 transgenic animals appear to possess an increased percentage of CD4+CD25+ cells. Further, while the CD4+CD25+ subset from transgenic animals does not appear inhibitory on a per cell basis, the expression of Foxp3 is still elevated in this subset relative to their CD25− counterparts. Interestingly, overexpression of Foxp3 in CD4+CD25− T cells confers suppressive activity on these cells, although they remain less effective than CD4+CD25+ T cells. Overall, the data suggest that the recently described transcription factor, scurfin, is a critical regulator of immune cell function and may work primarily through the generation and/or activity of CD4+CD25+ regulatory T cells.

The results from the Examples indicate that expression of scurfin (Foxp3 gene) can downregulate the immune system in part through regulatory T (T-reg) cell activity. Consequentially, if the expression of the endogenous Foxp3 gene can be induced in T cells it can be used to downregulate the immune response in a variety of autoimmune diseases such as Inflammatory Bowel Disease, Multiple Sclerosis, Rheumatoid Arthritis, Psoriasis, Diabetes, and Asthma or in other scenarios such as Graft versus Host disease. Furthermore, scurfin expression can be down-regulated to activate the immune system in cancer or AIDS.

Definitions

Prior to setting forth the Invention in detail, it may be helpful to an understanding thereof to set forth definitions of certain terms and to list and to define the abbreviations that will be used hereinafter.

"Scurfy" refers to an inherited disease in mice which exhibit a severe lymphoproliferative disorder (see, e.g., Lyon et al., *Proc. Natl. Acad. Sci. USA* 87:2433, 1990). The responsible gene (mutant forms of which are responsible for the disease) is shown in Sequence I.D. Nos. 1 and 3.

"Foxp3" refers to the forkhead domain-containing gene, which is mutated in the scurfy mouse mutant. "Foxp3" refers to the protein encoded by the mouse Foxp3 gene. "FOXP3" refers to the human ortholog of the murine Foxp3 gene. "FOXP3" refers to the protein encoded by the human FOXP3 gene. The cDNA sequences for murine Foxp3 and human FOXP3 are disclosed in U.S. patent application Ser. No. 09/372,668 wherein the mouse scurfy gene is designated Fkh$^{sf}$ and the human ortholog is designated FKH$^{sf}$. The genomic sequence for human FOXP3 is disclosed in Genbank Accession No. AF235087. Genbank Accession No. AF235097 and U.S. patent application Ser. No. 09/372,668, now U.S. Pat. No. 6,414,129, are incorporated by reference in their entireties for all purposes. The nucleotide sequence of AF235097 is:

```
  1   gatccaggtc tcccaaacct gtcatgttcc ccctttgggg acagtctgtg gtgtcacagt   (SEQ ID NO:23)

61   ggttacaatt gctagctcat ccttcaacgt tgttgttggc acgcgttctt cagggacacc 121   ccttggatct cccctgactc tcctcttatt ctcccactcc accactcccc atgccggact 181   gtactgtttt ccactctccc tcctccagcc agcacccagg gcttaccacc gaggtgttga 241   gtcccgaggt cacagggtct ctcagctcct tgcatgtgtt ccctgtctgg cggcagacag 301   gcatctcctt gataatgttc tctgggtctg tggccatctt cacatctgac agcccttgg 361   cccatgccga tgagctaact agccacatga aggcgaacac agccgtggcc agaaagtcct 421   aaggcaggca ggggtgagga agacagcact gtgagtggac tgcttcacgc taggccctgg 481   ggcctcctcg gatcacaggt ccccagaag aggcctgtct ctcccctgcc ttttcagctc 541   tcaagcccac aacactttca cctgaaggtg gccctcccag cttgagcttg tgtgtgtaca 601   tgacacagag gatgtgggag tgtgattgtg atatgtggct gtgggtgttg ggggagggg 661   aactctggga tgatttccga atctgtggaa agtaatgtgt cttctactt ttgtctgcat 721   gtgggaattt ttgtcatttt gtgtctaggc tgagggtatg tgagtacagt ggtgtaggaa
```

```
           -continued
 781   tcagtgtgtc tgtgtggcat gatgacaggc atgactgtca cagcgaacct ctgtgggcct
 841   cttcctttga tctaggctgt gtagttgtgt gagagtggga aggttctcag gtgtgggcct
 901   gtctgggatt ctgcataggc tgtatgtctc cgtgactcta tgactctgtg tcccggatgc
 961   ctggtgtgga ttaatagcag cagcaactat atgtgtggct gttatggtgg ctgtttgcat
1021   gtgggcctgt ctgggatttg gtgtggtctg tgagcatggc tgtgtccctg gggttccgtg
1081   tccccatggt ccctacatgc aagtggctgt ggggactcac cagcatgggc cctttgttat
1141   tctctcggta cttgttctgc aggaagatgt aggtggccag agcccccatg gagtagagga
1201   aggcaaacac ggccacggtg acaaagaatt cggctgacga ggagtagtcc ccaactaaga
1261   agaccttggt ggtgccccct cggcaggtgg gtgcatcaaa gtacacttgg tgcagcctgc
1321   aaacagaggt gggcaggtgt ggcccagccc ctcagaacac cctcaacccc cagcccaat
1381   catgggtccc cccatttctg acaaggcccc aggaagagga ggaaataacc attcatcgag
1441   cacctactat gtaccagtca catttcactg attgctcaaa acatcctggt gagataggtg
1501   ttattcatcc ctcactccaa cccaagcact ctggcctctt gattatttct agaacttgcc
1561   aggcatcctc cctccctagg atctttgttt gtactggctg ttcccttttgc caggaatgct
1621   tttcccctag atagcttcgg gtcttactcc ctcatctcct tttttttttt tttttttttt
1681   ttttgagatg gagtcttgct ctgtcaccag gctggagtgc ggtggcacaa tcccggctca
1741   ctgcaacctc tgcctcccgg gttcaagcga ttctcctgcc tcagcctcct gagtagctgg
1801   gattacaggc atgcgccgct acgcccagct aattttttgta cttttaatag gacgggggtt
1861   tcaccatgtt ggccaggata gtcttgatct cttgaccttg tgatctgccc gccttggcct
1921   cccagagtgc tgggattaca ggcgtgagcc actgcgcccg gcctccctca tctccttgaa
1981   gctttgctca actgtcacct tctcattgag accttccctg atctccctac ttaaaattaa
2041   attgaaacat tctctcaacc agcacttctt agcctggctt ccttgctcca cttttctcga
2101   tagtagtggt acccatctga cgtaccaggt atttttttt ttttaatct tggtttttgc
2161   tgtaactaca agagggcagg gcttttttcct gtgttttcac ctccgtttat ctccaggccc
2221   tggaacagtg ctggcaccta gcagacactc aagaaatgtt tatcaaatga aatgtacaga
2281   ggcggaaaca gaggctcagg gaagtgcatt aacttgccta aagtcacaca gctggcaagg
2341   gaatgtcaga gttgagatct gaaccttgtt ttctccctat ctcatgttga cttttctccc
2401   ccaccccagt tcaggtcccc gagagaaaaa aatgtatgca tagcagagga gaggccagcg
2461   actagataac aggaaaagac agacagaaag aaaggagggt aaagggatct tggaacaggg
2521   tgtgtgtatg tgagggaaga ggggaggtgt cctgggacta aggcctttcc tgtggtgtga
2581   tggaggagag gtggggggttg tagagagaaa atgtctgtgg gagaagttct ggagcacagt
2641   ctcagattgg aggccaggat cctgagactg agcaaatggt gccaatgcct ttgtgtagca
2701   aaggccctga gggaagaggc ttgcacttat tagtcaccta ctaagcagtt tacataaatg
2761   tctcattaat gacagcctcc agcaattctc taaagaaggc attattagac ccttttttaca
2821   gatgaataaa cagaggctta gcaaggttat tacttgccca aggttgtaca gctcctaaat
2881   gatggagcta ggagttgcat ctgggtttga gtttctgttt ctagtgggct gggtcaggag
2941   agggggtccc taagagggaa tgagaggtcc ttgggtatta gggcagtttg ggagggattt
3001   tgctcagggg gacccagggc caagactgtt tttctagggg acttgtgggc tagagcctta
3061   ggacccaaag ttctagacat gggaggcgtg ggggaggggc acaggggatg gttgtggtct
3121   tgtggatccc caaaggactg gctctaagca gtgtcccttg ctgccagctc cccctccttc
```

-continued

```
3181  cccagactct tttctccctt gcctttgtgg acccatggat acctggctgc ccctctgcct
3241  ctcaggccac actttcccgg catctcctct cttttccatc attgctcagg gcctgtgcta
3301  ggtttcttc tactttcact cttccatctc cccactgggt gatcacttga gcctacattt
3361  accctcagta ctcgaagacc cccagtttcc aactcaaccc ctgtcctctt tcctgagtcc
3421  cttaaattta ttttacttat tgaacagaca ctgatggagc acttattgtg tgccaggcac
3481  tgtgctaagc acctgatgaa tattaactca ttgaatgcta accacgaccc tgtgaggtag
3541  atattattag tattcctttt tacagatgag gaaattgaga cccagagtgg ttatgtgatt
3601  tggccaaata gtggggagt ctcagaaacc tgtgcgggga ttgtgtctgt gggtctctgt
3661  catcccaccc tgcaggaggt aaacatcatt gtgagggtag tgcccatgcc agccgtgctc
3721  attcttgtgc acctagcacc cagtgtattg cccggcacac agtgtgagct caataaatgt
3781  cagaattgtt taattgggtt taattttcc ctatatctaa gcagcacccc tcattattct
3841  attctctacc ataaaaccct acatgaggat ctcctcgagt ttctctcagt ctgctattat
3901  cctctttgtt aatttatttg ttataatgta ggctccatga aggtagggag ttgggtctgg
3961  ttttttttt tttggagatg gagtttcgct cttgttgccc aggctggagt gcaatggcgc
4021  gatttcggct cccaggttca agtgattctc ctgcttcagc ctcctgagta gccgggatta
4081  caggcatgca tgaccacgcc tggctaattt tgtattttta gtagagacgg ggtttctcca
4141  tgttggtcag gctggtctcg aactcctgac ctcaggtgat ccgcccacct cggcctctca
4201  aagtgctggg attacaggcg tgagccactg tgcctggcgg gagttgggtc tgttttagtt
4261  actatcatgc ttccagcact ttgagtagta ccagatataa aataagttct caaaaatgtg
4321  tatagaatga atgaatgggg attaaataat aatattggct aacattaatt gggtacctac
4381  tgggttaagg tatgtatata cacctgtctt acttttgtat cttgtttatt gcctgtccct
4441  tacccccttcg ctggaacaga gccagagggc cacagcctat gtctgccttg ctcaccacat
4501  agtcctagag tccagagcag tgccaggtac aaggcaggtg ctcagtgatc ccagtggatg
4561  tagcctcgag gtgggagctg ggcaggagct acttgcgggg ggaggtattg gccggttcca
4621  ccctgcccct tcctctccca ggtctgttgg tatcccaggg tgggagcaca cctgaagggg
4681  tactcgaact cgacctcgat gctgaggtca ctctcggtct tgttggcaca atccacgctc
4741  agctggagct ccccactgta gctgccgcat gtggcaaagg cgaagatggc gaagaccttg
4801  ggcagcaggg atggggatgg ccacagtgaa cctgtgtgca tgtgggaggg aggtgccctc
4861  ctctggacag atcggggcc cagcacaggc agcagcagat ggagcagtcc ccaccccac
4921  cccctaatca gggctcatcg ggaccaagga caagctgatt acaagggtat ggctgtctct
4981  tcctgtttct ctctctgtgt ctctctctgt ctctgccttt ccatgctgac ctccctcttc
5041  tctgtttgtc tctgttgttc tctgtgtatc tcactgtgtc tctgtttctc tcggtatctc
5101  tgtttctcta tgtgtctttg tctttctcag atgtctcttt gtctctctgt gtctctgatc
5161  ctctctgcct ctgcctatct gatctgtcga tgtctctttt tgtctctttt ttctctgtct
5221  gtgtaagtgt atgcctgtat gtctgtgtct ttctgtttct tggtctgttt gtctctgtct
5281  ctctgtcctg tctctcactc ggtctccgga tggttctctc tctgtctccc tcttgcctct
5341  gtgtgttggt ttctcttttt tctgagtgtc tctttctctc tgtgtctctc tctccctcac
5401  cctgttttcc tgcctctctc cctgcgtctg tttctctttg catctgtttt ctgtgtctcc
5461  ttttcttg tttctgtttg tctcttctct cttatgtctg tatctcttct catctccata
5521  tttcttttt ttttctcagt atttccatct ctgtctttat cattccctgt ccctcattct
```

-continued

```
5581  ctctgtcacc ttcactgtct ctgggtttct ctgactttgc atctctcacc cagcatctgc
5641  tacaggctcc acctccccca cccctccctc acttcaagag aggaggtagg acgtcacagt
5701  ctcccacttc acaacggggg taccctcagc cctatgtgac gtcacagctc atctgttttc
5761  tggcttcaga cccctgaaac ctcaccctgg agcccaattc ccccatcccc tacaaccccc
5821  gcactcatcc ctggctactc gcccctactc caccccctgct cttctggacc ccatgacctc
5881  cctctctccc tgcactctgc cccaacagcc cggaccacac tcacccattg cagcaccttc
5941  acaaagccga ggggctcctt gaccacccgg aactgacccc cagccaccag ctgaggagag
6001  aaacagtggg gaaggggtgg ggttgttgga ggtacaggga ggtgagcggc aaggctgccc
6061  atcaatgacc caggggatg gagcatgtga cctcggggag agggtgagaa ggagaaagtg
6121  acaccttggg gatggtgtga gccccagggt ccaaggactg gtgggaaggt ctgaagagat
6181  ggtgagtcag atggcagagg aagtcggggg tgagggagat ggggatgagg tcaggactag
6241  ttaaggaggg ggagcaggtt tgaaacgtaa aggcgagtcg gatggggaag gggttcgggt
6301  agagaatggg gatggagtgg ggtgcattcg ggtgggggg ttgtgatggt gaaggtgagt
6361  cataacgggg caggagtcgg tttggctcag gtgggggaag ggtctgcagg ggtaaaggtg
6421  tgttagacgg cggtggcggt agatatttga ggtgatgggg atggggaagg gttgggactg
6481  attggggggtg agtttctgag gtggcaaaga cgagagacat ggcggagagg gtctggactg
6541  attaaggtgg gggagggctg ggacacggct tcagtcgcta tgtgttgggg gtgaggaggc
6601  tgggggtttt ggaaggagta aaaccggatt gtcccctagg tgtgctctgg gggaaggggt
6661  ggtcgcctat gggggtacag tctctgtttg ggaggggcgg gtgccagccc tctcccccat
6721  ccccgccccc acaccttctg tcgctctatt cctagcttta tccgcagcac cccccatctt
6781  ccttccactc tcccctcccc ttgtcccttg ccctcactcc agcccccagg cccctattcc
6841  tcccctcgcg gtcgccagta ataaacgggg ctccggggc ccccgctgcg gcagtgagga
6901  cggccctcgc tgcggcaaag agcgcactcc ttttctccac ctccccttc ctcccccttca
6961  cctgccgcag accccatcc ccagcgccgg ggaccgggtc tccgctgcca gaccctggcc
7021  accacctccc agagtcggct ggcctgagcg accggccta ggcagccggg cggcggcggg
7081  ctctgtccac ggtgctggag cgcgtacctg attcaccacg tccatgtccg ccagcagcag
7141  catcagcaat gcaggggcg ggaggctcgg ctagcaaggg cggcgcgggg cgcggcgggg
7201  gcggcgcgcg ctcgttggaa cagcccaggc ggctgcagcc ccgcccctcg cgccccctcc
7261  ttgcccgcca cgcgcctgcg cacagcgggt tgtaccacag tctcaccggc agccattccg
7321  gcccggaggc tggagccgtg agagcgtgcg ggaatatgcg ttgggaaaac acaagtcgag
7381  ggccggggag aggagacctc cctgctcggt cctacagtgt gacaactttg ccaggctctt
7441  ttctgagttt gttaaacatg ttcactcatt taatgcttac agaagtccta cgttgtaggg
7501  actattaggc cgtttttaca gacgaggaaa ataattcccc agagagctta agtgactctc
7561  acaaggtcag ccagctacta gctggcagtg cccagagtcc ctgcagttta aacacggttc
7621  aaggccttcc aggttccttt ttcatagtct gcattttaag cacacccctga aactcctgcc
7681  cccatctagc catctcccctt atttctttct tcctctttgt caaattaatg cctactcgaa
7741  ctctaccact ttacctattt attccttagc tctctcttaa ttggaataac cctccttcct
7801  gcgactaaaa ctaggcccat caaggtcaac agtgatggct atgatgcaaa atccaaaata
7861  cagttggggc ttaagatgct caacttcggc caggcgcagt ggctcatgcc tgtaatccca
7921  gcactttggg aggccgaagt ggacagtgga tcacttgaag tcaggagttt gagactagcc
```

-continued

```
 7981 tggccaacat agtgaaaccc catctctatt aaaaatacaa aaattagctg gctgtggtgg
 8041 caggcgcctg taatcccagc cacttgggag gctgaggcag gagaattgct tgaacccagg
 8101 aggcggaggt tgcactgagg cgagattgca ccactgcact ccagcctggg caacagagcg
 8161 agactccatc tcaaaaacaa acaagcaaac aaaaatactg agatactgtt tttcatcttt
 8221 cagggtggtg agtatcaaaa agtttgataa cgttccgtat tggtaggttg gccagaaaca
 8281 agcgttctca taaatcgcct gtggaagttt cattggtata acgtgtagaa ggcaatcggg
 8341 caaaatctaa aaaaaaaaaa taacaaattc atttactgtt tggttcacct tcatacttct
 8401 aggaattcat cttacagata gactcataca tgtgctaaaa gatatatgta aagataata
 8461 catgactggg ctgtttattt tttattttt tttgagacgg agtctcactc tgttgcccag
 8521 gctggagtgc agtggcatga tctccgctta ctgcaacctc cgcctcccgg gttcaagcaa
 8581 ttctccctgc ctcaccctcc ctgagtagct gagattacag gcattcacca ccacgcccat
 8641 ctaattttt ttttttttt tgtagtttta gtagagatgg ggtttcgcca tattggctag
 8701 ggtggtcatg aactcctgac ctcatgtgat ctgcctgcct cggcctccca aagtgctggg
 8761 attacaggtg tgagccactg gccaggcca gggctgttta taataggata aagaatggac
 8821 actcccaaag tgctcattgt tggtagcctg tttaaataaa ctctgatact atgccgctgt
 8881 cattataata acatggaact atggaatgat tgccaagata tttagttaag taaaaaatgc
 8941 aagatgtcaa actgtgtggt aattgtgtac aaagagaaga gaagggttat atcagacaga
 9001 gaatagctaa catttaaatt gtggctgttt tctgtcaagt actctttaga gaactttgcc
 9061 tgtattactc acttaaattc ttactgtaac cctatgtgac aggtacgaca actatctttg
 9121 ttttacagct gaataaacta agaggcggag aggaattttc ctaagttcac acagctggta
 9181 aattggtaga accaggatat gaacccagga agtctggctc cagcacctgt tactcttagc
 9241 cactgtgcta acttatcagt acaccatctt tttttttca gcacaccatc ttgtatgtct
 9301 gtgaaagata cctgataata ctatttgctt ccagagggta gggaaacttt tcactttata
 9361 cccctttgta ccttttgaga ctccatctca aataaaataa aaaaataaac agcctggtag
 9421 tgtatcatct tatacataca cctttagca catatatgag tctacctgta agaaattcct
 9481 agaagtatga agctgaacaa aacagtaaat gaatttattt ttctagattt tgcccagttg
 9541 ccttctacac aggttatacc aatgaaactt ccacaagcga tttatgagaa cgcttgtttc
 9601 tggccaacct gccagtatgg aacattatca aactttttga tactcaccac cctgaaagat
 9661 gaaaaacagc atctcagtag ttttgttttg ttttgttttt gagacagagt ctcactctgt
 9721 tgcccaggct ggagtgcagt ggtgcaatct cagttcactg caacctccgc ctcctgggtt
 9781 caaacgattc tcctacctct gcctcctgag tagctgggat tacaagcaca aaccaccacg
 9841 tccggctatt ttttttttt ttttttttt tttttagtag agatgggggtt ttgccatgtt
 9901 ggccaggctg ttgtgaact cctgacctta agtgatccac tgtccacttg gcctcccaaa
 9961 gtgctgggat tacaggtgtg agccactgca tctggcctac cttttgaatt ttgaaccatc
10021 tgaatgaata tctttttttt gagacagggt ttccctgtgt tgcccaggct ggagtccagt
10081 ggcatgaata tggctcactg cagcctcgac ctcctgggct caagcgatcc tcctgcctca
10141 gcctcctatg tagctgggac cacaggcgtg agacaccatg cccagctaat ttttaaatat
10201 ttttgtagag acgaggtctc actttgttgc ccaggctggt cttgaactcc tgggctcaag
10261 tgatcctccc gcctcagcct cccaaagtgc tgagatgaca ggcatgagtc accatgccca
10321 gctcaatacc tgttttttta aacatgaaaa ttcacacata tatgtaatgg atacttccct
```

-continued

```
10381  gttgttgcct tattggggaa gcagtacaca ggaggggtta aaagcatgga tcttggcatc
10441  aaactgcttg aatttgaatg ccacctctga tacttcttgt ttgaccctgg acaggtaaga
10501  tggtttaaaa tgatacctat aaggttgttg cactgattca acgagatgat cactgtaatg
10561  cagttagcac agggcccaat aaatggttca ttttacctcc tacacatctc tggaatccac
10621  tcacttctca ccatctcctc tgccacctcc tctggctaag gcgaccatca ttcctgccaa
10681  ttttagcatc tccagtctct tcccctccc ttctgttttc agcatagccg tcagaacatc
10741  tatttaaaat gcaatgttaa ctatgtcact accctactca aatccctccc atggctcccc
10801  actgcttata ggaaaaatcc cagagtttgg gacctggcat tcaaggttcc acctgatctg
10861  gcctcagtgg cttctcccac ctcatccctc aacagtctcc cttcactctc tgtgccctgc
10921  ccatgacttg ctgttctcac ctaactccag cccaaccact ttaagccttt gtttcaaggc
10981  ctaatgtaac tcaatcttct cagtcctagt ctccaattct ggcttccctc aaatttcagt
11041  cctggcttga ttggcgcaga ttatacaaat gagacacccc tgttctggga gctgggaaga
11101  gttcctcccc gactggtggt ctcatcctgc accactccca atgctacctt caattcctct
11161  ggagtggggc tgactcccac tttggatgag acctgtcccg tgtttcaacc agttcagttt
11221  gccccgagag aaacccagag ccggtgcctg cacatagta aatgcctgat aagccttcag
11281  tgagcgaatg taaccccaaa ggctgggtga agagtaaagc tggggcaaga agcagagagg
11341  acctctggga tctgtgtggg ataagagtag gttactgtta ggtggtctca ggaaagccag
11401  gtgggccctg agtgggttcc ccagggctgg gagccctgac ctttgctgtc acctatgttg
11461  tctactgatg gatttaggtt ttctttcctt tctcaggcag aaagtgggag atgggagaca
11521  gagcgatctc aatttagcca ccctaaaatt cctgttgccg tcagaggacc cctctgccta
11581  agatgcatca cataccaggc cgattccaac ctccaggcct ctcccctggc aggattcttc
11641  tctgggtttc cttgtccttt ccttctcatc cgtctaccct tcctagtttg acctggctga
11701  gccctggtga aatctctgcc tctcttcctc tctgggtcca agcaccctc acacccgctc
11761  tctccctttt cctccatctc tgtccagtgc cctccccctc ccctctcc cactctgcct
11821  ccagcttttt ttggctgctg tctcttcctc ctcctcctcc tctccctcc ttccctgacg
11881  ctgaataatc aggcctggct gtcctggttt ctggaaatac ccgtgtgtgg gcagtggctc
11941  agggctagaa caggggatgg atggatgggg gccctgggc agccccagac ccccagtgca
12001  aagacaacaa aatccaggga tgtggtccat gcctgcctcc tgctggggag ggagggcag
12061  gaggtttatt gagcagttgg ggaggggtgg gaattcagag ggcgtggacg caggccatct
12121  cgtctcccaa gtcctcctca tcgaagcggg agaggatgga ctcctcgtcg ctatagagag
12181  agctggttcc ctgtgccagc aggtcactgg cagcattgtc catctcatcc agcgtcaggc
12241  gacacgcatc tgcaatctcc tgcttggcca gggccacgaa acgtgggtct cgagcaaaga
12301  ggcccagacc ctctgagata agcacctggg ggcacaggtg ggatcagtgt tgacggacgg
12361  cacagtgtgc acagaaggtt cagtgtggat aaatgacgtg cccatgaggg catgtaggga
12421  agtcagtggg ggacagggt gagcagaggt cgtagggcaa agggatatct acatgcacaa
12481  cacaggacct ggggactcct ttccgtcctc ctccagtacc cacctcctcc ccttctcccc
12541  catccgtctt gtctatatgc cctctggact cacagcctcc accaagctgt cggcactgcc
12601  cctcttccca tggctggggt ccgagtgggt tccaggcacg tgcagacagg tgaaggtgcg
12661  cagtgggcca ctggatctgc cgaggtaccc ctcccccgct gcgccctctt ccaccaacaa
12721  cagcggggca tacaggagcc gaccccgctg aggtggtgtt gcccaggaac cctgagccag
```

```
                                       -continued
12781  aataaacatc agaggggcag ggatggatga gtagggtatg agggtctagg actcaccgct
12841  gtgcctactt ctttccctca gtatacaact ggagtgaaat tgaatgggta taagtcaggc
12901  ttgagtttat ttatgtaaga gtgcaggagg cctgggttta aatgtcagct ctgccactta
12961  ctagctgcat gatctggggt aaacctctca ggacctcagt ttcctcacaa gtacagtgag
13021  cattgtgtgc attcattcat atgtgtcctg ttcttcagaa ggctctgagg ccaggcgcgg
13081  tggcttatgc ctgtaatccc agcactttgg gaggctgaga caggcggatc acctgaggtc
13141  aggggtttga gaccagcccg gccaacatgg tgaaacccca tctctactaa aaatgcaaaa
13201  attagccagg catggtggtg agcacctgta atcccagcta cttgggaggc tgaggcagga
13261  gaattgcttg gacccgggag gcaggggtta cagtgagcca agatctcaac actgtactcc
13321  agcctgggca gcagagcaaa actctgtctc aaaaaaaaaa aaaaaaaaaa aaaaaaaagg
13381  gcctgatatg tgctgtgttt gagaaattca gcctaggctg cccccatctc tccagacccc
13441  agaccccagc accacctcca cagcctcacc tgagcccctat tgggcccctga atttcgccca
13501  cgatgatagg tgcctgggat gggtaaatcc tcacaactgc cctggcgctg cagacactgg
13561  atggtgaagg agggcttccg acctgggggt gggtggggca ccaggggcaa atagcaatgt
13621  cagtgcttcc ccagatctct gtcctgcagg cccgtggggg cccttggat ccatccctgc
13681  tctcacctgc aggtgtgggg ggcagcagac ggcggcgtgg taccaggtgc ccatccatgt
13741  atctctgagc tctgtgaggt ggcaaaagga ctgagcacgg gggagtccct gcctgctcat
13801  ctaggtagga aagcctgtgt gggtgggagg gccaggggtg aacttgggtc tgggcctgga
13861  cctgggcctg ggagatgggg cacaaacagt cctccccgac ccagttccca ccccctcctcc
13921  accccagctc atgggttcat cccatgtggc atggccagtg taccgatcag ggacttcctc
13981  atcctcatct tgcttgtttt gccctttggt tcccttgggc tgagaatttc cttcttctgg
14041  gatggtgaaa atgagagccc cagagcctct cctggggaaa gggaggcacg ttaggcagac
14101  cagatccctc aatatgtggc cctggacccc tggttcctct catcccatgc cccaaccctt
14161  acagaaacac tgggcttttg gattttttg ttgaggacaa gtcacataaa attaaccatt
14221  aaccatttta aagtgaccat gggcttttgt ttaatagatg ttcatctaat taggactgaa
14281  agtttcaaaa aaatcaaagt tgacctgtag agagacacct tgaacacaaa actgggcatg
14341  tattaggagt gggggagcc tgtaaaagct aggcactta tttttttatt tctattttt
14401  attttctgag acgaggtctt actctgtcac ttaggctgga gtgcagcagc atgatctcag
14461  ctcactgcag cctcaacctc ccaggctcaa tttatcctcc cacctcagcc tcccaagtag
14521  ctgggactac aggcatgcgc caccatgctc ggctatttt ttatttttg tatggacggg
14581  gtctcattat gttgtgcagg ctggtcttgt actcctgggc tcaagcgatc ctcccacctt
14641  ggcctcccaa agtgctggga ttacgagtgt gagccaccgt gcctaggcaa gctagacact
14701  ctgaaatttt ttttaaaat tttctttaa tctgcttatg tattgtctag cagctaagtg
14761  tttgacatgc attacctcat ttcatccttt ctttatccct gtgaagtaag tgctttgtca
14821  tccccttaa acaggtgagg aaactgaggc tcatagaaac gaagtgacta ggcagggcac
14881  ggtggctcaa gcttgtaatc ccagcacttt gggaggctga ggtgggcaga tcacctgagg
14941  tcaggagttc gaaccagcc tggccaacat ggcaaaacct cgtctctact gaaaaaaaaa
15001  aaaaaaatta gccctggcatt atggcgcacg cctgtaatcc cagctactcg ggaggctcag
15061  gcaggagaat cgcttgaacc cgggaggcag aggttgcagt gagccgaaat tgtgccactg
15121  cactccagcc tgggagacag agcgggactc tgtctcaaaa aaaaaaaaaa aaaaagtga
```

```
-continued
15181  ttagctcaag gtcacttagc aaatggcaga ggcagaatgt gaactgaaac tcttggtttc
15241  acacaatgtg cttttgcat taaacctttg tattgccttt ctcatatgaa tctcttatca
15301  ccctctattc ttacctgagc ccttgaaaca cctccattct tcccaaattt ctgcttgaag
15361  gcctctaggc cctccctccc acccccctca acttcctgcc tcctgaattg cctctatcca
15421  gtgtctagtc cttgccttcc ctcacaatct acttccagac acttgataat acctgtgggt
15481  gttggatcca gcctggggca cactgggctg actggaggtg ggagtccccc tgtcatcatc
15541  actgggccca aaggagagtg aatctggaag tctgtccccg acaggcagag acacagaaat
15601  cccggagccc cggcgagctg agggctggga gaccatcgtg gcctgtggag agtcacagga
15661  ctgagtgttg catgcacttt gtggctaagt catttggtca tataacatgt ctcccccaca
15721  ggtccatgaa tgtgggcctt gccctccaac agcaatggta atgtcaaat aaataaatac
15781  gtaaataaat aaataaatat ttgcgatagg gtcttgtcct gtcaccaggc gggagtgcag
15841  tggcatgatc acagctcact gtggcctcat cctcccaggt tcaagcaatc ctcctgcctc
15901  agcctcccaa gtagctggga ctacaggctt gcaccaccac tcctagctaa tttttaaatt
15961  tttttgtaga gaggcggttt cactattttg ccaggactgg tcttgaaccc tagggttcaa
16021  gcgatccttc caccctggac tcccaaagtg ctgggattat aggcatgagc caccactccc
16081  agcctcaaat aaatattttt ctattgcaga gggggcttct ctggggagc ttcttcccag
16141  aagcagtgtc aaaatcactc aggggattga cgaagtattt tacaatcaag ttcctgggag
16201  agtgaaaact tgtccccact tgttagttt ccaagtcctt ttcatcttcc tcctccactc
16261  cctcctgccc ctcttcttcc tcctcctctg tgtcacaggt gagggcctgc cgcatctcag
16321  gacccaagtc ctgcaggctc cgcagaccag cctgtgggg tggagaaata ggtaagcagg
16381  cagctcaggg tctgaacttt ccctctgttt cccctgcagg cgggtagggt ggggaagga
16441  gtccttcagc caccctggcc ctccgtgagg cctggggcct cagtttcctt atctgtgaca
16501  tgggtttcac aagatcaaaa tgggggtcag cctcagccac agcactgcca cacgtgccca
16561  tccacactag gccctgcccc gaagacctga agggcggaag aggtgctagg ggcggcgtcg
16621  ttgcctagta gccctttttc tttcctccgc cggaatttgc ggaaatagtc ctggatcaga
16681  aatgtggcgt agaatttgcc cacggtgacc tcctcctcta ggggcaaggg agagaaggca
16741  agatcacaca ggggccctct gacccagccc acctcgccgc ctctctaccc accagcatgg
16801  acttccctc gccctctgcc cagcgctggt tttgtggtgg agagcgatca tctgccattc
16861  aggggctggc gcggggaact ggggcgggga tagctcaccg tctggtgggg ggatgacctc
16921  atctagcagc ttctgtttca tccgcttcca gatctttttg atgacaatcc gcagctcctg
16981  gttggcttgc tccaggttcc ctgcgttgga ggaggatgtg gggcatgagc caataggaag
17041  aacctccaca gctgcccct cactgttggg tgggggaac ttcacaagct gctaccgcag
17101  atgcacaccg cccccattgg acggggtggg gggaaacagg cctggagaat cctgtcaccc
17161  attctggggt tcagagctag gagtggggcc catgattcaa tgagtttgct ccttgcaccc
17221  tccccaggaa cgatcccact cctgccctc ccctacacct tctgttttga tcttcaggga
17281  tgtccggacc agggcaaaga gtgtggcgtt gaatgtcacc gtccatctg agttgagggg
17341  catgttcatt gccacaagtc tctgcaaaca cgagagacat gaaacccact ctgggaaaat
17401  gccgggtatg caggaacgaa tgtcaagggg cagaaacctc tgaggatgcg atcaaacacc
17461  cctcccacc caaggcagat cccttcccac ccttgccatg tgatagacag ttctctcagg
17521  agcctggggg tgggcaggtg cacagacctt gcaggccact cggtgtgggc acagcttccc
```

-continued

```
17581  aaatcccaga gggggctgga tacgtctcag cagggcaacc acatccaagt gtttgatgcg
17641  gccctggag gagttgggga ggtaccactg gattggcgat gccccacta gcccttctc
17701  aaggccccac cagctcatca ctacctcctc ctaccaatac cccagagctt gccagggaag
17761  aactggaggg cagtcagaga gggcagagga tggggcagtg gaaactttgg ggcatctatt
17821  gactgggtaa tgagatgcag cagtcggagg tttgggggct aggggactgt gtagggcaat
17881  acattgtccc ctggattcta ggtaagggta tagagggcat acttggcccc agggtcatat
17941  tcagaccaga tcctcttgaa ttcatcaagg tgatggggc ccaggatgga ccaatctctg
18001  gtgagataat caaagttgtc catgatcaca gccacaaaga gatttatgat ctgtgggcca
18061  gtgagcaagg gagcagttag gtgaagggca gaacactgtc atggacggat ggtgggaggc
18121  tggggcgggc ttatatggtc atgagtctct gggttgatct tgtcatcaga ccagccctct
18181  cacccactat gaagatctgg gctgcccacg tcacatccct gagcccctca gggccagccc
18241  ccgtgacggt ggtggtggtt gtgaggaaat ggttctcacc aggaaggcac agagcatgaa
18301  gaagctgatg aaataggcga tggcaaaatt gctaccacag gtaaactctt caccagggcc
18361  gaagtcagac tcaggatcac accgatttcc gggaaggctg gcaagcatta tctcctgcca
18421  tgcctcacca gtggcacacc tggtgggagt cacacagggg tagcatcctg aaggggaggc
18481  tatgaagtca tggtaaatgg agttggggga ggactgggga atgaggagat gacctacttc
18541  tcaccagggg ctacatctgg cacagataac atttcaatat tttaacagcc agtgtggcca
18601  tgttgacgac agtcatgttt gcatcttaca gatgaggcac tgagacctga aaggggagg
18661  cgtcttacag tcagaaagaa aatggctgag gctagaatac tctaacagac tcctcacatc
18721  atagccagga aacatctcgg gctgtatgga gccccatgct gccatattat tcccatagct
18781  caagcagtct ggggctcaga gagggtgggt gggcacccac gggcataagg tggcaggga
18841  gtgagtagat gtcacctgaa cagaagcagc acagcctgtg gaaaggtctg gaagttgttg
18901  tttcggttta tctgtgtgcc atcctgaaga gccaccttgc cgaacatctg tggacacatc
18961  aaggctgtgt cagtggggtg aacccatgcc ccacccattt cacacctcct aatacctaaa
19021  ggagcctcat aaccctgaca aacagggcat cactgctgat ctcatttcac agatgtgtag
19081  attgacccag gccgtccag cttgtctgtc tacctgccac ccctactttg gggctattct
19141  taacccatcc cctgccagca gaggagtgct taagggatgc ttcctagggt ccccacttgc
19201  ctgcatgcca atgacggcat agatgaagaa tatcattgcg atgagaagag ccacataggg
19261  caaggcctat agggatgggg gaggggggca gagaatagat gcacaggctc aggcaaagaa
19321  ctataagccc cagaatgcac tgctttccct ggcctgggcc tactgggaga tgcagtccat
19381  ctccaaagtg ccaaggactg tggtgtctct caaatgtgaa catagtgtta agtagataga
19441  gtaaggtcag tgagaccaga ggtgtgttgg aaactgagag cccagaaaaa agagaaaatt
19501  ggaataataa tttggaaatg ggtatggcat gttgggagat gtagttctga gggtggtaaa
19561  ggggcaggct gagaagtgtg aaatgggggc gaggtatggt caaagggatg gggtaggga
19621  ttacctggaa ggacttgatg aatgtccaga gcaatgtgcg gatcccttca cccttactga
19681  gaagcttgac cagccgcata actcggaaga ggcgaaagaa ggtaatgaa atgcgggagc
19741  tgtcctcaga gctctggggt gaggggtgca gtaggatgc tcagtttgca tttactccag
19801  ctatctccct atctcatgct ttggcccctcc cagtacccaa atcactcagg ccctagggta
19861  atccggaggg atggaggac agagggacat gggaaagaa gcagagagtc cctgttatta
19921  gggtgggcta cctcgccaag gtggccacca ttctggaggg agatatggcc aagaaaaagg
```

```
-continued
19981  tgatacagga gatgatgaca tcataggccc aaatgaacaa ggtgagatat gatggagcag
20041  atataggggg tgatggtggg gtcattacac aggggacaat gggaaagttt atatggtagt
20101  ggattaggat taggaaaaag tgggtaatgg gaatggaagg gagaggagag agtaaaggag
20161  gtgatggatc agagacattg gagccaatag aggaaatgat ggaaccagtg gtgtcataga
20221  gatgatggag atgagagaac cgatggagaa gccaatggag aagccagtga tggagatagg
20281  gaaccagcag cgttgtcagt tgaggtgaca gaaccatgta gtacccaatg gaggtgatgg
20341  agccaatgat atagtcaatg gtgatgacag agccatgaaa gagccagtgt cagagatgat
20401  gaagttggtg gagaaatgaa gccaatgaag tcatcagaaa agatggagcc aaagcaggag
20461  ccagtgaaca tgacggagcc aatggatggg ggatgtagag gcaatgaaag agataacaga
20521  aataacagga gaggcatttc aggagatggt ggagccagta gataggttac aaaatggaat
20581  gagaaagcca gtagagggg acttttgctg aacccaacag ggactcagaa gagatagagc
20641  tagaatgagg actgagtctc caggagtagg gaggatgtgc gtgggagcca cccacccacg
20701  tgaaagggaa ccccgggata gaggtgaggg aaggtgtata gggcgagagt ggattagtgg
20761  aaaggccagt tctcacattg acttcagtga cggcaatatc cactatgctg cccaccacaa
20821  taagagcgtc aaacgtgttc caggcatcag tgaagtaatg ctgcaagtag gagaaaagca
20881  gtgccctgtc ttctcaaagc tcgcaagcca gggtaggggg ccagtagtag taggggggcgc
20941  cggaggggg cagggcttcg cttggatcac acgatgggcc tgcacctgag tccctctcac
21001  tccctagact cacactccct ggctgctgcc cgcatcgcca acccagagc tctgcaatga
21061  gctccactcc caaggaattc atccactggt gggtggggct agagaagggg ggccaccttg
21121  ggcttgaagg cgatgatttt gagcaccatc tcaatagtga agaggccagt gaagaccatg
21181  ttgaggatgt ccatggcata gttgaaggga gcagtctgct catagtgctg caggagaaaa
21241  tcaggttgag atggagcctg aggcagagat gccgccacac ccaaccaaat attccctggc
21301  ctgggctgag gcgagtctgg ggacttgatt gcactgtgta ttggtcaaac ctcttgcact
21361  gtctgcctcc cattatggat actggaaagt ttagttcttg attactagct tttcttgtag
21421  ttaggcaagg ccaggttgac tagtgagaca taaacataaa tctgctgttg gttagcagct
21481  tgtgtaaaaa aaattttgct ttccgatgaa aggatcaaat aaggagaggc cccaggtgca
21541  gctctccctg ccttgagtgt ggttttgatg cctggagctg tgatcatgaa acaacaatca
21601  tgaaaatgaa tgccaacttg ctaagaatgg tgaagcagaa agatagagca tgggtcccgg
21661  atgaacaatg aacaaacagc ctacctctgc acttctcaat acatgaggta attaccacag
21721  ttcattgact ccaggaggca catcttttta catttttagaa tctctgaaat tggggcgcat
21781  tttataacaa atggcaactt acaatggcca ctggctactt ttttttttt ttccacattc
21841  ttacatctcc gaaatcagaa tgcaacttac aagtactggc catagactta aagaaatgtg
21901  gcaaatgtct ttatagctta agttgctgtt agttggcagg gggtttgtta tttgcagcct
21961  taaatgttcc caatggttcc caagggatta tgtggagata tagggtcag gagtctggcg
22021  ggggtcaggc agggatctca gacctgcatg gctagggcaa ctgtgttgag caggatgagc
22081  aggaacatca ggtactcaaa ggcagcagag ttcacagtgg cccacacacg atactgatgc
22141  gggttcttgg ggatgtaacg gcggagtggc tgggccttga ggcatattc cacacattga
22201  cgctgcatac cagggcaggg catgagtgag cagtggggtc ctgaggcaag gagggaaggg
22261  ttggtgacca tccataggg gtcaggggtc agaggtcacc tggttcttgt ccagctcaca
22321  gttttggtac tcctgctcgc cctgggcacg gaaagtgatg atgacgaagc ccacgaagat
```

```
22381  gttcatcatg aagaacgcaa tgatgatgat gtagacaatg aagaacactg agatctccac
22441  acggtaatta tagatggggc catggtcctc tgcatatgca tcgatggcct tgtatagcag
22501  tctgtgggag ccagaggggg ggtagaggtg ggggcaggtg aggggatatc ccagccccct
22561  cagacctgcc cccagtctac ttatcacaga caccccagag tttcctgcct ggcaccccaa
22621  agacccctaa atctcctgac ctaaccacct gggacctcca tacatactct aagagacctc
22681  taccaggccc tcaaagagtc caaatcctct gtcccatgcc ctcagaaacc cccatagagt
22741  cctccagaga atctccattc agaacctcaa agacccagaa atcccctaag tttccacaga
22801  ccttcaaatc cccttctcca accacttgga gaccccatg cgcctcccca gaacttccac
22861  acaagccccc aacgatctgt aaatttatcc ctgtcccatc aacttgaatc cccactccat
22921  ctccccacag agccccacaa tgagtatccc aaagacctgc acagctttct agaaatcgct
22981  gaatccctgc ttcatctctt cagagaccaa tcccagtccc ctcagacctc cactctgtcc
23041  ccccaaacca tctccaatcc tttccaggct tctatctagc tacctagtcc cttagaaacc
23101  gctgtccaat tcctggagac ccctcactca agtccccaaa gaaccccccac ccagcttctg
23161  ggaactccac ctctacagtc ctctgataca cccaccactc tccagaaaac cctatccagt
23221  ctcgagagac cttcgtcaca tccccaaggt acactcccac ccattcccag gagatcccaa
23281  cccaatcctg cagagacccc tgcctcatcc cctgataaac ccagggccct gtccctcacg
23341  caggccagcc ttcaaaggtg gagacagtga acagggccat catggctgaa aggacattgt
23401  caaagttgaa atcactgttg acccagagcc gctcccggac caggggccgt gacacgtctc
23461  catctgggta taccaggaag gagcccctgt ggatgtgcaa acaggttaga tgggtgagga
23521  ggggtgagga actggggaaa gggtctgggg tctccagcat ggaggcagca ggacatagtg
23581  gtggagcaat atgttctagg ttcaaatcct gtccctccat gtcctggctg ggtgaccttg
23641  cgcatttacc ctttctgtgc ttctgtttcc ccattctaag aaataaggat aataacagaa
23701  tcgatttcct ggcttgtcac aaggattaat aaatgtcaca agtcaataaa tgagactagt
23761  gtctggcaca tagttggcat catttcatca tcaccattat catcctcatc atcgcccacc
23821  aggaaaaagt aaaacgaata atagccaacg tttattagca gtaactatat gccaggcact
23881  gagctagatt ttcttttct tctcttcttt tctattctct cttttttttt gagacggagt
23941  cttgaaaaag actctgccca ggctggagtg cagtggcatg atcttggctc actgcaacct
24001  ccgcctcccg ggttcaagcg attctccctc ctcatcttcc agagtagctg ggattacagg
24061  tgcacaacac caagcccagc taatttttgt attttttagtg gagacggggt ttcaccatgc
24121  tgactaggct ggtgtcgaac tcccaacctc aggtgatctg cctgccttgg cctcccaaag
24181  tgctgggatt acaggcgtga gccacagcgc ccgggcccaag ctaggttttc tgtgtagcaa
24241  ctttacattg tacaaagtac attttccatg tagtagctca tttactcttc acaacagcct
24301  tgtgagatag gcactgttta gccccgtttt tcagttgagt gaaatggaac tgagtaagtt
24361  taagaaatgt acctaagtct catgaagtgg atttgaaccg taatgtctga cttcacagcc
24421  caggctttta gctactaccc tctacaggag tctcaagatg gaagctgggg gctcagggtg
24481  ggaatggtga ttgctaatgg gtctggagtg gaatgtaggt cacttgggga atgcggagag
24541  ggatttgggg gaggtatcgg gggccgccga agactggtg agatctgagg gcctctgcag
24601  ttcttgggac aattctggga ctatatcttt gggccttggt gagatctaga ggctctaaag
24661  tcttggggag gggtcctgag ctccgtggac ggcagggtct tgggcactca cttgcattct
24721  tgagggggtgt gtttggcctc gtccgtgcag gtgtagaatt tcccctgtag agaggatgtc
```

```
24781  tgtcaagtag gttcaccctt catcacactc ccgcccagac ccctgcctgg cattccctcc
24841  agtgtttgcc ccaccttgaa gagctgcacc ccgatgcagg cgaacataaa ttgcagaagt
24901  gtggtgacaa tcatgatgtt tccgatggtc cggatggcca caaatacaca ctgcaccaca
24961  tgctgcgggc acccaagcat atggctactg aacactacag gccacagtgg tcatgggca
25021  gggactctgg tcatagatgc agctgaggga cttgggctgg ggacatgtgg tgatgggtca
25081  gggatgtatg gttagcaaca tgtgttcaag aggcagtgtt atgggctaga gacgtgtggg
25141  catccaccag gaataagtgt ttgccgggtg gggatctgtg gccacctgtc agggagctgg
25201  gtctgagaaa tgtggccact ggtagaaaca tatggtcact tggaaggaac atgggtcagg
25261  ccacatggct agtggtcaga gatgtgtatt tatgtgtcgg gtccaggccg tatggtcatg
25321  catccgtgca aatggtcagt ttgatcagtg atcctggccc caggggcagg gcagggcctg
25381  ggtcctgtgg gtttgggtgg ggtggggtta ccttgagtcc cttggccctg ttgatggctc
25441  ggaggggccg cagtactcgg agtactcgca gaatcttcac caccgagatg gcgctggagc
25501  tggggaaggg gcaatcctca ggcattggcc ctggctgggc cctggctgtg agaggaatgg
25561  ggtgggctgg ggatctgtca cttactggat gccaaaggag atgagggaca cactgaccac
25621  cagcagatcc aacatattaa accagctacg gcagaaggag ccgcggtgca ggaaggcccc
25681  aaacactgtc atctggggac aggacaagag gctagactca gacctgggga tggtgggggt
25741  tgggggaggt ggggatgggg acaggagagg tgggctgcaa gaaccggtgg ggagagtgcc
25801  agggcaactg agggtaggac tggggtccca ttagtcacct ttagtagaat ctccacagtg
25861  aaaatggagg tgaaggcata atcgaagtaa cccagaatct ggggtgtgag aaagagcggg
25921  gagccactga gtcacggctg aggggatcc taggtgactt ctcaaaaggc ttggccatca
25981  gaaagattag ggttcaaatt tggacccttc tgcctctacc cagctacatg gcgcctttg
26041  gcctgcttaa cctctctgag cacagcttcc tcctcagtca atattgatc tcctccctgg
26101  tgcttccccg tgtgttgcac atgccgtaaa ggctggcatt gcatcagctg cgttaatgag
26161  cccctctctc ggctcaccta gggctcttct ccttatctcc accctgaccc agcttgtgcc
26221  cactaggaca cccctgggag tgtcccctca gctcctagct cccagccaaa ggctcacatg
26281  gttgcggaag gagtgggctc ggatgggtc ctcagcggcc agggacacac tgctgaggat
26341  gatgaacacc aggataagat tggtgaagac atgatggtgg atgagggtgt ggcagccctt
26401  cctcagcctg tggagaggga gtgggccatg gtcagaactc aggaccacag aattgttcag
26461  ggattccaag ggatacagtt ctggccctga cacaacaccc atgccccac tcccacccttg
26521  gctgctcctc catgctcctc cacctgccct agcccctcct gcctcacccc ctgccacttc
26581  cggcactcac gggttggttt ggctgaggca gaagaaggcg ctgccctcag ggatgggtac
26641  caccttctcc ttgggtacaa cttcctgcag gagttccaca cccctgcac cctcttcctc
26701  ttcttcctct tcttcctctt cttcctcctc ctcctcctcc tcatgtctg gcaccagaga
26761  aaagcaaaaa aaaattaatt gagcaagttg atgtaaagca cccagaacag tgtttgccac
26821  gtggtcaatt cttcccattt ccctgctaga atgtcagctc ctccaggaag gtattttagt
26881  ctgttttgta tgctgctatg tccacagcac ttagaacagt gcctgggaca cagtaggagc
26941  tcagtaaatg tgtgttgaaa gaatgttgta tatacagact attttataat aaaggctctg
27001  agaagttcag cagtaaacaa aacgtgtttc tcttcttctt gttttttcttt aaagatagg
27061  tcttactctg ctccccccagg ctggacttca gtggtgccat catggctcac tgcaaccttg
27121  aacttctggg ctcaagcaat cctcctacct tagcctcctg agtagctggg actacaggct
```

-continued

```
27181  tgcatcatca tgcttggcta attaatttct tttttagaga tggggtcttg ctatgttgcc
27241  caggctgcat ttcccttctt taacctcaat gttcccaaat gttgctgacc atacccaag
27301  tctgttattt tcaggatgat cttggaaaag gctgatctct ggagaggagg gtctcagggg
27361  tcaggagctg tctgcctgag ctctttcccc aaggtccac acctgctcca cctggccctg
27421  cccacttgcc tgctccttcc ctccttgcac cctcctcttc ctctttctcc acaccaggca
27481  cctgaggaca ggaagacggg agtcatcaat ggtgagggag acacaggaa tggacacagg
27541  ggaggcatgg aagaaatgta ataatagggg aaagaatagg cagaggatga aggttaaaga
27601  catgcacata tggctgggcg cagtggctca tgcctgtaat cccagcactt tgggaggctg
27661  aggcaggtgg atcacttgag gtcaggagtt cgagaccagc ctggccaaca tggtgaaacc
27721  ctgtctcttt caaaaataac aaaaattagc cgagtgtggt ggcgcatgcc tgtaaatccc
27781  agctacttgg gaggctgagg caggagaatc tcttggaccc aggaggcaga ggttgcagtg
27841  agccgagatg gcacaactgc actccagcct gggcgacaga gtgagactct atctcaaaat
27901  aaaacaacaa caacaaaaaa acagatatgc acacatagac aggtagtggt gggagtggga
27961  ggtgtagaca gtgcccaggc atctaactca ccaggccttc attctcctgt gggagatcct
28021  tctcattgct cttctccctg tgcgaggaaa tagggtgat tgctgcagat gggctaaggg
28081  ggatcactac agtcagaaca gaccttttctt gggtcccata gaactttctt gcttccgctc
28141  ttccccactg cccctcccaa cagtccgttc tcaaagcagc cagagggagc ctgttaaacc
28201  ctgtctggga tatcccaact ctgcccacaa ccctcccatg tctccttaat tcaggaaaaa
28261  ctacagtcct cacccctggcc cagaatgccc tcaatctggc cctccatttc ctccactgac
28321  cttcactcca taccactctc ctccttcctc actccattcc agcctcactg ttttattttt
28381  tttgagacgg agtctcactc tattgctcag gctagagggc agtggtgcga tattggctca
28441  ctgcaacctc cgcctcctgg gttcaagcga gcttgtccag ctaattttct tttgtatttt
28501  tagtagagac agggttttcac catattggcc aggctggcct cgaactccta agctcaggtg
28561  atccaccctc ctcggcctcc caaagtgctg ggattacagg cgtgagccac tgctcccggg
28621  catcgctggt attttttgaa agtgctaaga atgtggtcag gtgcggtggc tcacgcctgt
28681  aatctcagca ctttgggagg ctgaggcggg tggatcacct gaggttagga gttcaagacc
28741  agcctgcca acatggtgaa accccatctc tactaaaaat acaaaaaaat ttagctgagc
28801  atggtggtgt acgtctgtaa tcccagctac tcaggaggtt gaggcaggag aattgcttga
28861  acctgggtgg cggaggttgc agtgagctga gatagcacca ctgcactcca gcctggatga
28921  caagagtgaa actccatatc agaataaaaa aaaaaagtgc taagaacatt agcgccccag
28981  aagctttgca cttgccactc cccttccttg aatactcttc ccccagatat ttgcatggct
29041  cactccctca cttcattcag gtctctggtg aaatgtcact tcctcacaga gaccttcctt
29101  gctgacctta accccaaaga gcaatcttca tttcttgcta tccttttcatt ctgtttttctc
29161  tttattacat attattaaca tatattatat attcatttgt tttatttttc ttgccttcct
29221  caactagaat gttagttcca tgaaggcaag gactcttgtc tgccttgacc cctgttgtct
29281  cctcagcatc tagaacagga cctggcacac agtaggcagt caatagatgc atgttgaatg
29341  aatgaggact ggcagatggt atctggagat ggggattacc agggtgacta gaggcatctc
29401  tggtggtggg ggtgtctgag gggttccag tcagggatcc cagagagaga ctgtgttagg
29461  ggtggagcca gatctcaccc gcccttgtcc ttggcagtgc ctgcatctcc actggccagg
29521  ttgtccacag caatggcaag aaacacgttc aacaggatgt ctgggatgag cttaggctgc
```

-continued

```
29581  aaaggatgga gaagcaccct gcctatagac cacccagttc cccttaccca ccccgactcc
29641  accatcatcc agccccacaa agctccaagg atacagttgc cacagatgaa gagaatgatg
29701  aaatagatgc acaccaacat tcctgggaag aaggggccac catatgccat gataccatca
29761  tacatgacca cgttccagtc ctcacctgtc aggatctggg ggtgggaagt cactgtggag
29821  ctcttggacc ccctccaact ccagggtctc cccgacccac ccatcccatg gtctccagat
29881  cctacctgaa agacagtgag gagggcctgg gggaacgtgt caaaggtgct tcgcttggtg
29941  tgggtctggt caaagttgaa cttgccccca aacagctgca tgccaagcag ggagaagata
30001  atgatgaaga ggaagaggag aagcagcaag gatgcgatgg atttcattga attgagcagg
30061  gatgccacca gattgctcag agaagcccag tgtctgcagc agaaatggga gggggcaggg
30121  tcgatgccat gtccactgga catggctgga gcatcaggag ccagggcagg gctccagctt
30181  gagatgcacc tcggcaggtt gggctcaaat aggctttggt gtcaggggtta gaaatgattt
30241  tggagttggg gtgagatgag agtaagaagt gggggaagct gggccctgtg gtggctcacg
30301  cctgtaatcc cagcactttg ggaggccaag gcgtgtgggt catgaggtca ggagactgag
30361  accatcctgg ctaacacggt gaaacccccgt ctctactaaa aaaaaattag ccaggcatgg
30421  tggcaggtgc ctgtagtccc agctactcag gaggctgagg cagaagaatg gcgtgaaccc
30481  aggaggcgga gcttgcagtg agccaggatt gcactgcact ccagcctggg cgatagacag
30541  agactctgtc tcaaaaaaaa aaaaaaaaa aaaaaaaa agaagaagaa gtaaagaggt
30601  aggggaaagt tgagagtttg gggttagggt tggtggtagg ggtataatgg gagactggga
30661  gatgaggtta ggatggagtt ttttttttc ttatctttt tttttttttg agatgaagtc
30721  tcactgtgtt gcccaagctg gagtgcagtg gcacaatctc gtctcactgc aacctccacc
30781  ttccaggttc aagcgattct cctgcctcag cctcccgagt agctgggact acagtcactt
30841  gccaccactc ccggctaatt ttttgtatt tttagtagag acggggtttc actacattgg
30901  ccaggctggt cttgaactcc tgaccttgtg atccacccgc ctcagcctcc caaagtgctg
30961  ggattacagg cgtgagccac cgcgtccagc ctaggatgga ggtttaatgg aagttggtga
31021  agctagaatt gggtttcagc ttgggactgg gcctggtgtt ggggatgggg ttgtgatgta
31081  tttggggttg gagatggagt taagggtaag ttgtggttga gggctgggat agaggagggg
31141  atgggatgag actggggctg aggctggaaa tggagttgca gttgaagata gggtgatggt
31201  taagggttag ggacgtggga gttctctttg gggattgagg atggtattat ggttggtggt
31261  tagtgacagg gatggggctg ggagttaggg atgaggtggg agatggagtt gggcttggga
31321  atgggtgtta gcgttgtaaa tgggctcata ggtgacctgt ggttgggggt tgggatcaga
31381  gatggtattg tggttggggg ttgggatggg gtttggggctg gaatagtat ggcattgaaa
31441  tcggagacag ggttggggaa aaacgttaga gcaggagttg aggttgagga aggcaatgga
31501  aatggagtag acattctccc cagtggatga agacaggaac ttgtgtctgc tttgattcct
31561  ggtgtttccc tagggcttgg tagggtgcct ggcacacagc aggcactcaa tggatgtctg
31621  ctcaatgaat ggtgaagcag atgaagttat cattggagct tgggtggggg tgttgaggct
31681  gtgtttgagg cccttgtctt ccccctcccc taatacaaac ctggtgacct taaagatcct
31741  gaggaggcgc acacatcgga gcactgagat gcccaagggc tgcatggcgc ccacctccac
31801  caaggtggtc tctaggatgc ccccacagac cacaaagcag tcaaagcggt tgaagaagga
31861  agacacatag gcagagggcc ccagaccgta caatttgaga agcatctcca ccgtgaacag
31921  acagagcaac actttgttgg catactctgt ggggagagag gcagggatga tcgggctggc
```

```
31981   cagtttctgt ggtgacatgt ggggaggtaa ctagggacca tggggtgacc cacggtagct 32041   ggtatcaggc caggtgctgg ctgagggaag gcttagggct agggattggg gtgagtttgt 32101   aggtcagagt aggtgaagtt ttgagggget tggagatggg gatgaggggc agagtcgggg 32161   tgggggccag agtcagtgtc tatgagtcca gaagacccaa attcacaagt agagttagag 32221   tctagggttt cttcgggact ggggctggtt tgtgggttat gggttagaaa tgtgctcggt 32281   attcaggctg gggctgagat tataatgaat aatagtaaga gctgacactt ataaagtgtt 32341   agctatatgg tgggccatac aatgtcctaa gcacttttca ctttacatca tttactcctc 32401   ttcgctgctt catgaagtgg atactactat ctatcatctc cattttgtag atgtggagaa 32461   cttttccaga cagtgtgatg ataagagcct ggattctgga gccaggctgc ctgggttcta 32521   attctggctc tgccactcgc tagctgggtc ccgagattag tcgcttaacc cctcagtgcc 32581   ttgatgctca gtgttctgtg ccttagtatt taattcgcat aaggttgtgg tgaagaaatt 32641   gtcagtacac ataaagaaag gtgctgagaa aggagcttga ggcacacagc aagtgctacc 32701   tgtgtaagct acaaggtggg atgggacagg ctaagggctc tggatttatt tgggtagggg 32761   ggaaggcagt gtcttggggg ctgaggcgcc ctagaggttt tggatttaag cttctgggt 32821   agaaggaata ggaggctggg ggagacgact agcaggctgg gggtgtaccc tggatctggg 32881   tgagccacac aggctgcccg tggtgctcag aggcgatggt caacgtgttg aggaagacga 32941   gcaacagcac agcccagtag caggcattgg acttcactgc ccgacggcag cgtgcccgaa 33001   ggacccggtt ggctcggcgg aggcggcggc tgggggaagg ggagcccaca ggctgagatc 33061   acctacctaa gcctgccctg ggggggctcag gtggggatc caaaggtcat gagggcttgg 33121   aggtgggggg tttcaaagtt atgagtcaa ggatttgcac aactttccca actcaccaga 33181   ctctggtttt catgatcttg tttctgaaaa agaaggggga tgggaggtgt gtgtcgtaaa 33241   gggcagaagg ggtgtcagtg actggggcca gaggtcaagg actgagatcg aggcttgagg 33301   ctaaagaaag gacttgagtc agggtttgga ctggcttctg ggctgggtca ggggctgggg 33361   gccctcacag gcagcgtgta cagctggcca gagcccctc ctcctcatcc tcatcgcctt 33421   gggtctctgt catggaaccg gtgtcactgg ctgggaggct ggctgtaggc aaggtgggga 33481   tagtggtcag gacctgaaga ccccgaggtc caatctttgg cttcacctc tgcctaccca 33541   cccccacccc agcctggctg gaccccacc atggctgctg gtggagtgtg tggagcgagt 33601   agaatgactg aaccagcgca gacgtccacg cctcctattg gtcagctcgg ccagctgtgg 33661   ccctgcaggg agagaaagga caattaggga ggacatactg ggggcagggt tagggccatg 33721   tctagggtag gggtgtcatt tggagtcttt atagctgagg ctggtcttga ttctgcattt 33781   tgagccataa cttgggggct ggggctagag ttgttgcaga tcaggcctgg gtgggtctca 33841   ggagggcaga ccacatctaa ggcatgcagg gaatgggcca gattggagtt gcctacgatg 33901   gcccgcccgg ccctcttcag ccatagaacc aaggttgtca tcggcggagg ggtcctccat 33961   gtccagctct tcggcttgag tgatccagtc caggtagccc cgcaggtctt cctccatctg 34021   ctgcttctcc cgctgcttct ggaagtcccc gcgagctttc gctttctctc tctccttgga 34081   gaactccctg agggaggagg atagagggct aggggagga gccaatctga acaccttgct 34141   ttcatcactc cagccacact agcctcctag ctactctttg aatatgccaa gcacattcta 34201   gcctcagggc ctttgcactg accattctct ttgcttggaa tgcttttccc tcagataacc 34261   acatggtgca cccacctcat ctctttttt ttcttttccc cagatacagg gtctcactct 34321   atcactcagg gtggagtgca gtggtgtgat catagctcac cgcagcctcg acctcctggg
```

-continued

```
34381  ctcaagcgat ccttccacct cagcttcctg agtagctagg actacaggtg tgcgccacca
34441  tgcccagcta ttttttgttca ttttttgtaa agatgaagtc tcactatgtt gcccaggctg
34501  gtctcgaact cctgacctca agccatcctc ctgccttggc ctcccatagt gctgggatta
34561  caggcatgag ccactgcacc tggcctcttt cacattttta ctcaaataac accttgtcaa
34621  gacagccttt cctgacatcc ctatttataa tcacaagatc tctccattct tatcttttat
34681  ctttcctttc tttccacagt acatattcca tataaaacac tatatatatg tgtgtgccaa
34741  tatataaatg cacacactta ttttattgca tatgttgcta ctttctgtct ctccccatca
34801  gaatgtaaaa ccaggaaggc agagattttt gtcttttgtt ccactcctaa aatggtgcct
34861  cacatacaat agatgctcat gattgaatga aggagtattt cagatgggtt ttgaaggatg
34921  tctaggagtt tgccaggcac aaagaagtgg gcagtggctg aggggtggga agcagggagt
34981  gtctaggtcc ctcacccact caggacgcca agcacaaggt tgaggacgaa gaaggaccca
35041  aagatgacaa ggctcacaaa gtacacccag ggcagttcat accccatggc atcttgcatc
35101  tggggagaga aaaggcatgc atccctcagg gtaggcagac actcctgcgt gagtgtcagg
35161  gaggaaaggc aggtgcagcc tttgagctct gtgccacag tccacctcac ccagtagagc
35221  acatcggtcc agccttccat ggtgacacac tggaagactg tcagcatggc gaagaagaag
35281  ttgtcaaagt tggtgatgcc tccattgggc cctggccagc gcccgcggca ctcagtctgg
35341  ttcagcgtgc acgcacgccc tgatcccgaa gacgcacagg gcgatgggtc ctcctccgct
35401  tccatgtctg caggaagact ggagcttggg gcttcgaagc aggcccactc tcagtcgctg
35461  ccaccctgaa gccccgccca cttaggaagc tcgacttggg tcctagattt ttctctttct
35521  ctctttcttt ctttcttttt ttgagacggg gtctccctct gtcgcccagg ctggagtgca
35581  gtggcacgat ctcggctcac cacaacttcc gcctcccggg ttcaagcaat tctcctgcct
35641  cagcctcctg agtagctggg attaccggcg tgtgccacaa cgcccggcta atttttttg
35701  tatttttagt agagacgggg gtttcaccat attggtcagg ttggtctcga actcctgacc
35761  ttgtgatccg cccgcctcgg cctcccaaag tgctgggatt acaggcgtga gccaccgtgc
35821  ccgccagtc ctagatttt ctaaggcaac acttagctcc acttctaggg cagaaccctg
35881  cgagctccgt attctgaacc actgggaagc tagggatccc accaaccggg atttaaatcc
35941  tggcgtggag tcttgtaaat aacaatgagg caagagcctg ggggcggagt cttgtgaatt
36001  tggacgcgtc tcttgaaaat aggggagggg caaggcatgg gcgggagtct gggtaaatgg
36061  tctgagtgta tgagaacagt cgtggagaat aaaagctttt tttggtttgt ttttgttttg
36121  ttttttgagac cgagtctcac tctgtcgccc aggctggagc gcagtgagtg gtgcgatccg
36181  atctcagctc actgcaacct ccatctccca ggctcaagtg attctcatgc cgcagcctcc
36241  cgagtagctg ggattacaga catgcaccac cacgcccggc tcaactttgt attttttagta
36301  gagatggggt ttcactatgt tggccaggct ggtctcgaac tcctgacctc aagtgatcca
36361  tctgcctcgg cctcccaaag tgctgggatt acaggcgtga accacggcgc ccagccgagg
36421  ataaagtttt ttaaaattgt ttttgttatt attttttgga gactggatct cactattttg
36481  cacaggctgg tagcaaactc ctgggcgtaa gtgatcctcc cgcctcggcc tcccaaatgc
36541  cgggaataca ggtgtaagcc aaggcgcaga gttttttgttt tgttttgttt tgttttgag
36601  acggagtctc gctctgtcgc ccaggctgga gtgcagtggc gcatctcggc tcactgcaag
36661  ctccgcctcc tgggttcacg ccattctcct gcctcagcct caggttcacg ccattctcct
36721  gcctcagcct cccgagtagc tgggactaca ggcgcccgcc accatgccca gctaattttt
```

```
36781  tgtatttttt tagtagaggc agggtttcac cgtgttagcc aggatggtct cgatctcctg
36841  acctcgtgat ccgcccgcct cggcctccca aagtgctggg attacaggcg cagagtcttg
36901  tcttaagtgc ggggcacttg cacttaagtc ttaagtgcgg ggcaggacct tagcctgtgg
36961  gtacagtctc gtgatggggc ggagctatta gcgaggtggg gttgtagtct gatttagggc
37021  agagtcttga atatatgggt gggacttggt tatctgggga tggaacctga gcctgggggc
37081  cgaatcttgt gcatttcagt gggtttccct gagtgcagca ttggatctag gaaccgaagg
37141  aggggggcatg ttctgcctag gaggggcggg cagactaacc ggatcccagg aagtagcacg
37201  tcttgtgcat tcgtccaagg aacagctcga gcccaatgat ggcataaatg atgatgacga
37261  agagcacgag cagtgcaatg tgcagcagcg gcaccagagc cttcatgatg gaattgagca
37321  ctatgtgcag gcctgcgggg agggaggggg aggcagaaat aagggcgggg tcagctcagc
37381  cccacccca ccctccacct ccgacctcgg gggatgtgcc actcactcgg gaccccagac
37441  accagcctca gtggccgcag cacccgaaac gccctcaatg ccttcacatc gaagcctcct
37501  ggcttctccc cggtgtgcgg ggcgtcgcct ggccgtccgg ggccctgctc cagcagaacg
37561  ctgaacagcc tgatggggga gcaccgggca gggaggcgga ggtcaggcct tgggattccc
37621  ccctccaccc taaccttctc agaaaagcac aagtccctgt aactagaaat agaaatgggt
37681  tttaataata ttcctgattc tggctgccga atgggggcgg tctgaaagag tcgctttcct
37741  gagcccagaa ttcagcgggc ctgacgtag gaaggcgact agggtggggt gcctcccgca
37801  gacgcgcacc cgaccacgac gatgatgaag tcgagtaggt tccagccatt gcggatgtag
37861  gcgctggggt ggagcaccag cccgtaggcc acgatcttga gcaccgtctc cacagtgaaa
37921  atcaccagga atacgtactc cacctgctcc tgggggtggg accgggggc gggtcgggaa
37981  gtcgggagt tatttgaagg cgaggtttga cgggggcgtg gggagcatag tcaggaccga
38041  gggtggggct gagccaggca gggccatccg ggtcagagag ggggcggggt ctggctggaa
38101  ggagtgagct ctactgggc tctatttggc tggggaactgg ctggggcggg gcgggcctta
38161  ccaggttgtg gttggcagtg ttggagtcgt cctcagggaa gggatgtaa actcccaggg
38221  ccacgcagtt ggcaaagatg gtcagcagga tgaggatgtc gaagggcctc aggtggacac
38281  agtcaaggac cctggcagag tggcattgga acccccctac tcccttggga acctcccacc
38341  cagtgctgac ccttgacgcc caaggtgaca ggtcctggca ttctcgaccc ctgccctgac
38401  aaggccttga ctttgtccct cctggaaacc ttaaccatcc ccaactcttg ctgtgattca
38461  gtccttgact cttgaaccct ggtgaccttt gcctttctga acctgcccc caacccagtt
38521  cttgactctt gaccttgatg atctcagccc tcctctgttc cagccctgac ccaattcttt
38581  actcctggta ccctgatgac ccttacccct gggccctgcc cctgccttcc aggatgcttc
38641  cactccacga tgctgatgca ggaccgtcgc agaggattgg ccagggtgag gcagaagagt
38701  gcccgaggtg accgctgggc actggccact gccactgtct tgtgcttgct gtgctggttt
38761  cttcgcttag gggtccctag gcctgatgcc ccactgcttt caccttccac agctgggggc
38821  ccggggcaca gccccccattc gggaccaggg cctgcccat ggctggact gggctctggg
38881  gtggtgtcta tatggagaaa ctgtgtcagg gagggacagg gtattgggc aattgtggct
38941  gcttcctacc tgatcctgtc cctctgtttg aaggaaggag agaagagcat ggaaaattag
39001  ggagaactgg gagtagctgg gttaaggact gggaagtaag agtgttcgaa ttaagattag
39061  agtgagagtt tatagggag tgaaggtgag attacatttc caagtgaagt agggtttggt
39121  gtttaagttg ggggtagagt ttaaattgcc atggggtggg cgaatttaag gttaaatttg
```

-continued

```
39181  agtggtgggt tttgggttag ggtggggatg ggtttagaca taggtaggag tggagttttg
39241  tctaagggtt aggactgggt attttgaatt ggaattagaa ttaggataca ggttagggtc
39301  gaagttgagt tttgagtggg acttgaattt tgcattgggg ttttcagcta aggccactcc
39361  cagttcccat ggtctcgttt cagcctcaga gggcggtaga ttggcctggt taagattccc
39421  agctttggat gaaacaagct gcctgagttt aaatcctgac tttaccactt ggtagctatg
39481  tgttgccttg ggcaaattat gtaatctctt tgagcctcag tttccttatc tgtataataa
39541  ggatgataat aacagtacct aaaatatagc ggtgttatga ggattaaatg agttcagaat
39601  caaaagaatg cctggcacat agagttattc ccattttgca gatgagaaaa ttgagaagaa
39661  aaagttaagt gacttgctga agtggctgaa tggggagtca cactcagtct aactctagag
39721  ccctcatggc ttactaccac catcaagtat gtcttctctc tctttctctc ttttgttttt
39781  gtttttttt ttaaagggtc tgtgcacttt ctggaaagtc agagactgca atcactaaca
39841  gtattgacat cccgggggttg aggttgaggt taggtcactt taggtctgta tctggggtgg
39901  ggtttagact ctaacagggg tttgccttct ggctggtaga gtttgtgtta ggtttcaggt
39961  gggcgtttgg ataggggtca gagccaggat tgaggttggg tttcctttgg gaactaaggc
40021  tgtggatgag gctgagaggc catgggggggt ggtgtctggg tcaggctgag cgttagggct
40081  ctggtggcag agaggctgtt tgggctggc tgggatgggg aacagggtga tgtggttctt
40141  gtccctaga ggctctctgg gggtggggtc tgggtgggca atgggtgggt cagagggggct
40201  ctaccttgct ccaagggtct gcagggatgg aaggattctc tcaccttttcc cgccttcaga
40261  ttccgacatc tttctttcga gattgaaggg ccatctgcac acaacccccc tctcttcccc
40321  cagctttgga gggattaagg ccgcagggcg gggcaataac agtgttgtat gggagggtgg
40381  cggtgggggt gcaaatggga cgttgtgggg ccagagcctg gcaacagatg aaatatttac
40441  caaatatata cctgcagcaa acagtcaaac taaaataaga aaaacgatgt cattttccag
40501  tagtatatgg aattcgaagt ataggaaaa aacctaatat atgtgcaata tctctatgga
40561  aaaaagatca aatattatca attattatta tttttagaga cagggtcttg ctctgtcacc
40621  caggctggag tgcagtgcg tgatcatagc tcacagtagc gttgaattcc tgtgctcaag
40681  tgatcctctg acctcagcct ctgtagctgg gactgcaggt gtgcactacc atgcccaact
40741  attttttttt taaattttgg gttgcttcga actttatttg agaacaacag aagataaacc
40801  tatcaaaaga acacacaggt gggtgcgggg gcacggctag tggcggcggc cgggggcatc
40861  cgggctaagg cttttacttg gctgcagact ggtcggatt cgcagctcct aggccccccaa
40921  gctgggcccg tgactccaag gtgatctcgt tggactgcgt ggctagcttg ggcatggggg
40981  cctccacggt cagtgtgccc tcagggggaca gggaggagga gacccttggtg ggtccacac
41041  cggggggcag cgtgtatttc cgggtgaagc atcgggagat gtagccatgc tcgtcctgcc
41101  gctcctcgtg cttgctggtg atctccacca tgccatcctt ggtcttgacc gtcagctcgt
41161  cggaggcgaa gtagttgatg tccagggata cgcgccagcg gtccgctgtg ggccgattct
41221  ccgagacccc gccgctgagc tgccggctga gcgcgtagct gtaggcgggc gcggccaccg
41281  cggggctctc gaccgcggcg ggggcagggg acgcacgtag cggggccagc agctggtgcc
41341  caaccactgc gaccagcccg aaggcctggt caaagaggcg actgtgcggg taccagtcgc
41401  ggaagggggtc ccagctgggg tcccgcagga gcgagaaggg gacgcggcgc tcggtcatgc
41461  tggctggctc tgctggggac gtctgcttgg acaagtgtca attttttttt tttttttaa
41521  gagatggtgt attgctgtat tgcccatgcc ggtctcaaac tcctgacctc aagcgatcct
```

-continued

```
41581  cccgccttgg cctccaaaac tgctgggatt gcaggtgcgc gtcggctgtt caagaaatgg
41641  ttacatagat ttcttttgct ttatttattt atttagagac ggagtctcgc tctgttgccc
41701  aggctggagt gtaatggcgc aatctcagct cactgccacc ttcgcttccc cagttcaagt
41761  gattctcctg cctaagcctc ccgagtagct gggactacag gcatgtgcca ccatgcctgg
41821  ctaatttttc tcattttagt agagaggggg tttcaccatg ttggccaggc tggtctcgaa
41881  ctcctgacct caggtgatcc acccgactcg gcctcccaaa gtgctggtat acaggcgtg
41941  agccactgca cccagccggt tacatagata tttgctgtgt aattattctt tggagtgtac
42001  aaatgtgtat catattaaag cattttattga atgcatggac actagtaact ataacttaca
42061  tagtgctttc ttatcttatg tgtcaggcac atagtacaac gtgctttata taaattaatt
42121  ctgttttaat cctaaaaagc aggtactgtc aatagtccca ttttacagat gaggagacta
42181  agacacaggg aagtagtcgc tttgtgttaa aattctgccc ttaatgtgta cacttttata
42241  gcctagaaga tgaatgccgc cttaaacgaa tgagtcagga agccccttc tgtccggccc
42301  ctccactccc caccacacgg gttgttcctt tttcccttgg aagagcccac tggactgcag
42361  gtggaagaac tacagttccc agcagctatt gcaagctcaa cctccgtgca cactcacccc
42421  aggcctcaca tccggcatgc gccgtgctcg ctcacagaac tacactttcc aactctcccc
42481  acacgacccg tgacactctg tggaccgcga gcacggagca gggtttctac agctgctccc
42541  cactttctcg gacccggtcc tggacccagc ccccgactcc gacacggctc caccatggag
42601  gaggcggacc gaatcctcat ccattcgctg cgccaggccg gcacgtaagg acagagcccc
42661  cgcccacccc cgaagcccac atccgggact ctaaagccca ggaccccgtt tcccgggaac
42721  cttaaaaccc gggatcctga cattcagggc tccaactcca ggatcctaag accctcaccc
42781  ccttacacac acacacacac acacacacac acacgcac acacacacac gcacacacac
42841  accgccctcc ctgacaccga catcagaggc ctcccaaatc ctttaaccat gatatttggt
42901  acacccaaag ctctgggacc cagacacctt gagacgttac aaccttgaaa cctcaagacc
42961  cggaaccctg taatctgggg aatcttaaca tcagttccct gagaccctgt tatctggaga
43021  ccctaagaca cctgtgccct aagaaccagg gagcgtaaaa ccccaggacc ctggcactcg
43081  gggactccaa aaaatccctg gaccagatac ttgggatcct tcaaactcca gttccccaaa
43141  cacctggggc ttaaaaaaac ccaggattct tttttttttt ttccttttcc gagatggagt
43201  ctcgctctgt cgcctaggct ggagtgcagt ggggtgatct cagctcactg cagcctccgc
43261  ctcccaggtt caagtgattc tcctgcctca gcctcccaag tagctggtat tacagccgtg
43321  cgccaccttg cccggctaat ttttgtattt ttagcagaga cagggtttca ccatgttggt
43381  caggctggtc tccaactcct gacctcaagt gatctgcccg cctccgcctc ccaaagtgct
43441  gggattacag gtgtgagcca ccacgcccag ccaaaaaaac ccagaattct aaaatctgac
43501  atcagcattt ggtcaccctg acgcacgaag actcctccgt tcagaggccc taaaaaccca
43561  ggatgccaac atctagggag tctgatttt gtattgcttg aaactaggtg gtcttgatat
43621  tcagggatct tgatacccag ggaccctgac atttggaact tctgaaaaca gcagcctcct
43681  aaaatctagt cttctcaaaa ctctagcagc tcaatatgta tgcaaagaac atactatctg
43741  ggaaccaaga aacccagaga ttgtgccacc tggaccccttt caccttccca gactcccaaa
43801  ttttgatatt tttctaaact gagttctctt ccacccacca ttctcctact ccaagatctt
43861  aggacttgag gatttcccta gttcctggtt ttccaaatgg aagtcacagt caccaacatc
43921  caggatctgt ctgaactgta ggcatcctcc ctgcccgac cctggtacta gtgtttccaa
```

```
43981  aaggctgcag ggctcagcct gatccctgtt gcctgactat tcctgtgatc aagctggtcc
44041  ccttcttcag ggcagttcct ccagatgtgc agaccttgcg cgccttcacc actgagctgg
44101  ttgtagaggc tgtggtccgc tgcctgcgtg tgatcaaccc tgcggtgggc tctggcctca
44161  gccctctgct gcctcttgcc atgtctgccc ggttccgcct ggccatgagc ctggctcagg
44221  cctgcatggt gagtggccct cctcctaatg cacacatcct ctttcttcct cttttacaaa
44281  gtaaccaagt tcctttgcaa cacttgcctt tcctctgcaa cacttgcctt tcctctgcaa
44341  cacttgcctt tcctctgtca ttttcctgc ggcttagttt tcattagtgg ttaaggctgc
44401  tgactgtact gccaaactgc ctgagtagtt tagatcctag ccccaccact tggtaactgt
44461  gtgaccctaa cccttctggg ccccagtttt cctatttgtg aaatggagat gataaatgta
44521  gtgcttttat gaggagcaaa tgagtttatc cagtttgcac ctgggctgct cctggcttct
44581  atgttttaaa tttagctgca aaataccacc cccaccccat agtatccatt tcctagttcc
44641  agaaaatact ctgtctgggt catatactcc taaactaatc actctgtgct ctgattggcc
44701  cagtctggat gacatggtca ttccttttt tttttttttt ttgagatgga gtctcacttt
44761  gtcgcccaag ctggagtgca gtggtgcgat cttggctcac tgcaacctct gcctcccggg
44821  ttcaagcaat tctcctgcct cagcctcccg agtagctggg actacaggcg tgtgccacca
44881  cacccaacta attttcatgt ttttagtaga gacggggttt caccatgttg gccaggatgg
44941  ttttaatctc ttgacctcat gatccacctg ccttggcctc ccaaagtgct gggattacag
45001  gagtgagcca ccgtgcccag ccttttcttt tcttttttc ttttttttt tttttgatg
45061  tgaagtctct ctctgtcacc caagctggaa tgcagtggcg tgatctcagc tcacggctca
45121  ctgcaacctc cgtctcctgg gttcaagtga ttctcctgcc tcagcctccc gagtagctgg
45181  gactacaggc atgcaccacc atgctcagtt aattttgta ttttagtac agacggggtt
45241  tcactatgtt ggctaggctg gtcttgaact cctgacctcg tgatctgccc acctcggcct
45301  cccaaagtgc tgagattaca ggcgtgagcc actgcgcccg ccgacacgg tcattcctat
45361  aggacactgt gattagccac tccttcagga tcctgtggag ttgggataag gatgattacc
45421  caaagaaagg catgctggtt acccaaaaga gtgtctgcta tattacctct gtgggaacca
45481  catatcctgc ctctgctaag agcaattcca acaatgtctc tgtgacagaa taaataaagt
45541  gcttttcttt taaaaatat tttaatttt ttagaggtaa gtgtcttgct atattgccca
45601  ggctggtctt gaactcctgg cctcaagaga ttctcctgcc tctgcctcac tagtagctag
45661  gactataggc acatgccacc ctgcccgaga attttaaat ttttcgtaga tgggggtct
45721  cgcttttgta gagatgttgc ccaggctggt cttaagctcc tggcctcaag caatcttccc
45781  gccttggcct cctgagtagt tgggactaca ggcgtgcacc actgtgcctg gtaaagagcc
45841  attctgatga aacactcacc cattcccagt atagagctga gtccaggagt ccagttcctg
45901  tattcaagag ctgcaagtaa tgccactccc cctggctcac tcactctgtg actttgggcc
45961  agtcttttt tttttgaag cccaggctgg agtgcagtgg cacaatctcg gcttactgca
46021  acctcctccg cctcctgggt tcagcaatt ctcctgcctc agcctgccga gtggctggga
46081  ttacaggtgt ctgccactgt gcccggctaa tttttttgta ttttagtgg agacagggtt
46141  tcaccatctt ggccaggctg gtctcgaact cctgaccttg tgatccaccc acctcagcct
46201  cccaaagtgt tgggattaca ggtgtgagcc accgcgtctg gctctcttaa ccttttgag
46261  gctaagtttc cacatgtgta aaatgggtat aagaattgta gctactgtat agggttgctg
46321  tgaggattaa acatgagtta atgtgtgaaa agctggttat aataagcttt gcataaatgg
```

-continued

```
46381  gattactatt attggatagg tccgatctgg aacctgtgaa tacatagtga atggaaacac
46441  tttgaactga cccaggaagt atatggtggt ggagggacga tagagtaact accgtgaaaa
46501  ctttcattta gatataggg actgggtggc tagagttgtt aaatttgggc cttgcttatg
46561  cagtttctgt ctcttagcaa caggtctcag agctccatcc atcccttcgc tctcaggttc
46621  acccagctct caggagttgt cacattgttc tctctggggc tcttggtggc cttatgaggc
46681  aggcagtctg tccctggcc caggactgta tgtattctta aggttagcac ttaataggg
46741  ggaagttatg tcttctgttt gcagaggaga gtacacagca ggaggtgttg aggtgggggc
46801  tcaggcttcc tgcagttctc tgttcttccc tcagtgctgt ctctcttgga ttttgttcac
46861  ctgcttttgc ttacattgat tttagtgggg gttagtgact atggcttttc cagtggccag
46921  gaggtacatg tgggctgggc acgttggctc ttgcatgtaa tcccagcact tgggagtct
46981  gaggtgggag atcagttga gcccaggagc tcgagatcag cctgggcaac atagtgagac
47041  ccccatctct acaaaaaata aaaaaaaat agctgggcat ggtggcacac gcctgtggtc
47101  ccagctatgt gggaggctga ggtaggagga ttgcttgagc ctgggaggtc caggctgcag
47161  tgggctgtga ttgcgccact gcactctagc ttgggaaaca gagtgaaacc ccatctccaa
47221  aaaaaaaa aaaaaaaag actggggacg gtggctcctg taattccagc actttgggag
47281  gtggaggcgg gcagatctca ccagaggtca ggagtttgag accagcctgg ccaacctggc
47341  gaaaccctgt ctctactaaa aatacaaaaa ttagcctggt gtggtggtgt gtgcctgtaa
47401  tcccagctac tcaggaggct gaggcaggag aatcgcttga acccaggagg cggaggttcc
47461  agtgagtcga gattgcacca ctgcactcca gcctgagcga cagagcaaga ctcttgtttc
47521  caaaaaaata aaaacaggt acatatggtt gtctggcccc cagcagcctt ggtttatcag
47581  cagcaggcaa aaggagttct cttaatccag ctgtgtgctg tccctgtagc cccccgcaa
47641  ctcagcactg ccatgttctg gcatcttttc ttcatatgcc ctgctcctgg caacagtttc
47701  tgcaccttag ccacctccat attttggcac cttccccact cctggaatga gtttctatat
47761  cagtcacagc tctttgattg catattgtgg aaaaaatcca agtaaaata ccttaaaagc
47821  cagtggttat acttatttga ccttgagcct ccaaaataaa tatatcttgc attgtgaccc
47881  agtatactcc taagtataga ataatgatgg cttctaagtg tactctgtgc caggccctgt
47941  ggtaagtaac atggtgttaa ctcatttaat tctcaggaca accttctgct atatgtactg
48001  ttggtatacc ctctttcaga tgaagaaagt gaagcacaga gggattaagt gatctgcctg
48061  aggtcgtata gttggtaaga ggcaaagctt gggtttgaat ccaggaagtc tgctttcaga
48121  gtctatgcag ttccaaagca gtggcaactc tggaagaaaa aggctttcct aggccgggtg
48181  tggtgattcc cacctgtaat cccagcactt gggtggctg aggtgggcag attgcttgag
48241  cccaggagtt tgagaccagc ctggccaaca tggtgtagcc ctgtctacac tgaaaataca
48301  aaaattagcc gggtgtgtg gcatgcacct gtaatcccag ctactcggga ggctgcgtgg
48361  gaggatcact tgagcccagg aggcagaggt tccagtgagc caagatcacg ctactgcact
48421  ccagcctgag cgacagagcg agaccctgtc tcaaaaaaa aaaaaaaaa aggaaaaagg
48481  ctttctttct ctcctggcct gtttcctcag tccccatcag aaccctcatg agtccttttg
48541  ttctgagcta ttgtgcttct ggtcttttg tcctgtttat ttttaggcac tctttctata
48601  ataggtagat ttgctctttta cctatgatat gggctccaaa tatttttccc caacttgtca
48661  ttaactttg actttgctta ttctatttc tttaaatatt ttctttcttt tcatgtattc
48721  aaaagtaccc atcttttctt ttatggcctc tggattttga gtcatagaaa ggccagagct
```

```
48781  ttaatcttgt ttcttgttct ctgtagcgtt gactatcatc actctgtgac tcccccagg
48841  gcccagaggc cttggggagc tggggaggt tgggaggtg gtggttagtg agaaagtggg
48901  agcgttttca gcctaggccc aagtctccca gggcaggagg accctgcctg cttcctgata
48961  gccgcccacc aaccctcagg acctgggcta tcccttggag cttggctatc agaacttcct
49021  ctacccccagt gagcctgacc tccgagacct gcttctcttc ttggctgagc gtctgcccac
49081  cgatgcctct gaggatgcag accagcctgc aggtactggg tgtctggat gtgggcgggg
49141  gcggtgaggg gagaggaggg ccttctaggg gctgtagggc tgagagaggt agaggtggta
49201  aaaaggttga tgggtagggg tggcggtatg tgccttcagg agagctaggc aggaggatta
49261  ggcatcagag agggctaca gggcagggg caggggctg aggttgagct gaccccggtg
49321  gtgcgttggt gcggggaggg gcctccctga ctcaacccct gtgccctccc tctctctcac
49381  ttcgctctaa ccacttgggc ctcctgggtg ctactcaaac ataccccagt acactcccgc
49441  ctctgcacct ttgtatcgtt ggttaccttt ccctaggta ccctcatggt tcactccctt
49501  acctctttga ggttaacctc ctctccgcag ccctctcctg atccccacct ggctgcagtc
49561  tggatggtat tcaggatcct attcatgatc tctctcctct gctagcttgc cggctccctg
49621  agggcaggga cctttatcca gtttgttcca cgaagtagcc ctagtgtcta gaacagcgac
49681  ctgtacatag taggtgctcg gtgtttgttg aatgactgaa cgtgagaacg caagctggat
49741  agatgtgtat ctctggatgg gggtcaggag tggaggctgg tctcctaggg tatgcccttt
49801  tggatttgca gcattgacat ctgattcact tcctccctat ccccataggg tgactcagct
49861  attctcctcc gggccattgg gagccaaatt cgggaccagc tggcactgcc ttgggtcccg
49921  ccccaccttc gcactcccaa gctgcagcac ctccaggtga gaccctgac tcccatggat
49981  cttctcttgt ccccgtctgg gtgcccaggg ttttggcccc ctaccctgg caaccctcat
50041  cccacttcac cctggagatt ctgagcctgc tctcccacca gggctcggcc tccagaagc
50101  ctttccatgc cagcaggctg gtcgtgccag aattgagttc cagaggtggt gagcatgagg
50161  ctgtggggag gggtgaggag gaaggtgggg gggaacctca tagcgttgcc atgcggcagg
50221  gccagctgac tctgttcctg cctccagagc cacggagtt ccaggcgagt cccctgctgc
50281  ttccagtccc tacccaggtg cctcagcctg ttggaagggt ggcctcgctc ctcgaacacc
50341  atgccctgca gctctgccag cagacgggcc gggaccggcc aggggatgag gactgggtcc
50401  accggacatc ccgcctccca ccccaggtac agccagatgc ctggctccct gctgtctggg
50461  ctgctgctca ctgacactcc cgctggtcct ctgctctcct tccccacttt gtccctccct
50521  tccattgttt cccctctgtg tgtgcttacc tagctcccca cctgaaagaa cactggagtc
50581  agaaaaaagg agaacctggg acaagtcagt atccctcctc agagccttgg tttcctgtgc
50641  taaaatttgg ggtagtaata gtgctctcct ctcagggcag tagttagact gaataatgtg
50701  cttgagattc ctggcaactg gagcaatcca gattggctac ctgccttcat cattcattaa
50761  ttcattcatt catttggagt cttgctctgt cacccaggct ggagtgcagt ggcgtgatct
50821  cagcacactg caacctccat ctcccgggtt caagcgattc tcctgcctca gcctcccaag
50881  tagctgggat tacaggcttg caccaccaca cctggctaat ttttatattt ttagtagaga
50941  cagggttttg ccatgttggc taggctggtc tcgaattcct gacctcaggt gatctgccca
51001  ccttggcctc ccaaagtgtt gggattacag gcatgagcca ccgcacccgg ccctaatctt
51061  tctctgtttc tgcacttgtc actgatgttc attttttctgg tttctaggtt tttgcacaat
51121  ttctgcctgt ccccattatt ctagttctgt gttttttgctg ctcctctttc ttacctctct
```

```
51181  gtctcctcgt ttctgtactg aattcctctc ttgctctgtc tatctatctg ttccccttc
51241  tcctctgtct acttctttat ctgtcccctc ttcttctctg tgcaccttt tatctgtgtc
51301  cccttctgct ctgtccacct ctgtatctct cccttcctt gctgtccacc tatatatctg
51361  tcaccctct gcctctgttt acttcttaat ctctctcctc ttcctctctg tccacctctg
51421  tatctgttgc cccttccctc tgtcccctta tctctccctt cttcctctct gtccacctct
51481  gtatttgtcc ctcctcccct tctgtccatc tctttatctg tcctctcttc ttcttttttt
51541  ttgagacggt gtctcgctct gtcacccagg ctggactaca atggcatgat cagggctcaa
51601  ggcagcctca aattcccggg ctcaagcaat cttcccacct caggcatctg agtagctggg
51661  tctacaggtg cgtgcgcccg gctaattttt gtattttttg tagagatggg gttttgccat
51721  gttgaccagg ctggtctcga actcctgacc tgaagcaatc cacccacctt ggccttccaa
51781  agtgctggga ttacaggcat gagccaccat gccgagcccc ctcttcttct ctgtcaacct
51841  ctttgtcccc tcttcttctc tatccatctc tgtatctgtc ccctcttccc ctctgtccac
51901  ttatctgtcc cctcttcctc tgtccacctc tgcatctgtc ccctccttct ctctgtccac
51961  ctctctgtca ccctctccct ctgtccattt ctttatctgt cccctttttcc tctctgtcca
52021  cttctcttt tccctccctc cattctgctc tcctatttct gttccctctt cctctgtgtt
52081  cacccaggta tcagtacccc tcccccttctg tccacccttta catctgtccc ctcttcctct
52141  ctgtccacct ctgtatttgg ccccctccc cttctgtctg cctctttatc tgtctcctct
52201  tcctctgtgt ccacatctct gtctgcccct cttttcctcc acctctgtgt cggcccctc
52261  ctggtctgtc cactttttta tctgtcctct ctttctgtct tcacctctgt gtctttttac
52321  atttttattt ttttatcatt attattattt tttgagatgg agtctcgctc tgtcacccag
52381  gctggagtac agtggtacga tctcagctca ctgcaacctc tgcctcctgg gttcaagtga
52441  ttctcctgcc tcagcctccc acatagctag gactacaggc atgcaccacc acgcccagct
52501  aattttgta tttttagtag agacaggggt tcaccatgtt ggccaggatg gtctcgatct
52561  cttgacctca tgatccatct gcctcggcct cccaaagtgt tgtgattaca ggcgtgagcc
52621  accacgcctg gctgtctgtt tttgttttta tatctgtagt aattttcaaa cataaatgta
52681  gagagaatat tctagtgaat cctatgtacc attttgccaa cttttcttca tcttttctct
52741  cccaacttt tctttgttgc tgtattattt taaagcaaat ctcagacatc atgtcatttc
52801  agctctaaat acttaggact acatctctta actcataagg acattcagtt ttcaaggtaa
52861  ccactggacc attttcatgg ctaatgaagt taacaataat atcttgtggg ttttttttg
52921  ttttgttttg ttttgttttt tgttttttt tgttttgttt ttgagacgga gtctctctct
52981  gttgcccagg ctggagtgca atggcgtgat gtcgcttcac tgcaacctcc acttcctggg
53041  ttcaagccat tctcctgcct cagcccccaa gtagctggaa ttacaggagc acactaagtt
53101  ttgtattttt agtagagtcg gggttttacc atgttggcca ggctggtctt gatctcctga
53161  cctcaggtga tctacctacc ttggcctttc aaagggctag gattataggc atgagccact
53221  gtacccggcc aacaatgata tcttaatacc atccaatact tgagttcata atcagatttt
53281  cccattatct tgaaactctg ttgtccctct cttgcctctc tctctctgcc tctttctgtg
53341  cttggtacct ttgattccct gtctctgccc tgtcccccga tatcctgtct atgcttctct
53401  tggatttggg ggctctaggc ccacccccct ctcttcccac atccttctcc agcatgggga
53461  tctagtgggt ggagagaagt atgtctgtga gcaagaggag acccctgtcc tcgaggagat
53521  cccaggctgg tggagcagga gagtagagca gggcctgcct tagtgggaag gctggagggt
```

-continued

```
53581  ggggtgact  tgtctgtata  ctcttgtcag  ggggtccttg  gaggaggcag  ggccttgggt
53641  gctaggtggg  ccctacacc   ttcctgcttc  cccgcctt    tctcccagg   aggacacacg
53701  ggctcagcgg  cagcggctgc  agaagcaact  gactgagcat  ctgcgccaaa  gctggggcct
53761  gcttggggcc  cccatacaag  cccgggacct  gggagaactg  ctgcaggcct  ggggtgctgg
53821  ggccaagact  ggtgctccta  agggctcccg  cttcacgcac  tcagagaagt  tcaccttcca
53881  tctggtgggt  gcgcctgagg  acatgagatg  tgtggatggg  cgtggcaggc  ttggagggtg
53941  gctttttgtg  tcagcaccac  acctttatcc  acacaggttc  ctgtgttccc  actggacagg
54001  ccctcgcccc  actgtgggat  gggtacccag  aggggtcccc  tagcttatta  gggacttgac
54061  tggagaaaat  gtggataggt  gggaaccatg  caaaggtgtg  ggggtgttct  tggggcaaca
54121  ccccctttcc  tcaggcagtt  tcctttgagc  atatcttctg  tcctaagatg  ttcactctga
54181  gggcccccca  tccttctcat  gggcatttga  ggcttgagag  atgggcagg   tgggtaggag
54241  ctgtgacagg  gtcagggaga  tttctccacg  agcaagcact  ctggcccgag  gttgcagatg
54301  gtgcctttac  ccacatagtc  acagtctggc  caccatcggt  gcttcagtgg  gcatgcatgc
54361  cgcactgggg  gcagttctca  ggggaggctg  aggctgggcc  acgtgaggaa  gggccttccc
54421  tggcagccag  gatgcccctc  gtcactcccc  ttaggagccc  caggcccagg  ccactcaggt
54481  gtcagatgtg  ccagccacct  cccggcggcc  tgaacaggtg  agcagagtgg  tttggagggg
54541  ggtgtcccag  gcccttgctt  gtctactggg  cctgacaccc  caaccctgac  tggcctgggc
54601  ctcccaggtc  acgtgggcag  ctcaggaaca  ggagctcgag  tcccttcggg  agcagctgga
54661  aggagtgaac  cgcagcattg  aggaggttga  ggccgacatg  aagacccctgg  gcgtcagctt
54721  tgtgcaggta  aggggcgag   gaggggctgc  gcgttgggct  aggtcagaag  gagggcctcg
54781  gggtgtgagg  gactagatgg  ggcaagaggt  gctctgtaga  ggtctgcaca  tggcagaagg
54841  gttcctggga  gccattaggg  atctgtgggc  ctcttgaggg  tggctatgag  aatcaggcca
54901  gggtgagggt  ctgtgggcat  ctatgggca   ccgcgggtct  gcatgggcag  gggattgagg
54961  ggtcctcgga  gggtctgtgg  gcatctgtgg  ggtacccacg  ggtctgcatg  acagggat
55021  taggggtcc   tcggggtcct  tggcaccagc  gtggagctgt  tagagaggcc  tgtgggggcc
55081  acagggtgt   acagtcatct  gtggagctcc  atgggggctg  tggcatgtga  ctgggtatcc
55141  accggccagg  cagagtctga  gtgccggcac  agcaagctca  gtacagcaga  gcgtgagcag
55201  gccctgcgcc  tgaagagccg  cgcggtggag  ctgctgcccg  atgggactgc  caaccttgcc
55261  aagctgcagg  tggggttggg  gctgtagctg  ggcggagagg  ggcagggtgg  ggtggggtgg
55321  ggttggaggg  cccagcctgt  gtgacatgta  cccatccccc  accagcttgt  ggtggagaat
55381  agtgcccagc  gggtcatcca  cttggcgggt  cagtgggaga  agcaccgggt  cccactcctc
55441  gctgagtacc  gccacctccg  aaagctgcag  gattgcagag  aggtaagcag  tggggccctg
55501  ggctgtgggc  gggccaggggc aggctcggtc  cctctctagg  gggcatccc   tatgctctgc
55561  tcactgtctt  ctgcctgtgg  gctcatggca  gctggaatct  tctcgacggc  tggcagagat
55621  ccaagaactg  caccagagtg  tccgggcgc   tgctgaagag  gcccgcagga  aggaggaggt
55681  ctataagcag  ctggtaaggc  ctgtgtgagg  gacctgggta  gcttaggagg  gtgggggat
55741  ggtcctgggg  cagtgcctgc  tatatccctg  cctagatgtc  agagctggag  actctgccca
55801  gagatgtgtc  ccggctggcc  tacacccagc  gcatcctgga  gatcgtgggc  aacatccgga
55861  agcagaagga  agagatcacc  aaggtacact  gccagggcca  tggagggtgg  gtcatgtggg
55921  ctgtcaggca  tagtgtggcc  gcacagggac  ctcacaccct  caggcagagc  tgtccagtca
```

```
55981  cactctaaca cagaatagtc acacacaatc catcccagtc acccctgaca cagtgacaca
56041  gtccctgtct ggtacacatg aggaccctcc actgctagcc agcctgcccc aggcagggc
56101  tcatggctgc catggtgtct gccagatctt gtctgatacg aaggagcttc agaaggaaat
56161  caactcccta tctgggaagc tggaccggac gtttgcggtg actgatgagc ttgtgttcaa
56221  ggtgtggggc aggttgggcg ggggtgagtg gggtgaggct gggctgctgc cttgtgcatc
56281  tgctaattgg ctggctgggg tccagaccca ggccctgtgc gaggctggag gtgcactgat
56341  acccagggct ggctttgttt catggaggat gaagctagtg gggtggtggg agagggtggc
56401  cttcttaggg catggagatg gtcaagggca gcccactgat acctttgagg tccctgtgtc
56461  tggtcaggat gccaagaagg acgatgctgt tcggaaggcc tataagtatc tagctgctct
56521  gcacgaggtg aggggagaca tgtgcctggg gtggggctgc tgggggtggg tgggactggg
56581  tgcaagcctt ctgctcctgt tgtccccaga actgcagcca gctcatccag accatcgagg
56641  acacaggcac catcatgcgg gaggttcgag acctcgagga gcaggtgagg cctgggggca
56701  ggatggggag ccaaggcggg ccggggggac agttcctcag gttatgctga cagaggctgt
56761  ggagccacac acagccgatg gctggacacc cagccctgcc ccttagtgcc tgtgacctgg
56821  gacaggcaag tggcctactg tgagcccag cttccacccc aagggccctc ctgtctgcct
56881  cccagggcca tgggcagagg cttcagctta aagatgtagg gggaatcctg ccacatggcg
56941  aaggatgctt tgggtagagg gaacaccaca cgaggcctgg ccatgggaca gagcaggctg
57001  ttggagttgg tgggaggggc ccagagtggc tgtgatgggg gctggtgagc aggagctggg
57061  aaagggctg tgtgtgctga gggggcatgt gttcacattg cctcagatcg agacagagct
57121  gggcaagaag accctcagca acctggagaa gatccgggag gactaccgag ccctccgcca
57181  ggagaacgct ggcctcctag gccgggtccg ggaggcctga ggagccgccg cagaggtct
57241  ctccccagcc tcaggcaggg atttggggtg ctggaggcag tggccaagca catgccctag
57301  ctacttcctc cgctgtccag ttcctcctgc tgcggccttg acccagacc cctgcccact
57361  gaccgcaacc cttatatggg gtgatagtcc agcatgtggg gagctcggct gcagtttatt
57421  ggggacggta ctgtgggttg ggggccttgg atcccaaata aatgagtagt tcctctgcag
57481  tctaagctga ggcatggatc agggctcagg gaatgggagt gaggtgagtg gcaggggaga
57541  cacgggtat ttttggcaag gcagtgtgtg tggctgtgtg tgtctgcacg ggactcaaga
57601  gacccactgg ggggctgtgc gtgtgcatat gcgtgagata cacaggtgaa ttctaacagg
57661  ccgtgtgtgt gagcgagcac gtgttgggac ctcagatcct gagggtactg acgctgcttc
57721  tgtgtaggcc tctgggcaca ccctgtgtt gacagtgccc ctgtgggccc tgaggctggc
57781  tgtgggtgcg tgccttgggg tgtgtgggtt gtcagggctg tgcttgtgtg tgattgtgtg
57841  atgatgcagc tttgaggttg tttgagtgta ctgaggcagg ctctctgtgt tttggggttt
57901  gtgttgagtg agggacagga ttgtgacatt ttgtgtgtct gtgtgacttt tccagccctg
57961  aagtaatctg tgcgagcagc tgaggcaggc tctgtgtggc tggttgtgaa ggctctgttt
58021  ggctgcaggg ctcgactggg gggtgtgtct ggggcggagg tggggctgg ggccaggacc
58081  ggggcccctc tgagcagcct tggggcaaag gatatgatgg gggaggggt ggctgccagc
58141  ggggaacag gggccctggc aggcaagaca gtgaaacct cacttcttgg tccctgtggg
58201  cacatccagg gcctatcatc cctgccccca ccacctctgc ctcccaccag tttggcccct
58261  gttcgtccat cctcctttcc ttgatcttga ggtcagggc caggtgtagg gttggaacac
58321  ctgctgggcc tctggctccg tttcttgcgg aactccagct catccacggt ccacacagcc
```

-continued

```
58381   cccttctcgc tctccacccg cacaaagcac ttgtgcagac tcaggttgtg gcggatggcg
58441   ttctgtggaa ggccggggac agggagcagg tgggcgtcaa cctctgaggc cagcagccac
58501   caccaacaac ccacatcccg ttcctcccca atgtgcctat gagcccagac ccaggcctgc
58561   ccactttgag ctgcgatggc acttgaggcc atcccagtca ccgccacctc agaggagctc
58621   accttccagg tggcaggatg gtttctgaag aaggcaaaca tgcgtgtgaa ccagtggtag
58681   atctcattga gtgtccgctg cttctctgga gcctccagga tggcctgaa gttgggggt
58741   ggggtaaggg gcacattccc caaacttggg gtttagaggg gctatgacct accccgagcc
58801   atctgacatg ggggcggaat tgtaggggca ggtaatcagg acaggacta gatgtggggt
58861   gaagcatggg gtcaaagatg gggttagaaa agggggtgaag tgtcggttg ggcagggtta
58921   gatgggtgtg ggtatggttg ttctgggatt aggtaaggga tcaggactga ggttgggagt
58981   ggggtcttgt tcagggctag ggctgaagtg aggtgaaagg tctgggatgg agttggagtt
59041   ggggttctct gtggaggtga catttcaggg ttgggggaagg tgaagggtca gaagtggggt
59101   caaggatttg gaaggggtaa agggccaggc caacttaagg gtcagggaag gggtgggtta
59161   agagtcaggc tggggtggac tcaggtgggg ggtctagggg tgagggatgg gatgacttgg
59221   ctttaggtca gaagccagag atggttttgaa ttatcgagta tcttacgtgt cagggacatg
59281   gttaggtggt taggctcagg gcaaggatga ggttagttgt ggggttcggt gtggagtgag
59341   gctgagggtc agggaatttg atcagtttgg attcaggaat gggattacag agtcagcgat
59401   gatgattgca gtgaggctat cagtcaggat ggggctaggt cagggtttca gttcagagac
59461   agtcggggaa tatctggtat catgtagggg tgaggttcag gtttgggggtt aggtgtggcg
59521   ctaggatgaa ggttctgaga aggcattggg gaggctgaga tgaaggagtt gggatggggt
59581   gatgaagtta aggatcaaat gggtgttaca aggaaaggtt gggaatggtg cccagttggg
59641   ggtgtattga catactgggg tacgttgggg ccagggaagg gatgggggtt ggggttggcat
59701   aaaggctggg gaaggagtta gagtaagagc tggggtacgt ttagggcaag gtgcagagat
59761   ggggttagct ttaggctatt ttatgggtcc aggagagggt taggtatggg gctgaggtgg
59821   acatctggaa aggggtaggt ttagggtcag aatttggcat gctctggcct ggatggtggt
59881   ttaggtttgg atttgcggac aggtttgggg tgaagccagc atgaggggtc acatttgagg
59941   cacggcttgg ggatccttgg ggctggggct tgggaatgga ggaacccact ctgagggcac
60001   tcagagggag acaggagttt gggaggcagg tccccccaccc catctttgtc ttcctcctcc
60061   ttggggccga gctgccctgc ttacccagcg gatgagcgtg gcgtaggtga aggggggtcg
60121   catgttgtgg aacttgaagt agtccatgtt gtggaggaac tctgtcagag ggtggggatg
60181   aatcaagccc catgcaggac ctcctagcta gctccctgtc cctcccccct acaaggtgag
60241   tctacaggcc tgagatctca ccgtcaacac ccgtgtccac gggcacaggt actgtttgct
60301   gagcacctga cataagttgt atcatttatt ctttgcacca cttctgccaa aatagttctc
60361   cccgaggttg aaaagaagcg gagtaacttg cacaccaaag gatgcaagag gttaaatggc
60421   agagccagga tgacagtcaa ggtctctgat ccctgctaag cccacaggcc aggcctggtg
60481   gagagcagtg gataggtgag ctcgggcgaa tccaccccga ttttccttgg tcaggggagg
60541   aaaggaggtg ctcctggaat tacttagcag ggtccctccc ttctgatggc cgaatatagt
60601   agctggagtc cagagtgggt gaggcatggc cccaatcccc aagggagtca gggctagggg
60661   cccgacactc gagaccatat ggggggcttt caggccacgg acatcccgaa aggaagcttt
60721   tgtgagcgga tgcatttttcc caaaggctga gtggcggcag ctgcagtggt ggtggtggtg
```

-continued

```
60781  ggaaggggca gcatggagct cctttgcacc ctccacccag agcctgtcag gattaggagc
60841  ttgggggcac cgtgtagtgc aaggaccatt cttacctggg aatgtgctgt ttccatggct
60901  accccacagg tgcctccgga cagcaaacag gctgtcaggg gcctcccggg ggccagacca
60961  ggctgggacg acagggcctt ggctgccagc agctacgatg cagcaggagc ccttgtcgga
61021  tgatgcctgg gtgagggggga gaggctggtg acccagaggc ttaaacttcc cacttttttac
61081  tttctatttt atgttttttta tttttttttga tactgagtct tgctctgtcg cccaggctgg
61141  agtgcagtgg tgcaatctcg gctcactgca accccacct cccagattca agcaagtctt
61201  ctgcctcagc ctcccgagta gctgggacta caggtgcccg tcactacgcc cagctaattt
61261  ttgtattttt ggtagagatg gggtttcacc atgttagcca ggctggtctc gaactcctga
61321  cctcatgtga tccacccgct tcagcctccc aaagtgctgg gattacaggc atgagccact
61381  gcgcctggct ccactttatt tttaaatcag tgttttcaa agcaaggacg ccctcttcta
61441  aattccagtc tgaggtggaa tcccacaaaa cagcatgagc cgtatttatt agagcacagg
61501  tgcggatgtc gtatgtggcc actgatgctg ggaccatgaa ctggggttga atagggctct
61561  ttaccaccca actgtgacct tgggaaagtc acctaaaccc ccctggcctc aatattcctc
61621  atctgtacat tcgcatcatg agaaataaat taccaccagc aaagcgctca gaaacagtgc
61681  ctggcctcca gggctggctt catgggcgtg tgacctatgt ggttatgtgg caccctgtgc
61741  tttgtttaat gctctgtggt cgccatcttg aaatctgaac aagggccct gcaggttaca
61801  tagctggtcc tgctggcaca cagcctgcat ctggcaagtc tggctatttg catttgcttt
61861  aacaactcag gatcacagtg tttggggatc ttagagtcag aggtttttt ttttttttt
61921  ttcttgagac ggagtcttga tctgtcgcct aggctggagt gcagtggtat gatctcagct
61981  cactgcaaac tccgcctccc aggttcaagc aattctctgc ctcagcctcc caagtagttg
62041  ggactacaga cacctgccac cacgcctggc taattttttg tactttttagt agacacaggg
62101  tttcaccatc ttggcgaggc tggtcttgaa ctcctgacct cgtgatccac ccgcctcggc
62161  ctcccaaagt gctgggatta caggcgtgag ccaccacgcc cagccggggt cagagggttt
62221  gtaagtagaa ggggacagat ttccaggtct gggcatgttt ggagctgggg acaggggccc
62281  ctagctctca ggacctgaat gtgaggttag gttccctgca ccgtgcagac ctcctccctg
62341  cccccccagca gtctgagtct gccaccacca gtcctggggt cgctcaccac agatgaagcc
62401  ttggtcagtg ccattttccc agccaggtgg gcctgcatgg cactcagctt ctccttctcc
62461  agcaccagct gtgaaatggc acaaacatga ggcctcagcc tggcccttct ctgccacatc
62521  tttgcccagg ctacggtctt ccctgggagt gcccgctcct cttccttcct ttataccagc
62581  cctcgtccca ggtgaacttg gtttctggca catggtggac agaaggtttt gcgcactatc
62641  cctatccctt accctccacc gccctggcat tacctgctgc tccagagact gtaccatctc
62701  tctctggagg agacattgtg ccctgccctt tcatccaga agatggtccg cctggcagtg
62761  cctaagtagg gagaagattc catgcaggtg accacgacag gcctggtctg gctcaatgct
62821  ctgaatgggg agggcccaga ccctctggga gttctctcct ctgagcccca gctcccctcc
62881  cctctctacc tcagtctccc tctcacaccc ctcgttccct taacacatgc ccctcagcac
62941  ctactgcatg tcaggcctga actcaccact tgagcctggc cagagtgctg agataatgt
63001  tggaagtgtg gtgagttgag aatgggccag ggaggtgaga gtgggcaaag cattctgggt
63061  ggagggacgg cctgtgcaaa ggcctggctg caaggaggac aggacatgtg gggttgctgc
63121  taagggttgt gtgtagtgtg gtgtgtattt gtgtgtgtgt gtgtgtgaga gagagagaaa
```

-continued

```
63181  gagagagaga gagagagaga gagagagaga gagagagaga gagagagaga catatgggggg
63241  gactgagggg aggcagcagc agccatctag aggagctaga actttgggaa cagtggaata
63301  aggctggcat gttggcatga ggagtagcag ggcaaagcag gagtgcagat tctagagcct
63361  ggctacatgg gttcaaatcc cagctctgtc actcaggaac tgggagattt tgatcaagac
63421  acttaacctc tttggcctca gtctccttgt ctgtaaaatg ggggtaaata acagcacaaa
63481  cgtttcttat tatacatacg agaaaactga ggtcgagaga agctaagtaa tttgtccaag
63541  gtcacacagc cagtcaggga tggagctggg atttgaaccc acagtctcag agtttagctc
63601  ttgcatctta ctacttattg ggatgaagcc tgagctgaga tctgcaccct agacctctcc
63661  ccacaagcca gggccggtag actggcacag gcctgggcca ctcacttgag gaagtcctct
63721  ggctcttcga agaccttctc acatccgggc cacttgcaga caccatttgc cagcagtggg
63781  taggagctct ggggcacagc cgaaagggtg ctgggggggac agagggtgtc agggagggg
63841  ataggagggc gaggatcctt cccagccctg tccactgacc tgtccttcct gggtgcactg
63901  ggatttggga aggtgcagag cagtgccggc tccctggaca cccattccag gctggccacg
63961  ttgatccctg tgggtgggga cagggcacct atggaggctg tgggctgggc tctggagctt
64021  ggcccacaag gcctctcatt ttgagcttcc caccctcctg agcctcgaaa accctgactc
64081  ccagggggct ctgctgtccc caaagtccca ggcttctggc agagaagctt aaagacggcc
64141  attcgcaggt gctgacattt tgactagctt tgtaaagctc tgtggttttg tgattttgac
64201  attctgcatc tttaaggttc tgcacctgac gttttttgga gggtggagtt ccaagcctc
64261  tgagacctga caccttgac ccccagagta ctgcaattca gaatagccta cactgctcac
64321  agccaaggat ctggggactt ggggggttctg tgaagccatg gggtacgggc tgaggtgtta
64381  ccaggtggga ggccaggccg ggccttgagg gagaagaccc cagtggcggt ggtgggtggt
64441  gtgaggctga tcatggctgg gctctccagg gggtgcacct gcagcacagg ggtccgggcg
64501  tgggcatcca ccgttgagag ctgggggggca catgtgggct gtggttcagc ctgactcggg
64561  gcccctcccc acagttctcc cacctgctcc ctcctccctg cccattcacc gtccatacct
64621  ggtgcatgaa atgtggcctg tcctggagga gtgcctgtaa gtggggcaag gggcccagcc
64681  gtgccccgga gggtgccacc atgactaggg gcagtgtggg cagctgggca gaaaggcagg
64741  tgggtgagag gccatcctga tcctcactgt tctgtgtcta attcaaatac tctgcactgc
64801  aagcccacat ggtagatgct atgatcatcc cccttttaca cgtatggaaa ctgaggctca
64861  tggagatcga gtaacttttt aaagatcaaa cagctaataa gttgcagagc tggcctcagc
64921  cctgtcacct cacctacttg gccccagtcc tcttctcttg tcacatgggg atggggacac
64981  atagctatgc tcatgggact acaaatacggc ctcctcctct cctgagacag ggattgggag
65041  gtcggggaga gcctccaatc tctgaggcct ggcaggtggg gatttttcttg gccctgcaac
65101  atctgcataa gtcacagact tgcctgggac ccagaaacca cttcctgtgc cccagccagc
65161  cccccctcccg cccagtgcca cagtaaaggt cggcacctgt aggtccaggt accccaccct
65221  gcctgcccca tcctgggccc agggcctcac ctgcagctgc gatggtggca tggggttcaa
65281  ggaagaagag gaggcatggg ccccgcctcg aagatctcgg ccctggaagg ttccccctgg
65341  gccccgggcc cccagcaggt ctgaggcttt gggtgcagcc ctccagctgg cgaggctcc
65401  tggggatggg ccaagggcca aggaaggggc cgagggcttg ccaggcctgg ggttgggcat
65461  cgggtccttg tccaagggca ggctgcgtag acaataggg aaaggagtca cacgtgtgct
65521  agggcggtat gagatactcg accacctgag ccacgtggac actcctctgg tcaaagcagg
```

```
65581  cattggctgg gacatgtccc gagggggccc atagttgcac cccagctcta gacacacaca
65641  cacacacaca cacacacaca caccaagaac acaggtacat gtacataccc acacatgccc
65701  cacgtgcaga ggtccagcac ctggcttgcc tgcccacgct agcacagccc tggtgtggat
65761  gtgtcctcta tgagggcaat ggttgtttcc ccctccactt gagagctgtt tcaagcctca
65821  ggcctctagc cctccctgca ccctgcacag gctgtgtttg ctcatcttgc cggagctggt
65881  ctcggacttt ctcctcggag tcctattttg ccccagtgac taggcatgga ctcaaaagat
65941  tcatctggct gctgtgagtg gggctagtga ggaggctatt gtaacagtcc tggcaagtga
66001  tgatgctggc acagaatggg ctggtggcag tggagaaggc gagaagtggg tagattctga
66061  gacttaatct gaagctggat caggagcagt gctagcagct tggatgtagt gggcaagagg
66121  gagagtcaaa gtgacatggg ttttagcttg agcagctgga aggaccgagc tgacattacc
66181  tgagatgggg gacatggcgg ggagttggat tgggtgcaaa agtgcaggtg tagatagaca
66241  tgaagagtct ggcattaaat atgtgagtgg aggagctgag ggggcagctg aatacggggg
66301  tctggatctc agggcaagga ggcgagtcca ggagtgtgat catgcacgga tccagcatgg
66361  caagtgacag agaggaggag agatgggggtc tcttgagctg gggcctgtag aagcttctct
66421  acccagcccc catcagagtt cacccccaatt tctggccctc aagcctggct catgctacac
66481  cccctgcctc aaatgcccac tccttctcct ctttccctgt ccaagccacg caagacctgc
66541  tcttctattg tcctcacctt gaaagccctc acaatggct ccgggccccc tgctgagccc
66601  cagaaccttc cactccctga gggaagcact ggcttttcag gatcctataa tcctggtctg
66661  agaggaagcc agagctgaa gggactgccc agccaacccc attatacaga aggggatgct
66721  cagatgccga gttccgtagt cccatagtga cttgagaact ccacttcttt ctttaggaag
66781  tgtttccgtg tgcacatttt ataaactctc tggtgtgtgt gtgtgtgtgt ctccatctcc
66841  ccgttccacc tcacagcact gagttgggca cacagctgct gagagcagcc cggggagta
66901  tagaagggtt ctgggggagc agttgctcct tcctttcttt gctgtcacct cctgggggtg
66961  gttgtcagag ctgtggtgct gagggagatg agtgtgagaa tccaggtatt aagttcttag
67021  tctcctgggg gcttagaaca ttactgcgtg agaaacagga gtgtgggtct gtggaggctc
67081  cgaacaaggg cctgggagag cactggtgag atgagaaggt gagtgaatga atgaagccag
67141  agatggggtg atgctccttc aagccaagaa ataacaaaga ttgccagcaa ccaccagaag
67201  ctgggggaga ggcctggagc agcttctccc ttatggcccc cagaaggaac caaccctggc
67261  aacaccttga tcttggactc tggcctccag aactgtgaga tgatcaattt ctgttgctga
67321  agccactcag ttgtggtact ttgttatagc agccagaaca aactaatacc gatttcggtg
67381  caaatggatg ttttccacca ctctggcctg gcccatgtgg ctggcctgtg gtcacttctg
67441  aagctgcctg gacacttggc cagagctaag aattctcccc aaacacatgt gggatggcct
67501  gactcagcaa agcatagata cattctcaga cagggacatg gagatgatct gtctggggt
67561  agaggaccta gagggccggg ctgggcagcc ggcttcctgc actgtctgtt gggacgtccc
67621  tttctgactg ggtttctcag aagctgaatg ggggatgttt ctgggacaca gattatgttt
67681  tcatatcggg gtctgcatct gggccctgtt gtcacagccc ccgacttgcc cagatttttc
67741  cgccattgac gtcatggcgg ccggatgcgc cgggcttcat cgacaccacg gaggaagaga
67801  agagggcaga taccccaccc cacaggtttc gttccgagaa ctggctgccc tgtcctgcag
67861  caggcttggc ccaggtgggg tgacatgggt gctggtggat gtggtaggtg atgtccatct
67921  ggccactatg acaagcccct agctctgaag acctggccct tcttgggttg tggagaggac
```

```
-continued
67981  ccaggtttga agctctgaga gtgccaggca ggctccacag atactgggac ccctggggtc
68041  ttcaaata9t ataacaccag gacctcagaa tcatagaaca gcatttctta gatttaaagg
68101  atcctagaat ctcaaaacca cagactgtgg ggtctacggt cccaaagtct cagtatgtgt
68161  aggccagtgt ccctggtgtc caaactcctt ggaaccatct gaaagtcagg cagcttgctg
68221  cttcataggg cctcttgcct accaggcctg gaaacacagc cagcctccct agggcctcag
68281  tctccctgtc cactctggaa caacgttccc aaatacatgg ccactccgcc agagatggca
68341  acaggggag gaggaggttg aggctggtgt gcctttggtc tgggcctcat gggggagct
68401  ggaaaagcct cagccttcgc caatacagag cccatcatca gactctctag aggggcccca
68461  caatcaaggt tttcggggac cagcaccagc tctggggaca cacagcctga ctgactgaca
68521  tgcctccatc atcaccacgc tctggccaac taggcctcct gacctatgga gtccggggcc
68581  tcacctagcc cagctcttgt gaggctgggc cccacactgt gatcgtggat cgtccaacct
68641  gtgggaagtt ggggtccaac gtgtgagaag gcagaagggg gaatggtagc ccaggttccc
68701  cttccccctt ctgggtgctg aggggtaaac tgaggccttc agttggggag agagccagaa
68761  ccagggtccc acctagagtc ctgagatcta ggcttggatt tcaactctgc cgctgcattt
68821  cggtgaggcc ctgagatctc tggtcttcaa tttgcccttc tacactgagc acggagaggc
68881  gtggagtaga caagggccag ggccttcta cgctgtctgg ttaagtcatt aggtgtctgc
68941  agggcttcaa gttgacaatt gcccctctat ccaggggact ggctgagaga tagggataca
69001  tagagacaaa gagacacaca caaagagcga gcaagagaga acaagagata gtgagagaca
69061  ttgagagaaa tggacacatg catggagagc cagagtgcat gtgtgcgaga ggaggattgc
69121  ctcaaataag aacatttgct ggtctctggc tggttcaact gatgctgcct gaaataatca
69181  agaataaaga agggcaaggt gccaggggaca cccatggctg ggtattgaat tgtattgcaa
69241  agcaacaatc agcaaaacag tgtggccctg gtataagaac agatactggg gaagagaaca
69301  gaatagaaag cttggacatg gacccacata tggagagaac tgaatttgtg atgaatgtgg
69361  catttcaaac tggaggacca tggagtatgg tttaacaaat gtgtctgaga taattaggga
69421  gaagataaag ttattgagtg aatagtcagt ccattatccc aacaacccct ccctgcccag
69481  tttgaaatgt caccatcatc atataccccta aaatgcccag atccattcaa gatataagtt
69541  ttaacaccta atgctgatct tgggtttatt gtgtgtcagg ccttgtgcta agtatttact
69601  gtggttaaaa atttttaatct aaacaaagac tcctgaggaa ggtactatta taaccattgc
69661  agtacatatg aggaaatgga ggtatggaga ggttaagtgc ctggctaaaa atcacacata
69721  gggcttgggg tgacgctggg tttgtcccag acagtctggc tccagtaccc acactcttaa
69781  cctctatagt aaatggaaaa aatgaagcca taaagagac tagaagccaa cataggtgaa
69841  catttatctc attttcaagt aggaaaggac tttctaagca caaaaccaga gacagaagcc
69901  acagaaaaaa agactaacct atttgactgt ataaaccat cataagcatc acaaaaaaca
69961  ccataaacaa atagaaaaaa agcaaatgat gaattgggga aaatatttgc tatatatgta
70021  atggctgatg aaaggttaat aaccattcca aataaagagc tgtggcaaat caataaggga
70081  aaaataagat gaacaccccta ttaggagtaa ggacatgacc agacaaccaa aaaaaaaaaa
70141  aaaaaaagc atgaatggcc aatgaatagt aaaagtaatc acaagatgca aatttcaaca
70201  atgtgataat gtgttttct tacctgtcat gttgggaaat aattaaaaca taataatact
70261  cacctagggt tagcttaagt agagggagca taaaatagga caaccttttg gaaggagaat
70321  tagcagagag ggtcataaac tttaaaaatg cacgccccct ttgccccagc aactcccttt
```

-continued

```
70381  tcaggaatcc aaggaagcag tcagggatgt ttatagaaaa aaacgagaaa caaccggaat
70441  gtccaacaat cggcacttgg tcaaatcaat caaagttcat gctgatgtga ggacagtctt
70501  gtccatcatg aaagatcatg tgttcaaaca atttttagta agcttcaaaa acactactgt
70561  taattgaata aagcaggaac aaaaccaata tatagcatga ttctaatttg gttacagaaa
70621  tactaatagc taacacttcg tgagcactta ctttgtgcca aacgctgtgc taagcctgca
70681  gaatcgagct caccccagcc ctgaacaacc tgtttgcttc ctgaatatgg actctggtca
70741  cacacatgca gtcctggggt aggtccacac agctaaacta cggttgacaa tggtgtgaag
70801  tgctccctgc cccccgccc caagggtctc ctctaaagcg atacaagcaa agttcagtta
70861  agtgctcagc ttgccccggc accttgcaat cctcctgcta ctagggtgaa cagaactgat
70921  gctcactctc ataaaatgta aaggtcctcg gcgacattac tattattaaa cgccagctgt
70981  gtacaaagct ctaggctgga tgctggctgg gaaggcaggt gggggaaggc aagaaaagag
71041  agcgggagag atggaggaaa ggagatcgat ggagtgtggt caagatggag gagacagaga
71101  taggggagat ggtcagaggc caggagagat gcgggaaag agagtctgag tgtagcgaca
71161  gacagatggc gggagaaaga gaggcagaga aacatgtaaa agagcaagac agggtgagca
71221  gagagacaga gaaggatgag aggcatcaag agctaagaga caaagagatg agagagatgc
71281  agttgaaatt ttcagttgca cctggacagc atttcaagtt gttcaaagct ctgaaatcca
71341  taaagactgg cagctgacat atttttaaaaa tcctatccat ctacgtatca attgatgaat
71401  tcatttattt ttgccccctgc ccatgcatta agtacttcac ctttaagtct tctgccattt
71461  attctattat tattttttta aagaccttac ctggctggaa tcacggtagc tgggtacatc
71521  ccactgtacc agagggcccc tgacccccc gccgtgccta cctccctgcc atctcctcca
71581  atggggccca catctggtag gggagagcag ggacactcac cttggtgaag tggactgaca
71641  gaaaaggatc agcctggctt gtgggaaact gtcacgtatc aaaaacaact ttgcttttat
71701  accgagaaga aaaaccacgc tgtacggtgt ggaagccgca gacctctctc ttctaataat
71761  ccaaattttt ttcgatgagt gtgtgcgctg ataatcacgg ggtgggggg ggttctcata
71821  gttttttttt tctctctctc tgtgtttctc cttttcttga ttatgagact taaacggaaa
71881  ttttgaaatt ttgggttttt ttctttgccc tttacgagtc atctgaaaat atgatttctt
71941  cccctcacca cagaggtgag aggtatcaat gagataatag ggctcatgag aaaccacagt
72001  ttttaaaaca aaagtgtata gagtttgaaa aaaaaaaaac aagggaaaag aactaaaata
72061  aatcacaggg ccaacccgag gcaggcagag acaccattct gtgagtgaga ggatatttga
72121  gggtctctgg ggaaagaaag agaatctgaa gctctatgtg tggatgggaa atgccaggga
72181  aagagacaga atagggctgg gttcccagag gcctcgccct actccaggcc tcagtttccc
72241  tatagatgga attgatatgg tccccattgc ttgaactacc cggcgagggg agttctgcac
72301  cccctgcaac acccctccca cagagggtga ggggcatgta agttacttca tggaggagaa
72361  agcggagagc ccactgtcat cccctaaaat tcatggactt gaagagtcgg agaatccctg
72421  gctcccagaa tctactgaca gttactgaat gaggaaagag agaaaagtct cgcctcatca
72481  cgtttagggg cttgagtgcc ctgacccagc cactgtccca ctgggaaggt ccctagcagg
72541  tccccaatat taatgcatcc atcctcacga tgaaccccag aggcccattg ggaccctgac
72601  cctcttgttt caggaacatc atggcctgat gcttctgagg ccctcagcct ttggggtctt
72661  ttacttcaaa aagccccagt ttccaaggat ttaggattcc aaatatccgc catcatctca
72721  gtagctgatg tttatcttga attttccatg ggtcagatac agtgctgaac atgtctcaca
```

```
72781  agtgatcatg ttcaatcctc accatggccc cttgagctcc atctcatcat tattgtattc
72841  ctgttataca gatgagggaa acggaggtat aagtagtcaa gcaacttgcc caagatcaca
72901  gagctggcga gtgtgggtcc cgctttcttt ggtgctgggc tttgaaatcc ccaagctttc
72961  ctgaacttga tgttctcagg ttttaaattc taggatgtga tggcagggag atcctgggat
73021  ttggagagtc cttggagact tgaagcttgt gaggctttta ggttgtccag gaattggcgg
73081  ctgcatctct tgacctcagc aggcactcta ttcaaccact ggtcagcatg gtagaccagc
73141  ccccaggggc ttctcctgac aggccatggt gaagacttcc agctcccagc accctgcaaa
73201  gcccagggtt ctagtcgtcc aacaaccact ccagccctct acaagactgg cttcagacct
73261  ggggaagaga aattggaaag ggcttttat ttacatggta caaatctggt ggccaagatc
73321  cacccctca cccctttgcc ccctttcctc cccaacctt ctaagccctc gtaaaagga
73381  gggcctcttt cctcaactca gactcaccct tctggaaaag cccagaatgg gcctgatggc
73441  ctggctttgt gaagacaaga aaaaaaaaaa aaagaatag aaaaaaaag accttaaaaa
73501  aatcagccaa caacaattaa aaaaaaaaa aaacaccca accctcccca ccattagttc
73561  aaaacaaaac tttcgctggt tgaggcttct gagttggtgg dacacatctg agacccaaaa
73621  atggcttggg tgtgttggac agccagggga ggcaccaagg tgggatgagg tccctgctt
73681  ggaggcctgc agggaccctg tgaacagcag gtgttaaca gatgtcacgg catgtgggag
73741  ggagcaaggg aggggtgag gagcatgcat gtcaggaagg agtcctgggg agctgattct
73801  agtgatggcc ccaaggttaa tgaccccttg cagtgatggt cctaaggtta atgatccctt
73861  gcactgatgt tcccatagtt aataacccct tgctccctgc agacttgggt cggaatgttc
73921  cctacacctc ctgcgtaatt ataaaccagg ccagttctat cagcagaggc attgttccct
73981  gccccagcac ctgtccccct cctggaaaag ggggctagtt ttctctctca ggatcagagg
74041  tgtgggctgc attctcctta taccttcccc agaccatctg tcccttactg tcactcactc
74101  catgaaagag agtggccaga gatataggag gcaaacgaag tgaggatggt ggccgagaat
74161  gtgagctggc cccttgggca ggcccagggt gtgagaggga aatgctacgg ctgctgaaag
74221  ccaagatcct tgcagaatgg gggctgggt caggagggca gagagggta gaggtcgcta
74281  cctcccctct atactggact atatcctctc tcatggaggg cttctcggga aggagactgg
74341  gagggctggg agttggggt gagtaggcaa gattaaacgg gtcaggaaaa gtccccagag
74401  acagggccct ctgacaaaga cttgaaggag atgagggagg gagccagcta gatatctgag
74461  gaactccaaa ggaaacagcc agggcaaagg tcctgaggtg ggaatgtacc tgatttgttc
74521  aaggtctaca aggggctgg tgtggttagt gtggagagag caagaagaga agctggaggt
74581  gaggtcagaa aggggactcg gaggttagac cacgcaggac cttgtaggcc atggtaagga
74641  ctttggcttc aacgctgagt gaggaggaag gcatgacagg gttgcaagca gaggagaaac
74701  acaaaccgtg ttaggattta acaggaagcc cctgaatgct gagtgtacaa tggggtctag
74761  ggcctgaatg tggaagcagg ggaccagcaa ggagctggct actgcagtag tctaggtgac
74821  tggtgatagt gctggcagtg gaggtggtga gaagaggatg gatttggtaa atattttaa
74881  tagacagcca aaaggatttg ttgaagactg agagtcttgg agccagatcg ggacagacaa
74941  tgcccaaacc aggtgggcag gaaggagtcc ctggactatt tgccagcttg aacttttagg
75001  tgagaaaaaa ataaagttct gtcttgctta agcccccatt attttatgat ttttctgtta
75061  cttgcagctg aacatattca tttctaactc atggacatcc tgaacatgga gacctgggga
75121  gaggggctgc tggaaggatc acctccctcc taggatgctg tgaggttcta atgagataac
```

```
75181  agcatgctca gaacctggca ctcagtaggt gttcagtaaa tcttcccagg atggagaagg
75241  aatgtatgaa tggatgtgtt cagcggacaa aagctgcagt tgagttccca cagaaggtga
75301  gaccccaaag ggagagcgaa aggagtttac tagatggaag cagcagaagg aacagcactc
75361  ttgggagagg gaacagtaga agcagagatg gggggacaga agaagggag gtgaggcccc
75421  tgtggggtgt ggagtgtcag gttgggcaag aaggacaggg ctttgattgt gattccatta
75481  gtcagaagct acccatatgc ccaatcaact tctggtagca cacagtcagg tcagtgtttg
75541  ctgagctgaa atttaaaaaa gtgaatcctt cagaaagtta aatttcctat tcggccattc
75601  attcaacaat agtatcaagt cctggagagt gcttgcggct aacaatcagg ggcattcttg
75661  gcttgtggca ctgctcaaga aaaggttgta gttgggcagg gaggacccag taagtaacta
75721  actgcaacag gacagtcatt ttcactttcc tagttcacac accaaggtgt ggtctaggcc
75781  ttcaggggct ctgggtattc ctggggcaat ggggagtcac ggagggttag ggagagggta
75841  accccatccc tgagaagcac attttttccta atggctgcct gcgttctatg gttctgctgt
75901  ccggccaccc aatacctcag actctgtcta cacagcgtcc tcctctccag cctccttatt
75961  ggctactcat gcctcccttc acaccaccta cactgccccc gtcggctctg ctttttttccc
76021  catcttgcct ccaagtcctc cctccgtccc gctgcactat ctagcctcgg cattggctca
76081  tcccatacta gtactgtcct ttgaggtctc tacgccttca ccctggctcc ctcattggct
76141  atccgccagc tctcgtcctc gctcccgcct tcagcctcca cctccattgg ctcggctccc
76201  tacacacccg cctcttggtc tcctttagc cttcgtattg gctagctcca ccttggcacc
76261  acccccttcga agccgcagtg cacgctcaca agcctcccca ttggctcgct gcagccattg
76321  tcgtcatccc acgcgtggct ctccattggc tgttctctct ctctagctac cgttccaccg
76381  cctacgcaac ccgcgggatc tcccactttt tgggcctctg cgttcgttcc cggctgccct
76441  catcgcctgt agccattcca cttttcccac cgcccacatg cctctctcgc tcagacttcc
76501  gcattagctg tctgcttctg ttttcttcat catggatttc gcaccacccc cattccggcc
76561  tctccattga ttcctcgatc atcccgcccc ctacaccgcc cactcccggg catccccatt
76621  ggctgcgtgc ttctccggct ctcaattcgc tgtacgtcat ccgtgcatgg ctgcccattg
76681  gccctctgca atacttgtct tcatctcacc gcctatgccc ccgtgagccg tacccctccg
76741  cgctggcctt cccattggct gcccgccct tcaggcctg ccccgcgg tcccgccgcc
76801  ggtgccgtcg gtgccgccgc cgccgccgat atgcgcgta cggcccctgt ggagcccccg
76861  ctgcggcatt ccgcgcccc ctcgccggcc gcgggtgagc cccgcacctc ggtcgaggcg
76921  gcggtggccc cgcggagggt gctgttcgcc gacgaggcct tggggctgcc gctggcgcag
76981  ttgcgccgct accggccgtg gggcgggccc ggggcgggca agatggcggc ggcggccggg
77041  caagatggcg gcggcggcgg cggggccgac gaggacgacg atggcgagga tggggatgaa
77101  ggggaggagg aagaggaggc ttgccccgag ccctcaccgc tgtgcccgt ccccgctggc
77161  gggggtttt acctggtccc cacattttcg ctgccgcccg cgccgggccg tctggagcgc
77221  ttggggcgcg tcatggtgga gctggaggcg ctgctgccgc ctcccggagc ggtccccggg
77281  ggtgccgggg tgtgggtgcc tggggccgc ccgccggtgc tgcgcgggtt ggtacgcgtg
77341  ctgaaccgct ccttcgagaa ggcggtgcac gtgcgggcct cacacgacgg ctgggcttcc
77401  ttttgcgacc acccagcgcg ctacgtcccg cgcagcccgc cgtgggcagg agcgggagga
77461  acaggagcag gagatcccat cctggatccg gggctcggcc tgggtcccgg ccaggcatcc
77521  gcctcctcgc ccgacgacgg cggccgcacc gaccgctttg ccttccagct gccctttgct
```

-continued

```
77581  gagggcgcgg gcgatggggc gcgcctcgac ttcgtggtgc gctatgagac ccctgagggc
77641  actttctggg ccaacaacca cggccgcaac tacacagtcc tgctccggat cgcacccgct
77701  cccacaccca ctgatgccga agggctgccc cagcagcagc agctgccgca gctggagcca
77761  cagcccgagt gccagggtcc cgtggaggct gaggccaggc agctgaagag ctgcatgaag
77821  ccggtgaggc gcaggtaatg tcagccagcg ccacctccgc caacgcaggg ctgtgtctgg
77881  gatggaggac aagcattccg gcccaggaac ccctcaggcc tgctctccag gacagggagg
77941  agggtgcatt gagtcagtca gtcaaagagt gatggaggtc aaacacgtgc taggcactgt
78001  tttaactggg gttttattcc tccatttatt gagttccact gtaaagccct gaacaagaca
78061  gacatctacc ctaccctcaa ggattcatac aggctcctat gggagacagt ttgaaaaaac
78121  aagcaagcaa gcagatagga taaataggga caaagttagc tgctgaaggg agtaaggga
78181  tagattggga gggaatgact gtgtcagaca tgctgttaaa gggagggcct ttgaggaggt
78241  gagtcccgaa tgatgataaa aagagttat gcagatacgg tggggaggtg ggggagagtt
78301  tgtaggaaaa ggaacaggga ggacttttct gaggaggttt catttaaact aagtcctgga
78361  tgatgaataa cagttatgtg catatatgga acaagggtgt tctaggtaga ggaaacagca
78421  agtgcaaagt cctggggtgg aaatgagctt ggtgtgaatg atcagcagtg tgctggagtg
78481  gagagaactg caatgacata gtgtggacca agggctttgc cagtgggggg tagagcagat
78541  tctctttctg acagagcagg aaaccaggat tccagaggtg gagaaactgg ttgaggcagt
78601  gatggcacct ggctcttcca gttcacccat gcctgacctt gaagcctgtg cactctactg
78661  ttaacgctgt aatctacttt tgagtcctgt ggaggcgagg ggctgagccc atgctctcac
78721  aagaaagcag tggctctagc agagagacag aaccagatgg gtactggact tgaagttttt
78781  gtcccttgtt tttttgccac accacctgtg atcatttagg gacagggaga ataatcagt
78841  tataccccag ggggccccag aagatttccc taggtttcct ctatcaagct atgagttctt
78901  taagggcagc agctagtcct gattcttttt gcggtcacct aagtctggcc caggatcact
78961  agattctccc taaaatgtat acatttccct gttcctggga ggactgggaa tggaaatggg
79021  aaaatgcttt ttggaccttg tatgtatacg cttggtcaga agcccctggc tgcagtaaga
79081  catttgtggg ttctgctggt tctggtaagg ccttaggctg tgagtggttc agaaaggtct
79141  agctccggtc tggtgggcag atgtgcctgg gtaactgagc aggcaggcag gtacccactc
79201  acccacctgt gagccccacc ataatctgag acttcattta aaggggcag gcagcatggt
79261  tttcttaca gcattaagag tgtggattct ggcatagatt gcctgggttc aaatcctggc
79321  gctgccactt actggccttg tgaccttggc caacgcattt aactacacca tgcctcagga
79381  ccctcacctg taaaacagaa ttatagcatc tactttacgg gataagagta aaggtgctca
79441  gaaccgagtc tggctcaaag tagtatcata caggtgttag ctagtgtcag tatttaggga
79501  gccacaccta cagtttcctg gattcctctc ctaaattcgg ctccgcccat cagctgtgtg
79561  gccttgcctc cgtttccttc tctgctaagg gaaatgacag tcactttgca tggttggatt
79621  gaatgcagca acatgggca aggtaactga agcatggtgg taactgcaaa agataactgg
79681  ccagcattta ctgatttctg tgctatgaac atcagatcca ttctctccgt gaggcctgct
79741  gtgcatgctg tgttgtgtag gtgctatgat tatccccatt tagtagaggg gagacaggta
79801  gctcagagag atgagccagc ttgctcaaag cctctcagct agtgagtgac agggccaggg
79861  aagaaatgct agggacattt attttttct atttttttt ttttaaactg gtcctctaga
79921  aagcgtggca tgattcaggg caaattctgg atttcactct tggtgttccc agcatgtcgt
```

```
79981  gctttccttt taccttttt tttttttttg cttatcgag gtatacctac ataaagtgta
80041  ctgatattct gtgtatagcc cagtggattt gtacatatgt atgcacttgt gtagccacca
80101  cccagatgaa gatactgagc aggtccagta ccccagagct accttcattt ctatcacttt
80161  cccaagctgt catccccgcc ggctgtcatg ggaaccctgt ctgtaagatg cgacagtttg
80221  ggtaaaggag tttggtcatt ttaaagagtg tgaaaggcag agaacagaga aatcaaaacc
80281  ttgcagggcc aaggtgggtg gagagggtgt ttttcttta acatacatgg gcggttttaa
80341  ggagaaattg aagcagcctg ttcagacaat tgttttggta tctggcccca ggtctgtggt
80401  tcctaacatg acttgtgata ttattttaag tgggcagatg gcttttttgat agcttcttta
80461  tctttcgatc tcagctcttg caaaggggag gttggtgctc attgcaagat cagcgataag
80521  ggtttctttg taggtcggtg gctttcttgg tgagtacatt tcaacatatt attgttttag
80581  aacctgtgtg ctgccagtga cttgcagcac tgttgaagac tagccaccct ttgtgaccta
80641  gccctcttgg gaaatggcgg aggatctcag ggtatatccc ttacctgtgg gagccctatc
80701  agagggcttc ctgttgagga aatgttggct gtaggccctc tgtgcactga gcacagccac
80761  atcaggtgag ggcatgggag aagtccgtgg tagccatcag gatagagttc agaaacccaa
80821  atggctgctt tccctgggtt gctggaccag gcatttggta actctaaagc ttagagatga
80881  ttcatcgaca agcatttatt gactgcctac tgtgtgctgg gcacagtgct aggttccagc
80941  agggaaagag atgcagagtg gtcctaagat gtcacagggc ttgtgggatg gagtacagag
81001  gatttgttgt atgagacctg gctgagcccc tgctcttcgc caggcacttc actgagtact
81061  atattttcat gcaaggtctg gtttaattcc gacaacattc cctgtgaagt agagggtttt
81121  aaatttctct ttcctggatg agcaaactga ggctcccaga gtccaaagtc ctagggctgg
81181  tgtggggaaa agccctcctg atcttccttg gcacttgaca ctacccttg gaagtgtcct
81241  attcttctta aaagtaaaga ccaagagagc ctcaccatgg tcttcaagca ccctcccatc
81301  ccattcccca atctggcctc cactggctca tagtcttaac accagtggtc tttctgagct
81361  cctgtcacca tggtctttct gttactccaa agggcctcgc tcctttctgc tgcagggcct
81421  ttgcccctgc tgtttccttc accaggaaca tttatcccgt accccttgca gtctcctcca
81481  gtgttgatcc ctcagttcta agaggacttc cccaggggag cctgtccacc ccagtgtcct
81541  cgggcccctg gcttttttcat agcactcatc agcccagcac gtgctaagct ttgttagaga
81601  atgtcccatg gcagagcaga tgaacatcgc caccagtcga ggggtcatcg gccaccctgc
81661  ctagcagttc tactatattt ttttgatcca ctcgtttctc ctctgaagtg actctttcaa
81721  atgttcttta ccttcagact ttctctcctg cttcaaaaaa caaaacagaa gccataagaa
81781  tggaactccc tataacttgt ggcccccaag tctgcacgct gatttcctc ccctgtgtta
81841  cagatgacga ggagtccctt cttgctcagg ccacttctcc ctcctgtgct ctgggtccca
81901  gtttctgcta cttgctctag aatctgacat catcagtcac ttttctctc ctggcaggtt
81961  ttctgctgcc ctccttgctt gatcctctat tcacctttgc ctgtgccagc atcccttctg
82021  tctccgctga ccccacgttc tctccctcct gcttctggcc agcacctcat caccctcccc
82081  ttcactgctg accctgcag agttgcctgt acttgccttc tgcacttgct cacccccgta
82141  agtgttagcc cccggcatct gccagattct gcaggtggtt ttttagtttt cctcttgaag
82201  tggttgacca ctcctactta aaacactttg tcttccctg ccttgagacc acactctgct
82261  ggttttcctc ttaactctct ggcccttctc tttctcctgg ctcttccctt agcttcatgt
82321  atccaaactc ggcatctcca cttgactgat ggcccaaata attcctcaaa ctcaccttgt
```

```
82381  cggggactgc attcatcacc tctcccacag tgttcccaag cagcctctca ctcccctacc
82441  tccccacttg ctcgttttgc ttttcagcat ccttaagtaa gccctgcctg accctgtaga
82501  ttgggccagg gacccttatt ctagggcatt ctttcctttt ctaaaggcac tgatcgcagt
82561  ttgtagttat atctttatta ggggttgct ggatgactct ctgccccgct agactgtaag
82621  ctccgtgagg ggtagggaca tggtctgctt tcattcacca ctgtattcct gcaggcctgc
82681  cacagtgcct ggcacttagc aggtgctcaa taaatgtttg ttgaaataat gagtttgagt
82741  atttttttaa tgtcttcctc catactgaat tgtaagcttc ctagttgggt ttgctcacca
82801  tggtgtctcc aggatccgtc actggggctg atgcacagga aggcccactg tctttcagtg
82861  cacctataac tgaagggatg gggatccaac ctgctatctg agttggcagc ctcagggaa
82921  accagaataa ctggagttga acgggacaag tcagggcat cttagttttc tgtagagtga
82981  ggaattaatg tgaacgtgat cctcttttat gccacagaaa acttggtagg gcattatggt
83041  taaggacatg ggcctgaggc cacgtgctaa gaagtggca gagctgggat ctgagcctgt
83101  gtggtcctgc tctagtgctc cagctcttag ctactgtacc aggctgggtg atgcatttta
83161  ccagcagggc aacactgggc aagttgcttt cctttcagag cttcagtttc cctcaatgga
83221  aatttggagg gggttactgt taagtgcttt ataggtactt ttcaaatatt tctttgatct
83281  gctgaacaac tcactgatgt aggtattatt atccctcct tagagatgag gtaactgagg
83341  cacagagagg ttaagtaact tgccccaggt cacacagctg ataggtggca gagctggaat
83401  tgttcaaaat tgcatatcct aacccttat tgagttgtga aatcaattta ctgggtttca
83461  acaagcatta aaagaaaaa ggaaatagca taagaaatgc cagtgtatca ccacatgcag
83521  taaaggtaag tattgtttca ctcgaagaac aaccattttt cagttattta tatgtctgtt
83581  tacacgtgtg ggtgtgctgg gttatgatgt agaatggatt tcttactatg gtcgtggcc
83641  aaagaatgaa gtcatggctg ttgaagaagc tcatggcacg agaaactgct ctccctctac
83701  cccactggat cacccgcaag tcccagagtt gaggctgaca cacttgttgg ggaaggcaaa
83761  gcagtgcccc ataacttg gtggctttca cagccaccttc aaaccctgt tcttttcaga
83821  aagcagatgg ctcagggtaa ctgcaattct gagtatcgtg gggcaggttt ctgaagccac
83881  tcatccccc ggaaagtcag cgttatcttc aggttgacta catgggagcc ggggtctgct
83941  gagtttccct ttgggtttca gtgcctgacc cactttgggc tggcaaaatt ctttgaaaac
84001  atgaatgctg ggggtgctcc agaggactcg ggtggtggtg gcaatggcag tctgtgactg
84061  ctctgaaagt ctgctttgct tttctccaca gggcttgtca gcccctcaccc gctcgcttac
84121  tctgtgactg gcgaatcacc tttcttggct ttcttggctg gcctaggccg gggccaacac
84181  cacctctttc caaatcctca ccctctggtc tcctcgggc ctatcagctt ggcagccatt
84241  gtgtttcctg atggccggag gaatttgcac gcccaggaga ctggcgtgca ggcctgagat
84301  ggccccttt agtcgacacc agcttgacta gtgctcacta gcacccaaat gatgcatgtc
84361  caagattttc cagatctgtg tgccctggcc cctatggctc actgcccttg aggggatgcc
84421  acgtggtact tgtggggctg gtgccaaaag aacaggtttc cttcttgaaa acgagcaggc
84481  atactgcagg tacagttttg ttcttaatct tctccctccc cattttctta agaaccctc
84541  ttctctgtta ccgatcagtg agtcagtata catttgtact tgatttctct tactatcctc
84601  atgttgattg aagtcatagc tgcccttgag tttttactgt gaaagacggt tcaaagataa
84661  cttgtttctt tttaagccca caatttcaaa ctctcttcaa agtggagccc tcctggagtg
84721  tttgttacca gcgtggttgt gtagtcagtg agtgtagaga tgcagttcct tgagtttag
```

```
84781  tttttgcatt tgtaaaaagg aagggtgttg ttttgaagga tagatgtgaa ggttttcaaa
84841  tgccttggtg tgtcaatgag aggggcccat ggtggaggag gtgaacaata catgcttgtg
84901  ctttctgctt tcatatctga ctttggagaa cgacttgttt gcttctgtcg atgttgtgga
84961  tcttgggatt ggctcaatgg cgtgacctgc tttttggatg ttctcgccct cctcagccat
85021  ggaaagggtg ctctgggggc tgaaggattg attgtgtatt tgttttcctt tctccttcct
85081  ccaactgaat tgtggagtcc tttacctgct ggctagctga ttcctgagtg ttctccttt
85141  tctgtctcac atctatgact gcagtggctt ttagaagcct gtttgtaata tatgtccgga
85201  ctaggccaga tggaggagaa ggcttgcctg ctactgcgca caggtgggag ggctggcttt
85261  ctgtctgtct gtgggccttc ttgaagaggc ttggtttaga agatcctagg aggaggatgt
85321  tttctgtcat gaaggactat ggtaacaaaa agaagtaagt tagtgcagcc tggcagaaat
85381  tgtgttgaaa caaaagtcca aagacctgga ttttaggacc acggagggga ttggtgtgag
85441  accaagctgg tttgctctga atctctcttt ctcatctgtg atgtgtggga ggtggcagct
85501  gggctcccag agtcacccac cctaggccct gtagtattct gattcaagta cctctggtgg
85561  gatttgtgag tcctagacag tagagaaaga cagacggtcc cttctagact ctagatccgt
85621  atatatggtt caaatgttct ccccgagggt gtttatagaa agcagttctt gcagccattc
85681  tgtgtctagt ggcctcctag ccacgcatgt cccaggccca tggaggtagg gaaatgggga
85741  atgaatatgt gggcaaaggc aggtccaaag aaaagcctgc atgaaggagg agggagggat
85801  cttgtctagt attgatgcct ccctctatct acttctagaa aggatggaga tgggttgggt
85861  aagaccccag tctccctcat ccaagaagca gcagctgact gggtaagagc caaaaggcct
85921  gggttgtgat gtgaagtgta tgaccttgag ccatttactc agcctctgtt ttatcctctg
85981  taaaatggag acaatagtac tgcctgcttc agaggattac aagtacctgt ctcatagggt
86041  gattgtgagg attgaattaa cacatgttgc ccaggcaccg tggctcatgc ctgtagtact
86101  aggacttcgg gaggctgaga tgggaggatc gcttgagtcc aggagttcac gaccagcctg
86161  gtcaacgtag gaagacccca tctctaaaaa caaaatacaa aaaaacaaaa acaaaaacca
86221  aaaaaccccca aaaacttctt taaaaaaatg tgaagcactt agaacagtgt gtaatgccat
86281  agtaggtact atgtatgggt cagatggtga tactcgtttc tgtgaaggta attggttatg
86341  ggttttcaaa aagtttcaac caggccgggc acggtggctc atgcctgtaa ccccagcaca
86401  ttgggaggcc gaggagggtg gatcacctga ggtcaggagt ttgagaccag cctggccaac
86461  atggcgaaac cccgtctcta ttaaaaatac aaaaattagc tggctgtgat ggtgggtacc
86521  tgtaatccct gatacttgag aggctgaggc aggagaatca cttgaacctg ggaggcagag
86581  gttgcagtga gccgagatca tgctattgca ctccagcctg gcgacagaac gagactccat
86641  ctcaaaaaaa aaaatttttc aaccattgtc agaagtatca agaatgtcac attgcctctt
86701  aggaagaaaa aggtgtgggc attcgcccca gctcctctca ggttttagtc aatgcttccc
86761  tcatttacct taatctgtag acacttgata ctcattttca gaataagaac agtgacttct
86821  ccatgatgag atgccacccc tgggaggacc cacctgaaat gcactcggct tatgccactc
86881  agggatctga ctggcctggt gaaggaggag caagacccat aaatatctac agttgattca
86941  atcccagctg tgtgtcaggc cctgatttct ggctgtccat cctcattcct cttgactgcc
87001  ctgtgcttag tgcacatcct gactcccgg ggctctgttt tatgagtgag gaggtgaagc
87061  gacctgccag gctgatacgg ggacgagagg gttagcatag ggacccaggc ctctgtgacc
87121  tccctcccag tctccatttg cattccttcc tctgcctcac agtcttgtct acctgccatt
```

-continued

```
87181  tcttagaaaa ggtgttttg ttttgttttg ttttgttttg tttttgtgag ataatctctc
87241  actctgtcgc ccaggctgga gtgcagtggt gtgatttcgg ctcactgcaa tctctacctc
87301  ttgggttcaa gcgattttcc tgcctcagcc tcccaggtag ttgggattac aggcgcccac
87361  caccacgccc agctaatttt tatattttta gtagagacgg agtttcacca tgttggccag
87421  gctggtcttg aattcctgac ctcaggtgat ccacctgcct cggcctccca aactgttggg
87481  attacagatg tgagccaccg cgtctggccc ttttttttt tttgagactg agtttcactc
87541  ttgtccccta ggctggagtg caatggcgcg atcttggctc actgcaacct ccgcctccca
87601  ggttcaaatg attctcctgc ctcggcctcc caagtagttg ggactatggg cgtgcaccgc
87661  catgcccagc taatttttg tattttagt agagacaggg tttcatcatg ttgcccaggc
87721  tggtcttgaa ctcctaacct caagtggtct ccctgcctcg gcctcccaaa gtgctggaat
87781  tacaggtgta agccaccacg cccagccgaa aagatgggtt cttctatctt ttctctttcc
87841  atagccagga atgtatccta aagaaatgat acaagtgtcg ataaaactat gcccaatgct
87901  gtttgctggt ttgctttgca acctctaaat gaaagaactt agctgctcag taggaaggga
87961  atggtatgat atgagtatta agcagccatt tgaaatgttt gcaaaagtgt ataatgatgt
88021  ttcttactgt taaatggaca aagctagctg tgaaattatg tctgtagaat ctaaatgatt
88081  tcgtagaata tctggaagga aattttccag aatggtaaca gtagttgtct ctggctgatg
88141  tgtgattgtt tttcttgctt ctttagactt tcctgtattt tgcgaatttt ctataatgag
88201  gctgtaggac ttttaggatg aggggataaa caaaggcagc agaagagaaa acagcagctg
88261  tcaggtgaag gtgggctagc acagaggctc agaaggtgcc agtgggtggc agaagtgacc
88321  tctcagggta ttattagatc catgtactct ctcctctgcc ctgcaggcct gccgaggagg
88381  aactgaagac gaagaacatg gatgataaca cctttgccat gggtaagcaa ttggcaagct
88441  tcggaagttt tagcttgtat ttaccatgtc tttcttccta ctgttttct ttctataaaa
88501  atgaaaaagg ctgggctcag tggctcatgc ctgtaatccc agcactttgg gaggctgagg
88561  caggaggatt gcttgaggcc aggagttcga gatgagcctg gcaacatag tgagacctca
88621  tctcttaaaa aaaaaaaaa aagacgggca tgctggcatg catccgtagt ccctgctact
88681  cgggaggctg agctgggagg atcatttgag cctgggaggt tgatgctgca gtgagtcatg
88741  attgtgccac tgcaccccag ccttggtgac acatcgagac cctatctcaa aaaaaaatg
88801  aagggtacc ctctgcttta gattgtcaca gaaagcttca gaggcaaaac tgccagttgg
88861  ctaggatggc agattttctt aacaaaacca tacctacttg tatgcctgtc ttgcccaatg
88921  ctgcctttct cttccctcta gcagagcatc ctgatgtcca ggagtcagtg gtccactgg
88981  tagcccccac ccctctccgt ccatggcccc agatgacact tcaggtaagt gggtccttgc
89041  agccttggag tagacagccc aataggaggc tcacagtgtg actattgctg ggctgggtgg
89101  tgggcccac tagctctggg tcctccctgg gttggaggga gggcacaaaa ctcagaacct
89161  gatgggggag ggggagaatg cagttactca gctgggcttg tagaaatgtc atttgttaat
89221  ttagcaaaaa tttatggagt gcttgttctg tgctaagcac tgttacaaac atgcaaaaac
89281  gctctttgag ggggcttatg tgttagtagg gtgagacatg ataaagtaat agaatatatg
89341  gtactttagg tgatgatgag tgataaggaa aaatagaaag gaatagggag tgggtgagag
89401  actctgtgtg tgtgtgtgtg tgtgtgtgtg tgtgtgtgtg tgtgtgtgtg tgttgtgggc
89461  gggggtcggt tgcaactta gattgggtgg cctgggaagg ctttagtgat tagtgagatc
89521  tgagcgaaga tctgaggaag gtgagagagt gagccacgtg gataactaag ggaagaacat
```

-continued

```
89581  cccaggcgag tgtgaagttc ctgaggtgag gccatgacta acgtgtgtga gggacagtgt
89641  agaagccagc gcagcagggg cagaacgagg gaggggggaga gtggtgcggg gtgagggaga
89701  gaggtggctg aggacagatt gggtggtgcc tcacaggcca tggtgaagac tttggctttt
89761  actccgagtg aggggagcc gcaagagcat tgtggacgga ggagggatgt aatctgattt
89821  aggatttaac aggctccctc tggctgctgc ttggaaaata gacgtcagag taagggtgga
89881  aacaggcgac tcgtgaaggg gaggccactg cagtggtcca ggcgagagtg atggtaggta
89941  ggggaggtag agacattttg gagggtgtgt gtgtgtgtgt gtgtgtgtgt gtgaactttt
90001  taattacaaa aagtttcaaa catacaaaag taaaatagta taatgaacct acgtacacca
90061  tcccccagct tcagtaaata tcaacacgtg ctcattctta ttttatctgt accccgtctc
90121  ctccctccca ttccctctgg aattattttg gaagacatcc agacatcatc ccatccataa
90181  atacttctgt ttgtatctca gaaaattaag aactcttttt tgttttttt tttgagacag
90241  agtctcactc tgtcacctag gctggagtgc agtggtgtga tctcagctta ctgcaacctc
90301  tgcctcctgg gttcaagcaa gtacatccag ctaattttg tattttagt agagacggga
90361  tccgttgcct tggcctccca aagtgctggg attacaggtg tgagccatca cgtctggcca
90421  gaaaattaag aattcttaac cccacaatac tatcatcaca ccttagaaaa taaacggtaa
90481  ttcctcagta tcatcaagta tttggtcagt gttcaagttt tcttctctca taagtgttta
90541  ggatccaaac aaagttgaca tgttgcattt gattgatgtg tctctttaga tttttaaaat
90601  ctcccccact ttgtttcttt gcaatttgtt ggttgaagaa actttgcttg tcctgtagaa
90661  ttttccagtc tgggtctggc tgattacatc caggtggaaa tacatttctt actccatttt
90721  tattaattta ttaattatat taattaatgt aatcttatta aattatttta atttatcaaa
90781  ttgtattaaa cgaatgtatt taatctttta ttattaaatt aactagaatt aactctattt
90841  aattctatta ttcccacttc ctttattagc tagaattctt ctctaaagaa aaactgtccc
90901  acaccagcta tttggctact ttgagatata gtttgtgcag aaaaagcagt gtaaatattt
90961  aatttttcc attttattta ccagtttca gagaagtact actacaaagg tgaccaataa
91021  aaggattttt ggttttgtgt cattatgaac tcatgaattc taaacatatt tgaatgagtt
91081  tcaatccatt gcacttattt gtttgctttt tttgatgctt aaattgaact atccctggct
91141  agtaggagct tattgagatg ggctactctg tccttttgac acgccctcat cattctgtga
91201  gcctttctca catcttccat gacaatatgt gctaggttca tcctgtactc tccctgcccc
91261  aagcctggaa acagccattt cttcttgct tttcttttct ttattttctt tttctttttc
91321  tttctttcct ttccttcct ttctttcctt acctttcctt tctttctttc ctttcctttg
91381  tctctctctt tcttttcttt cttttacttt attttcttt ctttctttc ctctctctct
91441  ctctttcttt cttttttctt tttctttctt tttttttttt ttttttttga gtcagagtct
91501  ttctctgtcg cccaggctgg agtgcagtgg cacaatctcg gttcactgca acctctgcct
91561  tctgggttca agcaattctc ctgtctcagc ctcttgagta gctgggatta caggcacatg
91621  ccaccacacc cggctgattt ttgtattttt gcagagatgg ggtttcacca tgttggccag
91681  gctggtcttg aactcctgac ctgcctggtg atccacctgc cttggcctcc caaagtgctg
91741  ggattacagg cgtgagccac tgagcctggc cagaaacagc tatttcttta aggagcactg
91801  attcctttca gtggagagtg gcattcaaag gccaagattt gggggctcgg catgcttgct
91861  gctactagat tggtcattgt ttctaggccc tttcaaaaga tggagctagg aaataattgt
91921  tttttaaaga gaagatgata catcatgggt tcatatggac atcctggcta tgttttggga
```

```
-continued
91981  tttttttgca  ttttatttttt  tttaaaattt  ttttaattttt  taattttttga  ggggacatag
92041  taagtgtata  tatttatgga  gatgttttga  tataggcatg  cattgtgtaa  taatcacatc
92101  atggagaatg  aggtatgcat  ctcctcaagc  atttatcctg  tgtgttacaa  acaatccact
92161  tacactcttt  attttttttt  tttttgagac  aaagtctctg  tcgcccaggc  tgcagtgcag
92221  tggcacagtc  tcggctcact  gcaatctctg  ccctctgggt  tcaagtgatt  ctcctgcctc
92281  agcctcttga  gattacaggc  gcacaacacc  acgcccagct  aattttttgta  ttttttggtag
92341  agacggggtt  tcaccatgtt  ggccaggctg  gtctcgaact  cctagtttca  tgtgatccgc
92401  ccgccttggc  ttcctaaagt  gcttggatta  caggtgagag  ccactgtgcc  tggctactta
92461  cacttttagt  tattttaact  ggctctgttt  tgaaggtaag  ccagcagtat  ttagtgatga
92521  tcattcacca  aatattcaca  cccaccgaat  tcctcagctt  tataatctgc  aagaagccct
92581  gttttactgc  atccaattgt  gttattttac  catagatgac  agtctttgga  gtctagacag
92641  tgacagaggg  cgctttaagg  catttttata  tagaaacccc  tgtgggggctg  gctgtgggct
92701  gtcacacttc  ttactgtctc  tgcttgttcc  atccctcct   ctgcttcatt  cccttgcttt
92761  ttctctgccc  ccttgccccg  gccatggctc  caggttttctg  acgttccgat  gactggcaac
92821  cccgcagaag  aaggtgatgt  ccccagaagc  agtccacctg  tggcttttac  agaggtcctc
92881  caggcaccgg  ccatcaggat  tccccctcc   tccctctct   gtggcctggg  tggctccccc
92941  agagaccagg  cctcaggggcc  cgatgcgagc  gaggggggcca  ccgggcctttt  cctggagccc
93001  agtcagcagc  aggcagaggc  cacatgggga  gtatcgagtg  agaatggagg  ggggctggag
93061  gctgtgagtg  ggtcagagga  gctgctcggt  gaggacacca  tcgaccagga  gctggagcag
93121  ctctacctgt  ctcacctgag  ccgcctacgg  gctgctgtgg  ctgcgggtgg  ggcaggggggt
93181  ggtggggagg  gctccacaga  tggagggatg  tccccagcc   atccctggg   catactgacg
93241  gaccgcgacc  tgatcttgaa  gtggcctggc  cctgagcggg  ccctgaacag  cgccctggct
93301  gaggagatca  cgctgcacta  tgcccggctg  gggcgtggcg  tggagctcat  caaggacacc
93361  gaagaccctg  atgatgaagg  ggagggtgaa  gaggggctct  ctgtcacacc  ctccagccca
93421  gaagggggaca  gccccaagga  atcgcctcca  gaaatcctct  ccggggcccg  ttctgtggta
93481  gccacgatgg  gagatgtgtg  gctccccatg  ggcagagggc  tcaggatgtg  acggccctgt
93541  ggttctgggt  acagagggtc  agttcattgg  ggatcctgag  aaagggatgg  gcaaggacac
93601  cagctctttg  cacatgaata  gggtgatagc  tggggtgact  gagtccctgg  gggaggccgg
93661  gacagaagcc  cagatagagg  tcaccagtga  gtgggcaggc  agcttggatc  ccatatctgg
93721  caaggagcca  gcctctcccg  tccttctgca  ggggcaaaat  cccacccctcc  tcagtccctt
93781  gggggccgaa  gtctgtctct  ctagtgtagc  caggcctcat  gtgagctccc  aggatgaaaa
93841  ggatgcaggc  ccaagccttg  aaccccaaa   gaagtctccc  accctagcag  tccctgcaga
93901  atgtgtgtgt  gcactgcctc  ctcagctccg  ggggcccttg  acccagactc  tgggggtcct
93961  ggccgggcta  gtggtggtcc  ctgtggctct  gaacagcggt  gtgtccctcc  tggtgcttgc
94021  gctgtgcctc  tctctggctt  ggttctcata  ggctctgctt  gtgggatcag  cagaggctta
94081  agatgggata  catggcctgt  gcagtgaggg  gacctgggtc  ctttgcttct  gagaatgctc
94141  aactgaaaga  gaggccttct  catccccaag  ctctccagtc  aacacagggc  tccctgtggt
94201  gacaccagtg  gagatgaggg  aacgggtaga  tggtgtgagt  gagggggaact  tttagagtgg
94261  aactgggcat  gtcctccgcc  tacccccccga  gcctgtatttt  atttttgtat  aattctctgg
94321  atgagggaga  gtggtcgtga  gctggtcttg  gggcacaatt  acccagagat  atatttatta
```

```
94381  acagccaacc tgtgcaacct gctggagctt tatttttaat ttaatttata tagagtacct
94441  attattatat gccacaatag agctctatga gaaacagtgt cttgcggtgt agtgttctcc
94501  tgtttgggca tgagtgtgca gggtggtcac tttctgtggg aggatcacag tggggagttg
94561  ggggtgggac gtggtcgcct gctgctgctt caacatgtct ttccttgaag atgtgtgtct
94621  cctcgtctcg tggtcctaat ccatatggtt ctttgtcttt tccacattct gcctgtggga
94681  ccctacaggt gtgtatttgg atggtggtgg tgggagccag ggaggaagag tggcagccac
94741  atgagggttt ggtgtcagtc acatggttgc agtggtagct gtggtctcct gtggatgtgg
94801  ggacatcagt tgtgaatcag ccacaaggtt ttgaggttac tgaaaaaaca gcctttgaca
94861  ccagcaggga gacccccttag tccctgagat aaggaaggcc tcagaaagga aagaggagtt
94921  aatgtactgc agtacttggt agcacagttg ctgtccacag acatcacatt tctactaaaa
94981  acaggaagcc cagaagcttt gaaagaaaga tatatattta ttgcatgcaa ataaaaaact
95041  gctcaacaaa ataaaacacc acatatttat ttacttccct ttacagcaaa acctattgga
95101  agaaatatct atacgagctt tcttcagttc ttctatgatg cctttctgaa atagccccaa
95161  tcagatcttt tttgcccaac catttcagca aaactgctga agatattcac attgttatag
95221  ccatggttaa gtctcagatg tcatcttact tgggatattg gcagcatttg acatagttga
95281  tcatctctac cttgcaaccc tttcttcact tggtttccaa gataccacac tctcctcatt
95341  tcccttcttc ctcactggcc actgtgcaaa gctgtcagtt ctcttgaaac tgctttgtag
95401  gttcaatgca aatccaacca caattccaat agagttttgc ctgtgtgtag atcatgacac
95461  attaattctt aaatttatgt agaagtgcca agactagcca ggacactgat acttattgta
95521  atggtatatt cagatggcac gatattttg caagagtaga caaatcgacc aataaaaaaa
95581  cagtgatctc ggaaacagtg tagacacact cgtgtagaca cagaactggt gaccaaggaa
95641  gtgtgttaga ccagtgggga aatgattgga ttttgaataa atagaacaat tggttacccg
95701  cattgaaaaa tatgaacttg gatccctact ttacaacaca aataaaaata attctaagtg
95761  ggtttaaagc ctaaatgcga agggcaaaac caaagcgctt taagaataca atgaggcagg
95821  gccgggtgct gtggctcact cttgtaatcc cagcactttg ggaggtctag atgggcggat
95881  caggagtttg agaccaccag cctggccaac atggtgaaac cccgtctcta ctaaaaatac
95941  aaaaattagc tgggcatcca cctgtagtcc cagctgtttg ggaggctgag gcgggacaat
96001  cgtttgaact caggggggcag aggttgcagt gagccgagat ggcaccactg cactccagcc
96061  tgggccacag atcgagactc catctcaaaa acaaaacaaa acaaaaaaca aggcaaaaca
96121  ccttcgtata ctcatggtag caaagttttt cttcatcacg acacagaaac aaccataaat
96181  gaaaattacg aaacattcag tgaccttaaa attaggaatg tccattgatc aaaagacacc
96241  ataaagagag tgaaaacctt atgtagtagg ttgctatgaa taaaagcaaa acaaaaagga
96301  gtgaaaacac aagtgaaaaa ttgggaggag ataatggaat cacatataac tgatgaaggg
96361  ctcaaacctt agatgccaat aagcatctaa ataaattgtg gtatattcgc agaatggaat
96421  attgtataat gagaatggaa gatccataac tgcacgaaag catacagatg aatcacaaaa
96481  agccaaaaaa aagcttccac actgatccat ttatgcaaag ttcacaagca ggcaaaactc
96541  atgaattacc acctaaatgg tgacattgta agaaaagcg aggggctgat taccagagtc
96601  aggatagtgt tcacctctgg cagggggagg gatgtggctg agaagggggcc cagaggactt
96661  ctgggatgtc aataatggtt cactgcttga cctgggagac tgttcatgga tgtgcaattt
96721  attcatcatc attaaaacag acttatgggc tgggcgcggt ggctcacacc tataatccca
```

```
96781  gcactttggg aggctgaggc aggcatatca cttgaggtca ggagttcgag accagcctgg
96841  ccaatgtggg gaaacccgt ctgtactaaa agtataaaaa ttagccgggc gtggtggtgg
96901  gcgcctgtaa tcccagctac ttgggaggct gaggcgggag aatcactaga acccaggagg
96961  tggaggttgc agtgggccga gatcgcacca ctgcactcta gtctgggcaa cagagcgaga
97021  ctcttgtctc aaaaaaacaa aacaaccccc cccatacatt taggttttat acactcttat
97081  gcaaagacct cacaagtgaa gcagagtgca gtgggaagtg ggagtagcat gagtgtccga
97141  gactcctgca cacaggcttg cagagactcc agcctcctgg tgtgaaccac agtgtaggcg
97201  gcctccttcc tgcagaacaa tccctgggct ccgggtcttg ccttctgttt gtggagatcg
97261  actagtgggg aatcctctat cgtgtgcccc tgacaccagc catagagtgg ggcctcttgg
97321  gatggacagg acctgcccat attgtcctca gatgttgggg tccatctccc ctcaggcctc
97381  attcacaccc acaatagccc aggacacatg ggctttgggg cctggtgggc ctcataaaag
97441  cctggaaccc cgagcctggt tggtgtgacc ttgggcaagt cacccgtcct agaccagcct
97501  cagttcccca ttcataaagg gggctaatgc ccatcaagca gggtaggtgc aggctttggg
97561  gaaaacgttg tactgccctc ctcctgagcc catgttagac aggtcttata gtcaaggcag
97621  ggtaggaggg tggacaggaa caggggctgg agcgacacag tttgggacta aattgcccag
97681  ggtcacacag tgggcaagtg gcttcagccc tctgtgcctc cctttgctcg tctgtcatca
97741  gggtaataac ttttcctcct cacagggtta agtgaggaag aggtgagatg actcttcagt
97801  cactgagcag tgccaggcac agggcaagac tgagtacacg cccgttgtca ttccccctgg
97861  ctggagctct tgcaatcact gttatgcccc caccctgccc ctcccatta atctgttaat
97921  gtggtgaatt acattgataa gtttgtacat ctgtctttta aaattgagac gcaatcttgt
97981  tctgtcaccc aagctggagt gcagtggcac aatcacggct cactgcagcc tcaacctcct
98041  gggttcaagt gatcctccga cctcagcctc ccgagtagct gggactacag gcacatgcca
98101  ccatgcccag ctaattttta tatttttact agagacaggg ttttgccatg ttgcccaggc
98161  tggtctcgag ctcctcagct caagcaatcc acctgcctca gcctcccaaa gttttgggat
98221  tacaggcatg agcacgtcca gcctactttt ctctctctct ctctctctct ctctctctct
98281  ctctctctct ctgtctctct cctttctttc ttgacggagt ctcgctcttt ctcccaggct
98341  ggagtgaagt ggcacattct cagctcactg taacctctgc cccctgggtt caagagattc
98401  tcctgcctca gccttctgag tagctaggat tacaggcatg caccaccatg cccgactagt
98461  ttttgtgttt ttagtagaga cagggtttca ccatgttggc caggctggtc tcgaactcct
98521  gacctcaggt gatccacccg cctcagcctc ccaaagtgct aggattacag gtatgagcca
98581  ccacgactgg ccctactttt cttttttaaa attttagtgg tcagttacta gataaactct
98641  attttatca cccatttaca ggtgagggcc ttccatgttc ttatcagccc tgagctcagc
98701  cctttgccga ggccttcctg gtccacctct ccctcctcct tgtgactagg gccagcatct
98761  tagtctcaca gtggcccctt ctctctctgt cctcagcctt cagccctgct atcacccacc
98821  cgcatcctac aaccctctg cttcccctct tcagtgtttt ttgtccagga tgagaccaag
98881  tccaaacctg agcttcctgc taagtcaaag tgacttttc ctttcagtca gggaagcctg
98941  actaaagcgt ctggtccac ggtgaggtct tggtgtctcc aacagcgcag ccatggacgg
99001  ccaccctaca gtgataccctg cctttgccag caggggggcat cttatctcca agacagggaa
99061  agcctcagag aagacgggaa cagtcttaaa cgttaactgc ttgtagggtc acaggcctca
99121  gggtgcatga gctccaggct gggtgtccct tggagcctcc ctctctgcat gtggacaggt
```

-continued

```
 99181 gggggcagcc gagggcctgg cttttactgt tgttcggggt cttctacaga tgactctcct
 99241 cctcctcctc ttcctctttt tccttctacc aggaactcat ttccatcact aaagagaggt
 99301 tctcatattt ttaatcctct ttatctcact taaagggtcc attataggat ttttccacaa
 99361 gatgcactgg ctctgaggcc tgtgcccagg gcaggtcagg ctatagattg gccaggttgg
 99421 ccaggttggc caggttggct gagggcacca gcctggatcc tgaagacact ggagacagcc
 99481 ccaacagagc ctggggctca ggaaaaggcc accaacccc cagccagatc ctggccagct
 99541 gccagctccg cctccaccca gtcctctccc agggcctgaa cgccgggtct agaagctcca
 99601 ggcctggtgg tctggggggag acacgggccg ggaggatccc tcgaaagagg aggcaggaga
 99661 caatctctgt atggcttgag ggatgcacag ctgtggggtg aggcacgccc cacctagcac
 99721 aggcccactg acactgctgt gcagctgcag gcccagctgc tgccctctat gggctcagt
 99781 ctcctcacct gtgcaatggg catcattaca cccccaacgt gcaggggatg ctcgtgaatg
 99841 gaggggagcc gaggcgttga gaaagtagat ttggctcaag aggaggagga gcaggtcagg
 99901 gttggtgggg aaggatggat gcggccacct caggcatggc cggggctgcc ttcctcaaag
 99961 tgctcaggac agtcaggtgg gggaagttct gagtctgtga gcagaaccgt gggctgggga
100021 ccaggtgagg ttgtctctgt agtgttctgg ggtggccagc cactgtgcca ctattctttc
100081 ctgttggtcc tcatctctgc ccacggggag ccccaagatg ctccaagagc tcacagtgag
100141 ctcatgtgag ttactgtgac ccacatgcag tcattacagc catgtgtcat catcacaaca
100201 gccaccaggt taacacttgg ataatttatc caaataacga ctcacctgat gtgatttgca
100261 tgatatgcca tcatttatta ttatactcct attggatgtt taggtagtgt tcgatttgct
100321 tttttgccac tataaactat ctgtggtgag cattgtttcc catatatgta aacttgggag
100381 agacacagga atgttatat agtaaaacta tttgtaatag caaaatactg gaaacaaccc
100441 aattatacat catcaggaaa tgcataagta aattatgctg tattgacatc atggaatact
100501 acacagctat gagatggagt gaactaaggt acacaaagac acaatgttag gtgaaagaag
100561 ccagatacaa aagaggagat gatatatgct tttcatatat ggctcaaaac caaacaaaac
100621 tagtatttag gcatacatac acctgtgtta aaacagtttt acagaaaaca aggattctgg
100681 ccagtcgcgg tgactcacgt ctgaaacccc agcactttgg gaggccgagg tgggaggatc
100741 acttgagtcc aggagtttga gagcagcctg agcaacatgg agaacccat ctctacaaaa
100801 aatacaaaaa ttagctaggc atggtggcat gcgcccatag tcccagctac tcagaggcgg
100861 aggagggagg atcacttgag cctgggaggc agaggttgca gtgagccaag atcgggccac
100921 tgcactccag cctgggtgaa ggtatgagac cctgtctcaa acaacaaca acaaacaacc
100981 aaacaagcaa acccccacac aaggattttc aactgcttga ttgataccat ttaaaaaatt
101041 tatttaaaaa attgtcacag tagaatttac tttgggggag tttctatgaa ttttaatatg
101101 tgtagattca tgtaaccacc actgtaatta gtattcagaa cagttctatt accctaaaga
101161 actccattgt gcctcccctt agagtcactc cctctcctca cccctcacc cacgcaacac
101221 tccatcacta cattttttt tttttgagat agcggctcac tgcagccttg acctcctggg
101281 ctcaagtgat tctcccacct cagcctcccg agtagatggc actacagaca catgtgccac
101341 cacacccagc taaattttgt atttttttgta gagatggggt ttcgccgtgt tgcccagggg
101401 tctcgaactc cggagctcaa gtgatccgcc aacctcggcc tctcaaagtg ttgggagtac
101461 aggcgtgagc cactgcagct ggtcaggcct ttcaattaca atgttgaata gcaggagtaa
101521 gagtggacat tcttgcctca tttctgatct tagggagaaa gcatttagtt tttctctatt
```

-continued

```
101581  aagtatgatc taagccaggc agggtggctc acgcctgtaa tcccagcact ttgagaggct
101641  gagggggggt ggatcatgag gtcaggagat cgagaccatc ctggctaaca cggtgaaacc
101701  ccgtctctac taaaaataca aaaaattagc caggcgtggt ggcaggcgcc tgtagtccca
101761  gctactcggg aggctgaggc tgagaatggt gtgaactcgg gaggtggagc ttgcagtgag
101821  ctaagatcgt gccactgcac tccagcctgg gcaacagagc gagaatatgt ctcaaaaaaa
101881  aaaaaaaaaa gtatgatcta agctgtaggt tttttttttt ttttggtgga tgctttatat
101941  caggttaaga aagttatctt cttgtttgct aagagttttt tttaagatca tgaatcaatg
102001  ttgaattttg tcagaagctt tttctgcatg acatgatacg attatgtggt tcagttactt
102061  tcgaatgtca gtatggtaga ttgcatttat tgatttttat tttattttat tttaatttgt
102121  tttacttttt tgagacagag tctctctgtc accaaggccg gagtgtggtt gtgctgtatc
102181  agctcactgc aactgcctcc tgggttcaag caattctcgt gtctcagcct cccaagtagc
102241  tgggactata ggtgtgtgtc accacacctg actaattttt gtattttttag tagagatggg
102301  gtttccccat gttggccagg ctcatctcga actcctgggc tcaagcgatc cccccacctc
102361  agcctcccaa agtgctggga ttacaggcat gagccactgc acccggtcac attgattgat
102421  ttttgaatat tgtgtcagtt ttgcatcccc aggataagcc tcacttggtc atggtgtctt
102481  attttttgtat attggatttg aattggtaat attatgttga ggatttttttt ttcatctatg
102541  ttcatgaagg aagttgggct gtacttttcc catactttct tttttttctgg ttttggtatc
102601  agggtaatgc tatttgagaa gtgttcctgt cttattttttt gaagagattt tgtagaattg
102661  gtattatttc ttcttagatg tttgacacaa tttgccagtg aaaccatctg gacctggcaa
102721  ctttatcttc ttcttttttaa aaaagacttt ttttttttta aagagcagtt ttaggtttac
102781  agtaaacctg agaggaaggt acagacatat cccatatacc cctcacctcc acacatgcac
102841  agcctcccca ttatcagcaa ccctcaccag cgtggtgcat ttgttacaat tgatcattat
102901  caccccaatg atacatgagg tatcatattg gcctgaaatt ttctttttttt gttgtgtctc
102961  tgccaggttt tggtatcagg atgatgctgg cctcataaaa tgagttagga aggagtccct
103021  cttttttctat tgtttggaat agtttcagaa gcaatggtac tagcttctct ttgtaactct
103081  ggtagaattt ggctgtgaat ccatctggtc ctgggcttct tttggttggt aggttttttaa
103141  ttactgcctc aatttcagaa cttgttattg gtctattcag ggattcgaat gcttcctggt
103201  ttagtcttgg gagggtgtat gtatccagga atttatccat ttcttctaga ttttctagtt
103261  tatttgtgta gaggtatgta tagtattctt tgatggtagt ttgtatttct gtgggatcag
103321  tgctgatatc ccttttattg ttttttattg tgtctatttg attcttctct cttttcttct
103381  ttattaatct ggctagcagt ctatctattt tgttaatctt ttaaaaaaac cagctcctgg
103441  atttgttgat tttttgaagg gttttttcacc tctctgtctc cttcagttct gctctgatct
103501  tagttatttc ttgtcttttg ctagcatttg aatttgtttg ctcttgcttc cctagttctt
103561  ttaattgtga tattagggtg tcgatttttag atctttcccg ctttctcctg tgggcgttta
103621  gtgctataaa tttccttcta aacactgctt tagctgtgtc ccagagattc tggtacattg
103681  tgtctttgtt ctcattggtt tcaaataact ttatttctgc cttaatttca ttatttaccc
103741  agtagtcatt caggagtagg ttgttcagtt tccatgtagt tgtgtggttt tgagtgagtt
103801  tcttaattct gagctctaat ttgattgcac tgttgtctga gagactgttt gttatgattt
103861  ctgttctttt gcatttgctg aggagtgttt tacttcaaat tatgtggtca attttagaat
103921  aagtgcgatg tggtgctgag aagaatgtat attctgttga tgtggggtgg agagttctgt
```

-continued

```
103981 agatgtctat taggcccgct tggtccagag ctgagttcaa gtcctggata tccttgttaa
104041 ttttctgtct cactgatctg tctaatattg ccagtgaggt gttaaagtct cccactatta
104101 ttgtgtggga gtctaagtct ctttgtaggt ctctaagaac ttgctttatt tttatttatt
104161 tatttattta tttatttatt tatttattta tttatttatt ttttgagaca gagtctcgct
104221 ctgtcaccca ggctggagtg cagtggcgca atctcggctc acttcaagct ccatctcctg
104281 ggttcacgcc attctcctgc ctcagcctcc cgagtagctg ggactacagg tgcctgccac
104341 tatgcctggc taattttttt gtatttttag tagagacggg gtttcaccgt gttagccagg
104401 atggtctcga tctccagacc tcgtgatccg cccgcctcgg cctctcaaag tgcgggatt
104461 acaggcgtga gccaccgcgc ctggccaatt ttttgtattt tttagtagag cagggtttc
104521 accatgttag ccaggatggt ttcgatcttc tgaccttgtg atctaccgc ctcggcctcc
104581 caaagtgctg ggattagagg catgagccaa cgcgcctgac caagaacttg ctttataaat
104641 ctgggtgctc ctgtattggg tgcatatata tttaggatag ttacctcttc ttgttgcatt
104701 gatcccttta ccattatgta atgcccttct ttgtctcttt tgatctttgt ctcttttggt
104761 ttaaagtctg ttttatcaga gactaggatt gcaaccctg cttttttttt tttttttttt
104821 ttttttttgc tttccatttg cttggtaagt attccttcat cctttattt ttgagcctat
104881 gtgtgtcttt gcatgtgaga tggctctcct gaatatagcc caccgatggg tcttgactct
104941 atccaatttg ccagtctatg tcttttaatt ggggcattta gcccgttac atttaaggtt
105001 aatattgtta tgtgtgaatt tgatcctgtc attatgatgc tagctggtta ttttgcccat
105061 tcgttcatgc agtttcatag tgtcaatggt ctttacaatt tggtatgttt ttgcagtggc
105121 tggtactggt ttttcctttg catatttagt gcttccttca ggagctcttg taaggcaggc
105181 ctggtggcga gaaaatctct cagcatttgc ttgtctgtaa aggatttat ttctcctttg
105241 cttataaagc ttagtttggc tggatatgaa attctgggtt gaaaattctt ttctttaaga
105301 atgttgaata ttggcccca ctctcttctg gcttgtaggg tttctgcaga gatccactct
105361 tagtctgatg ggcttcccta tgtgggtaac ccgacctttc tctctggctg cccttaacat
105421 ttttctttg atttcaacct tggtgaatct gatgattatg tgtcttgggg ttgctcttct
105481 caagaagtat ctttgtgctg ttctctgtat ttcctgaatt tgaatcttgg cctgtcttgc
105541 taggttgggg aagttctact ggataatatc ctgaagggtg ttatccaact tggttccatt
105601 ctccccgtca ctttcaggta caccagtcaa atgtaggttt ggtcttttca catagtccca
105661 tatttcttgg aggctttgtt cgttcctttt tattctaatc ttgttttcat gctttatttc
105721 attaagttga tcttcagtct ctgatatcct ttcttccgct tgatcgattt ggctattgat
105781 acttgtgtat acttcatgaa gttctcgtgc tgtgttttc agctctatct ggtcgtttat
105841 gttcttctct aaattagtta ttctagttag caatttctct aaccttttttt caaggctctt
105901 agtttccttg cattgggtaa gaacatgctc ctttagctcg aaggagtttg ttattaccca
105961 ccttctgaag cctacttctg acagttcgtc aaactcattc tcggtccagt tttatttcct
106021 tgctggcaag gagttgtgat cctttggagg agaagatgca ttctgggttt gcaattttc
106081 agccttttg tgctggattt tcctcatctt tgtggattta tctcccttg gtctttgatg
106141 ttggtgacct tcagatgggg tttctgtgtg gatgtccttt tgttgatgt tgatactact
106201 cctttctgtt tgttagtttt ccttctaaca gtcaggcccc tctgctgcag gtctgctgga
106261 gtttgttgga gttccactcc agaccctgtt tgcctgggta tcaccagcag aggctgcaga
106321 acagcaaaga ttgctgcctt ttccttcctc tgggaagctt cgtcccagag gggcacctgc
```

```
106381  cagatgccag ccggagctct tgtatatgag gtatgtgtca gccctgctt gaaggtgtct
106441  cccagtcagg aggcatgggg gtcagggacc cacttgagga ggcagtctat cccttagcag
106501  agcttgagcg ctgtgctggg agatccgctg ctctcttgag agccagcagg caggaacatt
106561  taagtctgct gaagctgtgc ccacagccgc cccttccccc aggtgctctg tcccagaaag
106621  atgggagttt tatctataag cccctgcctg gggctgctgc ctttctttca gagatgccct
106681  tcccagagag gtggaatcta gagaggcagt ctggctacag cgggtttgcc aagcggccgt
106741  gggctctgcc cagtttgaac ttcccggagg ctttgttcat aatgtgaggg gaaaactgcc
106801  tactcaagcc tcagtaatga caaacgcccc tcccccacc aagcttgagc atcccaggtc
106861  aacttcagac tgctgtgctg gcagtgagaa tttcaagtca gtggatctta gtttgctggg
106921  ctccgtggtg gtgggacctg ctcagctaga ccacatggct ccctggcttt agccccttt
106981  ccagtggagt gaacggttct gtcttgctgg cattccaggc accactgggg tatgaaaaac
107041  aactcctgca gcaagctcca tatctgccca aacggttgcc cagttttgtg tttgaaacct
107101  agggccctgg tggcataggc acaggaggga atctcctggt ctgtgggttg agaagaccat
107161  gggaaaagca tagtatctgg gcctggatgc accgttcctc acagcacagt tcctcataac
107221  ttcccttggc taggggaagg agttccccga cccctactgc ttccccggta aggcagtgcc
107281  ccactctact tcggcttgcc ttccatgggc tgcaccccact gtctaatgag tcccagtgag
107341  atgagccggg tacctcagct ggaaatgcag aaatcaccca ccttctgcct tgatctcact
107401  gggagctgca gaccagaggt attactattt ggccatcttg ctattgctgc tgtttttttt
107461  tttttttttt tttttttttt tttaagacag agtctcactc tgtcacccag gcgggagtgc
107521  agtggtacaa cttcagctca ctgcacccctc tgactccag gctcaagcga tcatcccatc
107581  tcagcctctt gagtagctgg aactataggc acaagccacc gtggcccgat taattttgtt
107641  tttttgatat aagttttgta gagatgaggt ctcactatgt tgcccaggat gggattctct
107701  ggctcttaat aaataattgc ttttttaaatc tttcacaaag gaaaccttga gtgagtgaat
107761  aatcaaaagg tgatagattg tttagtttct attttctgtg gcatgaaggt cagtgatgct
107821  caggatgggt gtgagtaaga tgcttgtgct aagcatgctc cctgccccac agtcagtctg
107881  catgagccac tgtttctaat aagactgtgg atagagtgat ataatcacct ctaaccatat
107941  caaatgttac acgtaagttt cagattttga gacatgagtt gataagattt gaagttcaaa
108001  gaccatgact ttagtacttc ctgagtaatc aactgaaata tgttttacat atgtgttttc
108061  caaattgctg accattcatt ataagtgctt ctgaatttaa aggaggtact tgatgtatag
108121  gtaagaaatt accttaaat tctggaggtc taccctcaaa gtgtatacag aggtttaatt
108181  ggatgtaaga cacaggatca cctttagggt tctgtttttt tgtctattta ataaaaccca
108241  aactgtagta tgctttacat gcctttagaa tcatataaat aaactgctgt taagtaatgt
108301  tcccagttgt tatgtttctg ttacaggtga aaagcaatca cggagttaaa agaagacaag
108361  ctgaaatgat gcaggctgct cctatgttgg aaatttgttc attaaaattc tcccaataaa
108421  gctttacagc cttctgcaaa gtagtcttgc gcatcttttg tgaattttat ttctagcttt
108481  ctgatgctgt gaaatatgta tcattctttg aaatttata ttctaactgt ttcagctggt
108541  atgcagagac atcattcctt tttttttttt ctttttttct ctttccagac agagtctcac
108601  tctgttgctt aggctagagt gcagtggtgt gatctctgct cactgcaacc ccgcctcct
108661  ggatgcaagc aatttctgcc tcagcctccc gagtagctgg gattacagga gcccaccacc
108721  tacccagcca gattttgtat ttttagtaga gacggggttt cgccatcttg gccggggtgc
```

-continued

```
108781 tcttgaactc ctgacctcgt gatccaccca cctcggcctc ccaaagtgtt gggattacag
108841 gcgtgagcca ccgcgcccgg gcgagacata attcttatat attgattttc tatccagcag
108901 ccttgtgaaa tatgcttatg aattctaaaa gtttacttct agatggtttt cagtcttcaa
108961 catacagaat cataccatcc ttgaataaga acaattttgt ttctgccatt ttttttttct
109021 ttttccttt gtattttttg tagagacggg gttttgccat gtttcccggg ctgttcttga
109081 acttttgagt gcaagtgatg cacccgcctc acctcccaca gtgctgagat tactgacgtg
109141 ggccaccgtg ccgggcctgt tgttgccatt gtaaagagtt ttatttcctt ttctgattt
109201 atggcattgt gcagacccac ctgttaaaat ggtgacagtc aatatccttg tcttatccct
109261 gatgagaaac cgaaaaattt caacatttca ccatcctatt tactgtcctt tttttgtaga
109321 tggactttat cagagtaagt cattccattc tgttccaaat ttgctgagag tattcatttg
109381 aatatatgtt gagtttcatc agtgcatcta ttttgtttat aacagcattt ttttcccatt
109441 catctgttaa tgtagtgaat tagattgata actttgtaca ttttatctt ctatttaa
109501 aaatcgagac agggtctcat tctatcaccc aggctggagt gcagtggtgt tatcagagct
109561 cactgcatcc ttgaccttct tggctcaagt gatcctccca cctcaggctt ctaagtagct
109621 gtgactatag gtacatgtaa ccattcccag ctaattttc ttcttcttt ttttttttt
109681 tgtagtgatg agatttctc atgttgctta ggctggtctc gaacacctga gctcaggcaa
109741 tctgcccagc tcagcctcca aaaatactag tactacaggc atgagtcttg gcctggccag
109801 ttttttctat acaagggtct tctctatgta aagactaaac ttatctgtat ctttgtgagg
109861 gtgtgctaag ggcatgatga aatttatcat tctattgatt taagaaaac tatccttgac
109921 tttccagtgt gtaagtccat gaaagcataa ttatgttgaa agcatatatt gttatgggtg
109981 ttgagaaccc tgcactttct gctgctgtgg gagcatgtcc ttggaggtac ctttcgtctg
110041 ttttctcaac tccaaacatc ttaggaccat gggttgtgac tggtaaggaa tgtgtcttgc
110101 gagtttcaag atggagttga ttttcacatg gtgtcactct ggctctcctg tttctctaat
110161 actggcactt ctctttctgt gattctgatg ctacaaatga tagatatcgt tttagtattt
110221 tcttatgggt cctagagatt gtattcattt ttctttcagt ctctttctct gacttgttca
110281 catttaacaa tttcttttg gggtaggttg ctatttctgt tttcgcaggt ggtttacctg
110341 tcttctcagg cagtcaccgt ggtccttgtc cccatggtgg ggccggggca agagagggcc
110401 ctggagggga gggggttta gttgaagatg gagtgagttt tgaggggagc actacttgag
110461 tcccagaggc ataggaaaca gcagagggag gtcagattcc attatcctca gtggggatgg
110521 gaatcgaggg ttgggggcgt ggggctggga acggcagcct tccccaaccc gcagctgtac
110581 atgctccttg gctcccgcct cagtgcgcat gtccactggg cgtcttctgc tcagccgctt
110641 tacccacgtg gagaacgcca gggagctgtg agggtgtgtg gtctcgttcc tgtcgtctgg
110701 aatatttttc ctctactgag attcatctgg taggtctgca ggccagtcct cccggggtct
110761 gaagtgtgag tgagggtgaa gagcaggcag tgtgcttcgg gtgagtccgt tgggtcctgc
110821 ttcgtggtct gtggcctctg agggagaagg gcctcgaggc ttctgaaagg gaagggctc
110881 ctggcctctg aaagagaagg gccttgaggt cgtcctcctt ctctcaaagg ctgtgaggcc
110941 accatctgct tgtggtcgt gaaggggcca ggacaaggag gaaggtgggc catggagggg
111001 aggcggtcag gggctcaggt gaagaagggg cgattgctgg gtgtgctgtc agagggatgg
111061 aagtccggag gtgccaggaa tacccgatac aggggagatc cctgaatgag gtcccggaca
111121 ggtgcgagga gggcgataaa gaagggacct ggcacctggg aagactgcgg gctggtgagt
```

```
111181  gcccctgagc tttgtggagt ggggagcccc gagtgagaag catcgcaaga tctcacctcc 111241  gccatggaag gtctggcaac agtgggaagg actgggagag gctgtgcggt ccaatcaaac 111301  ttgatttgag agaagtgaat ggctctagta agtgggagtg tgcccaaagt agcaatcacg 111361  agaattatga ttcactaatg ttttcatgtg gagtccactt gtgaaactaa acctcatcag 111421  aaatgacctc tgccagtggg gcgccatggc ctgcgcctgt agtcccagtt actcgggacg 111481  ctgaggtggg aggatcccct tgagcaggag tcgatgctgc agtgagctgt gatcacgccg 111541  ctgcactctg ccagagcaac acagggagac tgcgggacca aagaaattt agaaaaaaaa 111601  tgtcctctgc gttttgtcac acgccttaag atgattgctc tgccagcttg gccagcataa 111661  gtggctttgt aggcactcag aaaaggtaca cacatatgct taactctggg acttattttg 111721  aaagtatttt caaaattaaa acgacaagtt aacatttatc catggaggtg atggaatata 111781  gcagccctt cgagggcatg ctcccaatca cggttgtctg ttttcagtgt gaaatatgag 111841  ttggcgagga agatcgacct atcggtctag accaagactc tatgtagagc cccctgaaat 111901  gattgggcct atgctggtga gtgcttaaac gttaattcgt tgttttctat tagcagaaat 111961  taattttgt gacagtattg ttgcattagt atggaaatgc tgataaaggt ctttcctgct 112021  cataaaaaat gatgatggcg tctcatgaag gaaacattga ttctggagaa tttttttcc 112081  tctagtgttc ttcagctttt gcccatgact tctttctcag gctttgtttg ttaatgacag 112141  attgtacaca tgtattccaa cactgagtat aatagcctcc aaagtcctcg tgcgtcactt 112201  ttctcatagt aaccttcctg tgggtcgagt aaccttattg ggcatagagc atagagttgg 112261  agaaatgtct ttaggcttag ttaggaccag aaatagctat gtattctgtg tatatatgta 112321  aaattttgta tcaataacga aacttatttt ttatttgcac acccacacgt attccccagc 112381  ccgagcagtt cagtgatgaa gtggaaccag caacacctga agaagggaa ccagcaactc 112441  aacgtcagga tcctgcagct gctcaggagg gagaggatga gggagcatct gcaggtcaag 112501  gtgagggaaa gggaagaaga acgtctgctg gtgtgtgcgt gtgtgtgtgt tcgtgtgtgt 112561  gtgtgtgcac gtgtgtgtgt gtgtgtgtta ggcattgtca cataggagga agaggaggaa 112621  agaaaacaat ggaagaatg cctgaaattg actggaaaag cgaggaggct atgtagtttg 112681  cagcttagct taggcaaatc cctcactatg ataaaagttc tcatctttat gaatgagaaa 112741  atggaggcgc tgggattgtg ttttatccaa gagcccttga ctggtgaata caaaatttgt 112801  attttgttcc aaggtttgtg tcttcctacc atctatgttg ctgtaaaaac ggaaatgatt 112861  ttgctgaaaa tgcttaaaac tcaaaggctt tactgtaagg tagcttagta ctgacccaag 112921  aatagaccca gttcagagga gcaggagcag ctccaaaaac cgagtcactg aatgtcagcc 112981  actgtttcct ttgattgatg tttttatatg gtacatttga taaaagctgg ataaatgagg 113041  atactgccat acaggtagct ggtttagtta ttttctaagt ggcttttagg aggtgattaa 113101  atcctttat ggttagaaaa agcaaaaag gaattatcct gagattaaca ttgagataga 113161  ataatttct cctagataaa atattttcaa acaaacatt tatgtaactg aggtcatgga 113221  ttattccagg gatgcactgt taaaaatttc tagaatctga ctgacaacaa tgcccattaa 113281  ttgctgtcct cccactccct tattctcagt gtgggacagt atattttctg tgattcacaa 113341  acaatgttat atttggtgct ttgttcttca cggggttcat ttatggaata ttacatttag 113401  gacctttgga cctaaatata actttatttg aacaaaatga gtttctatt tacctcaata 113461  agtaatgggt gtcatgactg taagattttc catagtcctc aaatccattc agctaatcga 113521  tccttcagaa attgacattg taattgtaac cgaaatccta tccatgtggt agacttgaga
```

-continued

```
113581  tttcttagct gatgcacact gctctcggta ctctatggct gaatataagc attatacatg
113641  tcctgtggtt tatccttaga ttgtcattta ggagaaaggt ctcaagctgg gctgaatgct
113701  gtgcacgcat agtcccagct acttgggagt ctgaggtgag aggattgctt gagccctgga
113761  gttgaagccc agcctgggaa acatagcaag accttatcac taataaataa ataaacaaac
113821  aaacaaacaa acagataact aaaggtttca tggtatagga aaacacagat gcaaagtttg
113881  tgcctagttg ctggtaatgt tgcaaacata actccttagt gaactgtacc acttaaaaat
113941  agttaagatg gtaaatttta gaatatgtgt atttttttacc ataattaaaa aaaacctcct
114001  gtcttcctaa agttcagtgt aattgtcata tattcttttta aattttttact gtatctattt
114061  tcaaggcata acattatgga aaatttgcaa gaatagtaca atgaactcct atacttttca
114121  cctagattca ccaattgtta atagctttcg cttcataggt ttcatatcac ttccctctct
114181  taccctgctt cccacacact cacacacaca cacatacaga tatatgttta ctgttattaa
114241  tgctgaattg tttcgataaa ttttcaggtg ttatgaccct ttacaccaag tacttgaggg
114301  tgtgtacatc atcagaacaa agaaaaagta attccttggt catcactgca gaaaaatcaa
114361  aatcaggaaa tttaacaatg agaaaatgca gtcatttatt acacagtgta tactcaaatt
114421  tcgccagttc tccagacaat ttcttttttc ctttttttttt ttttcctttg ttgagacgga
114481  gtctctctct gttgcccagg ttggagtgca gtagtgcaat cttggctcac tgcaacctac
114541  acctcccagg ttgaagggat tctcttgcct cagcctccca tgtagctagg actacagggc
114601  ctggccaccg tgcctgagta atgtttcctt ttttttgttt gtttgtattt tagtagaga
114661  tagggttcgc cctgttgtcc aggctggtct tgaacttctg acctcacctg atctgcccac
114721  cttggcatcc caaaatgttt ggattacagt tgtgatggaa caggaattaa aagaaattaa
114781  agaatgtgta agcaaaaact cagttgtatg taagaaaacc caatttcccc tgaggaagag
114841  aaagagctgg agtcctttaa aattaactgc ctgttttttcc ttctgtggct agtgagtctt
114901  atctctccct ttccgaggca ttgtgaagac cctgtttctc tagttgtgca gctgcaaggt
114961  cactagacag ataatctcaa gtggtaaaac atgttgttcc ttgaaaagta agaaataatg
115021  taatgcatgt ttcaattgag taactgtatt tgtttcccac ttctgtaata tgcttcccct
115081  gcacagatct cccctgccc cacgaaatgc ttaaaagata gcttgactct ttgtttgggg
115141  ctcagtcctt tggatgttaa tctgactagg tcggtgcatc taaataatta aataattcct
115201  cctcaacccc tcggtctctc tgattcctta attatcctgc agcatttctg gtgacccgga
115261  cagggattgg agatggcaga tttactgtct cctttgtctg tgggactaga gccccacggc
115321  caggggagac ctggtatcca aggcgtgccg taggggagct tcacctggat ggagactggc
115381  tctcccggca tcccagtggc ctagctggct gcacaacgga actggagacg gggctgcagc
115441  atgataccag cacttcaggt accacagtaa ggagaaaggg cccaaggcag gaaagcccat
115501  cccataggga tgaaggggag cttgatcacc tcccggggac cgaccactaa tccaacccag
115561  agtggctggg gggcagcagg agtggcctgc caatttggat gaacctcatg tcccctaat
115621  aaagtgaaag tggctcagtg gtggagaaaa tgggccaata gagtggcaag tgcagcaagg
115681  aagagcttgc tggcagggtg caagagtggc ttgccagccc aactgggagt gtgtgggtgt
115741  gtgtgtggac ctacccagga catgagagag gctcgtttcg tctgatgagg agtcctgggg
115801  taggagtggt gtgtaggtgt gtgaatgtgg gagcctaact aggctcaccc aggacacggg
115861  agaggcccgt tttgtccgat gaggagtcct gggcaggg acatgtgtga aagtgtgtga
115921  aagagacggt ctcgggagag gccaatgcgg ggagtgacgt ggggaagcac agatcccta
```

```
115981  gcgtgggctg tgtgctctga ggcaagtgcg ggggaaatca gacctaggac gttgtgtaca
116041  gctgatagga ccagctccat ggccacagca ggctgtgaga ggggaaggca cgttcctggc
116101  taagcagcct ctgaaactcc cataatagga cccagtctag tggacccgag agtgaaagtg
116161  agagtgaaag tgcgccacaa gggaggaaat gggaggaaaa gtgttgaaac caactccttt
116221  ggagtgcatg atgaaaaaat ttaaaaaaag atttagaggt gattatggga tgaaactgga
116281  tgctcaaaag ttaaggacat actgtgaatt agaatagccc tcttttagtg tcagatggcg
116341  ggccgaaggc actacagaga aattggccat gtgttttaag gtggtgacta gggtcagagg
116401  acagccaggg cattcagacc tagtctttac attgatgact aaatgaatgc agccctgcct
116461  agcagtttat tgtagaatgc tcgcagctca tgccaagaga accagctgc tctgacggct
116521  acagagttaa agggaaagtc acagaggctt gtaactccaa aagtaaaaag tgaaaagtaa
116581  aagccaaaag tgaaagtaaa aatcagctgc cctggcagct atggaaacaa aagaaaagtc
116641  tgaggaagga gaaaactggt tttgcaagaa ccacaggagg gaatagagac ccctcctccc
116701  tacattccaa tctaccccc tttactaagg ctaactgccc ctaaggagtt aagttcaaag
116761  agatacaggc tcccagtctc acagaaggag aaatcagagc tccaggaagt taaagtgaaa
116821  agctagaaaa gtcaggtagg ccgtctcagg tctggccatg ccgaagttat gcttacgcct
116881  cttacgagga caaaaggacc cccactagga cccagatgat gcagtctggc ttcaacacct
116941  acgaaggtgc cgagaaacac ttctgcaaaa gctaaaggat agtaaaagaa aaagacaacc
117001  aatataaaaa atctcagagg tgctccaggg tgcagataaa agcaccagcc agttttaaga
117061  aagactttgt gaggcatttt gggtgtacac tccgtttaac cccaaggctg ctgaaaatca
117121  gtgcatggtg aatacaacat ttgtaagtca gggccaagga gatattaggc ataaattgca
117181  gaagttagaa gctccgtagg tgtgaatgct actcagctta ttaaagtggc taccaaggtg
117241  tacattaact gagatcagga ggcaaagaag aaagctgatc ggaggcttaa gaaaggctaa
117301  tttactagca gcagccctta caggaagaga agctggctct ttgcaaggag acatggacgc
117361  gggtgtgaac gcagtcatgg aaaaggctag tctggacagg agtttgaaag ccggccgagg
117421  ctagagagag attaatgtgc acggtgcaaa aggaaaggac actagaagga taaatgtcaa
117481  aagagtaagg agaatggtca atggcctaac acccaagagc ggcgttcggt tgctagttgt
117541  ggtgcttccg aggcagatcc tgatctgatc ggcttagcgg ggggccgaga atttagcaga
117601  ctgagacaga ccgggctcca tccttttagg ccccggggag cctatggtct ctatggaagt
117661  agggggccga tcaatggatt tttttggtcg atattggtgc tgatttctct gtggtaaccc
117721  acccgattag ccccccccca caaagaactg tgctactatc gtaggggta caggggccaa
117781  agaaaagaga cccttttgca aatccaggag atgtattatt aggggacaag aagtgcagca
117841  tgagtttcta tatatgccaa attgtcgagt gcccttgtta ggaagagact tactccagaa
117901  actgcaggca caaatttcct ttacacctaa agggaatatg acactggagt ttggaaagtc
117961  taaggcaatg gtattgactc taactgtcac aaaggctgag gaatggcggc tctgtgaact
118021  gtgtgccaga aggctaccgg agccagacct acacaataag tggggaatgc ttttcaagga
118081  accaggtgta taggctgagg acaaccccc tggacttgct gcaaacagac ccctggtggt
118141  agtagagctt aaccctcatg ctgccctggt acgagtccgt caatatccct acccagagag
118201  gcaattgatg gcataacaaa acatttaaat cggctgtatg aacataggat tatagtgaaa
118261  tgcaagtcct tctggaatac tcctctgctg cctgtgcgca agccaaatgg tgaatacagg
118321  ccagtttaca aagtgtccag ggacaaggca aaagtctgtt ttcggggaggt tggatatcta
```

-continued

```
118381  ggattcatgg tatcccaagg ccagcgcagg cttggaagtg catgcaagga ggctgtatgt
118441  gcattgccca ccccagtttc aaggcagcag gtcaagaaat ttctgggtgc agtgggattc
118501  tgccgaatct ggattccaaa cttctccctt acagcaaggc ccttatatga ggctaccaaa
118561  ggaaaagaaa gagagcccct cgtataggaa aaggaacagc aaaaggcctt caaagatata
118621  aaggaagctc tcatccaagc cctggcgcta gggttgccag atgtaaaaag cccttctttt
118681  gatatgtgga tgaacggaag ggaatggcag ctggagtctt cactcagttg ttgggctctt
118741  gacattggcc ggtagcatac ttatccaagc gactggactt ggtggcctta ggttggcccc
118801  actgcctcag ggcgctggca gctatgcaa tccttataga agatgccaac aagctagccc
118861  taggtcagaa gacaatagtc tgggtgccac acgctatagt caccttaatg gagcaaagag
118921  gacatcgttg gctgtccaac tctagaatgc taaagtatca agggcttctg tgtgaaaatc
118981  cccagataac actggaaact ataaatacgg cctgtggagg accctgattg gaatgatggt
119041  gggttgcctc actgctggca ggaccttccc cactgttgca taaatacggt gaacgagccg
119101  ggaagatctc agagatacca ccttggagag cccagatgtt gaatacttca ctgatggtag
119161  cagtttcata acagatgagg tgtgatatgc agggtatgca gtagtgaccc aatactcggt
119221  ggttgaggct caagccttac cttctgggac ttctgcttag aaggctgaat taatagcatt
119281  aaccagagca ctgttattgg ccaaggggaa gaaagtaaac atatgtaatg attcaagata
119341  tgcttttgca accctgcatg cccatggggc aatacacaaa gagagaggac tattggctac
119401  tgaaggaaaa gaaataaaaa ataagagga aattttgcaa ttattagaag ccatatgggc
119461  tccagagaag gtggctgtta ttcattgcaa aggacaccaa atcgggaaga gctatgaggt
119521  gcccagcaac agaaaggcag accaagaggc taggcaggca gcaatgagaa aggctttacc
119581  tgaagaaaga actctagcaa tgcctctcct tatagagccc cctttattgg aggtaaccaa
119641  ttactcttca agggaaaaag cttggtttgg tcaggaaaca ggaaaatata ttaaaaatgg
119701  atggtggctg ttctctgacg ggaggctagc tgtcccagaa acaaaagccc aaggtttgt
119761  gaagcagatc catcaaggaa cacacattgg aaggacgact agaaactttg ataggtcggc
119821  atttctatgt gccacggctc tctgccatcg cccatgctgt ttttgaacaa tgtctatcct
119881  gtgcccggaa taatccaaaa caaggaccta ctcgacttcc cggaattcag gaagcaggaa
119941  ctgttccttg tgagaacctg cttgtagagt tcactgagtt acctctagca ggaggttact
120001  ggtatatgct agtgtttgtt tacaccttct ctgggtaggc tgaggccttc cccaccagaa
120061  ctgaaagggc acgagaggtg acaaaggtgc tactaaaaga catcatacca agatttgggt
120121  tgcctttaac cctaggatca gacagtggtc ctgcatttgt ggcagaagta gtacaaaagc
120181  tgactcaact tttaaagatc aaatggaaac tgcacacagc ctactccacca cagagttcag
120241  ggaaggtgga acggatgaac cggacactca aacagctact aaaaaagttt agccaggaaa
120301  ctcacttacg atgggatcag gtcttgccca tggtcctcct ccaggtcagg tgtacaccta
120361  caaaacaaac tgggtactca ccctatgaaa tattgttcgg aaggccaccc ccaattatta
120421  atcaaattag aggggattta aaggagttag gagagttaac ccttaggaga cagatgcagg
120481  ctttaggagt gggaatgtag gaggtgcata gctgggtaag ggaaaggata cctgtaagtc
120541  taacagaccc agtgcatcca cataagccag aggactctgt ctgggttaaa aggtggaatc
120601  caacaacctt ggggcccta tgggatgggc cccatattgt gatcatgtct acttccactg
120661  ctgttaaagt tgcaggtgtc acaccttgga ttcaccatag ccgcctgaaa ccagtggcag
120721  cagtgactcc cgacgatgac cagtggatta gccaacaaga cccagattgt cccacccgaa
```

-continued

```
120781 tgctcctacg gcaaaaccca accaccggta agaaggacga ctgccctgct ctgaccacac
120841 cagaggctgg tcagtctaca tatggctgaa gcttgaggat cctacaagct ctgctctagt
120901 cacatcctgg aagctgacta gtctatgcat ggccgaagct aagaggacca tctccggata
120961 attaaatgta aatacaattt ataagcctag ttataattct gtcaatactg attgttctgt
121021 tgttattact gcaaatgctg caaatgtcta tgctcagaag aaggtttgcc atgcccatgt
121081 gtagtgtaaa catgtttcta ttacgtacac tgatgttgtt accatttctg cctatactaa
121141 aaggggagaa atcttgagaa ggatgcccac attgtgtaca cactacctgg gtaaaaaata
121201 ccatagttaa aattctactg taccatacct actataaatg tacaggaatc aagttaagaa
121261 cctacacata caaccagaaa cagtctgcaa tggtttaaca caagagaggc ttagcaggac
121321 cagccctaaa catctgtatg agaaccaca aatcagatgc cctgactgta acattcagtg
121381 gtctacacta acacagctct aacacttata ttcaggaagg actgctctgc taaggagtat
121441 gtcaaccaaa ccaaattgta agacaaggac atgcaatcct ttaaatttta ctatcttaaa
121501 gccagagcta cctttctcgt ctacaggaca gacagcacta ttacaggtaa acagacaagg
121561 agcaggcctt ggagttccac tactaattgt caaaaagact agaaggactc aaatgcgtcc
121621 aaccccgcaa tttcgggtcc gtaagtcatt ctataagcat tttgttcagt cagtgcctga
121681 gcttccccca tcaaccaaaa acttatttgc ccaatcagct gcaaacatag ctggcagctt
121741 atgaatttcc tcatgctatg tatgtggagg aaataatatg ggggaccagt ggccatggga
121801 ggcaaaggaa ttaatgccac aagataactt cactttgcct aaccctgcca gtgaaccaac
121861 agcctcagcc agtgtttggt tgttaaaaac ctccataatt gaaaaatact gtattgcccg
121921 ttggggaaag gctttcacag agagagtagg agaaacaacc tgcctagggc aacagtatta
121981 tgataagact aaaaacaaaa ctctatggag aaatgcccag aatgactcct acttaccaga
122041 tccaaaccct ttctctcggt tctctactct aagccactct tggcatctct agaggctcca
122101 aatgcttgga aagcaccctc tggcctatat tggatctgtg gcacataggc atattggcaa
122161 ctgctggcta aatggacagg ggcgtgtgtg ttaggaacaa tcaagccatc cttctttcta
122221 attcctctaa agcaaaggga actcttaggt tatccagttt atgaggaaaa taaaagaaga
122281 actagaagaa gcatattcac aaaaatagac acaaatgtca aaaaggatgt agacatagga
122341 gactggaagg ataatgaatg gcctcatgaa acaatcacta atatattatg gccaactacc
122401 tgggcacagg atgggtcatg gggatatcac accacaatct atatgctcaa ctgcgtcata
122461 aggttgcagg cagtccttga aattataacc aatgaagcat caagggcact agatttattg
122521 gcaatacaag caacacaaat gagaaatgct atacatcaaa atagattggc tttagattac
122581 ctcttagcct cagaaggagg agtatgtgga aaatttaatt taaccaactg ttgcctagaa
122641 atcgatgata atggctgagc tgtcatggaa atcacagcta gaatgcgcaa gttggcccat
122701 gttccagttc agacttggtc cggatggtcc ttggatttgt tgtttggagg atagttctca
122761 acctttggag gattcaaaac tctcattggt gggttttttgt ttaatcttgg catctgcctc
122821 atcctccctt ttattttacc cctgattatt aggagtattc agtcaactat aaaggcaata
122881 gtaacccgac acactacctc acagttgatg gcattaacca aacatcagct gctgccagta
122941 gaagaagaag cccagctcca cgaagaggtg gcaaataatg gtgcttgcta tgaacacctt
123001 tgttatgaaa agcaccaaag gggggaaatg aaacaggaat tagaagaaat taaagaatgt
123061 gtaagcaaaa actcagttgt ttgtaagaaa acccaactcc ccctgaggaa gagaaagagc
123121 tggagtcctt taaaattaac tgcctgtttt tccttctgtg gctagtgagc cttatctccc
```

-continued

```
123181  cctttcccag gcattgtgaa gactgtttct ctagctgtgc agcagtaagg tcactagaca
123241  gataatctca agtcgcaaaa catgttgttc cttgaaaagt aagaaatgat gtaatgcatg
123301  ttttaattga ataactgcct ttgtttcttg cttctgtaat acgcttcccc tgcacagatc
123361  tcacctgccc cacgaaatgc ttaaaaggta gcttcactct ttgtttgggg ctcagtcctt
123421  tggatgtaat ccaactgggt cggtgcacct aaataattaa ataattcctc ctcaacccct
123481  tggtctctct gattccttaa ttatcccgca gaagtgagac cccacgccca acgcagataa
123541  ttttattgat agaattcctt tttctgatcc ggagtcaagt tcaggatcac atcttgcatg
123601  tgcttttcag gtgtttttag tttcctttaa tctggaatgt ttccttaatt tgtctttgtc
123661  attcatgata cagacatttt tgaagaggat agaccagttg gtttccagaa tgttctgcag
123721  tttgggcttt ttcatgtctt ttttaaagac cttttttaaa ctcagcattt attgctggct
123781  agtcatgcca tataacagtc taagtgctag gagtgtaagt gctgtgagag acaggatttc
123841  agccttgaat catttaatat gagaaggaca atcagaggta gaataacaaa gtgcaaagga
123901  ggcagcagag ttgtctgagg gcagtctctg gaaaggaaga gggtaatatt tggaacacct
123961  tgttttcctg ttttctgcta acagactcct gaaataatgt tcatgggatt cttatcaaca
124021  tatttattat tatactagct aaagctttta tataataaca ccgagagcat gaatattatt
124081  ttcttattca tatttcatgt tttactgctt aaattgatat gtattttta tttttaatgg
124141  ccgaagcctg aagctgatag ccaggaacag gttcacccaa agactgggtg tgagtgtgga
124201  gatggtcctg atggccagga gatgggcctg ccaaatccag aggaggtgaa aaggcctgaa
124261  gaaggtaggg aatccattag gcatgcacat tgtagggtgt ctgtttccac agtatcgtat
124321  cataattatt attacatttt tgagatggag tcttgctctg tccaccaggc tggagtgcag
124381  tggtggcatc tcggctcatt ggaaattccg ccttctgggt tcaagtgatt ctcctgtatg
124441  agcctctcgc ggagctgggc ttatggacat acaccaatgt gcccagctaa ttttgtatt
124501  tttagtagag acagggtttc attatgttgc acaggttgtt cccgaactcc tgacctcagg
124561  tgatccactt aacttaacct ttgaaattgc caggattaca tgcgagagcc accatacgcg
124621  accaaggcat tatttttta ataacacagg taacaatact gcctctttag taagagagtt
124681  cttatatgaa ggttatttga aacgtagttc aggccccagc acccgactga tagactgtca
124741  gatagggaaa caaactgagt caaagctatg ttgaattaaa agttttgagt ataaatcctt
124801  aaaccagtag ctcacaattt tcagatgctt ttgtaaaggt ctgcttttaa tcaatacata
124861  acacgtttgt aacacccatc acttggtgtg aaaaatgctg aagcactcat gcgggttcta
124921  ataccagctc ttacagcctt ggcgagattc tgagtgagtc cttccttc taaacctatc
124981  tttggttctt atgaaaatag tgagtttaag tcagagattt taaaccatt ttgcattccg
125041  tttctttcat actctgatcc tgttgcatag aatgcgtggg acacagagat catctgcttc
125101  gcatggtttg ttaatcacaa atcatgaaac cctggcccga gtcatctgaa aatctctgaa
125161  ttgagatttc attgtcagta agacagtgag cgggccctct gcttcatcct agttttccg
125221  tgtggagagc tgaatacgta gtgtaagatc ttgtgaaatt gtgaattctc cctcttcttg
125281  gtttgtttgt ttgtttggga cagagtctca gtgtgtcacc caggctggag tgcagtgatg
125341  caatttcagc tcactgcaac ttctggctcc caggctaaag ccgtcctccc acctcagcct
125401  cccgagtggc tggaactaca tgcacaagcc accgtgcctg actacatttt tttgttttca
125461  tttttgtaga gatgaggtct cactgtgttg cccaggcagg gtttctctgg cttttaatga
125521  acaattgctt ctttttttc cttttattta tttattatac tttaagtttt agggtacatg
```

-continued

```
125581 tgcacgttgt gcaggttagt tacatacgta tacatgtgcc atgctggtgc gctgcaccca
125641 ctatctcatc atctagcatt aggtacatct cccagtgcta tccctccccc ctcccccac
125701 ccgacaacag tccccagggt gtgatattcc ccttcctctg tccatgtgat ctcattgttc
125761 agttcccacc tatgagtgag aatatgcgt gtttggtttt ttgttcttgc gatagtttac
125821 tgagaatgat gatttccagt ttcatccatg tccctacaaa ggacatgaac tcatcatttt
125881 ttagggctgc atagtattcc atggtgtata tgtgtcacat tttcttaatc cagtctatcg
125941 ttgttggaca tttgggttgg ttccaagtct ttgctatcgt gaataatgcc gcaataaaca
126001 tacgtgtgca tgtgtctta tagcagcatg atttatagtc ctttgggtat atacccagta
126061 atgggatggc tgggtcaaat ggtacaattg cttcttaaat ctttccccac ggaaaccttg
126121 agtgactgaa ataaatatca atggcgaga gaccgtttag ttcctatcat ctgtggcatg
126181 taggtcagtg atgctcagca tgggtgtgag taagatgcct gtgctatgca tgctccctgc
126241 cccactgtca gtcttcatga gccactattt ctaataagac ggtagacaca catacgatat
126301 aatcatctct aatcatatca aatgttacat gtaagttca gctttagaga catgaattga
126361 taagatttaa agttgaaaga ccatgactct agtacttcct gagtaatcaa ctgaagtatg
126421 ctttacacat gtgttttcca aattgctgac tgttaattgt aagtgcttgt gacttgaaag
126481 gaagcacttg atgttcaggg gggaaattcc ttttaaattc tgcaggtcta cgctcaaagt
126541 ttatgcagag gttcaattgc gtgtaagaca cgggatcacc catagggttc tgttttagt
126601 ccatttaata aaacccaaac tgtagtgtgc tttgtatgcc tttagggtca tctgaataat
126661 ctgttgctaa gtcatgttcc caatcgttgt gtttctgtta caggtgaaaa gcaatcacag
126721 tgttaaaaga agacacgttg aaatgatgca ggctgctcct atgttggaaa tttgttcatt
126781 aaaattctcc caataaagct ttacagcctt ctgcaaagaa gtcttgcgca tcttttgtga
126841 agtttatttc tagcttttg atgctgtgaa atatgtatca ttctttgaaa tcgtgtattg
126901 taactctctg agctggtatg tagagacatc gttctttttt ttttcttct ttctttgtcc
126961 tctttgaga cggagtcttg ctctgtcgcc caggctggag tgcagtggcg cgatctctgc
127021 tcactgcaac cccgcctccc ggattcaagc aattgtctgc ctcagcctcc cgagtagctg
127081 ggattatagg cacccaccag cacgcctggc taagttttgt gttttacta gagatgggct
127141 ttcgccatct tggccggggt gctcttgaac tcctgacctc gtgattcacc tgccttggcc
127201 tcccaaagtg ctgggattac aggcatgagc ctccgcgccc ggtggagaca taattcttac
127261 atattggttt tctatccagt ggccttgtga aatatgcttg tgaattctaa agtttacttc
127321 taggtcgttt tcagtcttca atatacagaa acatatcatc ctggaataag agcagttttg
127381 tttccgccat ttttttttct ttccctttt gtattttttt gtagagacgg ggttttgcca
127441 tgtttcccgg gctgttgttg aacttttgag tgcaagtgat gcacccacgt catctcccac
127501 agtgctggga ttactggcgt gggccaccgt ggcgggcccg tcgttgccat tgtaaagagt
127561 tttatttcct ttctgattt tatggcattg cgcagaccca cccgttacaa tggtgacagt
127621 ggacatcctt gtcttatccc tgatgagaaa ccgaaaaatt tcaacatttc accatcctat
127681 tcactctcct tttttgtag atggacttta tcagagtgag tcattccatt ctgttccaaa
127741 tttgctgaga gtattcattt gaatatatgt tgattttcat caaacagtgc atctatttcg
127801 attaccacag cgttttttcc cattcatgtg ttaatatagt gaattcgatt gataaatttg
127861 tacgttttta ggttcgatta ttaaaacttg agacagcgtc tcactctgtc accgaggctg
127921 gagtgcagtg gtgttatcag agctcgctgc agccttgacc tcctgggctc aggcgctcct
```

-continued

```
127981  cccacctcag cctcctgagt agctgtgagt ataggtacat gccaccatgc ccagctaatt
128041  tttcgatggt ttttgtttg tttttgtag tgatgagatt ttctgatgtt gcttaggctg
128101  gtctcgaagt cctgagctca ggtgatctgg ccagctcagc ctcccaaaat actaggatta
128161  caggcgtgag ccttggcctg gtctggtttt tcttatatag gggtcttatc tatataaga
128221  ctaaagttaa tctgtgcctt tgtgcgggtg ggctaagagc atgatgactt ttatcattct
128281  attgatttaa agaaaactat ccttgactta ccagtgtgta aggccatgaa agcataattc
128341  tgttgaaagc atatattgtt aatgggtgtt gggaaccgtg cactttccgc tgctgtggga
128401  gcatgtcctt ggaggtacct ttcatctgtt ttctcaactc caaacatctt aggaccatgg
128461  gttgtgactg gtaggactat gtatcttgct gctttcaaga cggagtatat tttcacgtgg
128521  tttcactctg gctgtcctgt ttccctaata ctgtcacttc accctctgtg attctgatgc
128581  tacaaatgat agatatcgtt ttagcatttt cttacgggtc ctagcgattc tattcatttt
128641  tctttcagtc tctttctctg acttgttcac aatgaacaat ttccttttgg gataggttgc
128701  tatttctgtt ttcgcaggtg gtttacctgt cttcccagcc agtcacagtg gtccttgtcc
128761  ccatggtggg tccgggggcaa gagagggccc tgggttgggg gtggggttca gttgaagatg
128821  gggtgagttt tgaggggagc actacttgag tcccagaggc ataggaaaca gcagagggag
128881  gtgggattcc cttatcctca atgaggatgg gcatggaggg tttgggggcgt ggcgctggga
128941  acggcagccc tccccagccc acagccgcgc atgctccctg ggctcccgcc tcagtgcgca
129001  tgttcactgg gcgtcttctg cccggcccct tcgcccacgt gaagaacgcc agggagctgt
129061  gaggcagtgc tgtgtggttc ctgccgtccg gactctttt cctctactga gattcatctg
129121  gtaggtctgc aggccagtca tcccgggggc tgaagtgtga gtgagggtgg agagggcctt
129181  gggtgggtca ggcgggtccc gcttcctggt ctgtggcctc cgaggagaaa gggccacgag
129241  gtcgtcctcc ttcccttcac aggctgcgag gccaccggcg gcttcgtggt cgtgaagggg
129301  cctggacggg gaggaaggtg ggccgtggag gggaggcggt cagggggctca ggtgaagatg
129361  gggtgagtgc tgttgggggg atggaagtcc cgaggtgccg ggaaccccg acgacacagg
129421  gcagattccc tgaatggggc ctccggcggg ggcgaggcgg gcggtgaaga aggggcctgg
129481  cacctgggaa ggctgcggcc tggtgagcgc cccccccagc ggtgtggagt gcggagcgcc
129541  tgagtgagaa gcactgcaag gtctcacctc cgccatggaa ggtccgaaaa cagtgggaag
129601  gagtgggcga ggcagtgcgg tccaaccaaa cttgttgtga gggggggtga atggctctag
129661  gaagtgggag tgtgcccaaa gcagcaatca cgagaattgt gattcactag gttttcgtg
129721  gggagtgcac ttgtgaaact aaacctcatc agaaatgacc tctgtctgcg gggcgcagtg
129781  gcgctcgcct acgtagtccc agttactcgg gacactgagg tgggaggatc ccttgagcgg
129841  gaggtcgagg ctgcagtgag ctgtgatcac gccgctgcac tccagcctga gcaacacagc
129901  gagaccgcgt gtccaaaaga aatttagaaa aaaatgtcct ctgccttttg ccacacgcct
129961  taagatgatt gctctgccag cctggccagc agaagtggct ttgtaggcac tcagacagcg
130021  tacacacgta tgcttaactc tgggacttat cttgagagta ttttcaaaag taaaacggca
130081  agtttacatt tatccatgga agtgatcgaa tatagcagcc ctgtggagcg cacgttccca
130141  atcacggttg tctgttttca gtgtgaaata tgagttggcg aggaagatcg acctatcggc
130201  ctagaccaag acgctacgta gagcctcctg aaatgattgg gcctatgcgg gtgagtgctt
130261  aaacgttaat tcgatgtttt ctattagtag aaattaattt ttgtgatagc gttgttgcat
130321  tagtgtggaa atgctgataa aggtctttcc tgctcataaa aaatgatgat ggcatctcat
```

```
                                           -continued
130381   gaaggaaaca ttgattctgg aggatttttt ttttcctctc gtgttcttca gcttttgccc 130441   atgacttctt tctccggctt tgtttgttaa tgacagattg tacacatgta ttccaacaca 130501   gagtacaata gcctccaaag tcctcgtgcg tcacttttct cacagtaacc tccctgtggg 130561   tggagtaacc ttattgggca tagagcatag agttggagaa atgtctttag gcttagttat 130621   gaccagaaat agctatgtat tctgtgtata tatgtaaaat tttgtatcaa taacgaaact 130681   tattttctat ttgcacaccc acacgtattc cccagcccga gcagttcagt gatgaagtgg 130741   aaccagcaac acctgaagaa ggggaaccag caactcaacg tcaggatc
```

"Molecule" should be understood to include proteins or peptides (e.g., antibodies, recombinant binding partners, peptides with a desired binding affinity), nucleic acids (e.g., DNA, RNA, chimeric nucleic acid molecules, and nucleic acid analogues such as PNA), and organic or inorganic compounds.

"Nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally-occurring nucleotides (such as deoxyribonucleotides and ribonucleotides), or analogs of naturally-occurring nucleotides (e.g., α-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be either single stranded or double stranded.

"Isolated nucleic acid molecule" is a nucleic acid molecule that is not integrated in the genomic DNA of an organism. For example, a DNA molecule that corresponds to a gene that has been separated from the genomic DNA of a eukaryotic cell is an isolated DNA molecule. Another example of an isolated nucleic acid molecule is a chemically-synthesized nucleic acid molecule that is not integrated in the genome of an organism.

"Promoter" is a nucleotide sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

"Vector" refers to an assembly which is capable of directing the expression of desired protein. The vector must include transcriptional promoter elements which are operably linked to the genes of interest. The vector may be composed of either deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

"Isolated" in the case of proteins or polypeptides, refers to molecules which are present in the substantial absence of other biological macromolecules, and appear nominally as a single band on SDS-PAGE gel with coomassie blue staining. "Isolated" when referring to organic molecules means that the compounds are greater than 90% pure utilizing methods which are well known in the art (e.g., NMR, melting point).

"Cloning vector" refers to nucleic acid molecules, such as a plasmid, cosmid, or bacteriophage, that has the capability of replicating autonomously in a host cell. Cloning vectors typically contain one or a small number of restriction endonuclease recognition sites at which foreign nucleotide sequences can be inserted in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

"Expression vector" refers to a nucleic acid molecule encoding a gene that is expressed in a host cell. Typically, gene expression is placed under the control of a promoter, and optionally, under the control of at least one regulatory element. Such a gene is said to be "operably linked to" the promoter. Similarly, a regulatory element and a promoter are operably linked if the regulatory element modulates the activity of the promoter.

"Recombinant host" refers to any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for $\text{Fkh}^{sf}$" or a "$\text{Fkh}^{sf}$ anti-sense oligonucleotide" is an oligonucleotide having a sequence (a) capable of forming a stable triplex with a portion of the gene, or (b) capable of forming a stable duplex with a portion of an mRNA transcript. Similarly, an "anti-sense oligonucleotide specific for "$\text{Fkh}^{sf}$" or a "$\text{Fkh}^{sf}$ anti-sense oligonucleotide" is an oligonucleotide having a sequence (a) capable of forming a stable triplex with a portion of the $\text{Fkh}^{sf}$ gene, or (b) capable of forming a stable duplex with a portion of an mRNA transcript of the $\text{Fkh}^{sf}$ gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

Abbreviations: YAC, yeast artificial chromosome; PCR, polymerase chain reaction; RT-PCR, PCR process in which RNA is first transcribed into DNA at the first step using reverse transcriptase (RT); cDNA, any DNA made by copying an RNA sequence into DNA form. As utilized herein "$\text{Fkh}^{sf}$" refers to the gene product of the $\text{Fkh}^{sf}$ gene (irrespective of whether the gene is obtained from humans, mammals, or any other warm-blooded animal). When capitalized "$\text{FKH}^{sf}$" the gene product (and gene) should be understood to be derived from humans.

As noted above, the present invention relates generally to pharmaceutical products and methods and, more specifically, to methods and compositions useful for diagnosing scurfy-related diseases, as well as methods for identifying compounds which can modulate the immune system.

Thus, as discussed in more detail below this discovery has led to the development of assays which may be utilized to select molecules which can act as agonists, or alternatively, antagonists of the immune system. Furthermore, such assays may be utilized to identify other genes and gene products which are likewise active in modulating the immune system.

Scurfy

Briefly, the present invention is based upon the unexpected discovery that a mutation in the gene which encodes $\text{Fkh}^{sf}$ results in rare condition (scurfy) characterized by a progressive lymphocytic infiltration of the lymph nodes, spleen, liver and skin resulting in gross morphological symptoms which include splenomegaly, hepatomegaly, greatly enlarged lymph nodes, runting, exfoliative dermatitis, and thickened malformed ears (Godfrey et al., *Amer. J. Pathol.* 138:1379, 1991; Godfrey et al., *Proc. Natl. Acad. Sci. USA* 88:5528, 1991). This new member of the winged-helix family represents a novel component of the immune system.

Methods which were utilized to discover the gene responsible for scurfy are provided below in Example 1. Methods for cloning the gene responsible for murine scurfy, as well as the human ortholog, are provided below in Examples 2 and 3. Methods for confirmation of gene identity and correlation with gene function, as determined using transgenic mice, are also provided in the Examples.

Also provided by the present invention are methods for determining the presence of $\text{Fkh}^{sf}$ genes and gene products. Within one embodiment, such methods comprise the general steps of (a) contacting a $\text{Fkh}^{sf}$ specific nucleic acid probe under hybridizing conditions with either (i) test nucleic acid molecules isolated from the biological sample, or (ii) nucleic acid molecules synthesized from RNA molecules, wherein the probe recognizes at least a portion of an $\text{Fkh}^{sf}$ nucleotide sequence, and (b) detecting the formation of hybrids of said nucleic acid probe and (i) or (ii). A variety of methods may be utilized in order to amplify a selected sequence, including, for example, RNA amplification (see Lizardi et al., *Bio/Technology* 6:1197-1202, 1988; Kramer et al., *Nature* 339:401-02, 1989; Lomeli et al., *Clinical Chem.* 35(9):1826-31, 1989; U.S. Pat. No. 4,786,600), and nucleic acid amplification utilizing Polymerase Chain Reaction ("PCR") (see U.S. Pat. Nos. 4,683,195, 4,683,202, and 4,800,159), reverse-transcriptase-PCR and CPT (see U.S. Pat. Nos. 4,876,187, and 5,011,769).

Alternatively, antibodies may be utilized to detect the presence of $\text{Fkh}^{sf}$ gene products. More specifically, within one embodiment methods are provided for detecting the presence of an $\text{Fkh}^{sf}$ peptide, or a mutant form thereof, in a biological sample, comprising the steps of (a) contacting a biological sample with an anti-$\text{Fkh}^{sf}$ antibody or an antibody fragment, wherein said contacting is performed under conditions that allow the binding of said antibody or antibody fragment to the biological sample, and (b) detecting any of the bound antibody or bound antibody fragment.

Such methods may be accomplished in a wide variety of assay formats including, for example, Countercurrent Immuno-Electrophoresis (CIEP), Radioimmunoassays, Radioimmunoprecipitations, Enzyme-Linked ImmunoSorbent Assays (ELISA), Dot Blot assays, Inhibition or Competition assays, and sandwich assays (see U.S. Pat. Nos. 4,376,110 and 4,486,530; see also *Antibodies: A Laboratory Manual,* supra).

Nucleic Acid Molecules, Proteins, and Methods of Producing Proteins

Although various $\text{FKH}^{sf}$ or $\text{Fkh}^{sf}$ proteins and nucleic acid molecules (or portions thereof) have been provided herein, it should be understood that within the context of the present invention, reference to one or more of these proteins should be understood to include proteins of a substantially similar activity. As used herein, proteins are deemed to be "substantially similar" if: (a) they are encoded by a nucleotide sequence which is derived from the coding region of a gene which encodes the protein (including, for example, portions of the sequence or allelic variations of the sequence); (b) the nucleotide sequence is capable of hybridization to nucleotide sequences of the present invention under moderate, high or very high stringency (see Sambrook et al., *Molecular Cloning: A Laboratory Manual,* 2d ed., Cold Spring Harbor Laboratory Press, N.Y., 1989), or has at least 50%, 60%, 70%, 75%, 80%, 90%, 95%, or greater homology to the sequences disclosed herein, or, (c) the DNA sequences are degenerate as a result of the genetic code to the DNA sequences defined in (a) or (b). Further, the nucleic acid molecule disclosed herein includes both complementary and non-complementary sequences, provided the sequences otherwise meet the criteria set forth herein. Within the context of the present invention, high stringency means standard hybridization conditions (e.g., 5×SSPE, 0.5% SDS at 65° C., or the equivalent). For purpose of hybridization, nucleic acid molecules which encode the amino-terminal domain, zinc finger domain, middle domain, or forkhead domain (see Example 10) may be utilized.

The structure of the proteins encoded by the nucleic acid molecules described herein may be predicted from the primary translation products using the hydrophobicity plot function of, for example, P/C Gene or Intelligenetics Suite (Intelligenetics, Mountain View, Calif.), or according to the methods described by Kyte and Doolittle (*J. Mol. Biol.* 157: 105-32, 1982).

Proteins of the present invention may be prepared in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance or decrease the biological activity of the mutant or wild-type protein. Moreover, due to degeneracy in the genetic code, for example, there may be considerable variation in nucleotide sequences encoding the same amino acid sequence.

Other derivatives of the proteins disclosed herein include conjugates of the proteins along with other proteins or polypeptides. This may be accomplished, for example, by the synthesis of N-terminal or C-terminal fusion proteins which may be added to facilitate purification or identification of proteins (see U.S. Pat. No. 4,851,341, see also, Hopp et al., *Bio/Technology* 6:1204, 1988.) Alternatively, fusion proteins (e.g., FKH or Fkh-luciferase or FKH or Fkh-GFP) may be constructed in order to assist in the identification, expression, and analysis of the protein.

Proteins of the present invention may be constructed using a wide variety of techniques described herein. Further, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); and Sambrook et al. (supra). Deletion or truncation derivatives of proteins (e.g., a soluble extracellular portion) may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al. (*Molecular Cloning: A Laboratory Manual*, 2d ed., Cold Spring Harbor Laboratory Press, 1989).

Mutations which are made in the nucleic acid molecules of the present invention preferably preserve the reading frame of the coding sequences. Furthermore, the mutations will preferably not create complementary regions that could hybridize to produce secondary mRNA structures, such as loops or hairpins, that would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for indicative biological activity. Alternatively, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion. Mutations may be introduced for purpose of preserving or increasing activity of the protein, or, for decreasing or disabling the protein (e.g., mutant Fkh).

Nucleic acid molecules which encode proteins of the present invention may also be constructed utilizing techniques of PCR mutagenesis, chemical mutagenesis (Drinkwater and Klinedinst, *PNAS* 83:3402-06, 1986), by forced nucleotide misincorporation (e.g., Liao and Wise *Gene* 88:107-11, 1990), or by use of randomly mutagenized oligonucleotides (Horwitz et al., *Genome* 3:112-17, 1989).

The present invention also provides for the manipulation and expression of the above described genes by culturing host cells containing a vector capable of expressing the above-described genes. Such vectors or vector constructs include either synthetic or cDNA-derived nucleic acid molecules encoding the desired protein, which are operably linked to suitable transcriptional or translational regulatory elements. Suitable regulatory elements may be derived from a variety of sources, including bacterial, fungal, viral, mammalian, insect, or plant genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, a transcriptional terminator, and a ribosomal binding sequence, including a translation initiation signal.

Nucleic acid molecules that encode any of the proteins described above may be readily expressed by a wide variety of prokaryotic and eukaryotic host cells, including bacterial, mammalian, yeast or other fungi, viral, insect, or plant cells. Methods for transforming or transfecting such cells to express foreign DNA are well known in the art (see, e.g., Itakura et al., U.S. Pat. No. 4,704,362; Hinnen et al., *Proc. Natl. Acad. Sci. USA* 75:1929-33, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al., *Molecular Cloning: A Laboratory Manual*, 2nd ed., Cold Spring Harbor Laboratory Press, 1989; for plant cells see Czako and Marton, *Plant Physiol.* 104:1067-71, 1994; and Paszkowski et al., *Biotech.* 24:387-92, 1992).

Bacterial host cells suitable for carrying out the present invention include *E. coli, B. subtilis, Salmonella typhimurium*, and various species within the genera *Pseudomonas, Streptomyces*, and *Staphylococcus*, as well as many other bacterial species well known to one of ordinary skill in the art. Representative examples of bacterial host cells include DH5α (Stratagene, LaJolla, Calif.).

Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615, 1978), the T7 RNA polymerase promoter (Studier et al., *Meth. Enzymol.* 185:60-89, 1990), the lambda promoter (Elvin et al., *Gene* 87:123-26, 1990), the trp promoter (Nichols and Yanofsky, *Meth. in Enzymology* 101:155, 1983) and the tac promoter (Russell et al., *Gene* 20:231, 1982). Representative selectable markers include various antibiotic resistance markers such as the kanamycin or ampicillin resistance genes. Many plasmids suitable for transforming host cells are well known in the art, including among others, pBR322 (see Bolivar et al., *Gene* 2:95, 1977), the pUC plasmids pUC18, pUC19, pUC118, pUC119 (see Messing, *Meth. in Enzymology* 101:20-77, 1983 and Vieira and Messing, *Gene* 19:259-68, 1982), and pNH8A, pNH16a, pNH18a, and Bluescript M13 (Stratagene, La Jolla, Calif.).

Yeast and fungi host cells suitable for carrying out the present invention include, among others, *Saccharomyces pombe, Saccharomyces cerevisiae*, the genera *Pichia* or *Kluyveromyces* and various species of the genus *Aspergillus* (McKnight et al., U.S. Pat. No. 4,935,349). Suitable expression vectors for yeast and fungi include, among others, YCp50 (ATCC No. 37419) for yeast, and the amdS cloning vector pV3 (Turnbull, *Bio/Technology* 7:169, 1989), YRp7 (Struhl et al., *Proc. Natl. Acad. Sci. USA* 76:1035-39, 1978), YEp13 (Broach et al., *Gene* 8:121-33, 1979), pJDB249 and pJDB219 (Beggs, *Nature* 275:104-08, 1978) and derivatives thereof.

Preferred promoters for use in yeast include promoters from yeast glycolytic genes (Hitzeman et al., *J. Biol. Chem.* 255:12073-080, 1980; Alber and Kawasaki, *J. Mol. Appl. Genet* 1:419-34, 1982) or alcohol dehydrogenase genes (Young et al., Hollaender et al. (eds.), in *Genetic Engineering of Microorganisms for Chemicals*, Plenum, N.Y., 1982, p. 355; Ammerer, *Meth. Enzymol.* 101:192-201, 1983). Examples of useful promoters for fungi vectors include those derived from *Aspergillus nidulans* glycolytic genes, such as the adh3 promoter (McKnight et al., *EMBO J.* 4:2093-99, 1985). The expression units may also include a transcriptional terminator. An example of a suitable terminator is the adh3 terminator (McKnight et al., ibid., 1985).

As with bacterial vectors, the yeast vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include leu2 (Broach et al., ibid.), ura3 (Botstein et al., *Gene* 8:17, 1979), or his3 (Struhl et al., ibid.). Another suitable selectable marker is the cat gene, which confers chloramphenicol resistance on yeast cells.

Techniques for transforming fungi are well known in the literature, and have been described, for instance, by Beggs (ibid.), Hinnen et al. (*Proc. Natl. Acad. Sci. USA* 75:1929-33, 1978), Yelton et al. (*Proc. Natl. Acad. Sci. USA* 81:1740-47, 1984), and Russell (*Nature* 301:167-69, 1983). The genotype of the host cell may contain a genetic defect that is complemented by the selectable marker present on the expression vector. Choice of a particular host and selectable marker is well within the level of ordinary skill in the art.

Protocols for the transformation of yeast are also well known to those of ordinary skill in the art. For example, transformation may be readily accomplished either by preparation of spheroplasts of yeast with DNA (see Hinnen et al., *PNAS USA* 75:1929, 1978) or by treatment with alkaline salts such as LiCl (see Itoh et al., *J. Bacteriology* 153:163, 1983). Transformation of fungi may also be carried out using polyethylene glycol as described by Cullen et al. (*Bio/Technology* 5:369, 1987).

Viral vectors include those which comprise a promoter that directs the expression of an isolated nucleic acid molecule that encodes a desired protein as described above. A wide variety of promoters may be utilized within the context of the present invention, including for example, promoters such as MoMLV LTR, RSV LTR, Friend MuLV LTR, adenoviral promoter (Ohno et al., *Science* 265:781-84, 1994), neomycin phosphotransferase promoter/enhancer, late parvovirus promoter (Koering et al., *Hum. Gene Therap.* 5:457-63, 1994), Herpes TK promoter, SV40 promoter, metallothionein IIa gene enhancer/promoter, cytomegalovirus immediate early promoter, and the cytomegalovirus immediate late promoter. Within particularly preferred embodiments of the invention, the promoter is a tissue-specific promoter (see e.g., WO 91/02805; EP 0,415,731; and WO 90/07936). Representative examples of suitable tissue specific promoters include neural specific enolase promoter, platelet derived growth factor beta promoter, human alphal -chimaerin promoter, synapsin I promoter and synapsin II promoter. In addition to the above-noted promoters, other viral-specific promoters (e.g., retroviral promoters (including those noted above, as well as others such as HIV promoters), hepatitis, herpes (e.g., EBV), and bacterial, fungal or parasitic (e.g., malarial) -specific promoters may be utilized in order to target a specific cell or tissue which is infected with a virus, bacteria, fungus or parasite.

Mammalian cells suitable for carrying out the present invention include, among others: PC12 (ATCC No. CRL1721), N1E-115 neuroblastoma, SK-N-BE(2)C neuroblastoma, SHSY5 adrenergic neuroblastoma, NS20Y and NG108-15 murine cholinergic cell lines, or rat F2 dorsal root ganglion line, COS (e.g., ATCC No. CRL 1650 or 1651), BHK (e.g., ATCC No. CRL 6281; BHK 570 cell line (deposited with the American Type Culture Collection under accession number CRL 10314)), CHO (ATCC No. CCL 61), HeLa (e.g., ATCC No. CCL 2), 293 (ATCC No. 1573; Graham et al., *J. Gen. Virol.* 36:59-72, 1977) and NS-1 cells. Other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1), SP2/0-Ag14 (ATCC No. 1581), HIT-T15 (ATCC No. CRL 1777), Jurkat (ATCC No. Tib 152) and RINm 5AHT$_2$B (Orskov and Nielson, *FEBS* 229(1):175-178, 1988).

Mammalian expression vectors for use in carrying out the present invention will include a promoter capable of directing the transcription of a cloned gene or cDNA. Preferred promoters include viral promoters and cellular promoters. Viral promoters include the cytomegalovirus immediate early promoter (Boshart et al., *Cell* 41:521-30, 1985), cytomegalovirus immediate late promoter, SV40 promoter (Subramani et al., *Mol. Cell. Biol.* 1:854-64, 1981), MMTV LTR, RSV LTR, metallothionein-1, adenovirus E1a. Cellular promoters include the mouse metallothionein-1 promoter (Palmiter et al., U.S. Pat. No. 4,579,821), a mouse $V_K$ promoter (Bergman et al., *Proc. Natl. Acad. Sci. USA* 81:7041-45, 1983; Grant et al., *Nuc. Acids Res.* 15:5496, 1987) and a mouse $V_H$ promoter (Loh et al., *Cell* 33:85-93, 1983). The choice of promoter will depend, at least in part, upon the level of expression desired or the recipient cell line to be transfected.

Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719-30, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer. Expression vectors may also include sequences encoding the adenovirus VA RNAs. Suitable expression vectors can be obtained from commercial sources (e.g., Stratagene, La Jolla, Calif.).

Vector constructs comprising cloned DNA sequences can be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841-45, 1982), or DEAE-dextran mediated transfection (Ausubel et al. (eds.), *Current Protocols in Molecular Biology*, John Wiley and Sons, Inc., N.Y., 1987). To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. Other selectable markers include fluorescent proteins such as GFP (green fluorescent protein) or BFP (blue fluorescent protein). The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass.).

Mammalian cells containing a suitable vector are allowed to grow for a period of time, typically 1-2 days, to begin expressing the DNA sequence(s) of interest. Drug selection is then applied to select for growth of cells that are expressing the selectable marker in a stable fashion. For cells that have been transfected with an amplifiable, selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production. Cells may also be selected for transfection based on their expression of GFP by sorting for GFP-positive cells using a flow cytometer.

Protocols for the transfection of mammalian cells are well known to those of ordinary skill in the art. Representative methods include calcium phosphate mediated transfection, electroporation, lipofection, retroviral, adenoviral and protoplast fusion-mediated transfection (see Sambrook et al., supra). Naked vector constructs can also be taken up by muscle cells or other suitable cells subsequent to injection into the muscle of a mammal (or other animals).

Numerous insect host cells known in the art can also be useful within the present invention, in light of the subject specification. For example, the use of baculoviruses as vectors for expressing heterologous DNA sequences in insect cells has been reviewed by Atkinson et al. (*Pestic. Sci.* 28:215-24, 1990).

Numerous plant host cells known in the art can also be useful within the present invention, in light of the subject specification. For example, the use of *Agrobacterium rhizogenes* as vectors for expressing genes in plant cells has been reviewed by Sinkar et al. (*J. Biosci.* (*Bangalore*) 11:47-58, 1987).

Within related aspects of the present invention, proteins of the present invention, may be expressed in a transgenic animal whose germ cells and somatic cells contain a gene which encodes the desired protein and which is operably linked to a promoter effective for the expression of the gene. Alternatively, in a similar manner transgenic animals may be prepared that lack the desired gene (e.g., "knockout" mice). Such transgenics may be prepared in a variety non-human animals, including mice, rats, rabbits, sheep, dogs, goats and pigs (see Hammer et al., *Nature* 315:680-83, 1985, Palmiter et al., *Science* 222:809-14, 1983, Brinster et al., *Proc. Natl. Acad. Sci. USA* 82:4438-42, 1985, Palmiter and Brinster, *Cell* 41:343-45, 1985, and U.S. Pat. Nos. 5,175,383, 5,087,571, 4,736,866, 5,387,742, 5,347,075, 5,221,778, and 5,175,384). Briefly, an expression vector, including a nucleic acid molecule to be expressed together with appropriately positioned expression control sequences, is introduced into pronuclei of fertilized eggs, for example, by microinjection. Integration of the injected DNA is detected by blot analysis of DNA from tissue samples. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., 1983, ibid), which allows regulated expression of the transgene.

Animals which produce mutant forms of Fkh$^{sf}$ other than the naturally occurring scurfy mutant ("sf"), or in genetic backgrounds different from the naturally occurring mutant, may be readily produced given the disclosure provided herein.

Proteins can be isolated by, among other methods, culturing suitable host and vector systems to produce the recombinant translation products of the present invention. Supernatants from such cell lines, or protein inclusions or whole cells where the protein is not excreted into the supernatant, can then be treated by a variety of purification procedures in order to isolate the desired proteins. For example, the supernatant may be first concentrated using commercially available protein concentration filters, such as an Amicon or Millipore Pellicon ultrafiltration unit. Following concentration, the concentrate may be applied to a suitable purification matrix such as, for example, an anti-protein antibody bound to a suitable support. Alternatively, anion or cation exchange resins may be employed in order to purify the protein. As a further alternative, one or more reverse-phase high performance liquid chromatography (RP-HPLC) steps may be employed to further purify the protein. Other methods of isolating the proteins of the present invention are well known in the skill of the art.

A protein is deemed to be "isolated" within the context of the present invention if no other (undesired) protein is detected pursuant to SDS-PAGE analysis followed by Coomassie blue staining. Within other embodiments, the desired protein can be isolated such that no other (undesired) protein is detected pursuant to SDS-PAGE analysis followed by silver staining.

Assays for Selecting Molecules Which Modulate the Immune System

As noted above, the present invention provides methods for selecting and/or isolating molecules which are capable of modulating the immune system. Representative examples of suitable assays include the yeast and mammalian 2-hybrid systems (e.g., Dang et al., *Mol. Cell. Biol.* 11:954, 1991; Fearon et al., *Proc. Natl. Acad. Sci. USA* 89:7958, 1992), DNA binding assays, antisense assays, traditional protein binding assays (e.g., utilizing $^{125}$I or time-resolved fluorescence), immunoprecipitation coupled with gel electrophoresis and direct protein sequencing, transcriptional analysis of Fkh$^{sf}$ regulated genes, cytokine production and proliferation assays.

For example, within one embodiment proteins that directly interact with Fkh$^{sf}$ can be detected by an assay such as a yeast 2-hybrid binding system (see, e.g., U.S. Pat. Nos. 5,283,173, 5,468,614, 5,610,015, and 5,667,973). Briefly, in a two-hybrid system, a fusion of a DNA-binding domain- Fkh$^{sf}$ protein (e.g., GAL4- Fkh$^{sf}$ fusion) is constructed and transfected into a cell containing a GAL4 binding site linked to a selectable marker gene. The whole Fkh$^{sf}$ protein or subregions of Fkh$^{sf}$ may be used. A library of cDNAs fused to the GAL4 activation domain is also constructed and co-transfected. When the cDNA in the cDNA-GAL4 activation domain fusion encodes a protein that interacts with Fkh$^{sf}$, the selectable marker is expressed. Cells containing the cDNA are then grown, the construct isolated and characterized. Other assays may also be used to identify interacting proteins. Such assays include ELISA, Western blotting, co-immunoprecipitations, in vitro transcription/translation analysis and the like.

Within another aspect of the present invention, methods are provided for determining whether a selected molecule is capable of modulating the immune system, comprising the steps of (a) exposing a selected candidate molecule to cells which express Fkh$^{sf}$, or, mutant Fkh$^{sf}$, and (b) determining whether the molecule modulates the activity of Fkh$^{sf}$, and thereby determining whether said molecule can modulate the immune system. Cells for such tests may derive from (a) normal lymphocytes, (b) cell lines engineered to overexpress the FKH$^{sf}$ (or Fkh$^{sf}$) protein (or mutant forms thereof) or (c) transgenic animals engineered to express said protein. Cells from such transgenic mice are characterized, in part, by a hyporesponsive state including diminished cell number and a decreased responsiveness to various stimuli (e.g., Example 8).

It should be noted that while the methods recited herein may refer to the analysis of an individual test molecule, that the present invention should not be so limited. In particular, the selected molecule may be contained within a mixture of compounds. Hence, the recited methods may further comprise the step of isolating the desired molecule. Furthermore, it should be understood that candidate molecules can be assessed for their ability to modulate the immune system by a number of parameters, including for example, T-cell proliferation, cytokine production, and the like.

Candidate Molecules

A wide variety of molecules may be assayed for their ability to modulate the immune system. Representative examples which are discussed in more detail below include organic molecules, proteins or peptides, and nucleic acid molecules.

1. Organic Molecules

Numerous organic molecules may be assayed for their ability to modulate the immune system. For example, within one embodiment of the invention suitable organic molecules may be selected either from a chemical library, wherein chemicals are assayed individually, or from combinatorial chemical libraries where multiple compounds are assayed at once, then deconvoluted to determine and isolate the most active compounds.

Representative examples of such combinatorial chemical libraries include those described by Agrafiotis et al., "System and method of automatically generating chemical compounds with desired properties," U.S. Pat. No. 5,463,564; Armstrong, R. W., "Synthesis of combinatorial arrays of organic compounds through the use of multiple component combinatorial array syntheses," WO 95/02566; Baldwin, J. J. et al., "Sulfonamide derivatives and their use," WO 95/24186; Baldwin, J. J. et al., "Combinatorial dihydrobenzopyran library," WO 95/30642; Brenner, S., "New kit for preparing combinatorial libraries," WO 95/16918; Chenera, B. et al., "Preparation of library of resin-bound aromatic carbocyclic compounds," WO 95/16712; Ellman, J. A., "Solid phase and combinatorial synthesis of benzodiazepine compounds on a solid support," U.S. Pat. No. 5,288,514; Felder, E. et al., "Novel combinatorial compound libraries," WO 95/16209; Lerner, R. et al., "Encoded combinatorial chemical libraries," WO 93/20242; Pavia, M. R. et al., "A method for preparing and selecting pharmaceutically useful non-peptide compounds from a structurally diverse universal library," WO 95/04277; Summerton, J. E. and D. D. Weller, "Morpholino-subunit combinatorial library and method," U.S. Pat. No. 5,506,337; Holmes, C., "Methods for the Solid Phase Synthesis of Thiazolidinones, Metathiazanones, and Derivatives thereof," WO 96/00148; Phillips, G. B. and G. P. Wei, "Solid-phase Synthesis of Benzimidazoles," *Tet. Letters* 37:4887-90, 1996; Ruhland, B. et al., "Solid-supported Combinatorial Synthesis of Structurally Diverse β-Lactams," *J. Amer. Chem. Soc.* 111:253-54, 1996; Look, G. C. et al., "The Indentification of Cyclooxygenase-1 Inhibitors from 4-Thiazolidinone Combinatorial Libraries," *Bioorg and Med. Chem. Letters* 6:707-12, 1996.

2. Proteins and Peptides

A wide range of proteins and peptides make likewise be utilized as candidate molecules for modulating the immune system.

a. Combinatorial Peptide Libraries

Peptide molecules which modulate the immune system may be obtained through the screening of combinatorial peptide libraries. Such libraries may either be prepared by one of skill in the art (see, e.g., U.S. Pat. Nos. 4,528,266 and 4,359,535, and Patent Cooperation Treaty Publication Nos. WO 92/15679, WO 92/15677, WO 90/07862, WO 90/02809), or purchased from commercially available sources (e.g., New England Biolabs™ Phage Display Peptide Library Kit).

b. Antibodies

Antibodies which modulate the immune system may readily be prepared given the disclosure provided herein. Within the context of the present invention, antibodies are understood to include monoclonal antibodies, polyclonal antibodies, anti-idiotypic antibodies, antibody fragments (e.g., Fab, and F(ab')$_2$, F$_V$ variable regions, or complementarity determining regions). As discussed above, antibodies are understood to be specific against Fkh$^{sf}$ if they bind with a K$_a$ of greater than or equal to $10^7$M, preferably greater than of equal to $10^8$M. The affinity of a monoclonal antibody or binding partner, as well as inhibition of binding can be readily determined by one of ordinary skill in the art (see Scatchard, *Ann. N.Y. Acad. Sci.* 51:660-72, 1949).

Briefly, polyclonal antibodies may be readily generated by one of ordinary skill in the art from a variety of warm-blooded animals such as horses, cows, various fowl, rabbits, mice, or rats. Typically, Fkh$^{sf}$, or a unique peptide thereof of 13-20 amino acids (preferably conjugated to keyhole limpet hemocyanin by cross-linking with glutaraldehyde) is utilized to immunize the animal through intraperitoneal, intramuscular, intraocular, or subcutaneous injections, in conjunction with an adjuvant such as Freund's complete or incomplete adjuvant. Following several booster immunizations, samples of serum are collected and tested for reactivity to the protein or peptide. Particularly preferred polyclonal antisera will give a signal on one of these assays that is at least three times greater than background. Once the titer of the animal has reached a plateau in terms of its reactivity to the protein, larger quantities of antisera may be readily obtained either by weekly bleedings, or by exsanguinating the animal.

Monoclonal antibodies may also be readily generated using conventional techniques (see U.S. Pat. Nos. RE 32,011, 4,902,614, 4,543,439, and 4,411,993 which are incorporated herein by reference; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988).

Other techniques may also be utilized to construct monoclonal antibodies (see William D. Huse et al., "Generation of a Large Combinational Library of the Immunoglobulin Repertoire in Phage Lambda," *Science* 246:1275-81, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728-32, August 1989; see also Michelle Alting-Mees et al., "Monoclonal Antibody Expression Libraries: A Rapid Alternative to Hybridomas," *Strategies in Molecular Biology* 3:1-9, January 1990).

A wide variety of assays may be utilized to determine the presence of antibodies which are reactive against the $Fkh^{sf}$ (or the mutant forms of $Fkh^{sf}$ described herein), including for example countercurrent immuno-electrophoresis, radioimmunoassays, radioimmunoprecipitations, enzyme-linked immuno-sorbent assays (ELISA), dot blot assays, western blots, immunoprecipitation, Inhibition or Competition Assays, and sandwich assays (see U.S. Pat. Nos. 4,376,110 and 4,486,530; see also Harlow and Lane (eds.), *Antibodies: A Laboratory Manual*, Cold Spring Harbor Laboratory Press, 1988).

Once suitable antibodies have been obtained, they may be isolated or purified by many techniques well known to those of ordinary skill in the art (see Harlow and Lane (eds.), *Antibodies: A Laboratory Manual*, Cold Spring Harbor Laboratory Press, 1988). Suitable techniques include peptide or protein affinity columns, HPLC or RP-HPLC, purification on protein A or protein G columns, or any combination of these techniques.

Antibodies of the present invention may be utilized not only for modulating the immune system, but for diagnostic tests (e.g., to determine the presence of an $FKH^{sf}$ or $Fkh^{sf}$ protein or peptide), for therapeutic purpose, or for purification of proteins.

c. Mutant $Fkh^{sf}$

As described herein and below in the Examples, altered versions of $Fkh^{sf}$, may be utilized to inhibit the normal activity of $Fkh^{sf}$, thereby modulating the immune system (see generally, nucleic acid molecules and proteins above).

Further mutant or altered forms of $FKH^{sf}$ or $Fkh^{sf}$ may be utilized for a wide variety of in vitro assays (e.g., in order to examine the effect of such proteins in various models), or, for the development of antibodies.

3. Nucleic Acid Molecules

Within other aspects of the invention, nucleic acid molecules are provided which are capable of modulating the immune system. For example, within one embodiment antisense oligonucleotide molecules are provided which specifically inhibit expression of $FKH^{sf}$ or $Fkh^{sf}$ nucleic acid sequences, or, of mutant $FKH^{sf}$ or $Fkh^{sf}$ (see generally, Hirashima et al., in *Molecular Biology of RNA: New Perspectives* (M. Inouye and B. S. Dudock, eds., 1987 Academic Press, San Diego, p. 401); *Oligonucleotides: Antisense Inhibitors of Gene Expression* (J. S. Cohen, ed., 1989 MacMillan Press, London); Stein and Cheng, *Science* 261:1004-12, 1993; WO 95/10607; U.S. Pat. No. 5,359,051; WO 92/06693; and EP-A2-612844). Briefly, such molecules are constructed such that they are complementary to, and able to form Watson-Crick base pairs with, a region of transcribed $Fkh^{sf}$ mRNA sequence. The resultant double-stranded nucleic acid interferes with subsequent processing of the mRNA, thereby preventing protein synthesis.

Within other aspects of the invention, ribozymes are provided which are capable of inhibiting $FKH^{sf}$ or $Fkh^{sf}$, or mutant forms $FKH^{sf}$ or $Fkh^{sf}$. As used herein, "ribozymes" are intended to include RNA molecules that contain antisense sequences for specific recognition, and an RNA-cleaving enzymatic activity. The catalytic strand cleaves a specific site in a target RNA at greater than stoichiometric concentration. A wide variety of ribozymes may be utilized within the context of the present invention, including for example, the hammerhead ribozyme (for example, as described by Forster and Symons, *Cell* 48:211-20, 1987; Haseloff and Gerlach, *Nature* 328:596-600, 1988; Walbot and Bruening, *Nature* 334:196, 1988; Haseloff and Gerlach, *Nature* 334:585, 1988); the hairpin ribozyme (for example, as described by Haselhoff et al., U.S. Pat. No. 5,254,678, issued Oct. 19, 1993 and Hempel et al., European Patent Publication No. 0 360 257, published Mar. 26, 1990); and *Tetrahymena* ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates), or chimerics thereof (e.g., DNA/RNA/RNA).

4. Labels $FKH^{sf}$ or $Fkh^{sf}$, (as well as mutant forms thereof), or, any of the candidate molecules described above and below, may be labeled with a variety of compounds, including for example, fluorescent molecules, toxins, and radionuclides. Representative examples of fluorescent molecules include fluorescein, Phycobili proteins, such as phycoerythrin, rhodamine, Texas red and luciferase. Representative examples of toxins include ricin, abrin diphtheria toxin, cholera toxin, gelonin, pokeweed antiviral protein, tritin, Shigella toxin, and Pseudomonas exotoxin A. Representative examples of radionuclides include Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212. In addition, the antibodies described above may also be labeled or conjugated to one partner of a ligand binding pair. Representative examples include avidin-biotin, and riboflavin-riboflavin binding protein.

Methods for conjugating or labeling the molecules described herein with the representative labels set forth above may be readily accomplished by one of ordinary skill in the art (see Trichothecene Antibody Conjugate, U.S. Pat. No. 4,744,981; Antibody Conjugate, U.S. Pat. No. 5,106,951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, Jakoby and Wilchek (eds.), *Methods In Enzymology*, Vol. 34, *Affinity Techniques, Enzyme Purification: Part B*, Academic Press, New York, 1974, p. 30; see also Wilchek and Bayer, "The Avidin-Biotin Complex in Bioanalytical Applications," *Anal. Biochem.* 171:1-32, 1988).

Pharmaceutical Compositions

As noted above, the present invention also provides a variety of pharmaceutical compositions, comprising one of the above-described molecules which modulates the immune system, along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, the pharmaceutical composition (or, 'medicament') is provided in sterile, pyrogen-free form.

In addition, the pharmaceutical compositions of the present invention may be prepared for administration by a variety of different routes. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

Methods of Treatment

The present invention also provides methods for modulating the immune system. Through use of the molecules described herein which modulate the immune system, a wide variety of conditions in warm blooded animals may be readily treated or prevented. Examples of warm-blooded animals that may be treated include both vertebrates and mammals, including for example humans, horses, cows, pigs, sheep, dogs, cats, rats and mice. Such methods may have therapeutic value in patients with altered immune systems. This would include such patients as those undergoing chemotherapy of those with various immunodeficiency syndromes, as well as patients with a T cell mediated autoimmune disease. Therapeutic value may also be recognized from utility as a vaccine adjuvant.

Therapeutic molecules, depending on the type of molecule, may be administered via a variety of routes in a variety of formulations. For example, within one embodiment organic molecules may be delivered by oral or nasal routes, or by injection (e.g., intramuscularly, intravenously, and the like).

Within one aspect, methods are provided for modulating the immune system, comprising the step of introducing into lymphoid cells a vector which directs the expression of a molecule which modulates the immune system, and administering the vector containing cells to a warm-blooded animal. Within other related embodiments, the vector may be directly administered to a desired target location (e.g., the bone marrow).

A wide variety of vectors may be utilized for such therapeutic purposes, including both viral and non-viral vectors. Representative examples of suitable viral vectors include herpes viral vectors (e.g., U.S. Pat. No. 5,288,641), adenoviral vectors (e.g., WO 94/26914, WO 93/9191 WO 99/20778; WO 99/20773; WO 99/20779; Kolls et al., *PNAS* 91(1):215-19, 1994; Kass-Eisler et al., *PNAS* 90(24):11498-502, 1993; Guzman et al., *Circulation* 88(6):2838-48, 1993; Guzman et al., *Cir. Res.* 73(6):1202-07, 1993; Zabner et al., *Cell* 75(2): 207-16, 1993; Li et al., *Hum Gene Ther.* 4(4):403-09, 1993; Caillaud et al., *Eur. J. Neurosci.* 5(10):1287-91, 1993; Vincent et al., *Nat. Genet* 5(2):130-34, 1993; Jaffe et al., *Nat. Genet.* 1(5):372-78, 1992; and Levrero et al., *Gene* 101(2): 195-202, 1991), adeno-associated viral vectors (WO 95/13365; Flotte et al., *PNAS* 90(22):10613-617, 1993), baculovirus vectors, parvovirus vectors (Koering et al., *Hum.*

*Gene Therap.* 5:457-63, 1994), pox virus vectors (Panicali and Paoletti, *PNAS* 79:4927-31, 1982; and Ozaki et al., *Biochem. Biophys. Res. Comm.* 193(2):653-60, 1993), and retroviruses (e.g., EP 0,415,731; WO 90/07936; WO 91/0285, WO 94/03622; WO 93/25698; WO 93/25234; U.S. Pat. No. 5,219, 740; WO 93/11230; WO 93/10218). Viral vectors may likewise be constructed which contain a mixture of different elements (e.g., promoters, envelope sequences and the like) from different viruses, or non-viral sources. Within various embodiments, either the viral vector itself, or a viral particle which contains the viral vector may be utilized in the methods and compositions described below.

Within other embodiments of the invention, nucleic acid molecules which encode a molecule which modulates the immune system (e.g., a mutant $Fkh^{sf}$, or, an antisense or ribozyme molecule which cleaves $Fkh^{sf}$) may be administered by a variety of alternative techniques, including for example administration of asialoosomucoid (ASOR) conjugated with poly-L-lysine DNA complexes (Cristano et al., *PNAS* 92122-126, 1993), DNA linked to killed adenovirus (Curiel et al., *Hum. Gene Ther.* 3(2):147-54, 1992), cytofectin-mediated introduction (DMRIE-DOPE, Vical, Calif.), direct DNA injection (Acsadi et al., *Nature* 352:815-18, 1991); DNA ligand (Wu et al., *J. of Biol. Chem.* 264:16985-987, 1989); lipofection (Feigner et al., *Proc. Natl. Acad. Sci. USA* 84:7413-17, 1989); liposomes (Pickering et al., *Circ.* 89(1):13-21, 1994; and Wang et al., *PNAS* 84:7851-55, 1987); microprojectile bombardment (Williams et al., *PNAS* 88:2726-30, 1991); and direct delivery of nucleic acids which encode the protein itself either alone (Vile and Hart, *Cancer Res.* 53: 3860-64, 1993), or utilizing PEG-nucleic acid complexes.

Representative examples of molecules which may be expressed by the vectors of present invention include ribozymes and antisense molecules, each of which are discussed in more detail above.

As will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

The following examples are offered by way of illustration, and not by way of limitation.

EXAMPLES

Example 1

Identification of the Gene Responsible for the Scurfy Mutant

A. Cloning of a Scurfy Gene

The original scurfy mutation arose spontaneously in the partially inbred MR stock at Oak Ridge National Laboratory (ORNL) in 1949. Backcross analysis was used to fine map the peri-centromeric region of the X chromosome containing the mouse Scurfy mutation. A physical map covering the same region was generated concurrently through the isolation of overlapping yeast and bacterial artificial chromosomes (YACs and BACs). Once the candidate region was narrowed down to ~500 kilobase pairs (kb), large-scale DNA sequencing was performed on 4 overlapping BAC clones. All the transcription units in this 500 kb region were identified through a combination of sequence database searching and the application of computer exon prediction programs. Candidate genes were then screened for Scurfy-specific mutations by comparing the sequences of cDNAs obtained by the Reverse Transcription-Polymerase Chain Reaction (RT-PCR) procedure from normal and Scurfy-derived RNA samples. In one gene, referred to here as Fkh$^{sf}$, a two base pair (bp) insertion was found in the coding region of the Scurfy cDNA, relative to the normal cDNA. The insertion was confirmed by comparing the DNA sequences of PCR products derived from the genomic DNA of several mouse strains, including the Scurfy mutant. Again, the two bp insertion was found only in the Scurfy sample, establishing this as the probable cause of the Scurfy defect.

The mouse Fkh$^{sf}$ gene is contained within the BAC clone 8C22, and has been completely sequenced. It spans ~14 kb and contains 11 coding exons. The locations of exon breaks were initially identified by computer analysis of the genomic DNA sequence, using the GenScan exon prediction program; exon locations were then confirmed by direct comparison of cDNA sequences derived from normal mouse tissues to the genomic sequence.

The length of cDNA obtained is 2160 bp; the coding region spans 1287 bp of that, encoding a protein of 429 amino acids. FIG. 1 shows the nucleotide sequence of the mouse Fkh$^{sf}$ cDNA; translation is predicted to initiate at position 259 and terminate at position 1546. FIG. 2 shows the amino acid sequence of mouse Fkh$^{sf}$.

B. Generation of Fkh$^{sf}$ Transgenic Mice

The identity of the Fkh$^{sf}$ gene as the true cause of the Scurfy phenotype was confirmed in transgenic mice. Briefly, a 30 kb fragment of the normal genomic DNA, including the ~7 kb coding region of the Fkh$^{sf}$ gene, as well as ~20 kb of upstream flanking sequences and ~4 kb of downstream sequences (FIG. 5) was microinjected into normal mouse one-cell embryos. Five individual founder animals were generated, each with distinct integrations, and a male animal from each transgenic line was crossed to a female sf carriers. Male offspring carrying both the transgene (normal Fkh$^{sf}$) and sf mutation (mutant Fkh$^{sf}$) were analyzed.

Figure 6:
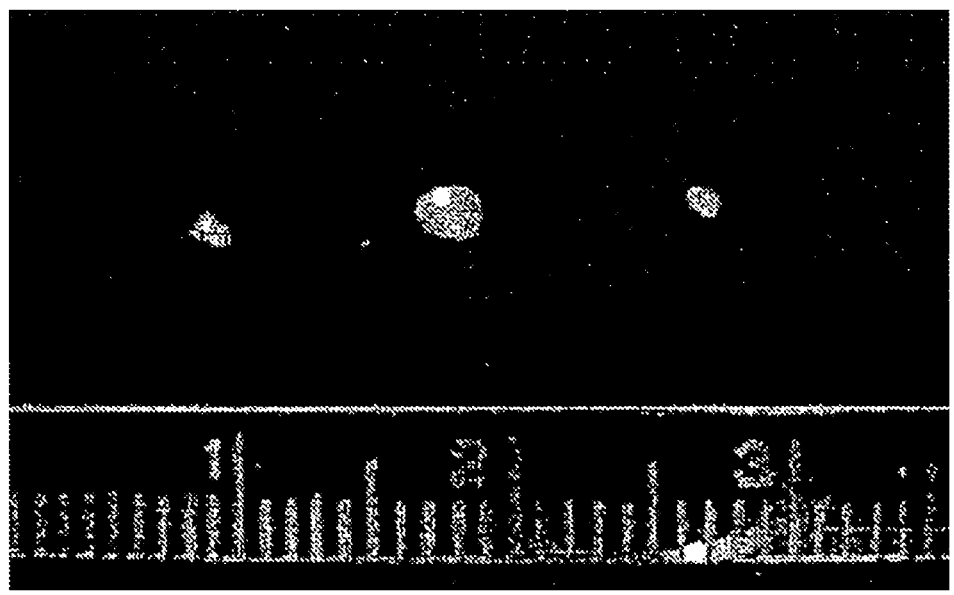
FIG. 6 is a photograph which demonstrates that the FKH$^{sf}$ transgene corrects the defect in scurfy animals.

Analysis consisted of examination of animals for runting, scaly skin, fur abnormalities and other hallmarks of the scurfy phenotype. In addition, lymphoid tissues (thymus, spleen and nodes) were harvested and their size and cell number examined and compared to both normal animals as well as scurfy mice. For all five transgenic lines, male sf progeny that carried the transgene were normal in size and weight and appeared healthy in all respects. Lymph node size in these transgenic mice was similar to (or smaller than) that of normal animals (FIG. 6) and there was no sign of activated T cells. These parameters are extremely different from sf mice and indicate that addition of the normal Fkh$^{sf}$ gene can overcome the defect found in scurfy mice, thus confirming that the mutation in the Fkh$^{sf}$ gene is the cause of Scurfy disease.

Example 2

Generation of FKH$^{sf}$ cDNA

A complementary DNA (cDNA) encoding the complete mouse Fkh$^{sf}$ protein may be obtained by a reverse-transcriptase polymerase chain reaction (RT-PCR) procedure. More specifically, first-strand cDNA is generated by oligo dT priming 5 ug of total RNA from a suitable source (eg., mouse spleen) and extending with reverse transcriptase under standard conditions (eg., Gibco/BRL SuperScript kit). An aliquot of the first-strand cDNA is then subjected to 35 cycles of PCR (94° C. for 30 sec, 63° C. for 30 sec, 72° C. for 2 min) in the presence of the forward and reverse primers (Forward primer: GCAGATCTCC TGACTCTGCC TTC; Reverse primer: GCAGATCTGA CAAGCTGTGT CTG) (0.2 mM final concentration), 60 mM Tris-HCl, 15 mM ammonium sulfate, 1.5 mM magnesium chloride, 0.2 mM each dNTP and 1 unit of Taq polymerase.

Example 3

Generation of the Human Ortholog to Murine FKH$^{sf}$

A human FKH$^{sf}$ cDNA encoding the complete FKH$^{sf}$ protein may be obtained by essentially the same procedure as described in Example 2. In particular, starting with total spleen RNA, and utilizing the following oligonucleotide primers (Forward primer: AGCCTGCCCT TGGACAAGGA C; Reverse primer: GCAAGACAGT GGAAACCTCA C), and the same PCR conditions outlined above, except with a 60° C. annealing temperature.

FIG. 3 shows the nucleotide sequence of the 1869 bp cDNA obtained to date (including an 1293 bp coding region); translation is predicted to initiate at position 189 and terminate at position 1482. FIG. 4 shows the sequence of the 431 amino acid human FKH$^{sf}$ protein. Comparison of the predicted coding region of the human gene to the mouse cDNA sequence reveals nearly identical exon structure and 86.1% amino acid sequence identity across the entire protein.

Example 4

Methods for Detecting Scurfy Mutations

As noted above, the Scurfy mutation was originally discovered by directly sequencing cDNAs derived by RT-PCR of sf and normal mouse RNA samples, and confirmed by sequencing the same region from genomic DNA. The nature of the mutation (i.e., a 2 bp insertion) lends itself to a number of different mutation detection assays. The first is based on differential hybridization of oligonucleotide probes. Such a hybridization-based assay could allow quantitative analysis of allele-specific expression.

As an example, a 360 bp DNA fragment is amplified from 1$^{st}$ strand cDNA using the following oligos:

```
DM05985 (forward): CTACCCACTGCTGGCAAATG      (ntd. 825-844 of FIG. 1)

DM06724 (reverse): GAAGGAACTATTGCCATGGCTTC   (ntd. 1221-1199)
```

The PCR products are run on an 1.8% agarose gel, transferred to nylon membrane and probed with end-labeled oligonucleotides that are complementary to the region corresponding to the site of the Scurfy-specific 2 bp insertion. Two separate hybridization reactions are performed to detect the normal and Scurfy PCR products, using the oligonucleotides below (the site of the 2 bp insertion is shown in bold):

```
Normal:   ATGCAGCAAGAGCTCTTGTCCATTGAGG     DM07439

Scurfy:   GCAGCAAGAGCTCTTTTGTCCATTGAGG     DM06919
```

The Scurfy mutation can also be detected by a cold Single-Strand Conformation Polymorphism (cSSCP) assay. In this assay, the same PCR products described above are run on 20% acrylamide (TBE) gels after strand denaturation. The Scurfy insertion causes a shift in strand mobility, relative to the normal sequence, and the separate strands are detected after staining with ethidium bromide.

Example 5

FKH$^{sf}$ Gene Expression

Semi-quantitative RT-PCR has been used to analyze the pattern of mouse and human Fkh$^{sf}$ gene expression in a wide variety of tissues and cell lines. Levels of expression are normalized to the ubiquitously expressed DAD-1 gene. In short, the Fkh$^{sf}$ gene is expressed, albeit at very low levels, in nearly every tissue examined thus far, including thymus, spleen, sorted CD4+ and CD4-CD8– T-lymphocytes, as well as kidney, brain, and various mouse and human T-cell lines and human tumors. Absence of expression, however, was noted in freshly sorted mouse B-cells.

As expected, no differences in level of expression were observed in normal vs. Scurfy tissues in the RT-PCR assays.

Example 6

In Vitro Expression of FKH$^{SF}$

Full-length mouse and human Fkh$^{sf}$ cDNAs, as well as various sub-regions of the cDNAs are cloned into vectors which allow expression in mammalian cells (such as the human Jurkat T-cell line), E. coli or yeast. The E. coli or yeast systems can be used for production of protein for the purpose of raising Fkh$^{sf}$-specific antibodies (see below).

Example 7

Generation of Anti-FKH$^{sf}$ Antibodies

Protein expressed from vectors described in Example 6 are used to immunize appropriate animals for the production of FKH$^{sf}$ specific antibodies. Either full length or truncated proteins can be used for this purpose. Protein can be obtained, for example, from bacteria such as E. coli, insect cells or mammalian cells. Animal species can include mouse, rabbit, guinea pig, chicken or other. Rabbit antisera specific for FKH$^{sf}$ has been generated, as determined by biochemical characterization (immunoprecipitation and western blotting).

Example 8

Assay for Function of an FKH$^{SF}$ Gene

Since loss of function of the FKH$^{sf}$ protein results in the phenotype observed in scurfy animals (wasting, hyperactive immune responsiveness and death), assays are described for assessing excessive expression of the FKH$^{sf}$ protein. Transgenic animals (described in Example 1) are examined for their state of immune competence, using several different parameters. Animals are examined for the number of lymphoid cells present in lymph nodes and thymus (FIG. 7) as well as the responsiveness of T cells to in vitro stimulation (FIG. 8).

Scurfy mutant animals have roughly twice as many cells in their lymph nodes as normal animals, whereas mice which express excess levels of the normal FKH$^{sf}$ protein contain roughly one-third as many cells (FIG. 7). Further, the number of thymocytes is normal (FIG. 7) as is their cell surface phenotype as assessed by flow cytometry using standard antisera (not shown), indicating that there is no developmental defect associated with excess FKH$^{sf}$ protein.

Normal, scurfy and transgenic animals are further examined for their proliferative responses to T cell stimulation. CD4+ T cells are reacted with antibodies to CD3 and CD28 and their proliferative response measured using radioactive thymidine incorporation. Whereas only scurfy cells divide in the absence of stimulation, normal cells respond well following stimulation. FKH$^{sf}$ transgenic cells also respond to stimulation, however the response is significantly less than that of normal cells (FIG. 8). This indicates that CD4+ T cells that express excess FKH$^{sf}$ have a diminished capacity to respond to stimuli.

Example 9

Human FKH$^{sf}$ cDNA Sequence is Related to JM2

Figure 9:
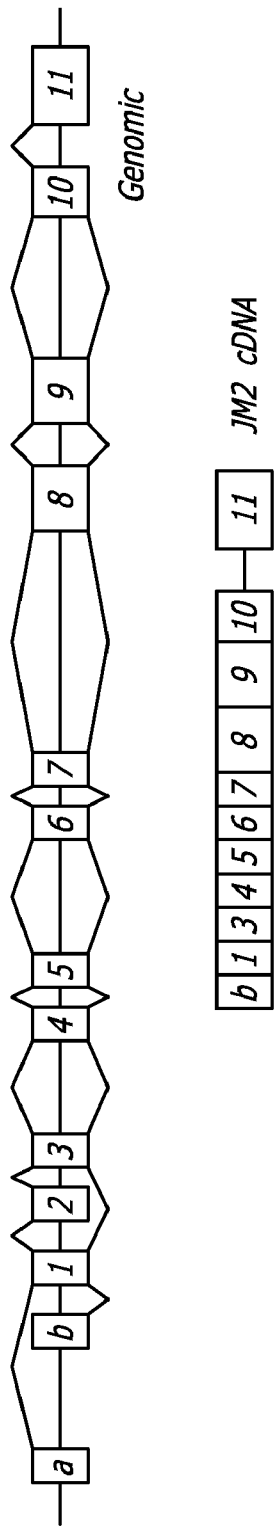
FIG. 9 is a comparison of FKH$^{sf}$ and JM2 cDNAs.

A modified version of the human FKH$^{sf}$ cDNA sequence exists in the GenBank public sequence database. This sequence is called JM2 (GenBank acc. #AJ005891), and is the result of the application of exon prediction programs to the genomic sequence containing the FKH$^{sf}$ gene (Strom, T. M. et al., unpublished—see GenBank acc. #AJ005891). In contrast, the structure of the FKH$^{sf}$ cDNA was determined experimentally. The GAP program of the Genetics Computer Group (GCG; Madison, USA) Wisconsin sequence analysis package was used to compare the two sequences, and the differences are illustrated in FIG. 9. The 5' ends of the two sequences differ in their location within the context of the genomic DNA sequence, the second coding exon of FKH$^{sf}$ is omitted from JM2, and the last intron of the FKH$^{sf}$ gene is unspliced in the JM2 sequence. These differences result in a JM2 protein with a shorter amino-terminal domain, relative to FKH$^{sf}$, and a large insertion within the forkhead domain (see below) at the carboxy-terminus.

Example 10

The FKH$^{sf}$ Protein is Conserved Across Species

The FKH$^{sf}$ protein can be divided into sub-regions, based on sequence motifs that may indicate functional domains. The two principal motifs in FKH$^{sf}$ are the single zinc finger (ZNF) of the $C_2H_2$ class in the middle portion of the protein, and the forkhead, or winged-helix domain at the extreme carboxy-terminus of the protein. For the purposes of characterizing the degree of homology between FKH$^{sf}$ and other proteins, we have split the protein up into four regions:

Amino-terminal domain: residues 1-197 of FIG. 2 residues 1-198 of FIG. 4

Zinc finger domain: residues 198-221 of FIG. 2 residues 199-222 of FIG. 4

Middle domain: residues 222-336 of FIG. 2 residues 223-336 of FIG. 4

Forkhead domain: residues 337-429 of FIG. 2 residues 337-431 of FIG. 4

Using the Multiple Sequence Alignment program from the DNAStar sequence analysis package, the Lipman-Pearson algorithm was employed to determine the degree of similarity between the human FKH$^{sf}$ and mouse Fkh$^{sf}$ proteins across these four domains. The results are shown in FIG. 10. The similarity indices ranged from 82.8% to 96.4%, indicating that this protein is very highly conserved across species.

Example 11

Identification of Novel FKH$^{sf}$-related Genes

The unique features of the FKH$^{sf}$ gene sequence may be used to identify other novel genes (and proteins) which fall into the same sub-class of forkhead-containing molecules. The FKH$^{sf}$ protein is unique in its having a single zinc finger domain amino-terminal to the forkhead domain as well as in the extreme carboxy-terminal position of the forkhead domain. A degenerate PCR approach may be taken to isolate novel genes containing a zinc finger sequence upstream of a forkhead domain. By way of example, the following degenerate primers were synthesized (positions of degeneracy are indicated by parentheses, and "I" indicates the nucleoside inosine):

```
Forward primer:
CA(TC)GGIGA(GA)TG(CT)AA(GA)TGG

Reverse primer:
(GA)AACCA(GA)TT(AG)TA(AGT)AT(CT)TC(GA)TT
```

The forward primer corresponds to a region within the zinc finger sequence and the reverse primer corresponds to a region in the middle of the forkhead domain. These primers were used to amplify first-strand cDNA produced as in Example 2 from a variety of human tissues (including liver, spleen, brain, lung, kidney, etc.). The following PCR conditions were used: forward and reverse primers at 0.2 mM final concentration, 60 mM Tris-HCl, 15 mM ammonium sulfate, 1.5 mM magnesium chloride, 0.2 mM each dNTP and 1 unit of Taq polymerase, subjected to 35 cycles (94° C. for 30 sec, 50° C. for 30 sec, 72° C. for 2 min). PCR products were visualized on a 1.8% agarose gel (run in 1×TAE) and subcloned into the TA cloning vector (Invitrogen, Carlsbad, Calif.); individual clones were sequenced and used for further characterization of full-length cDNAs.

Alternatively, the unique regions of the FKH$^{sf}$ gene (i.e., the "Amino-terminal" and "Middle" domains) may be used to screen cDNA libraries by hybridization. cDNA libraries, derived from a variety of human and/or mouse tissues, and propagated in lambda phage vectors (eg., lambda gt11) were plated on agarose, plaques were transferred to nylon membranes and probed with fragments derived from the unique regions of the FKH$^{sf}$ gene. Under high stringency conditions (eg., hybridization in 5×SSPE, 5×Denhardt's solution, 0.5% SDS at 65° C., washed in 0.1×SSPE, 0.1% SDS at 65C) only very closely related sequences are expected to hybridize (i.e., 90-100% homologous). Under lower stringency, such as hybridization and washing at 45°-55° C. in the same buffer as above, genes that are related to FKH$^{sf}$ (65-90% homologous) may be identified. Based on results obtained from searching public databases with the unique sequences of FKH$^{sf}$ any genes identified through low- to mid-stringency hybridization experiments are expected to represent novel members of a "FKH$^{sf}$ family".

Example 12

Overexpression of the Wild-type FoxP3 Gene Results in Decreased Numbers of Peripheral T Cells The original breeding stocks for scurfy mice were obtained from Oak Ridge National Laboratory (ORNL), with mice subsequently derived by caesarian section into SPF conditions. Transgenic mice were generated by oocyte microinjection by DNX Transgenic Services (Cranbury, N.J.), as described (Brunkow et al., *Nat. Gen.* 27:68-72, 2001). For the 2826 mouse line, a 30.8 kb cosmid construct was generated from mouse BAC K60 for injection. This cosmid contains the entire Foxp3 gene along with approximately 18 kbp of 5' sequence and 4 kbp of 3' sequence. Expression of the gene parallels that of the endogenous gene with respect to tissue distribution (Brunkow et al., *Nat. Gen.* 27:68-72, 2001). The Ick-Foxp3 transgenic animals were generated using the Ick pacmotor to drive expression (Garvin et al., *Int. Immunol* 2(2):173, 1990). Both transgenic and scurfy mice were backcrossed onto the C57B1/6 background (JAX) for 4-6 generations for all studies. No differences in responsiveness or phenotype were noted during backcrossing. Northern blot analysis was performed as described previously (Brunkow et al., *Nat. Gen.* 27:68-72, 2001).

Initial experiments involving the Foxp3 transgenic mice demonstrated that in 5/5 lines generated from distinct founder animals, the expression of the wild-type Foxp3 transgene prevented disease in sf/Y mutant mice (Brunkow et al., *Nat. Gen.* 27:68-72, 2001). Further analysis demonstrates that the copy number of the transgene is directly correlated to the expression of the gene at the mRNA level (Brunkow et al., *Nat. Gen.* 27:68-72, 2001). This is likely due to the fact that the transgene construct consisted of a large genomic fragment including a substantial portion of 5' sequence and much of the regulatory region. In analyzing the various transgenic lines, it also becomes clear that there was a direct relationship between the expression of the Foxp3 gene and the number of lymph node cells (Brunkow et al., *Nat. Gen.* 27:68-72, 2001). The relationship between transgene copy number and cell number is shown for three of the founder lines, with the scurfy mutant animal (sf/Y) and normal littermate controls (NLC) for comparison (see, Table 1 below). Lymphoid cell number from transgenic (lines 2826, 1292 and 2828), normal littermate control and scurfy mutant (sf/Y) mice were determined for various tissues from representative age-matched (4 week old) mice. The approximate transgene copy number was determined by Southern blot analysis and correlated well with Foxp3 gene expression (Brunkow et al., *Nat. Gen.* 27:68-72, 2001). Although there is a less dramatic, but consistent, difference in the number of splenic cells in the transgenic mice as well, the number of thymocytes is not significantly affected. For reasons of simplicity, except where noted, the remainder of the experiments utilized the 2826 transgenic line. Animals from this line are generally healthy and survive for greater than one year under SPF conditions. The line has approximately 16 copies of the transgene and by northern blot analysis is expressed at ten to twenty times the level of the endogenous gene in lymphoid tissues (Brunkow et al., *Nat. Gen.* 27:68-72, 2001). The transgene, like the endogenous gene, is only poorly expressed in non-lymphoid tissues, a likely consequence of its expression under the control of its endogenous promoter. Lymph node cell number in mice from this line range from 15-50 percent of normal, with the number of cells accumulating with age. Splenic cell number is less dramatically affected although generally decreased, with a range of 25-90 percent of normal.

TABLE 1

| Genotype | Transgene Copy Number | Cell Number (×10⁶) | | |
|---|---|---|---|---|
| | | Thymus | Lymph Node | Spleen |
| NLC | NA | 121.4 | 1.5 | 84.4 |
| 2826 | ~16 | 111.8 | 0.5 | 60.8 |
| 1292 | ~9 | 98.6 | 1.0 | 76.4 |
| 2828 | ~45 | 108.5 | 0.4 | 61.1 |
| Scurfy | NA | 64.4 | 4.7 | 109.5 |

Example 13

Thymic Phenotype of Scurfin-Transgenic Mice

The role of the Foxp3 gene in thymic selection remains unclear. Deletion of superantigen-specific Vβ-bearing thymocytes appears normal in both sf/Y as well as 2826 transgenic mice. Consistent with this, overexpression of the Foxp3 gene using its own endogenous promoter (2826 line) also does not appear to result in any gross changes in thymic development or selection. The number of thymocytes (Table I) and their distribution amongst the major phenotypic subsets is indistinguishable from littermate control animals. *Thymus*, lymph node and splenic tissues were collected as described (Clark et al., *Immunol* 162:2546, 1999) and were resuspended in staining buffer (1% BSA, 0.1% sodium azide in PBS) at a cell density of 20×10⁶/mL. Cell aliquots were treated with 2% normal mouse serum (Sigma) to block non-specific binding then stained by incubation on ice for 30 minutes with combinations of the following fluorochrome-conjugated anti-mouse monoclonal antibodies (mAbs): CD3, CD8β, CD4, CD25, IgG2a control (Caltag Laboratories, Burlingame, Calif.); CD28, CD45RB, CD44, CD62L, CD69, CD95 (PharMingen, San Diego, Calif.). The fluorescence intensity of approximately $10^5$ cells was examined using a MoFlo™ flow cytometer (Cytomation, Fort Collins, Colo.) with dead cell exclusion by addition of propidium iodide (10 μg/mL).

A more detailed examination of the CD4⁻8⁻ subset also reveals a normal distribution of gamma-delta cells and CD25⁺ cells. Importantly, the fraction of CD4⁺8⁻ expressing the maturation markers CD69 and HSA is identical in 2826 and control animals, suggesting that the maturation process is normal.

Overexpression of the Foxp3 gene in the thymus alone has a significantly different phenotype from the 2826 mice noted above. Transgenic mice expressing Foxp3 selectively in the thymus (16.5 and 8.3) under control of the Ick proximal promoter were crossed to sf/+ carrier females. Male scurfy mice (sf/Y) that carried the thymus-specific transgene (16.5 and 8.3) succumbed to disease at the same time and in the same manner as non-transgenic liftermates. Sf/Y transgenic animals expressing Foxp3 under its endogenous regulatory sequences (2826) did succumb to disease. Cell number is derived from mice that carried the transgene in addition to the wild-type Foxp3 gene.

Transgenic animals that express the Foxp3 gene exclusively in thymus (under the control of the Ick proximal promoter) are unable to rescue sf/Y mice from disease (see, Table 2 below). Two separate founder animals were crossed to scurfy carrier females in an attempt to prevent disease. In each case sf/Y mice carrying the Ick proximal promoter -Foxp3 transgene developed an acute lymphoproliferative disease that was identical both in severity and time course to that seen in non-transgenic sf/Y siblings. In each case expression of the transgene was restricted to the thymus with no detectable expression in peripheral organs, including spleen. The Northern Blot analysis was carried out as presented in Example 1. Further, thymic expression of the Ick-driven transgene was substantially greater than that of the gene in 2826 transgenic animals or of the endogenous gene in normal littermate control mice. Hence it appears that the fatal lymphoproliferative disease seen in sf/Y mice does not arise as a consequence of scurfin mediated developmental defects in the thymus.

TABLE 2

| Genotype | Disease in Sf/Y mice? | Cell Number (×10⁶) | |
|---|---|---|---|
| | | Thymus | Lymph Node |
| NLC | NA | 79.0 | 2.9 |
| 2826 | No | 100.1 | 2.2 |
| 16.5 | Yes | 110.4 | 2.7 |
| 8.3 | Yes | 32.2 | 2.9 |

Although transgenic (non-sf) animals carrying the Ick-driven transgene appear generally normal, high level expression of the transgene within the thymus does have phenotypic consequence in normal (non-sf) animals. Significantly increased expression of the transgene in otherwise normal mice leads to a relative decrease in the percentage of double-positive thymocytes and a corresponding increase in the percentage of double-negative (DN) cells, as well as a decrease in overall thymic cell number (see, Table 2). T cell development still occurs in these animals as assessed by the generation of CD4 and CD8 single positive cells and by the presence of relatively normal numbers of peripheral T cells in both lymph node and spleen (see, Table 2). CD69 expression on CD4⁺8⁻ cells from the thymus is similar in transgenic and wild-type littermates, suggesting positive selection likely proceeds normally, whereas within the DN compartment, the fraction of cells expressing CD25 is diminished relative to wild-type animals. These transgenic animals indicate that overexpression of the Foxp3 gene within the thymic compartment specifically can alter thymic development, but this appears to have no effect on regulating peripheral T cell activity.

Example 14

Altered Phenotype of Peripheral T Cells from Scurfin-Transgenic Mice

In addition to a decrease in the number of peripheral T cells in 2826 mice, there is a slight reduction in the percentage of CD4⁺8⁻ cells in both the lymph node and spleen relative to NLC. Whereas the CD3 levels appear normal on peripheral T cells, there are a number of other surface markers with altered expression levels. For CD4⁺8⁻ cells in the transgenic mice, the most consistent changes are a small decrease in the expression of CD62L and CD45RB as well as an increase in the expression of CD95. By comparison, cells from sf mutant animals have a very different phenotype. CD4⁺8⁻ cells from these mice are large and clearly activated. They are predominantly $CD44^{H1}$, $CD45RB^{LO}$, $CD62L^{LO}$ and partially CD69⁺ (Clark et al., *Immunol* 162:2546).

CD4⁻8⁺ cell numbers were also reduced in both the spleen and lymph nodes of scurfin-transgenic mice. This decrease is typically more dramatic (50-75%) than the decrease in the CD4⁺8⁻ compartment (25-50%). CD4⁻8⁺ T cells display relatively minor and variable changes in the level of CD62L, CD45RB and CD95 on the cell surface in comparison to NLC. In contrast to CD4$^+$8$^-$ T cells, there is a more pronounced increase in the percentage of CD4$^-$8$^+$ T cells that were also CD44$^{HI}$. Overall, the CD4$^-$8$^+$ cells do not express surface markers at levels that characterize them as specifically naive, activated or memory.

Example 15

Histological Analyses of Scurfin-Transgenic Mice

Whereas peripheral T cells in 2826 mice are clearly decreased in number, a determination was made whether the architecture of the lymphoid organs was also perturbed. Histological examination of the major lymphoid organs (thymus, lymph node and spleen) indicated that the most significant changes were found in the mesenteric and peripheral lymph nodes. Tissues for histological analysis were removed from mice approximately 8 weeks after birth and immediately fixed in buffered 10% formalin. Paraffin-embedded sections were processed for hematoxylin and eosin staining and comparative histopathology performed on representative mice. As expected, the thymus appears relatively normal, with a well-defined cortico-medullary junction, although there appears to be a slight reduction in the size of the thymic medulla. Transgenic animals had smaller peripheral lymph nodes, lack robust and normally distributed lymphoid follicles, lack distinct margins between follicular and interfollicular areas and had more obvious sinuses than those found in the lymph nodes of the normal liftermate control mice. Even though the spleen and Peyer's patches appear approximately normal in size and microarchitecture, there is a moderate decrease in total cell number and no or minimal evidence of germinal centers in these tissues. The changes noted here reflect a hypocellular state distinct from a number of other targeted mutations in which the lymph nodes fail to develop. Therefore, while T cells are capable of development in an apparently normal manner, their representation within the peripheral lymphoid tissues, particularly the lymph nodes, is substantially decreased.

Example 16

Decreased Functional Responses of CD4$^+$8$^-$ Cells from Scurfin-Transgenic Mice The phenotypic and cell number data suggest that there are specific defects in the biology of CD4 T cells from 2826 transgenic animals. The functional responses of T cells from these animals to several stimuli were evaluated, including anti-CD3 and anti-CD28. Lymphocytes were isolated from various tissues from NLC, 2826 transgenic or scurfy (mutant) mice and CD4 cells were purified by cell sorting. Thymus, lymph node and splenic tissues were removed from appropriate animals, macerated between sterile microscope slides, filtered through a sterile 70 µm nylon mesh and collected by centrifugation. CD4$^+$ T lymphocytes were sort purified from these tissues by positive selection using the MoFlo. Sort purities as determined by post-sort analysis were typically greater than 95%. Cells were cultured at 37° C. in complete RPMI (cRPMI) (10% fetal bovine serum, 0.05 mM 2-mercaptoethanol, 15 mM HEPES, 100 U/mL penicillin, 100 µg/mL each streptomycin and glutamine) in 96-well round-bottomed tissue culture plates. Culture wells were prepared for T cell activation by pre-incubation with the indicated concentrations of purified antibody to CD3 (clone 2C11) in sterile PBS for 4 hours at 37° C. Purified α-mouse CD28 (clone 37.51) or α-mouse KLH (control antibody) was co-immobilized at 1 µg/ml final concentration.

T cells were cultured at a cell density of 1 to 5×10$^4$ cells/well in 200 µL of cRPMI for 72 hours. Supernatant (100 µl) was removed at 48 hours for analysis of cytokine production. Wells were pulsed with 1 µCi/well of $^3$[H]-thymidine (Amersham Life Science, Arlington Heights, Ill.) for the last 8-12 hours of culture and then harvested (Tomtec). Proliferation data reported are based upon mean value of triplicate wells and represent a minimum of 3 experiments. Cytokine levels were determined by ELISA assay according to the manufacturer's direction (Biosource International, Camarillo, Calif.).

To test for proliferation and IL-2 production, a single cell suspension of Balb/c spleen cells was generated to used as stimulator cells. These cells were irradiated (3300 rads) and incubated a 10:1 ratio (stimulator:effector) with scurfin-transgenic or NLC spleen cells. To some cultures, IL-2 was added at 100 U/ml. For proliferation assays, cells were pulsed after five days and harvested as above. Both proliferation and IL-2 production are significantly diminished in cells from the transgenic animals compared to their littermates. Although transgenic animals increase their responsiveness with increasing stimulation, they rarely reached the levels achieved by NLC. This is particularly true for IL-2 production, in which cells from 2826 mice consistently produce low to undetectable amounts of this cytokine. Similar results were seen whether the cells were derived from the spleen or the lymph nodes.

As expected, cells from scurfy animals were hyper-responsive to stimulation and produce increased amounts of IL-2. The effect of the transgene was independent of strain and have remained constant during the back-crossing of the animals onto C57Bl/6 through at least generation N6. T cells from transgenic mice remained responsive to anti-CD28 in this assay whereas stimulation with anti-CD3 and control Ig results in generally poor responses that were lower than, but similar to NLC responses. Addition of high doses of IL-2 is able to partially overcome the proliferative defect in CD4$^+$8$^-$ T cells from 2826 mice, but generally fails to restore the response to that of wild-type animals.

In contrast to peripheral T cells, but consistent with the phenotypic data above, the proliferative response of thymic CD4$^+$8$^-$ cells is approximately comparable between transgenic and NLC mice. IL-2 production by thymic CD4$^+$8$^-$ cells however, is reduced substantially from the transgenic animals. The reduction in IL-2 production by thymocytes is somewhat more variable than that seen in lymph node or spleen and may suggest that the IL-2 produced is also consumed during the culture. Alternatively, thymocytes may produce other growth factors less affected by the expression of the Foxp3 gene. Nevertheless, the data generally support the conclusion that a major defect in the transgenic animals is in the ability of both thymic and peripheral T cells to produce IL-2.

Example 17

Altered Functional Responses of Scurfin-Transgenic CD4$^-$8$^+$ T CELLS

The ability of transgenic T cells to generate and function as cytotoxic T cells (CTL) was determined in an in vitro assay. A single cell suspension of Balb/c spleen cells was generated to use as stimulator cells. These cells were irradiated (3300 rads) and incubated at a 10:1 ratio (stimulator:effector) with scurfin-transgenic or NLC spleen cells. To some cultures, IL-2 was added at 100 U/ml. For generation of CTL, splenic T cells were stimulated in a similar manner in the presence of 100 U/ml of IL-2. After five days, cells were either assayed in the JAM assay (Matzinger, P. *J immunol* 145(1-2):185 (1991)) or re-stimulated on a new stimulator layer. Cells were approximately 95% CD4⁻8⁺.

Transgenic T cells were stimulated in a mixed-lymphocyte culture containing increasing numbers of irradiated allogeneic stimulator cells in the presence or absence of IL-2. The proliferative response of either transgenic or NLC effector cells was then measured. T cells from the transgenic animals responded poorly in the absence of exogenous IL-2, consistent with the data for purified CD4⁺8⁻ cells (above). In the presence of exogenous IL-2, transgenic T cells displayed an increased proliferative response, but still required a higher number of stimulator cells to reach a similar level of proliferation as control cells. The ability of mixed T cell populations to respond to stimulation in this assay may reflect the presence of both CD4⁺8⁻ and CD4⁻8⁺ T cells in these cultures.

As a direct indicator of CD4⁻8⁺ activity, the cytotoxic ability of T cells were assayed in a standard target cell lysis assay. CD4⁻8⁺ T cells were generated using allogeneic feeder cells in the presence of IL-2 and assayed to determine the ability of these cells to lyse target cells. Balb/c spleen cells were stimulated with PMA (10 ng/ml) in the presence of ionomycin (250 ng/ml) for 24 hours to allow for efficient loading of cells with $^3$[H]-thymidine. After 24 hours, $^3$[H]-thymidine (5 µCi/ml) was added to PMA+Ionomycin-stimulated Balb/c spleen cells. Cells were incubated at 37° C. for 18 hours and then washed. CD4⁻8⁺ effector cells were plated with target Balb/c cells at increasing ratios ranging from 1.5:1 to 50:1 (effector:target) in a 96-well flat-bottom plate (experimental) in a final volume of 100 µl. The cells were pelleted by centrifugation and incubated at 37° C. for four hours. A plate containing labeled Balb/c cells alone was harvested immediately and used to determine total counts (TC). A second plate containing labeled Balb/c cells alone was also incubated at 37° C. for four hours to determine spontaneous release (SR). After four hours of incubation, cells were harvested onto glass fiber and counted in a scintillation counter.

Percent lysis was determined as follows: {[(Total-SR)−(Experimental −SR)]/(Total counts−SR)}* 100=% lysis. At higher effector-to-target ratios (50:1 and 25:1), scurfin-transgenic CD4⁻8⁺ cells were as effective at lysing target cells as cells generated from NLC, while at the intermediate ratios (12.5-3:1), transgenic cells were significantly reduced in their cytolytic function in comparison to NLC. However, the transgenic cells were still effective with 50-60% lysis at these intermediate ratios. Overall, these data suggest that scurfin-transgenic T cells possess cytolytic activity, but are less effective than NLC. In addition, exogenous IL-2 was required to generate functional CD4⁻8⁺ T cells, presumably due to the poor endogenous production of this cytokine.

As a further indicator of T cell responsiveness, the functional responsiveness of 2826 transgenic animals to antigen in vivo was addressed. Contact sensitivity responses using Oxazalone as the challenging agent were carried out on 2826 mice and their littermate controls. Age-matched animals were treated on the left ear with 2% Oxazalone (diluted in olive oil/acetone), using a final volume of 25 µl. After 7 days, ear thickness was measured using spring-loaded calipers and mice were challenged on the right ear with 2% Oxazalone (8 µl per ear). Ear thickness was measured at 24 hours and is reported as change in ear thickness compared to pre-challenge. Control mice were challenged only. Thickness of ears following initial priming (prior to challenge) was no different from untreated ears. Mice were subsequently treated with PMA (10 ng/ml; 8 µl/ear) on the priming ear. Ear thickness was measured at 18 hours and is reported as thickness compared to pre-treatment.

In these studies, transgenic animals made a consistently poor response to Oxazalone at all times examined, whereas control animals responded normally. The transgenic animals however responded normally to challenge with PMA, indicating that they were capable of generating an inflammatory reaction to a strong, non antigen-specific challenge. Further studies using animals transgenic for both a TCR and Foxp3 will examine in vivo responses in greater detail.

Example 18

Scurfy T Cells can be Inhibited by Wild Type T Cells in Vivo

It has previously been reported that adoptive transfer of CD4⁺8⁻ T cells from sf mice into nude mice transfers disease as measured by the wasting and skin lesions characteristics of sf. However, grafting of sfthymus into normal mice does not transmit the disease suggesting immunocompetent mice are capable of inhibiting sf cells (Godfrey et al., *Am. J. Pathol.* 145:281-286, 1994). To better understand the mechanism of inhibition either 3×10⁶ sf CD4+ T cells or wildtype CD4⁺ T cells or a mix of sf and wildtype CD4⁺ T cells were adoptively transferred into syngeneic C3H-SCID mice.

C3H SCID mice were purchased from The Jackson Laboratory (Bar Harbor, Me.). All animals were housed in specific pathogen free environment and studies were conducted following PHS guidelines. The original double mutant strain, sf (sf) and closely linked sparse-fur (Otc$^{spf}$), were obtained from Oak Ridge National Laboratory. The double mutants were backcrossed to *Mus musculus* castaneous to obtain recombinants carrying either (Otc$^{spf}$) mutation or sf mutation (Brunkow et al., *Nat Gen* 27:68-72, 2001). Prior to cloning of sf gene carrier females for sf mutation were identified by the amplification of genomic DNA with primers 5'-ATTTTGATT ACAGCATGTCCCC-3' (SEQ ID NO:15) and 5'-ACGGAAACACTCTTATGTGCG-3' (SEQ ID NO:16) (primers for microsatellite marker DXMit136 which was found to be inseparable from sf phenotype during backcrossing).

The single mutant sf strain was maintained by breeding carrier females to F1 males of (C3Hf/rlx101/RI) or (101/RIx C3H/RI). Sf males were used at age 15-21 days and wildtype control animals were used at 6-12 weeks of age. Scurfy or wildtype CD4⁺ T were purified by cell sorting. The cells were resuspended in 0.9% saline, pH 7.2 and mixed at different ratios in a final volume of 200 µl and injected into SCID mice via tail-vein. Mice were monitored weekly for weight loss. Approximately 50 µl of blood was collected by eye-bleeds. Red blood cells were lysed and leukocytes were stimulated at 5×10⁴ cells/well for 48 hours with immobilized anti-CD3 (5 µg/ml) and anti-CD28 (1 µg/ml).

Figure 11A:
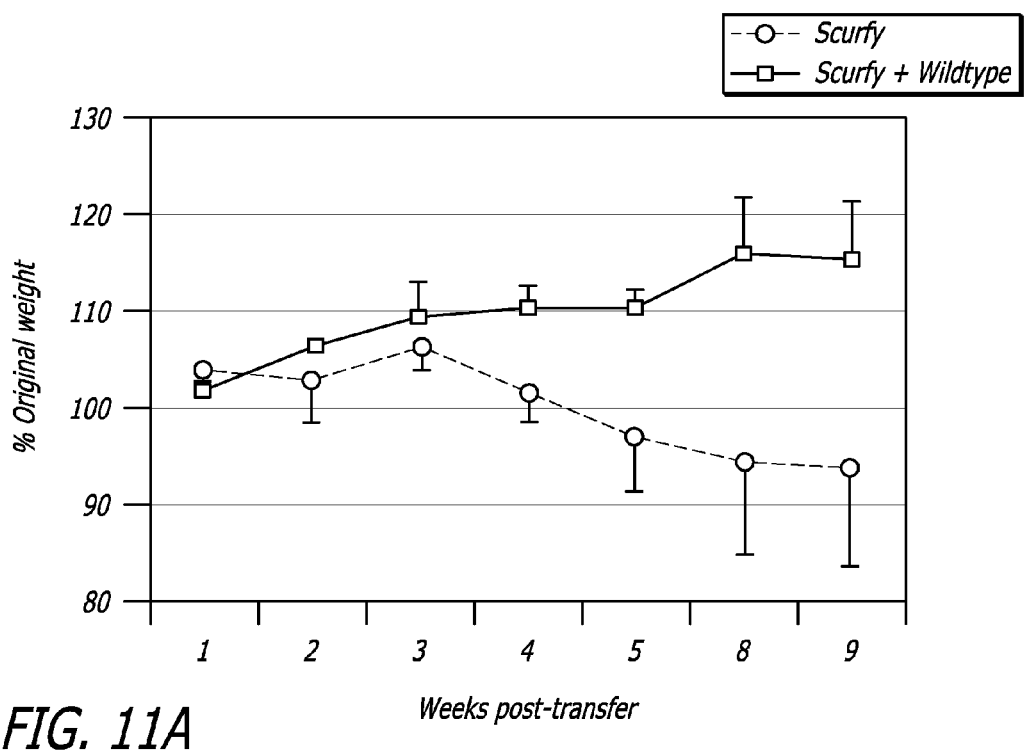
FIG. 11A is a graph monitoring the weight of both scurfy and wild-type mice. The mice were monitored for weight loss at regular intervals for 10 weeks. Each data point is an average of 3 mice except after week 5 when one of the three mice died in sf CD4 transfer group (indicated by an arrow on the graph). The data is representative of more than 3 independent experiments.

Mice that received sf T cells showed signs of wasting (seen as weight loss) 3-4 weeks post-transfer that became progressively worse, whereas the mice that received a mixture of sf and wildtype T cells showed a normal weight gain corresponding to their age (FIG. 11A). Mice that received only wildtype T cells showed a similar weight gain with age. In addition, mice receiving only sf T cells developed an inflammatory reaction around, but not within, the eye that persisted throughout the experiment. If the disease was allowed to progress, the recipients of sf T cells only died 8-16 weeks after transfer. Recipients of a mix of sf and wildtype T cells remained healthy throughout the experiment (experiments done up to 16 weeks).

Figure 11C:
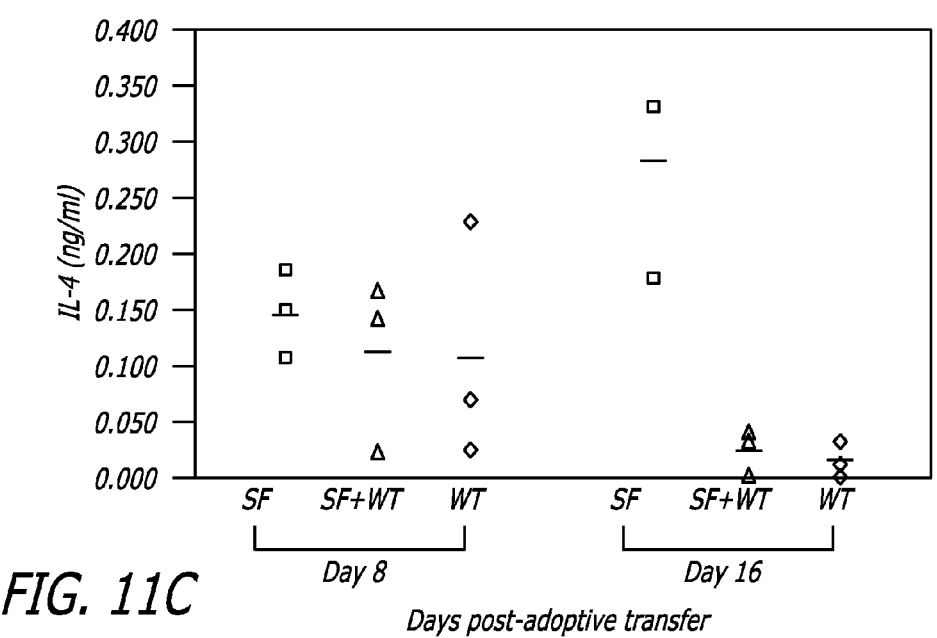
FIG. 11C is a graph depicting IL-4 production from $5 \times 10^4$ PBMC from C3H/SCID mice receiving either sf CD4$^+$ T cells or a mixture of WT and sf CD4$^+$ T cells or WT CD4$^+$ T cells were stimulated with 5 µg/ml anti-CD3 and 1 µg/ml anti-CD28 immobilized onto round bottom plates. Supernatants were harvested at 48 h and IL-4 levels were measured by ELISA.
Figure 11B:
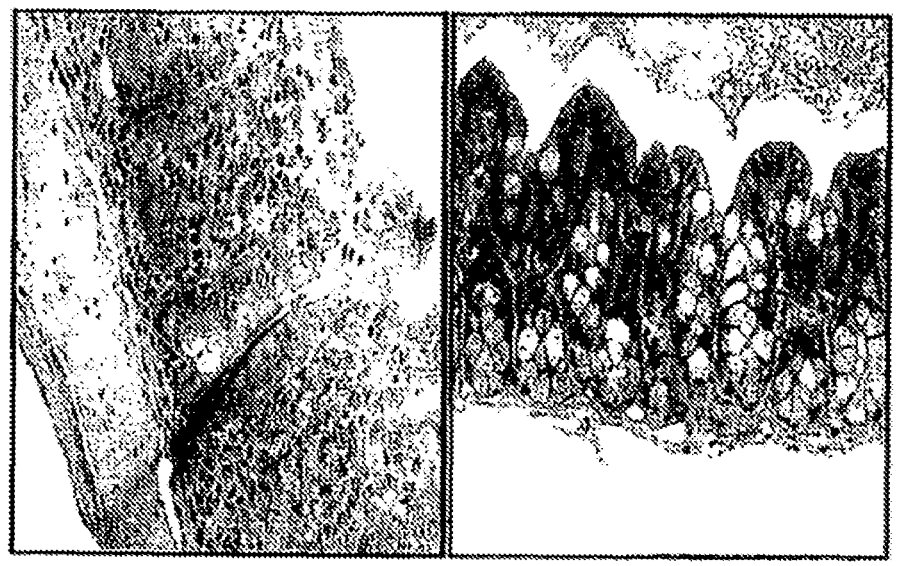
FIG. 11B is a photograph of a tissue section. Large intestines from C3H/SCID mice receiving either sf T cells (left panel) or a mixture of WT and sf T cells (right panel) were fixed in formalin, sectioned and processed for hematoxylin and eosin staining.

Histological examination of the large intestine of mice receiving sf T cells showed crypt abscesses, thick epithelium, increased epithelial cellularity and cellular infiltrates in the colonic wall, consistent with proliferative colitis (FIG. 11B). In comparison, the intestine of mice receiving a mixture of sf and wildtype T cells (or wildtype cells alone) appeared normal, correlating with the lack of wasting in these mice.

For the histological examination, tissues were removed from C3H/SCID mice receiving either sf T cells, wildtype T cells or a mixture of sf and wildtype T cells. Intestines were flushed with cold PBS and immediately fixed in 10% formalin. Paraffin embedded sections were processed for hematoxylin and eosin staining and comparative histopathology (Applied Veterinary Pathobiology, Bainbridge Is., Wash.).

Cellular infiltration and inflammation was also noted in a number of other organs (including kidney, liver and skin) from mice that received sf T cells only and such cells were not found in animals that received wildtype cells. Further, the lymph nodes and spleen from sf-recipient animals were substantially enlarged compared to their controls, indicating a marked lymphoproliferative process. Lymph nodes were collected from 6-12 weeks old mice and macerated in DMEM+ 10% FBS in between the ground glass ends of sterile microscope slides. The cells were filtered through 70 μM nylon mesh, collected by centrifugation and resuspended at ~50× $10^6$ cells/ml in complete media.

$CD4^+$ T cells from sf mice have been shown to be hyperproliferative and to secrete large amounts of cytokines such as IL-2, IL-4 and IFN-γ (Blair et al., *J. Immunol.* 153:3764-774 (1994); Kanangat et al., *Eur. J. Immunol.* 26:161-165 (1996)). To monitor the activation status of the $CD4^+$ T cells that were transferred into the SCID animals, IL-4 secretion by PBMC of recipient mice was measured. PBMC from various recipients were stimulated with anti-CD3 and anti-CD28 in vitro for 48 hours and secreted IL-4 was detected by ELISA kit (BioSource International, Camarillo, Calif.) according to manufacturer's instruction. At an early time point post-transfer (8-10 days), IL-4 was produced by PBMC from all the recipients (FIG. 11c). At later time points (2 weeks or more), PBMC from recipients of sf T cells secreted significant amounts of IL-4 whereas the PBMC of mice receiving either wildtype T cells only or a mixture of sf and wildtype T cells secreted little IL-4. Lack of weight loss, tissue infiltrates and suppression of IL-4 secretion in mice receiving a mixture of sf and wildtype T cells indicated that wildtype T cells were inhibiting the activation and disease progression normally associated with the transfer of sf CD4+ T cells.

Example 19

SF Cells are Regulated by $CD4^+$ $CD25^+$ T-Regulatory Cells

There have been numerous reports that the $CD4^+CD25^+$ subset of peripheral $CD4^+$ T cells (T-reg cells) is involved in regulating other T cells, both in vivo and in vitro (Roncarolo et al., *Curr. Opin. Immun.* 12:676-683 (2000); Sakaguchi, S., *Cell* 101:455-458 (2000); Shevach, E. M., *Ann. Rev. Immun.* 18:423-449 (2000)). It was therefore of interest to determine if such T-reg cells were responsible for the inhibition of disease seen after co-transfer of sf and wildtype $CD4^+$ T cells in vivo. Two million sf $CD4^+$ T cells were mixed at different ratios either with wildtype $CD4^+CD25^-$ T cells or with wildtype $CD4^+CD25^+$ T-reg cells and injected into C3H/SCID mice. The recipients were monitored for weight loss and IL-4 secretion by PBMC as described in Example 1. For isolating T-reg cells these were stained with anti-CD4-FITC (Caltag Laboratories, Burlingame, Calif.) and anti-CD25-biotin (Caltag) for 30 min on ice. The cells were washed twice with PBS and stained with strepavidin-APC (Molecular Probes, Eugene, Oreg.) for 20 min on ice. Cells were washed twice and positive sorted for $CD4^+CD25^+$ T cells.

Figure 12A:
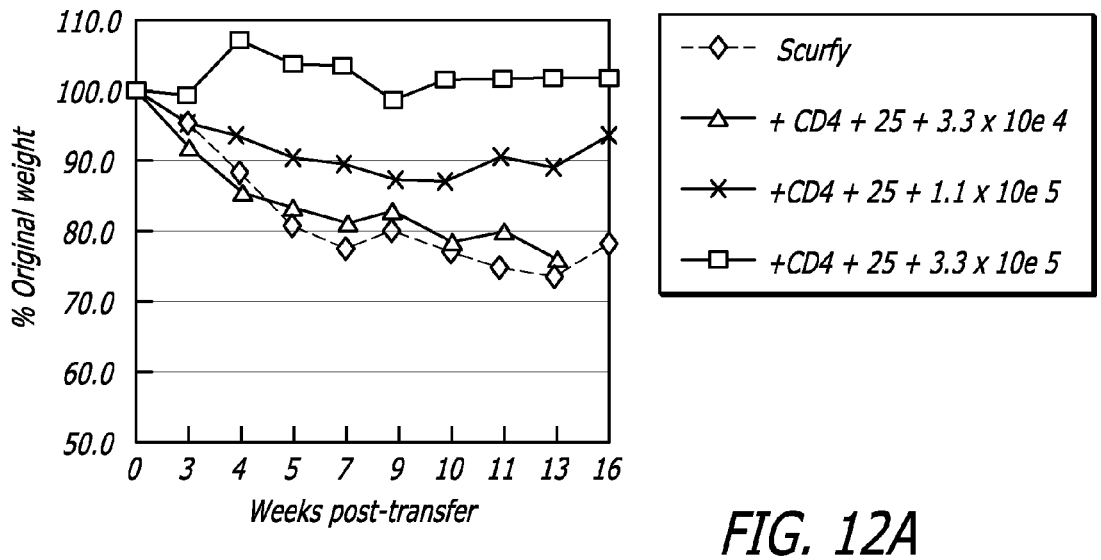
FIGS. 12A and 12B are graphs depicting the weight loss of mice treated with either CD4+CD25+ or CD4+CD25− T-regulatory cells. CD4+CD25+ T-regulatory subset mediates the suppression of disease caused by sf T cells in vivo. A mixture of $4 \times 10^6$ sf T cells and varying numbers of wildtype CD4+CD25+ (a) or CD4+CD25− (b) T cells was transferred into C3/SCID mice via tail-vein injection. These mice were monitored for weight loss over a period of time. Each data point is an average of 3 mice except sf CD4 transfer group and sf CD4+$1.1 \times 10^6$ CD4+CD25− T cells which have 2 mice each in the group. Also, arrows on the graph indicate mice that died or were sacrificed due to disease progression.
Figure 12B:
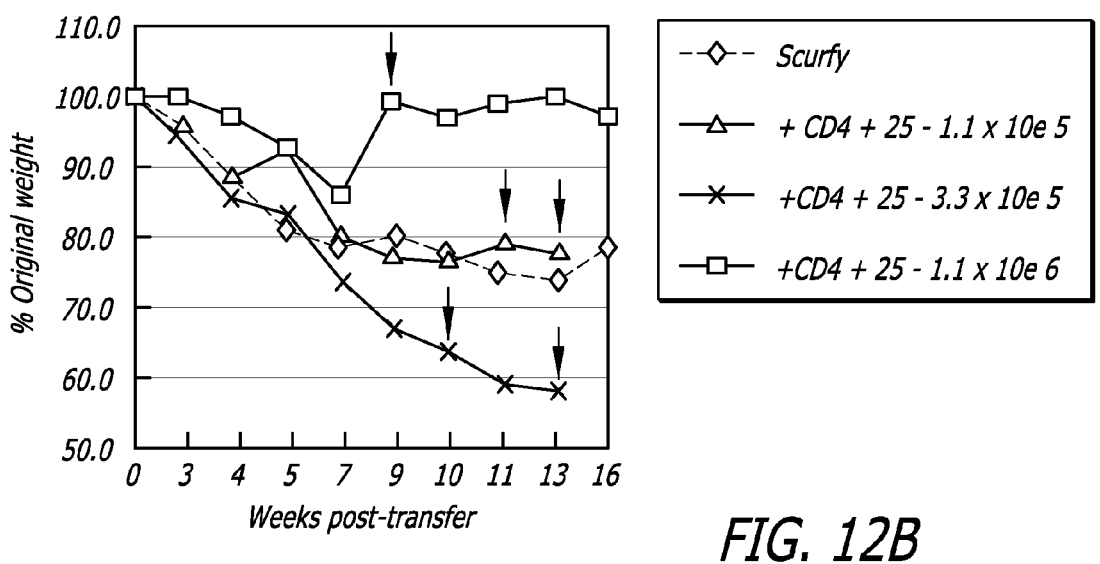

As before, mice receiving sf T cells alone showed signs of wasting (FIG. 12) and IL-4 production. However, mice that received a mixture of sf T cells and higher doses (110,000 or more) of wildtype $CD4^+CD25^+$ T-reg cells showed a marked reduction in signs of disease such as weight loss. In comparison, mice that received a mix of sf and $CD4^+CD25^-$ T cells showed signs of disease at all doses except when the number of $CD4^+CD25^-$ T cells was greater than 1.1 million. The small amount of suppression seen with higher numbers of $CD4^+CD25^-$ T cells may indicate that there are additional mechanisms of suppression or that $CD4^+CD25^-$ T cells give rise to $CD4^+CD25^+$ T-reg cells post-transfer. It seems unlikely that the mechanism of inhibition by $CD4^+CD25^-$ T-reg involves in vivo competition for lymphoid space, since as few as $1.1 \times 10^5$ T-reg can inhibit the activity of $2 \times 10^6$ sf T cells.

Figure 13:
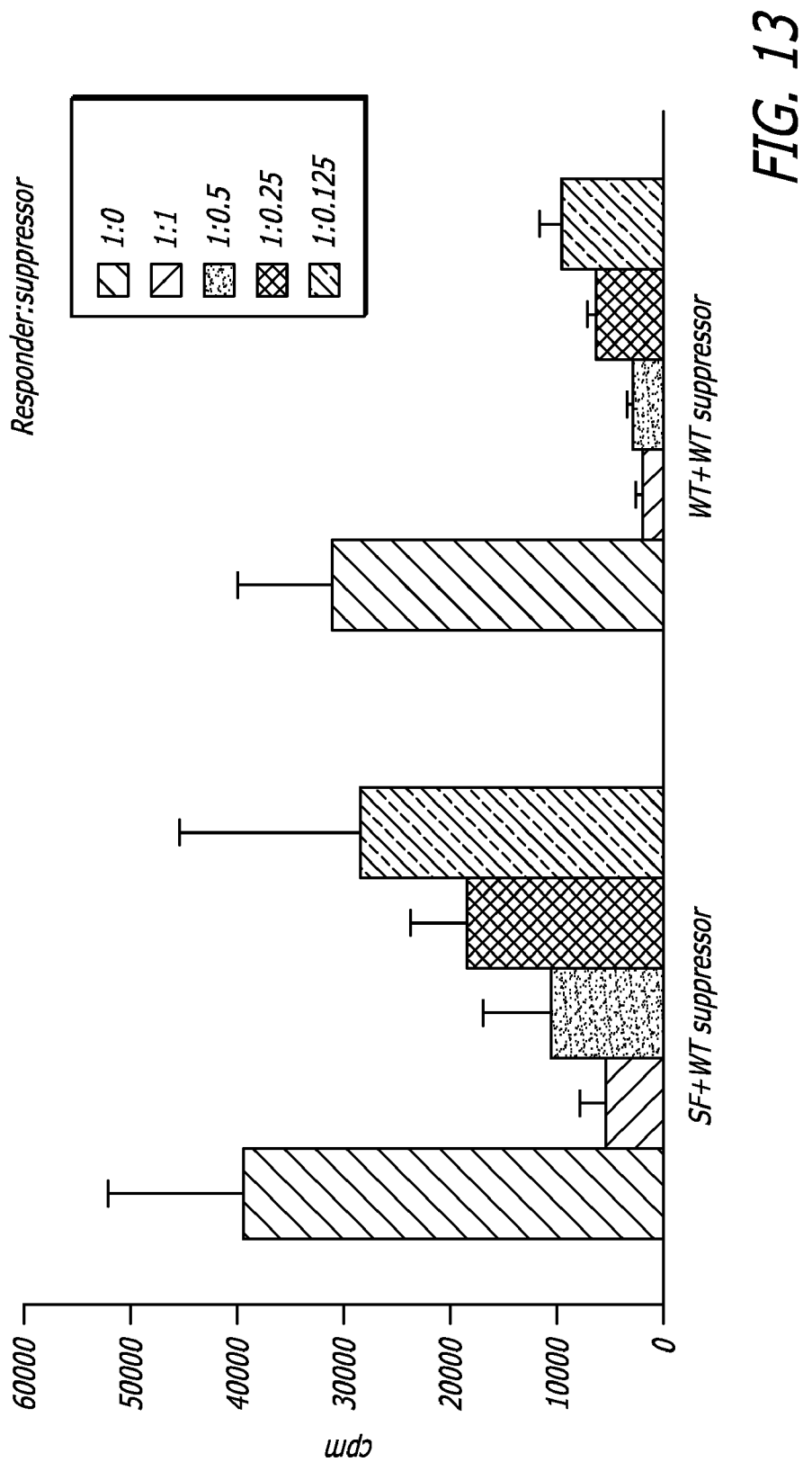
FIG. 13 depicts a graph of a proliferation assay that determines the suppressor activity of CD4+CD25+ T regulatory cells. Sf CD4+ T cells can be inhibited by CD4+CD25+ T-regulatory cells in vitro. $5 \times 10^4$ WT or sf CD4+ T cells were stimulated with anti-CD3 (1 µg/ml) and $5 \times 10^4$ mitomycin C treated Thy-1$^-$ APC. CD4$^+$CD25$^+$ T-regulatory cells were added at various ratios to the assay. The cells were cultured for 72 h and pulsed with [$^3$H] thymidine for final 8 hrs of the culture. Data is mean of triplicates.

In order to better understand the mechanism of inhibition of sf CD4+ T cells by $CD4^+CD25^+$ T-reg cells, in vitro mixing experiments were conducted. Sf $CD4^+$ T cells or wildtype $CD4^+CD25^-$ T cells were activated with anti-CD3 in presence or absence of $CD4^+CD25^+$ T-reg cells at various responder:suppressor ratios. FIG. 13 shows that the proliferative responses of wildtype $CD4^+$ T cells stimulated with APC and anti-CD3 were suppressed significantly by the addition of $CD4^+CD25^+$ T-reg cells. These $CD4^+CD25^+$ T-reg cells also inhibited the proliferative responses of sf $CD4^+$ T cells. However $CD4^+CD25^+$ T-reg cells were less effective in inhibiting sf $CD4^+$ T cells than wildtype $CD4^+$ T cells. This result, like that seen with co-transfer in vivo, indicates that the hyper-responsive state of sf T cells can be regulated by T-reg cells.

For APC, spleens were collected in a similar fashion as lymph nodes and stained with anti-Thy-1-FITC or anti-Thy1-PE (Caltag). Cells were washed and negative sorted for Thy-1. The cells were sorted using a MoFlo flow cytometer (Cytomation, Fort Collins, Colo.) and Cyclops (Cytomation) software at a rate of 10-20,000/min. Cell doublets and monocytic cells were eliminated on the basis of forward and side scatter gates, and dead cells were excluded by propidium iodide (10 μg/ml) stain. The purity of the sorted cell population was routinely 90-99%. Thy-1⁻ APC were treated with mitomycin C (Sigma, 50 μg/ml) for 20 min at 37° C. and washed three times with DMEM+10% FBS before using in proliferation assays. For regulatory T cell assays, CD4+ T cells were stimulated at $5 \times 10^4$ cells/well in 200 ul DMEM+ 10% FBS with soluble anti-CD3 (2C11; Pharmingen) at 1 μg/ml and an equal number of mitomycin C treated Thy-1⁻ APC from spleens. For T-reg assays MoFlo sorted $CD4^+CD25^+$ T cells were added at various ratios.

Cultures were incubated 72 hour at 37° C. and pulsed with 1 μCi/well with [³H] thymidine (Amersham Life Sciences, Arlington, Ill.) for the last 8-12 hours of culture. For in vitro preactivation, $CD4^+CD25^+$ or $CD4^+CD25^-$ T cells were stimulated at $5 \times 10^4$ cells/well in 200 μl DMEM+10% FBS with soluble anti-CD3 (1 μg/ml for wildtype cells or 10 μg/ml for Foxp3 transgenic cells), 4 ng/ml rIL-2 (Chiron) and an equal number of mitomycin-C treated Thy-1⁻ APC from spleens. The cells were harvested at 72 hours, stained with CD4-FITC or CD4-PE and positively sorted for CD4 using a MoFlo flow cytometer as described above. These cells were then added to the regulatory T cell assay as previously described at the same ratios as freshly isolated CD4⁺CD25⁺ T cells.

Example 20

TGF-β does not Inhibit SF CD4⁺ T Cells

Recent studies have implicated a critical role for CTLA-4 and secretion of TGF-β in regulatory function of CD4⁺ CD25⁺ T-reg cells in vivo (Read et al., *J. Exp. Med.* 192:295-302, 2000); Takahashi et al., *J. Exp. Med.* 192:303-310, 2000). To test whether sf cells were sensitive to inhibition with TGF-β, CD4⁺ T cells were stimulated with or without the addition of exogenous TGF-β. For the TGF-β assays, anti-CD3 (at varying concentrations, Pharmingen) and anti-CD28 (1 µg/ml, Pharmingen) were immobilized on plastic. TGF-β (R&D) was added at a final concentration of 2.5 ng/ml. Cultures were incubated for indicated time periods at 37° C. Individual wells were pulsed with 1 µCi/well with [³H] thymidine (Amersham Life Sciences, Arlington, Ill.) for the last 8-12 hours of culture. Proliferation data are mean value of triplicate wells and represent a minimum of three experiments.

Figure 14A:
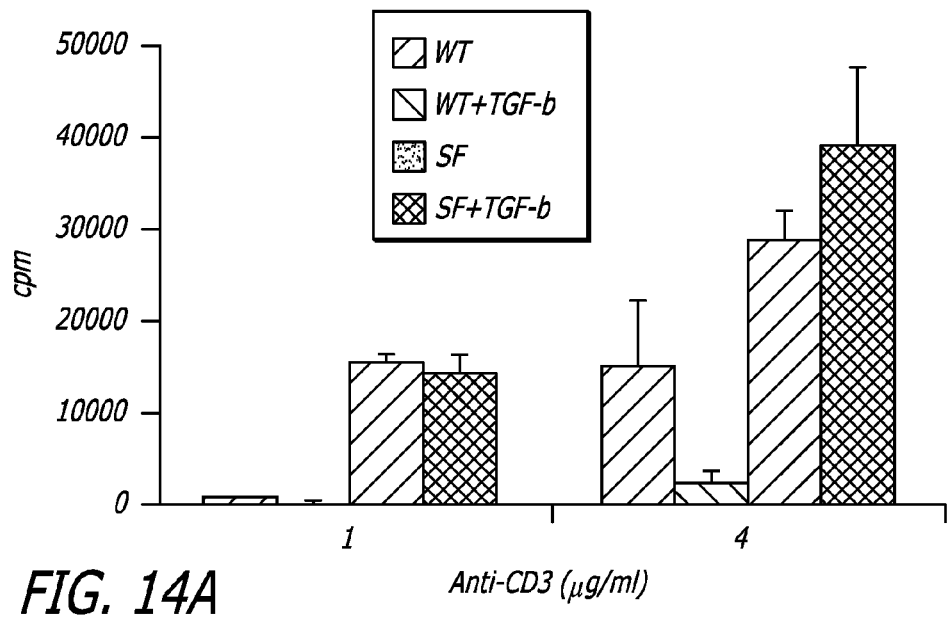
FIG. 14A depicts a graph of a proliferation assay in which $5 \times 10^4$ WT or sf CD4+ T cells were stimulated with immobilized anti-CD3. TGF-β was added at a final concentration of 2.5 ng/ml at the beginning of the assay. The cells were cultured for 72 h and pulsed with [$^3$H] thymidine for final 8 hrs of the culture. Data is mean of triplicates.
Figure 14B:
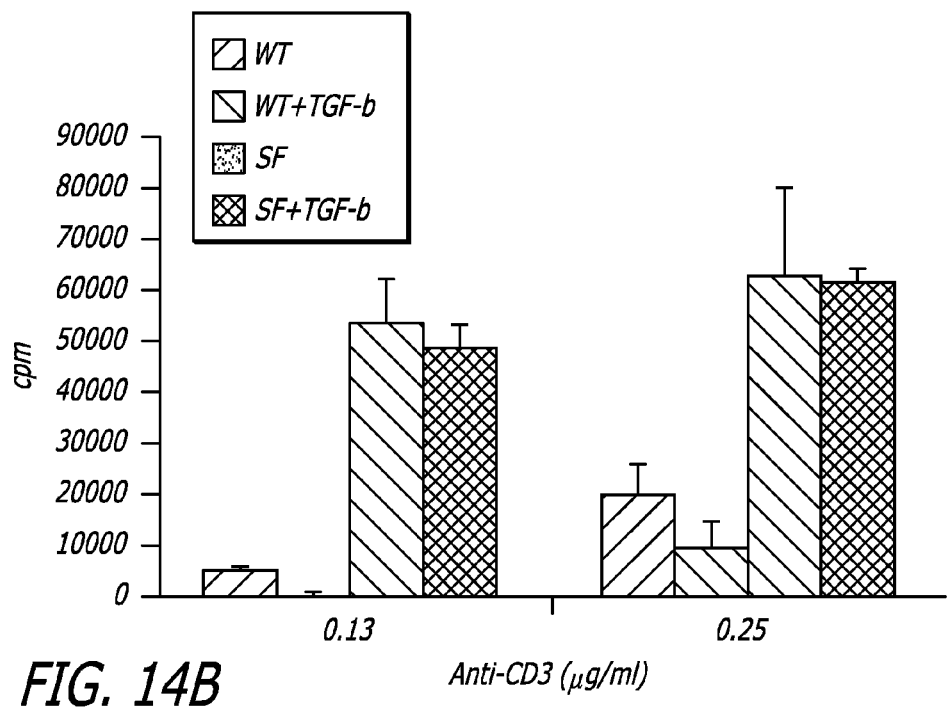
FIG. 14B depicts a graph of a proliferation assay in which $5 \times 10^4$ WT or sf CD4+ T cells were stimulated with immobilized anti-CD3 (varying concentrations) and anti-CD28 (1 µg/ml). TGF-β was added at a final concentration of 2.5 ng/ml at the beginning of the assay. The cells were cultured for 72 h and pulsed with [³H] thymidine for final 8 hrs of the culture. Data is mean of triplicates.

As expected, wildtype CD4⁺ T cells stimulated with either anti-CD3 alone (FIG. 14A) or with the combination of anti-CD3 and anti-CD28 were inhibited significantly by TGF-β (FIG. 14B). However, sf cells stimulated either with anti-CD3 or anti-CD3/CD28 were not sensitive to inhibition with TGF-β, regardless of the dose of anti-CD3 or TGF-β. The lack of TGF-β inhibition was specific to T cells since proliferation and cytokine production by B cells as well as monocytes, both stimulated with LPS, from sf mice were sensitive to TGF-β inhibition. It is worth noting however, that high levels of exogenous IL-2 can largely overcome the inhibitory effect of TGF-β on T cells, potentially by downregulating TGF-β receptor expression (Cottrez et al., *J. Immunol.* 167:773-778, 2001). T cells from sf animals produce extremely high levels of IL-2 upon stimulation, and this may contribute to the lack of inhibition by TGF-β on T cell function of sf mice. Additionally, the role of TGF-β production by T-reg cells in in vitro assays is not clear. Most experimental systems do not point to a role for TGF-β in this system, although the in vivo data does indicate an important role for TGF-β in inhibitory activity of CD4⁺CD25⁺ T-reg cells (Read et al., *J. Exp. Med.* 192:295-302, 2000).

Example 21

FoxP3 Expression is Upregulated in CD4⁺CD25⁺ T-reg Cells

The Foxp3 gene is expressed at highest levels in lymphoid tissues such as thymus, lymph node and spleen (Brunkow et al., *Nature Genetics* 27:68-72, 2001). The lymphoid expression of Foxp3 seems to be predominantly in CD4⁺ T cells, since the level of expression in CD8⁺ T cells as well as B cells was significantly lower or undetectable (Brunkow et al., *Nature Genetics* 27:68-72, 2001).

To assess if Foxp3 plays a role in CD4⁺CD25⁺ T-reg cells, the expression of Foxp3 transcript in CD4⁺CD25⁺ and CD4⁺CD25⁻ T cells from normal as well as Foxp3 transgenic mice (~16 copies of Foxp3 transgene) was compared. CD4⁺CD25⁺ or CD4⁺CD25⁻ T cell populations were collected as described above. Oligo dT primed first-strand cDNA was synthesized from these cells using the SuperScript Preamplification System (Gibco-BRL, Rockville, Md.) and used as a template for real-time RT-PCR using an ABI Prism 7700 instrument. Foxp3 expression was measured using the primers 5'-GGCCCTTCTCCAGGACAGA-3' (SEQ ID NO:17) and 5'-GCTGATCATGGCTGGGTTGT-3' (SEQ ID NO:18) at a final concentration of 300 nM and with internal TaqMan probe 5'-FAM-AGCTTCATCCTAGCGGTTTGCCTGAG-AATAC-TAMRA-3' (SEQ ID NO:19) at a final concentration of 100 nM. Dad1 was used as an endogenous reference (Hong et al., 1997). Dad1 primers were 5'-CCTCTCTG-GCT-TCATCTCTTGTGT-3' (SEQ ID NO:20) and 5'-CCG-GAGAGATGCCTTGGM-3' (SEQ ID NO:21), used at a final concentration of 50 nM and TaqMan probe 5'-6FAM-AGCT-TCATCCTAGCGGTTTGCCTGAGAATAC-TAMARA-3' (SEQ ID NO:22) at a final concentration of 100 nM. Other components of the PCR mix were from the TaqMan Universal Master Mix (PE Applied Biosystems). PCR cycling conditions were 50° C. for 2 min; 95° C. for 10 min; and 40 cycles of 95° C. for 15 seconds, 60° C. for 1 minute.

Data was collected by ABI Prism 7700 Sequence Detection System Software, Version 1.6.4. A standard curve was generated with a dilution series (1×, 1:10, 1:100, 1:1000, 1:10,000) of a standard cDNA sample which was run at the same time as the unknown samples. The software determines the relative quantity of each unknown based by plotting a curve of threshold cycle (CT) versus starting quantity and using the $C_T$ to calculate the relative level of unknown sample. Each sample was run in duplicate and mean values used for calculations. Data is expressed as normalized Foxp3 expression, which was obtained by dividing the relative quantity of Foxp3 for each sample by the relative quantity of Dad1 for the same sample.

Figure 15A:
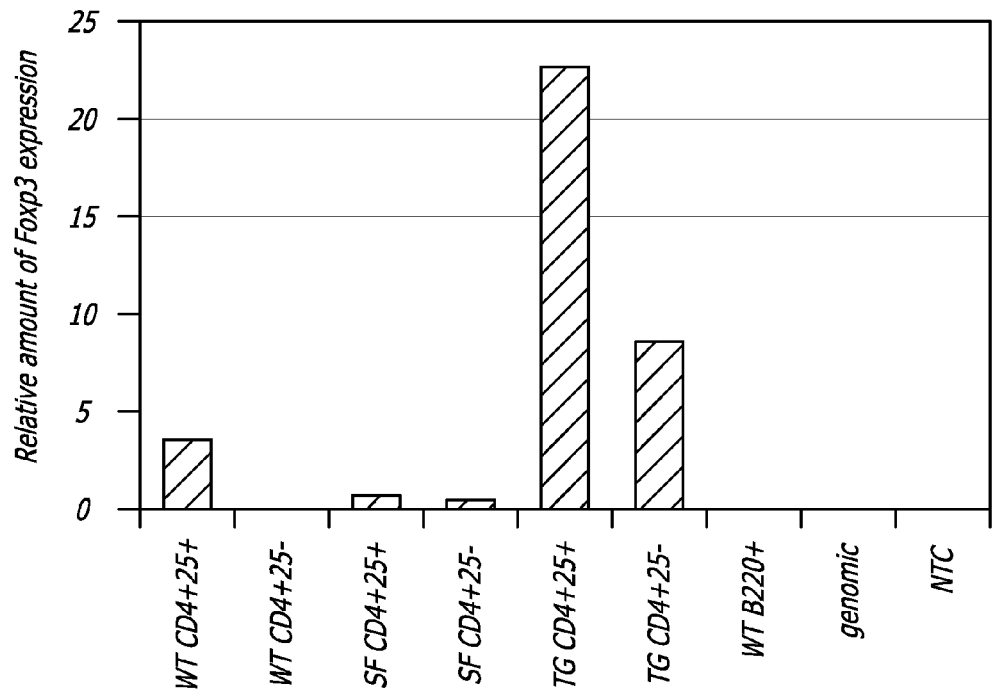
FIGS. 15A and 15B are graphs examining Foxp3 expression in cDNA samples from various cell subsets using a real-time RT-PCR method in which Dad1 served as an endogenous reference gene. Normalized Foxp3 values were derived from the ratio of Foxp3 expression to Dad1 expression.

Interestingly, the level of Foxp3 expression in CD4⁺CD25⁻ T cells was nearly undetectable whereas CD4⁺CD25⁺ T-reg cells expressed the highest amounts of Foxp3 so far described (FIG. 15A). The level of Foxp3 expression in T cell subsets of Foxp3 transgenic mice was also determined. These animals have ~16 fold the amount of Foxp3 message found in wild-type animals. In Foxp3 transgenic mice, Foxp3 expression was detectable in both CD4⁺CD25⁻ as well as CD4⁺CD25⁺ T cells, but similar to wildtype cells, CD4⁺CD25⁺ T cells expressed significantly greater levels of Foxp3. A subset of CD4⁺ cells in sf mutant animals also expresses CD25, although this population is large in size and expresses CD69, indicating they are likely cells previously activated in vivo. Nonetheless, it was determined that these CD4⁺CD25⁺ cells from the sf mutant animals do not show enhanced amounts of Foxp3 message, indicating that these cells are likely not T-reg in nature.

Figure 15B:
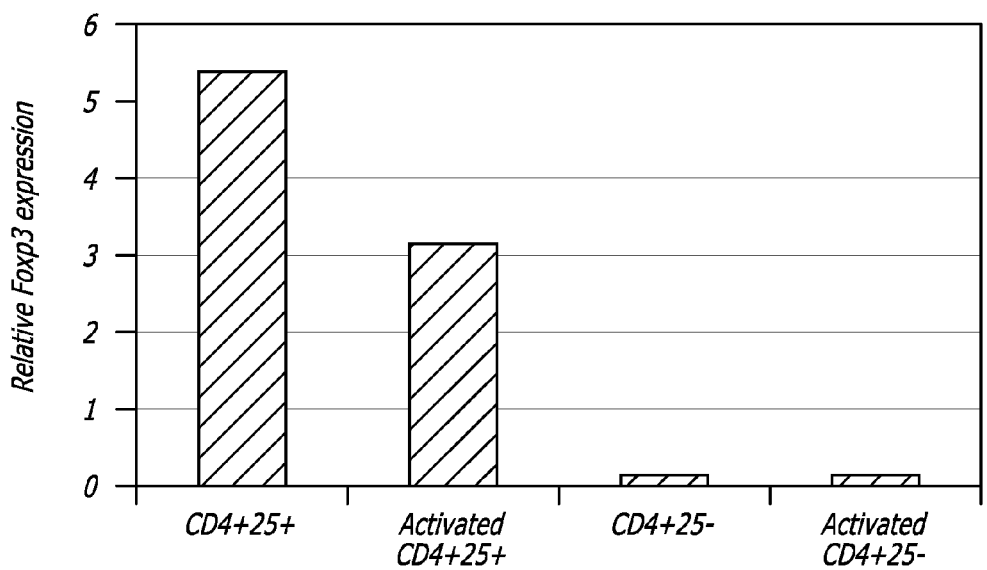

CD4⁺CD25⁺ T-reg cells express certain markers such as CTLA-4, OX-40, GITR (McHugh, R. S. et al. *Immunity* 16: 311-23, 2002); Shimizu, J. et al. *Nature Immunology* 3: 135-42, 2002) that are characteristics of activated T cells. To assess if Foxp3 expression in CD4⁺CD25⁺ T-reg cells was due to activation of T cells, Foxp3 expression was measured in CD25+ and CD25− subsets of CD4 T cells before and after in vitro activation (FIG. 15B). CD4+CD25− T cells did not express any Foxp3 even after in vitro with anti-CD3 and IL-2. Interestingly, the expression of Foxp3 in CD4⁺CD25⁺ T-reg cells decreased slightly after activation. This indicated that Foxp3 unlike any other markers reported so far on CD4⁺CD25⁺ T-reg cells was specific to this subset and was unrelated to the activated/memory phenotype of these cells.

Example 22

Figure 16A:
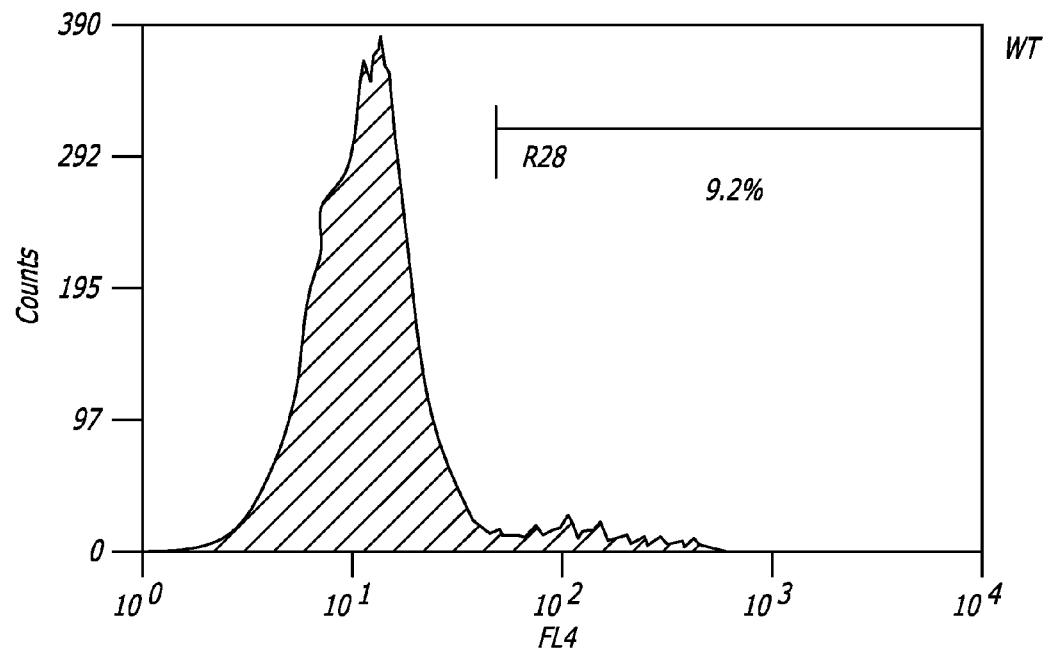
FIG. 16 depicts the level of CD25 surface expression on CD4+ T cells from WT animals, Foxp3 transgenic animals, and scurfy animals. Lymph node cells from sf, Foxp3 transgenic or littermate controls were examined for the expression of CD25 expression on CD4+ T cells. Data is representative of six individual mice examined.
Figure 16B:
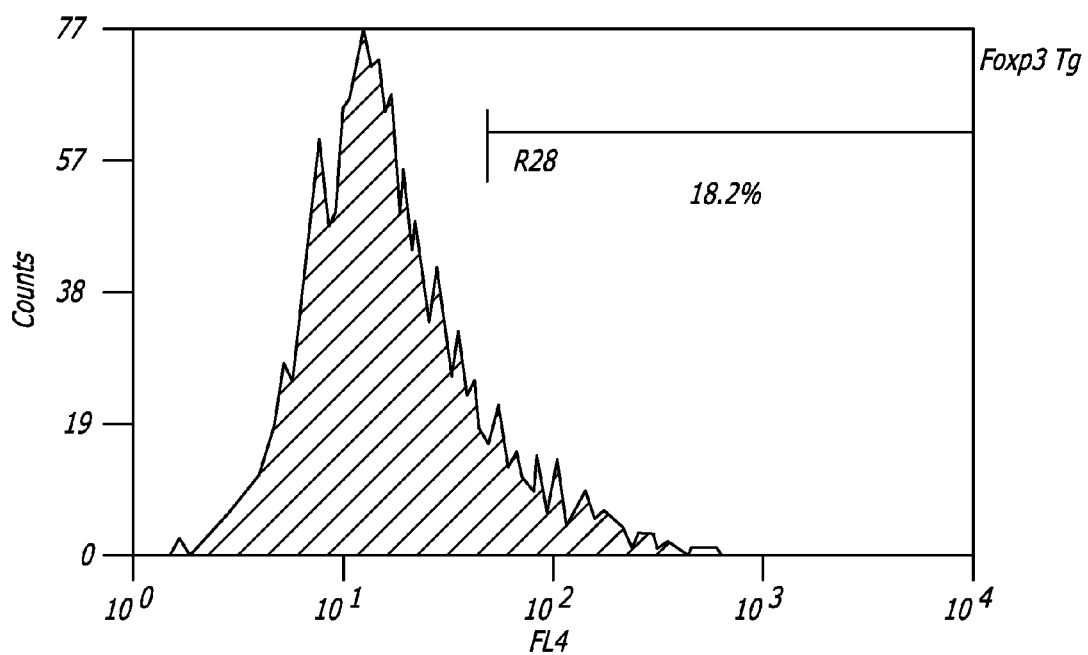
Figure 16C:
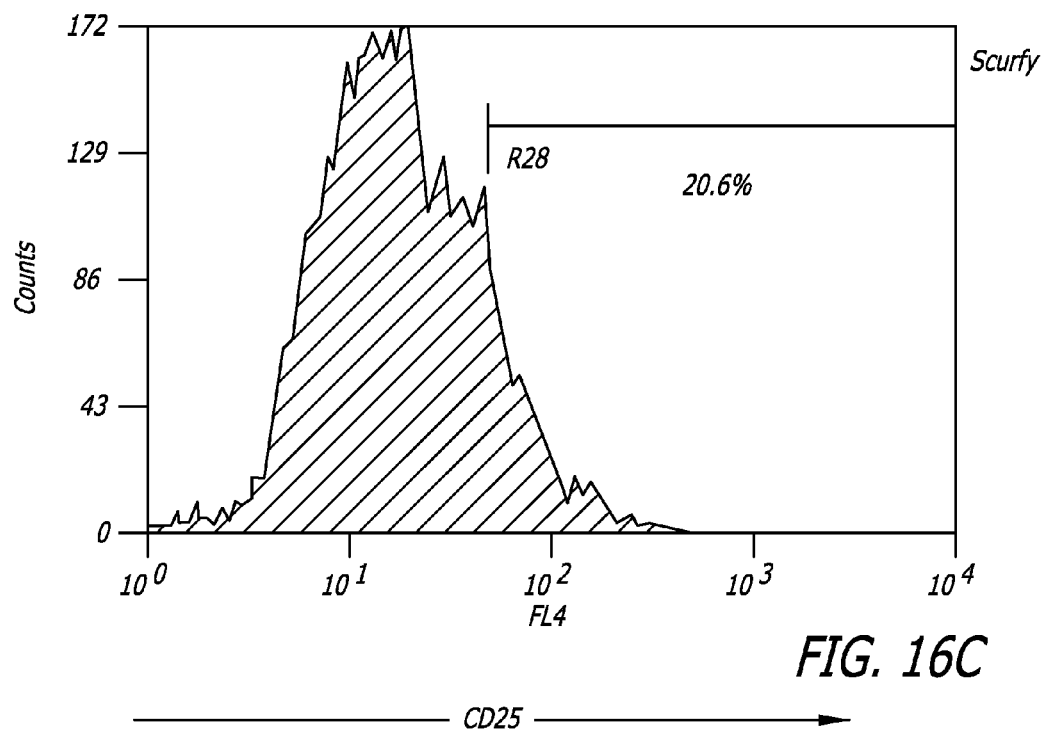
Figure 17:
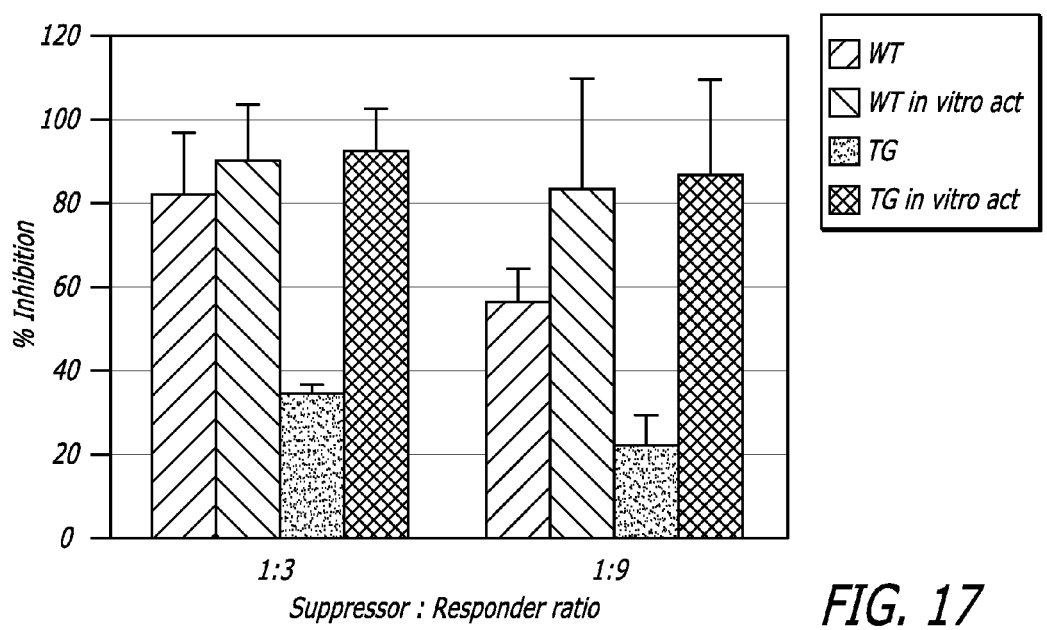
FIG. 17 is a graph depicting the level of proliferation in $5\times10^4$ WT CD4+ T cells were stimulated with anti-CD3 (1 μg/ml) and $5\times10^4$ mitomycin C treated Thy-1⁻ APC. CD4+ CD25+ T-regulatory cells from WT or Foxp3 transgenics were added at various ratios to the assay. The cells were cultured for 72 h and pulsed with [³H] thymidine for final 8 hrs of the culture. Data is mean or triplicates.

Overexpression of FoxP3 Leads to an Increased Number of CD4⁺CD25⁺ Cells But Does Not Lead to an Increase in Regulatory Activity The relatively exclusive expression of Foxp3 within the T-reg subset might indicate that this transcription factor is either required for the generation of this subset or is directly involved in its function. To determine if Foxp3 plays a role in CD4⁺CD25⁺ T-reg cell function, the functional activity of CD4⁺CD25⁺ and CD4⁺CD25⁻ T cell subset from Foxp3 transgenic mice was examined. These animals have 16 fold more Foxp3 message than found in wildtype animals, with very high amounts in the CD4⁺CD25⁺ subset. Additionally, there were fewer total CD4⁺ cells in these transgenic animals and those cells are hyporesponsive relative to their littermate controls. Whereas there were a slightly increased percentage of CD4+CD25+ T cells in the transgenic mice, the expression of CD25 was more diffuse and, unlike in wildtype animals, these cells did not comprise a distinct subset of cells (FIG. 16). A comparison of functional activity of CD4⁺CD25⁺ T-reg cells from wildtype and Foxp3 transgenic mice showed that although cells from the transgenic mice do display regulatory activity, there was no significant increase in suppressive ability relative to their wildtype counterparts on a per-cell basis (FIG. 17).

Under the T-reg assay conditions the CD4⁺CD25⁺ T-reg cells were activated at the same time as the responders. Since CD4⁺ T cells from Foxp3 transgenics were hyporesponsive to TCR stimulation it was likely that the Foxp3-Tg CD4+ CD25+ T-reg cells were not getting activated to the same extent as the wildytpe CD4⁺CD25⁺ T-reg cells during the assay. This raised the possibility that if CD4⁺CD25⁺ T-reg cells from Foxp3 transgenics were activated to the same extent as wildtype cells they would exhibit higher regulatory activity.

To address the issue CD4⁺CD25⁺ T cells were pre-activated in vitro with anti-CD3 in the presence of APC and IL-2 for 72 hours according to the previously published protocol (Thornton et al., *J. Immun.* 164:183-190, 2000). Based on our previous observations the T cells from Foxp3 transgenic mice were activated with a higher dose of anti-CD3 in vitro to give comparable proliferation as the wildtype cells. These preactivated T cells were then tested in a T-reg assay. As reported by others, preactivation of CD4⁺CD25⁺ T cells in vitro made them much more potent suppressors. However, preactivation of Foxp3 transgenic T-reg cells gave them comparable suppressor activity as wildtype T-reg cells (FIG. 17). This suggested that there was no intrinsic defect in T-reg cells from Foxp3 transgenics however overexpression of Foxp3 beyond a threshold level did not further enhance T-reg activity.

Example 23

CD4⁺CD25⁻ T Cells from Foxp3 Transgenic Mice Show Regulatory Activity

Figure 18A:
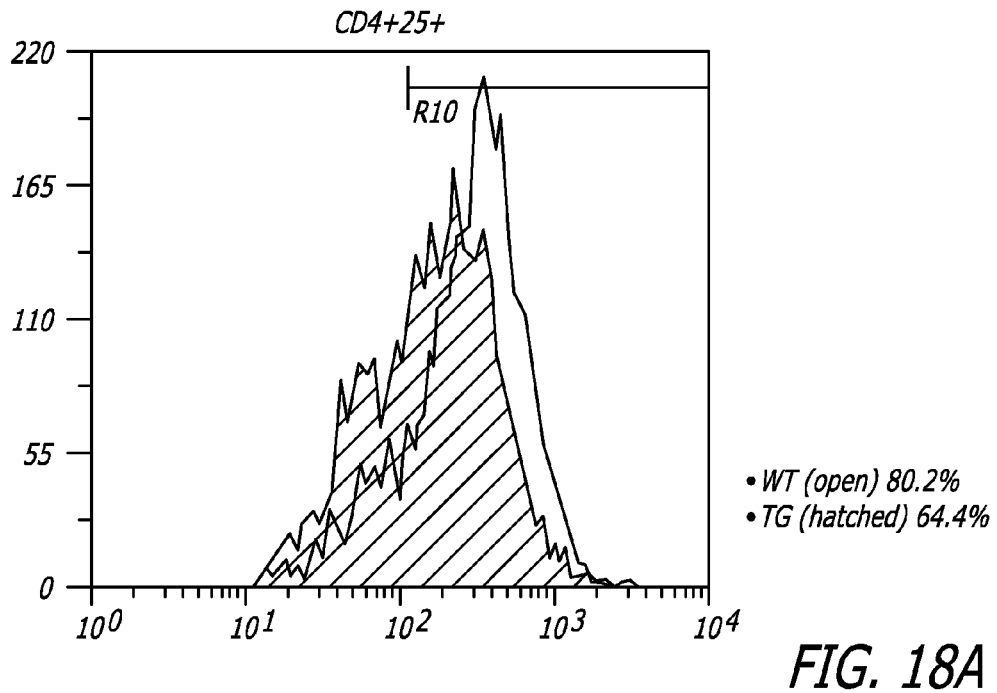
FIG. 18 is a FACS plot evaluating the expression of surface markers associated with T regulatory cells and the suppressive activity of these cells.
Figure 18B:
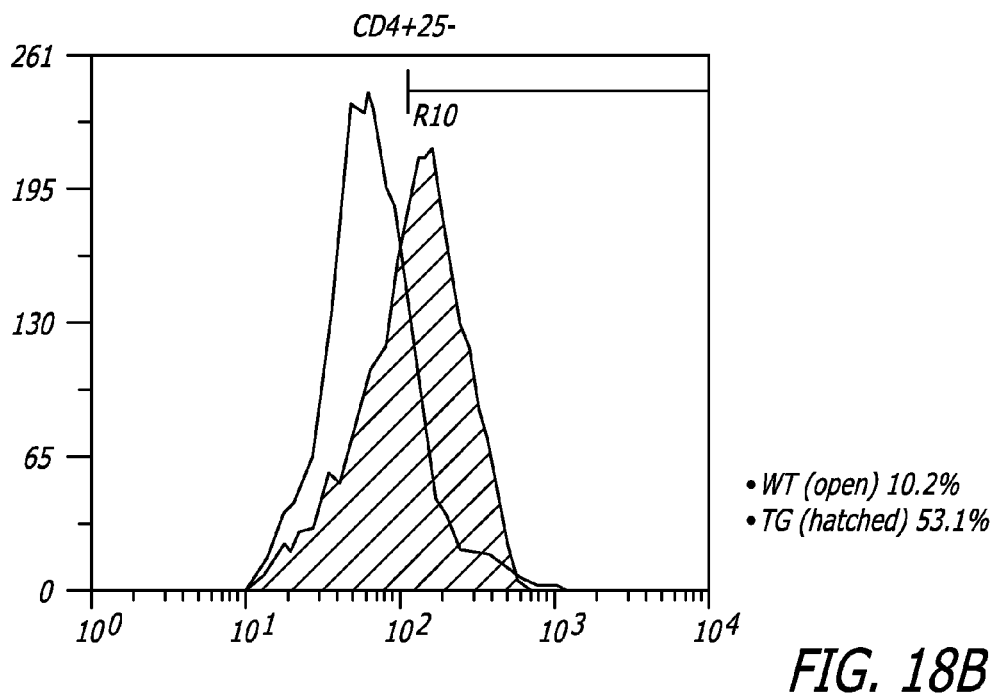
Figure 19:
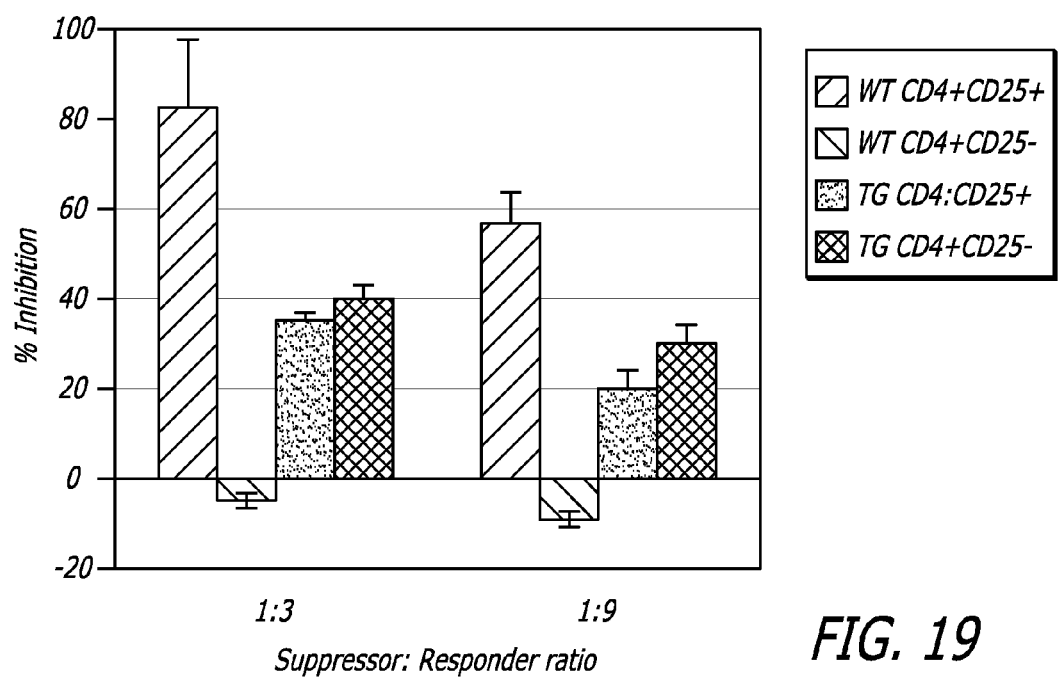
FIG. 19 is a graph depicting the level of T cell inhibition in freshly isolated CD4+CD25⁻ T cells from Foxp3 transgenic as tested in T-reg assays.

Since CD4⁺CD25⁻ T cells from Foxp3 transgenics express Foxp3 at levels higher than wild-type CD4⁺CD25⁺ T cells, we next evaluated expression of surface markers associated with T regulatory cells and the suppressive activity of these cells. Interestingly, the CD4⁺CD25⁻ T cells from Foxp3 transgenics also expressed GITR (TNFRSF18) that has recently been shown to modulate T-reg activity (FIG. 18). These cells did not express other activation associated T cell markers such as OX40, CTLA4 or Ly-6A/E (data not shown). More importantly, when freshly isolated CD4⁺CD25⁻ T cells from Foxp3 transgenic were tested for function in T-reg assay they had significant suppressive activity (FIG. 19). This activity usually ranged from comparable to lower than that of CD4⁺ CD25⁺ T cells from the same mice. As expected, such suppressive activity was never detected with wild-type CD4⁺ CD25⁻ T cells. In contrast to the CD4⁺CD25⁺ T cells, the suppressive activity of CD4⁺CD25⁻ T cells from Foxp3 transgenic could not be enhanced by preactivation with anti-CD3 and IL-2 in vitro (data not shown). This further supports the idea that the expression of Foxp3 commits a T-cell to the T-reg lineage without a direct correlation with regulatory activity.

The gene mutated in sf mice (Foxp3) has a critical role in the regulation of peripheral T cell responses. Loss of function mutations in the gene leads to a potentially fatal T cell mediated autoimmune disease both in mice and humans (Bennett et al., *Nature Genetics* 27:20-21 (2001); Lyon et al., *Proc. Nat'l. Acad. Sci. USA* 87:2433-2437 (1990); Wildin et al., *Nature Genetics* 27:18-20 (2001)). Additionally, overexpression of scurfin in transgenic mice leads to decreased peripheral T cell numbers and inhibition of a variety of T cell responses including proliferation and IL-2 production. Inhibition of IL-2 production by scurfin is not the sole explanation for hyporesponsivess since addition of exogenous IL-2 does not completely restore normal T cell response in mice overexpressing scurfin. To better understand the immunoregulatory mechanisms that may be controlled by the Foxp3 gene, further studies were conducted on the expression of this gene and the biological role of scurfin-expressing cells.

As shown in this Example, wildtype T cells can inhibit disease caused by adoptive transfer of sf CD4+ T cells into SCID mice. These observations are very similar to those made by several other groups characterizing the activity of regulatory T cells. Similar to the observation made by Powrie et al., the disease caused by sf cells was inhibited by even a small number of CD4⁺CD25⁺ T cells. CD4⁺CD25⁻ T cells were less effective at inhibiting sf T cell activity in this model, which may be due to a subset of these cells developing into a T-reg cell subset and making the appropriate inhibitory factors or due to additional mechanisms of inhibition. In addition, the in vitro hyper-responsive state of sf T cells can be inhibited by the presence of wildtype CD4⁺CD25⁺ cells, but not by the addition of TGF-β. Generally, data from in vitro T-reg experiments suggest a direct cell-cell interaction is required with no involvement of cytokines such as TGF-β (Thornton et al., *J. Exp. Med.* 188:287-296 (1998); Thornton et al., *J. Immun.* 164:183-190 (2000)). Additionally, TGF-β has no inhibitory effect on activated T cells (Cottrez et al., *J. Immunol.* 167:773-778 (2001)) making it unlikely that CD4⁺ CD25⁺ T-reg cell inhibition of sf cells in vivo is mediated by TGF-β.

To assess whether the Foxp3 gene product plays a role in CD4+CD25+ T-reg cell function we measured the expression of Foxp3 in CD4+CD25+ T-reg and CD4+CD25− T cells and measured the regulatory activity of CD4+CD25+ T-reg cells from mice overexpressing the Foxp3 gene. In both wildtype and Foxp3 transgenics, CD4+CD25+ T-reg cells expressed the highest level of Foxp3 mRNA of all different cell populations tested to date. A comparison of functional activity of CD4+CD25+ T-reg cells from wildtype and Foxp3 transgenic mice showed no increase in regulatory activity in cells from transgenic mice, even following an optimal stimulation of these cells. Importantly however, CD4+CD25− T cells from Foxp3 transgenic animals did have suppressive activity. While it is not possible to phenotypically identify a subset of T-reg cells in sf mutant mice (due to the high level of endogenous activation), CD4+CD25+ cells isolated from mutant animals neither expressed the Foxp3 gene nor did they display any suppressive activity in vitro.

These results indicate that although expression of Foxp3 can commit a T cell to the T-reg cell lineage, over expression of Foxp3 beyond a threshold level does not lead to further enhancement of regulatory activity. Furthermore, expression of Foxp3 by itself is likely not sufficient to generate T-reg cells, as CD4+CD25− from Foxp3 transgenic mice have comparable Foxp3 expression to wild-type T-reg cells but less suppressive activity. This effect on regulatory activity is unlikely due to an effect on CTLA-4 expression since there is no increase in CTLA-4 expression in Foxp3 transgenic mice and sf mutant animals express normal levels of CTLA-4.

Example 24

Modulation of Scurfin Expression

Antibodies or NCEs that modulate scurfin expression are identified using the following methods:

The scurfin promoter is cloned into commercially available Luciferase reporter vector (Promega, Madison, Wis.). This construct is then transfected into cells, such as a murine or human T cell line. Agents, such as antibodies generated against T cells, cytokines, receptors, or other proteins, in addition to small molecules, peptides, and cytokines, will be used to treat the transfected cells. The level of Luciferase activity is then determined using commercially available Luciferase assay systems (Promega) according to manufacturer's instruction to identify agents that either increase or decrease the expression of scurfin.

In an alternative approach, agents such as those described above are incubated with primary T cells under conditions that allow for the modulation of scurfin expression. The scurfin expression will be measured using the RT-PCR method described above in Example 21. Agents identified by either of the above methods will be used directly for the treatment of an autoimmune disease. Alternatively, T cells will be isolated from patients of an autoimmune disease, treated with the specific agents identified above to induce scurfin expression and transferred back into the patients to suppress the activation of other T cells.

In summary, the results of the Examples show that Foxp3 expression is predominantly seen in CD4+CD25+ T-reg subset and correlates with a basal level of regulatory activity. Over-expression of this gene can confer a regulatory function on CD4+ cells that lack CD25, indicating that this factor may be directly involved in commitment to this functional lineage.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for identifying a test compound that modulates the level of expression of scurfin comprising the steps of:
   (a) providing a composition comprising a reporter gene ligated to a ~20 kb fragment of genomic DNA normally contiguous to and upstream of mouse or human scurfin coding DNA, wherein said fragment of genomic DNA comprises a promoter region;
   (b) measuring the level of expression in the absence of said test compound, to obtain a predetermined level of expression;
   (c) contacting the composition with said test compound;
   (d) determining the level of reporter gene expression; and
   (e) comparing the level of reporter gene expression in (d) with said predetermined level of expression and thereby determining if the test compound modulates the expression of scurfin, wherein said scurfin comprises the amino acid sequence set forth in SEQ ID NO:2 or SEQ ID NO:4.

2. The method of claim 1, wherein the level of reporter gene expression is decreased.

3. The method of claim 1, wherein the level of reporter gene expression is increased.

4. The method of claim 1, wherein the test compound is a small molecule.

5. The method of claim 1, wherein the test compound is selected from the group consisting of an organic molecule, a natural product, a peptide, and an oligosaccharide.

6. The method of claim 1, wherein the test compound is from a library of compounds.

7. The method of claim 6, wherein the library is selected from the group consisting of a random peptide library, a combinatorial library, an oligosaccharide library and a phage display library.

* * * * *